US012637433B2

(12) United States Patent
Fairlie et al.

(10) Patent No.: US 12,637,433 B2
(45) Date of Patent: May 26, 2026

(54) HISTONE DEACETYLASE INHIBITORS

(71) Applicant: THE UNIVERSITY OF QUEENSLAND, St Lucia (AU)

(72) Inventors: David Fairlie, St Lucia (AU); Ligong Liu, St Lucia (AU); Robert Reid, St Lucia (AU); Jeffrey Mak, St Lucia (AU)

(73) Assignee: THE UNIVERSITY OF QUEENSLAND, Queensland (AU)

( * ) Notice: Subject to any disclaimer, the term of this patent is extended or adjusted under 35 U.S.C. 154(b) by 392 days.

(21) Appl. No.: 18/259,052

(22) PCT Filed: Dec. 23, 2021

(86) PCT No.: PCT/AU2021/051558

§ 371 (c)(1),
(2) Date: Jun. 22, 2023

(87) PCT Pub. No.: WO2022/133551

PCT Pub. Date: Jun. 30, 2022

(65) Prior Publication Data

US 2024/0109847 A1 Apr. 4, 2024

(30) Foreign Application Priority Data

Dec. 23, 2020 (AU) ................................ 2020904810

(51) Int. Cl.
*C07D 239/91* (2006.01)
*C07D 231/56* (2006.01)

(52) U.S. Cl.
CPC ......... *C07D 239/91* (2013.01); *C07D 231/56* (2013.01)

(58) Field of Classification Search
CPC ............................ C07D 239/91; C07D 231/56
See application file for complete search history.

(56) References Cited

U.S. PATENT DOCUMENTS

| | | | |
|---|---|---|---|
| 5,512,681 A * | 4/1996 | Boswell | C07D 235/02 548/251 |
| 2014/0045850 A1 | 2/2014 | Mallais et al. | |

FOREIGN PATENT DOCUMENTS

| | | |
|---|---|---|
| CN | 112028829 A | 12/2020 |
| WO | 2003076422 | 9/2003 |
| WO | 2009055917 A1 | 5/2009 |
| WO | 2018057933 | 3/2018 |
| WO | 2018213364 | 11/2018 |
| WO | 2018237007 | 12/2018 |

OTHER PUBLICATIONS

Qi, J Cell Biochem, 2018, 119:3081-3090. (Year: 2018).*
McCann, Islets, 2019, vol. 11, No. 5, 112-118. (Year: 2019).*
Lou, Cell Reports, 2019, 29, 749-763. (Year: 2019).*
Parra, Current Opinion in Pharmacology, 2010, 10 ;454-460. (Year: 2010).*
Zhou, Theranostics, 2022, vol. 12, Issue 5, 2080-2094. (Year: 2022).*
S. Zhang et al., "Electrochemical Formation of N-acyloxy amidyl radicals and their application: Regioselective Intramolecular Amination of sp2 and sp3 C—H Bonds", Organic Letters, Jun. 4, 2018, vol. 20, No. 12, pp. 3443-3446.
International Search Report for PCT/AU2021/051558 mailed Feb. 17, 2022, 5 pages.
Written Opinion of the ISA for PCT/AU2021/051558 mailed Feb. 17, 2022, 6 pages.
Olson et al., "Hydroxamate-Based Histone Deacetylase Inhibitors Can Protect Neurons from Oxidative Stress via a Histone Deacetylase-Independent Catalase-Like Mechanism", Chemistry & Biology 22, 2015, 439-445.

* cited by examiner

*Primary Examiner* — D Margaret M Seaman
(74) *Attorney, Agent, or Firm* — NIXON & VANDERHYE, PC

(57) ABSTRACT

The present application is directed towards compounds, pharmaceutically acceptable salts or prodrugs thereof, which are inhibitors of Histone Deacetylase (HDAC) binding or function. The compounds especially may have some selectivity for inhibiting Class IIa versus Class I HDACs. The present application also relates to methods of using the compounds and to uses of the compounds, especially in relation to the prevention of a disease, disorder or condition associated with Class IIa HDAC activity. In one form, the compounds are (ortho-phenyl) phenyl hydroxamates. In another form, the compounds are as provided in Formula (I), wherein R1 is a phenyl or cycloalkenyl which may be optionally substituted. Formula (I)

(I)

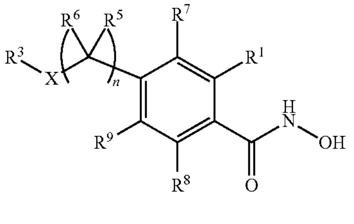

5 Claims, 3 Drawing Sheets

HISTONE DEACETYLASE INHIBITORS

CROSS-REFERENCE TO RELATED APPLICATIONS

This application is the U.S. national phase of International Application No. PCT/AU2021/051558 filed Dec. 23, 2021, which designated the U.S. and claims priority to AU 2020904810 filed Dec. 23, 2020, the entire contents of each of which are hereby incorporated by reference.

TECHNICAL FIELD

The present invention relates, inter alia, to compounds, pharmaceutical compositions of said compounds, and uses of said compounds. The compounds are especially for binding to class IIa histone deacetylases (HDACs) to inhibit interaction with proteins and peptides.

BACKGROUND ART

It will be clearly understood that, if a prior art publication is referred to herein, this reference does not constitute an admission that the publication forms part of the common general knowledge in the art in Australia or in any other country.

In eukaryotic cells, DNA is wound around proteins called histones, and the resultant protein/DNA complex is called chromatin. The DNA is wound around the histones, at least in part, through electrostatic interactions, as DNA carries a negative charge and histones carry a positive charge.

Histone acetyltransferases (HATs) catalyse acetylation of the terminal amino group of lysine in histones, which decreases the positive charge carried by the histone, and in turn relaxes the wound DNA structure of chromatin. Relaxation of the chromatin wound DNA structure allows for increased access for the DNA to transcription factors, thus promoting transcription. The reverse reaction, histone deacetylation, is mediated by histone deacetylases (HDACs) and increases the positive charge carried by the histone by deacetylating the terminal amino group of lysine, and in turn tightens the wound DNA structure of chromatin.

Acetylation of the terminal amino group of lysine is now known to also occur in many other proteins and is considered to be a common posttranslational modification. Deacetylation of enzymes and proteins facilitates epigenetic and posttranslational regulation of many genes and proteins that influences transcription, translation and the functions of multiprotein complexes.

Histone deacetylases are also now referred to as lysine deacetylases since they are now known to remove the acetyl group from numerous acetylated proteins, not just histones, including either in the nucleus or the cytoplasm. As such compounds that bind in the lysine-binding groove of HDACs can potentially block interactions with lysine-containing proteins that would normally bind in that site. Consequently, ligands that bind to HDACs may be viewed as affinity probes that deny protein-protein interactions such as denying binding between an acetylated lysine residue in one protein and zinc in a HDAC. Inhibition is therefore not just a measure of blockade of catalytic function of a specific HDAC but also a measure of blockade of non-catalytic protein interaction with a specific HDAC. Compounds that can bind tightly to a specific HDAC can thus potentially exert an effect on a HDAC-binding protein either by catalysing the enzymatic deacetylation reaction or by blocking binding of the lysine component of any protein that interacts with the HDAC at its zinc-bound location. As such, small molecules that bind in the catalytic binding site of a given HDAC may be inhibitors of HDAC enzyme function or inhibitors of HDAC binding to proteins.

HDACs represent promising molecular targets, as these proteins have been found to be involved in a wide range of diseases and conditions including cancers, neurodegenerative diseases, immune disorders, inflammatory diseases (and inflammation), kidney dysfunction (including renal fibrosis/injury) and liver dysfunction, and cardiovascular diseases. However, as HDACs are found throughout the body, it is difficult to achieve a selective effect.

Mammalian HDACs contain eighteen isoforms that can be divided into four classes. Class I HDACs includes HDAC1, HDAC2, HDAC3, and HDAC8 and are the most studied and well characterized. They are constitutively nuclear and have the most robust, classical deacetylase activity of all HDAC enzymes. Class II HDACs are further subdivided into class IIa and class IIb. Class IIa HDACs include HDAC4, HDAC5, HDAC7, and HDAC9 and shuttle between the nucleus and cytoplasm. Class IIb HDACs include HDAC6 and HDAC10 and are mainly cytoplasmic. Class III HDACs are called sirtuins and are structurally and functionally distinct from class I, II, and IV HDACs in that their deacetylase activity is $NAD^+$ dependent as opposed to $Zn^+$ dependent. HDAC11 is the only known human deacetylase in class IV.

Class I HDACs are ubiquitous in human organs and tissues. However, class IIa HDACs are more abundant in skeletal muscle, brain, heart, ovary, colon, thymus and placenta and less toxic to cells (Wang et al, Mol. Cell. Biol. 1999, 19 (11), 7816-7827; Grozinger et al, Proc. Natl. Acad. Sci. 1999, 96 (9), 4868-4873; Fischle et al, J. Biol. Chem. 1999, 274 (17), 11713-11720; Dequiedt et al, Immunity 2003, 18 (5), 687-698; Xie et al, Am. J. Hypertens. 2019, 32 (5), 515-523). Therefore, selective binding to class IIa HDACs over class I HDACs is likely to be more organ or tissue specific with less off-target effects.

However, it is extremely difficult to develop inhibitors that are selective for individual HDAC isoforms. In part, this is because all HDACs have similar structures with a long tubular active site to accommodate a lysine side chain.

HDAC inhibitors have been reported, for example, in WO2018/213364. However, the compounds in WO2018/213364 were tested against HDAC1, HDAC2, HDAC3, HDAC6, HDAC8, HDAC10 and HDAC11, and it was concluded that some compounds showed selective inhibition of HDAC6. As outlined above, these specific isoforms cover HDAC classes I, IIb and IV and class IIa was not investigated.

Similarly, HDAC inhibitors have been disclosed in WO2009/055917. While WO2009/055917 discusses the benefits of identification of inhibitors for specific HDAC isoforms, the patent is particularly directed towards HDAC inhibitors selected from the group consisting of HDAC4, HDAC5, HDAC6, HDAC7, HDAC8, HDAC9 and/or HDAC11. Furthermore, the only biological activities provided relate to compounds with an $IC_{50}$ value, specifically for inhibiting catalytic enzymatic activity for removing the acetyl group of lysine in an activated substrate, of less than or equal to 12 μM against one or more of HDAC4, HDAC5, HDAC6, HDAC7, HDAC8, HDAC9 and/or HDAC11 (without providing selectivity data or activity against any one isoform). As outlined above, these specific isoforms cover HDAC classes I, IIa, IIb and IV.

WO2018/057933 discusses compounds, compositions and methods for reducing oxidative stress in cardiomyocytes. In some embodiments the compound or composition is said to be a selective inhibitor of the catalytic enzymatic action of class IIa HDACs. However, the only compound disclosed in that document is TMP195 (N-(2-methyl-2-(2-phenyloxazol-4-yl)propyl)-3-(5-(trifluoromethyl)-1,2,4-oxadiazol-3-yl)benzamide).

SUMMARY OF INVENTION

In one aspect, the present invention is directed, inter alia, to compounds or a pharmaceutically acceptable salt or prodrug thereof which are inhibitors of HDAC binding or function, especially inhibitors of Class IIa HDACs.

With the foregoing in view, the present invention in some forms resides broadly in N-hydroxy-biphenyl-carboxamides, especially (ortho-phenyl) phenyl hydroxamates.

In a first aspect, the present invention provides a compound of Formula (I), or a pharmaceutically acceptable salt or prodrug thereof:

Formula (I)

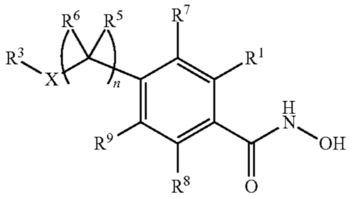

wherein,

X is —N($R^2$)—, —O—, —C($R^{2a}$)$_2$—, —S— or —Se—;

$R^1$ is selected from phenyl or cycloalkenyl, wherein said phenyl or cycloalkenyl are optionally substituted by one or more of the group consisting of: F, Cl, $CFH_2$, $CHF_2$, $CH_3$ and $CF_3$;

$R^3$ is selected from the group consisting of: $R^4$, —CO—NH—$R^4$, —CO—$R^4$, —C($R^{19a}R^{19b}$)$R^4$, —CO—C($R^{19a}R^{19b}$)$R^4$, —CO—C($R^{19a}R^{19b}$)—NH—$R^4$, —CO—C($R^{19a}R^{19b}$)—$NH^2$, —C($R^{19a}R^{19b}$)—CO—NH—$R^4$, —CO—C($R^{19a}R^{19b}$)—CO—NH—$R^4$ and H;

$R^2$ is selected from the group consisting of: H and $R^{10}$; or $R^2$ together with $R^3$ and the nitrogen to which they are bonded form a heterocyclyl or heteroaryl, wherein said heterocyclyl or heteroaryl is optionally substituted;

$R^e$a is selected from the group consisting of: H and $R^{10}$; or one $R^e$a together with $R^3$ and the carbon to which they are bonded form a heterocyclyl, heteroaryl, aryl, cycloalkyl or cycloalkenyl; wherein said heterocyclyl, heteroaryl, aryl, cycloalkyl or cycloalkenyl is optionally substituted;

$R^4$ is selected from the group consisting of: heterocyclyl, heteroaryl, aryl, cycloalkyl, cycloalkenyl, alkyl, alkenyl and alkynyl; wherein said heterocyclyl, heteroaryl, aryl, cycloalkyl, cycloalkenyl, alkyl, alkenyl and alkynyl are optionally substituted;

$R^{10}$ is selected from the group consisting of: heterocyclyl, heteroaryl, aryl, cycloalkyl, cycloalkenyl, alkyl, alkenyl and alkynyl; wherein said heterocyclyl, heteroaryl, aryl, cycloalkyl, cycloalkenyl, alkyl, alkenyl and alkynyl are optionally substituted;

$R^5$ and $R^6$ are each independently selected from the group consisting of: H, alkyl, alkenyl, alkynyl, halo, aryl, cycloalkyl, cycloalkenyl, heterocyclyl and heteroaryl; wherein said alkyl, alkenyl, alkynyl, aryl, cycloalkyl, cycloalkenyl, heterocyclyl or heteroaryl are optionally substituted; or $R^5$ and $R^6$ together with the carbon to which they are bonded form a cycloalkyl, cycloalkenyl or heterocyclyl; wherein said cycloalkyl, cycloalkenyl or heterocyclyl are optionally substituted;

$R^7$, $R^8$ and $R^9$ are each independently selected from the group consisting of: H, F, Cl, $CH_3$ and $CF_3$;

$R^{19a}$ and $R^{19b}$ are each independently selected from the group consisting of: H, $C_{1-6}$alkyl, and $C_{1-6}$haloalkyl; or $R^{19a}$ and $R^{19b}$ together with the carbon to which they are bonded form a cycloalkyl, cycloalkenyl or heterocyclyl; wherein said cycloalkyl, cycloalkenyl or heterocyclyl are optionally substituted; and n is 0 or 1.

Advantageously, the inventors have found that the combination of a phenyl ring substituted by a —CO—NH—OH group, and ortho substituted by a phenyl group provides some selectivity for inhibiting Class IIa versus Class I HDAC. More particularly, this combination provides selectivity for HDAC7 (a representative class IIa HDAC) against HDAC1 (a representative class I HDAC). Affinity for class IIa HDACs (or HDAC7) may be improved through modifying the substitution at the position on the phenyl para to the —CO—NH—OH group. The inventors have found that HDAC1 provides a good representation for activity against HDAC Class I more generally. Achieving selectivity is very difficult, at least in part because all HDACs have the capacity to interact with the acetylated terminal nitrogen atom of lysine.

In addition to acetyl cleavage of substrates, class IIa HDACs are also postulated to mediate biological effects through active site or surface binding/recognition of protein partners. Inhibitors that block class IIa HDAC processing of substrates must first bind to them and so are also capable of blocking substrate binding in the cavity/active site, but active site binding affinity can be formally established using a published assay (Meyners et al, Chemistry 2017, 23(13), 3107-3116).

In an embodiment of the first aspect, the present invention provides a compound of Formula (Ia), or a pharmaceutically acceptable salt or prodrug thereof:

Formula (Ia)

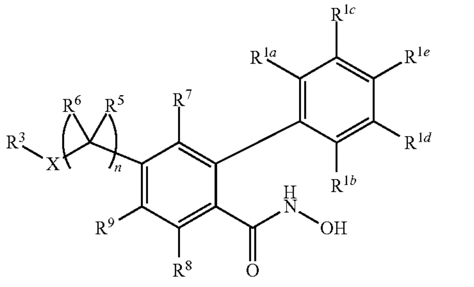

wherein,

X is —N($R^2$)— or —O—;

$R^{1a}$, $R^{1b}$, $R^{1c}$, $R^{1d}$, $R^{1e}$ are each independently selected from the group consisting of: H, F, Cl, $CH_3$ and $CF_3$;

$R^3$ is selected from the group consisting of: $R^4$, —CO—NH—$R^4$, —CO—$R^4$, —C($R^{19a}R^{19b}$)$R^4$, —CO—C($R^{19a}R^{19b}$)$R^4$, +($R^{19a}R^{19b}$)—CO—NH—$R^4$, —CO—C($R^{19a}R^{19b}$)—CO—NH—$R^4$ and H;

$R^2$ is selected from the group consisting of: H and $R^{10}$; or $R^2$ together with $R^3$ and the nitrogen to which they are bonded form a heterocyclyl or heteroaryl, wherein said heterocyclyl or heteroaryl is optionally substituted;

$R^4$ is selected from the group consisting of: heterocyclyl, heteroaryl, aryl, cycloalkyl, cycloalkenyl, alkyl, alkenyl and alkynyl; wherein said heterocyclyl, heteroaryl, aryl, cycloalkyl, cycloalkenyl, alkyl, alkenyl and alkynyl are optionally substituted;

$R^{10}$ is selected from the group consisting of: heterocyclyl, heteroaryl, aryl, cycloalkyl, cycloalkenyl, alkyl, alkenyl and alkynyl; wherein said heterocyclyl, heteroaryl, aryl, cycloalkyl, cycloalkenyl, alkyl, alkenyl and alkynyl are optionally substituted;

$R^5$ and $R^6$ are each independently selected from the group consisting of: H, alkyl, alkenyl, alkynyl, halo, aryl, cycloalkyl, cycloalkenyl, heterocyclyl and heteroaryl; wherein said alkyl, alkenyl, alkynyl, aryl, cycloalkyl, cycloalkenyl, heterocyclyl or heteroaryl are optionally substituted; or $R^5$ and $R^6$ together with the carbon to which they are bonded form a cycloalkyl, cycloalkenyl or heterocyclyl; wherein said cycloalkyl, cycloalkenyl or heterocyclyl are optionally substituted;

$R^7$, $R^8$ and $R^9$ are each independently selected from the group consisting of: H, F, Cl, $CH_3$ and $CF_3$;

$R^{19a}$ and $R^{19b}$ are each independently selected from the group consisting of: H, $C_{1-6}$alkyl, and $C_{1-6}$haloalkyl; or $R^{19a}$ and $R^{19b}$ together with the carbon to which they are bonded form a cycloalkyl, cycloalkenyl or heterocyclyl; wherein said cycloalkyl, cycloalkenyl or heterocyclyl are optionally substituted; and n is 0 or 1.

In an embodiment of the first aspect, the present invention provides a compound of Formula (I), or a pharmaceutically acceptable salt or prodrug thereof:

Formula (I)

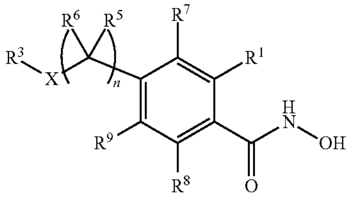

wherein,

X is —N($R^2$)—, —O—, —C($R^{2a}$)$_2$—, —S— or —Se—;

$R^1$ is selected from phenyl or cycloalkenyl, wherein said phenyl or cycloalkenyl are optionally substituted by one or more of the group consisting of: F, Cl, $CFH_2$, $CHF_2$, $CH_3$ and $CF_3$;

$R^3$ is selected from the group consisting of: $R^4$, —CO—NH—$R^4$, —CO—$R^4$, —C($R^{19a}R^{19b}$)$R^4$, —CO—C($R^{19a}R^{19b}$)$R^4$, —CO—C($R^{19a}R^{19b}$)—NH—$R^4$, —CO—C($R^{19a}R^{19b}$)—$NH^2$, —C($R^{19a}R^{19b}$)—CO—NH—$R^4$, —CO—C($R^{19a}R^{19b}$)—CO—NH—$R^4$ and H;

$R^2$ is selected from the group consisting of: H and $R^{10}$; or $R^2$ together with $R^3$ and the nitrogen to which they are bonded form a heterocyclyl or heteroaryl, wherein said heterocyclyl or heteroaryl is optionally substituted by one or more $R^{25}$;

$R^{2a}$ is selected from the group consisting of: H and $R^{10}$; or one $R^e$a together with $R^3$ and the carbon to which they are bonded form a heterocyclyl, heteroaryl, aryl, cycloalkyl or cycloalkenyl; wherein said heterocyclyl, heteroaryl, aryl, cycloalkyl or cycloalkenyl is optionally substituted by one or more $R^{25}$;

$R^4$ is selected from the group consisting of: heterocyclyl, heteroaryl, aryl, cycloalkyl, cycloalkenyl, alkyl (especially $C_{1-12}$alkyl, more especially $C_{1-6}$alkyl), alkenyl (especially $C_{2-12}$alkenyl, more especially $C_{2-6}$alkenyl) and alkynyl (especially $C_{2-12}$alkynyl, more especially $C_{2-6}$alkynyl); wherein said heterocyclyl, heteroaryl, aryl, cycloalkyl, cycloalkenyl, alkyl, alkenyl and alkynyl is optionally substituted by one or more $R^{30}$; wherein $R^{30}$ is selected from the group consisting of: —$R^{21}$ aryl, —$R^{21}$-heterocyclyl, —$R^{21}$-heteroaryl, —$R^{21}$-cycloalkyl, —$R^{21}$-cycloalkenyl, —$C_{1-6}$alkyl, —$C_{1-6}$haloalkyl, =O, halo, nitro, —$R^{21}$—$NR^{22}R^{23}$—$R^{21}$—N($R^{22}$)—CO—$R^{23}$, —$R^{21}$—CO—$NR^{22}R^{23}$, —$R^{21}$—CO—$R^{24}$, —$R^{21}$—O—$R^{24}$, and —$R^{21}$—N($R^{22}$)—CO—$R^{24}$; wherein $R^{21}$ is selected from the group consisting of: a bond, $C_{1-12}$alkylene, and -cycloalkylene; $R^{22}$ and $R^{23}$ are each independently selected from the group consisting of: H, $C_{1-6}$alkyl, $C_{1-6}$haloalkyl, and OH; $R^{24}$ is selected from the group consisting of: H, OH, $C_{1-6}$alkyl, $C_{1-6}$haloalkyl, —O—$C_{1-6}$alkyl, and —O—$C_{1-6}$haloalkyl;

$R^{10}$ is selected from the group consisting of: heterocyclyl, heteroaryl, aryl, cycloalkyl, cycloalkenyl, alkyl (especially $C_{1-12}$alkyl, more especially $C_{1-6}$alkyl), alkenyl (especially $C_{1-12}$alkenyl, more especially $C_{1-6}$alkenyl) and alkynyl (especially $C_{1-12}$alkynyl, more especially $C_{1-6}$alkynyl); wherein said heterocyclyl, heteroaryl, aryl, cycloalkyl, cycloalkenyl, alkyl, alkenyl and alkynyl is optionally substituted by one or more $R^{10a}$; wherein $R^{10a}$ is selected from the group consisting of: —$R^{10b}$-aryl, —$R^{10b}$-heterocyclyl, —$R^{10b}$-heteroaryl, —$R^{10b}$-cycloalkyl, —$R^{10b}$-cycloalkenyl, —$C_{1-6}$alkyl, —$C_{1-6}$haloalkyl, =O, halo, nitro, —$R^{10b}$ $NR^{10c}R^{10d}$, —$R^{10b}$—N($R^{10c}$)—CO—$R^{10d}$, —$R^{10b}$—CO—$NR^{10c}R^{10d}$, —$R^{10b}$—CO—$R^{10e}$—$R^{10b}$—O—$R^{10e}$ and —$R^{10b}$—N($R^{10c}$)—CO—$R^{10e}$; wherein $R^{10b}$ is selected from the group consisting of: a bond, $C_{1-12}$alkylene, and -cycloalkylene; $R^{10c}$ and $R^{10a}$ are each independently selected from the group consisting of: H, $C_{1-6}$alkyl, $C_{1-6}$haloalkyl, and OH; $R^{10e}$ is selected from the group consisting of: H, OH, $C_{1-6}$alkyl, $C_{1-6}$haloalkyl, —O—$C_{1-6}$alkyl, and —O—$C_{1-6}$halo alkyl;

$R^5$ and $R^6$ are each independently selected from the group consisting of: H, alkyl (especially $C_{1-12}$alkyl, more especially $C_{1-6}$alkyl), alkenyl (especially $C_{1-12}$alkenyl, more especially $C_{1-6}$alkenyl), alkynyl (especially $C_{1-12}$alkynyl, more especially $C_{1-6}$alkynyl), halo, aryl, cycloalkyl, cycloalkenyl, heterocyclyl and heteroaryl; wherein said alkyl, alkenyl, alkynyl, aryl, cycloalkyl, cycloalkenyl, heterocyclyl or heteroaryl are optionally substituted by one or more of $C_{1-6}$alkyl, $C_{1-6}$haloalkyl, halo, =O, aryl, cycloalkyl, cycloalkenyl, heterocyclyl and heteroaryl; or $R^5$ and $R^6$ together with the carbon to which they are bonded form a cycloalkyl, cycloalkenyl or heterocyclyl; wherein said cycloalkyl, cycloalkenyl or heterocyclyl are optionally substituted by one or more of $C_{1-6}$alkyl, $C_{1-6}$haloalkyl, OH, =O and halo;

$R^7$, $R^8$ and $R^9$ are each independently selected from the group consisting of: H, F, Cl, $CH_3$ and $CF_3$;

$R^{19a}$ and $R^{19b}$ are each independently selected from the group consisting of: H, $C_{1-6}$alkyl, and $C_{1-6}$haloalkyl; or $R^{19a}$ and $R^{19b}$ together with the carbon to which they are bonded form a cycloalkyl, cycloalkenyl or heterocyclyl; wherein said cycloalkyl, cycloalkenyl or heterocyclyl are optionally substituted by one or more of $C_{1-6}$alkyl, $C_{1-6}$haloalkyl, OH, =O, $NH_2$, and halo;

Each $R^{25}$ is independently selected from the group consisting of: —$R^{26}$-aryl, —$R^{26}$— heterocyclyl, —$R^{26}$-heteroaryl, —$R^{26}$-cycloalkyl, —$R^{26}$-cycloalkenyl, =O, —$C_{1-12}$alkyl, —$C_{1-12}$haloalkyl, halo, —$R^{26}$—$NR^{27}R^{28}$, —$R^{26}$—N($R^{27}$)—CO—$R^{28}$, —$R^{26}$—CO—$NR^{27}R^{28}$, —$R^{26}$—CO—$R^{29}$, —$R^{26}$—O—$R^{29}$, —$R^{26}$—S—$R^{29}$, and —$R^{26}$—N($R^{27}$)—CO—$R^{29}$; wherein $R^{26}$ is selected from the group consisting of: a bond, $C_{1-12}$alkylene, and -cycloalkylene; $R^{27}$ and $R^{28}$ are each independently selected from the group consisting of: H, $C_{1-6}$ alkyl, $C_{1-6}$haloalkyl and OH; and $R^{29}$ is selected from the group consisting of: H, OH, $C_{1-6}$alkyl, $C_{1-6}$haloalkyl, —O—$C_{1-6}$alkyl, and —O—$C_{1-6}$haloalkyl; and n is 0 or 1.

In an embodiment of the first aspect, the present invention provides a compound of Formula (Ia), or a pharmaceutically acceptable salt or prodrug thereof:

Formula (Ia)

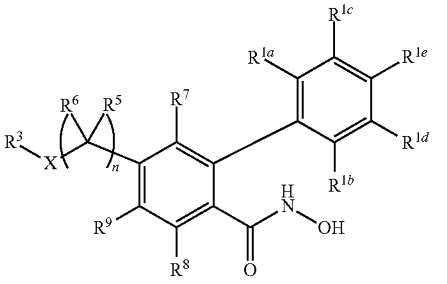

wherein,

X is —N($R^2$)— or —O—;

$R^{1a}$, $R^{1b}$, $R^{1c}$, $R^{1d}$, $R^{1e}$ are each independently selected from the group consisting of: H, F, $C_1$, $CH_3$ and $CF_3$;

$R^3$ is selected from the group consisting of: $R^4$, —CO—NH—$R^4$, —CO—$R^4$, —C($R^{19a}R^{19b}$)$R^4$, —CO C($R^{19a}R^{19b}$)$R^4$, —C($R^{19a}R^{19b}$)—CO—NH—$R^4$, —CO—C($R^{19a}R^{19b}$)—CO—NH—$R^4$ and H;

$R^2$ is selected from the group consisting of: H and $R^{10}$; or $R^2$ together with $R^3$ and the nitrogen to which they are bonded form a heterocyclyl or heteroaryl, wherein said heterocyclyl or heteroaryl is optionally substituted by one or more $R^{25}$;

$R^4$ is selected from the group consisting of: heterocyclyl, heteroaryl, aryl, cycloalkyl, cycloalkenyl, alkyl (especially $C_{1-12}$alkyl, more especially $C_{1-6}$alkyl), alkenyl (especially $C_{2-12}$alkenyl, more especially $C_{2-6}$alkenyl) and alkynyl (especially $C_{2-12}$alkynyl, more especially $C_{2-6}$alkynyl); wherein said heterocyclyl, heteroaryl, aryl, cycloalkyl, cycloalkenyl, alkyl, alkenyl and alkynyl is optionally substituted by one or more $R^{30}$; wherein $R^{30}$ is selected from the group consisting of: —$R^{21}$ aryl, —$R^{21}$-heterocyclyl, —$R^{21}$-heteroaryl, —$R^{21}$-cycloalkyl, —$R^{21}$-cycloalkenyl, —$C_{1-6}$alkyl, $C_{1-6}$haloalkyl, =O, halo, nitro, —$R^{21}$—$NR^{22}R^{23}$, —$R^{21}$—N($R^{22}$)—CO—$R^{23}$, —$R^{21}$—CO—$NR^{22}R^{23}$, —$R^{21}$—CO—$R^{24}$, —$R^{21}$—O—$R^{24}$, and —$R^{21}$—N($R^{22}$)—CO—$R^{24}$; wherein $R^{21}$ is selected from the group consisting of: a bond, $C_{1-12}$alkylene, and -cycloalkylene; $R^{22}$ and $R^{23}$ are each independently selected from the group consisting of: H, $C_{1-6}$alkyl, $C_{1-6}$haloalkyl, and OH; $R^{24}$ is selected from the group consisting of: H, OH, $C_{1-6}$alkyl, $C_{1-6}$haloalkyl, —O—$C_{1-6}$alkyl, and —O—$C_{1-6}$haloalkyl; $R^{10}$ is selected from the group consisting of: heterocyclyl, heteroaryl, aryl, cycloalkyl, cycloalkenyl, alkyl (especially $C_{1-12}$alkyl, more especially $C_{1-6}$alkyl), alkenyl (especially $C_{1-12}$alkenyl, more especially $C_{1-6}$alkenyl) and alkynyl (especially $C_{1-12}$alkynyl, more especially $C_{1-6}$alkynyl); wherein said heterocyclyl, heteroaryl, aryl, cycloalkyl, cycloalkenyl, alkyl, alkenyl and alkynyl is optionally substituted by one or more $R^{10a}$; wherein $R^{10a}$ is selected from the group consisting of: $R^{10b}$-aryl, —$R^{10b}$-heterocyclyl, —$R^{10b}$-heteroaryl, —$R^{10b}$-cycloalkyl, —$R^{10b}$-cycloalkenyl, —$C_{1-6}$alkyl, —$C_{1-6}$haloalkyl, =O, halo, nitro, —$R^{10b}$—$NR^{10c}R^{10d}$, —$R^{10b}$—N($R^{10c}$)—CO—$R^{10d}$, —$R^{10b}$—CO—$NR^{10c}R^{10d}$, —$R^{10b}$—CO—$R^{10e}$, —$R^{10b}$—O—$R^{10e}$ and —$R^{10b}$—N($R^{10c}$)—CO—$R^{10e}$; wherein $R^{10b}$ is selected from the group consisting of: a bond, $C_{1-12}$alkylene, and -cycloalkylene; $R^{10c}$ and $R^{10d}$ are each independently selected from the group consisting of: H, $C_{1-6}$alkyl, $C_{1-6}$haloalkyl, and OH; $R^{10e}$ is selected from the group consisting of: H, OH, $C_{1-6}$alkyl, $C_{1-6}$haloalkyl, —O—$C_{1-6}$alkyl, and —O—$C_{1-6}$halo alkyl;

$R^5$ and $R^6$ are each independently selected from the group consisting of: H, alkyl (especially $C_{1-12}$alkyl, more especially $C_{1-6}$alkyl), alkenyl (especially $C_{1-12}$alkenyl, more especially $C_{1-6}$alkenyl), alkynyl (especially $C_{1-12}$alkynyl, more especially $C_{1-6}$alkynyl), halo, aryl, cycloalkyl, cycloalkenyl, heterocyclyl and heteroaryl; wherein said alkyl, alkenyl, alkynyl, aryl, cycloalkyl, cycloalkenyl, heterocyclyl or heteroaryl are optionally substituted by one or more of $C_{1-6}$alkyl, $C_{1-6}$haloalkyl, halo, =O, aryl, cycloalkyl, cycloalkenyl, heterocyclyl and heteroaryl; or $R^5$ and $R^6$ together with the carbon to which they are bonded form a cycloalkyl, cycloalkenyl or heterocyclyl; wherein said cycloalkyl, cycloalkenyl or heterocyclyl are optionally substituted by one or more of $C_{1-6}$alkyl, $C_{1-6}$haloalkyl, OH, =O and halo;

$R^7$, $R^8$ and $R^9$ are each independently selected from the group consisting of: H, F, $C_1$, $CH_3$ and $CF_3$;

$R^{19a}$ and $R^{19b}$ are each independently selected from the group consisting of: H, $C_{1-6}$alkyl, and $C_{1-6}$haloalkyl; or $R^{19a}$ and $R^{19b}$ together with the carbon to which they are bonded form a cycloalkyl, cycloalkenyl or heterocyclyl; wherein said cycloalkyl, cycloalkenyl or heterocyclyl are optionally substituted by one or more of $C_{1-6}$alkyl, $C_{1-6}$haloalkyl, OH, =O, $NH_2$, and halo;

Each $R^{25}$ is independently selected from the group consisting of: —$R^{26}$-aryl, —$R^{26}$— heterocyclyl, —$R^{26}$-heteroaryl, —$R^{26}$-cycloalkyl, —$R^{26}$-cycloalkenyl, =O, —$C_{1-12}$alkyl, —$C_{1-12}$haloalkyl, halo, —$R^{26}$—$NR^{27}R^{28}$, —$R^{26}$—N($R^{27}$)—CO—$R^{28}$, —$R^{26}$—CO—$NR^{27}R^{28}$, —$R^{26}$—CO—$R^{29}$, —$R^{26}$—O—$R^{29}$, —$R^{26}$—S—$R^{29}$, and —$R^{26}$—N($R^{27}$)—CO—$R^{29}$; wherein $R^{26}$ is selected from the group consisting of: a bond, $C_{1-12}$alkylene, and -cycloalkylene; $R^{27}$ and $R^{28}$ are each independently selected from the group consisting of: H, $C_{1-6}$ alkyl, $C_{1-6}$haloalkyl and OH; and $R^{29}$ is selected from the group consisting of: H, OH, $C_{1-6}$alkyl, $C_{1-6}$haloalkyl, —O—$C_{1-6}$alkyl, and —O—$C_{1-6}$haloalkyl; and n is 0 or 1.

In some embodiments of compounds of Formula (I) or Formula (Ia), one or more of the features of paragraphs [0023] to [0058] may apply (the features of paragraphs [0023] to [0058] may apply alone or in combination with features of any others of paragraphs [0023] to [0058]).

In one embodiment, the compound or the pharmaceutically acceptable salt or prodrug thereof of the first aspect, is the compound or the pharmaceutically acceptable salt. In one embodiment, the compound or the pharmaceutically acceptable salt or prodrug thereof of the first aspect is not a prodrug. The compound of Formula (I) may be a compound of Formula (Ia).

In one embodiment, $R^1$ is

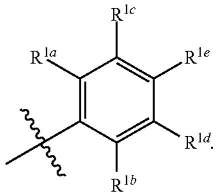

In another embodiment, $R^1$ is cyclohexenyl or cyclopentenyl, optionally substituted by one or more of: F, $C_1$, $CFH_2$, $CHF_2$, $CH_3$ and $CF_3$. In one embodiment, $R^{1a}$, $R^{1b}$, $R^{1c}$, $R^{1d}$, $R^{1e}$ are each independently selected from the group consisting of: H, F, $C_1$, $CFH_2$, $CHF_2$, $CH_3$ and $CF_3$.

In one embodiment, $R^{1a}$ and $R^{1b}$ are each independently selected from the group consisting of: H, $CH_3$, F and Cl; most especially $R^{1a}$ and $R^{1b}$ are H. In one embodiment $R^{1e}$, $R^{1d}$ and $R^{1e}$ are each independently selected from the group consisting of: H, F, $C_1$, and $CH_3$; most especially $R^{1c}$, $R^{1d}$ and $R^{1e}$ are H. In one embodiment, $R^{1a}$, $R^{1b}$, $R^{1c}$, $R^{1d}$ and $R^{1e}$ are each H.

In certain embodiments, $R^7$, $R^8$ and $R^9$ are each independently selected from the group consisting of: H, F, Cl and $CH_3$; more especially selected from the group consisting of: H, F and Cl; most especially $R^7$, $R^8$ and $R^9$ are H.

In one embodiment, n is 1. In another embodiment, n is 0.

In one embodiment, $R^5$ and $R^6$ are each independently selected from the group consisting of: H, $C_{1-12}$alkyl (especially $C_{1-6}$alkyl), $C_{2-12}$alkenyl (especially $C_{2-6}$alkenyl), $C_{2-12}$alkynyl (especially $C_{2-6}$alkynyl), halo, aryl, cycloalkyl, heterocyclyl and heteroaryl; wherein said $C_{1-12}$alkyl, $C_{2-12}$alkenyl, $C_{2-12}$alkynyl, aryl, cycloalkyl, heterocyclyl or heteroaryl are optionally substituted; or $R^5$ and $R^6$ together with the carbon to which they are bonded form a cycloalkyl or heterocyclyl; wherein said cycloalkyl or heterocyclyl are optionally substituted.

In one embodiment, $R^5$ and $R^6$ are each independently selected from the group consisting of: H, halo, aryl, cycloalkyl, heterocyclyl and heteroaryl; wherein said aryl, cycloalkyl, heterocyclyl or heteroaryl are optionally substituted (especially by one or more of $C_{1-6}$alkyl, $C_{1-6}$haloalkyl, halo, ═O, aryl, cycloalkyl, heterocyclyl and heteroaryl). In another embodiment, $R^5$ and $R^6$ are each independently selected from the group consisting of: H, halo, aryl and heteroaryl; wherein said aryl, or heteroaryl are optionally substituted (especially by one or more of $C_{1-6}$alkyl, $C_{1-6}$haloalkyl, halo, ═O, aryl, cycloalkyl, heterocyclyl and heteroaryl). In a further embodiment, $R^5$ and $R^6$ are each independently selected from the group consisting of: H and heteroaryl; wherein said heteroaryl is optionally substituted (especially by one or more of ═O, aryl or heteroaryl). In a further embodiment, $R^5$ and $R^6$ are each H.

In certain embodiments, $R^5$ and $R^6$ together with the carbon to which they are bonded form a cycloalkyl (especially a 3 to 6 membered cycloalkyl ring) or heterocyclyl (especially a 3 to 6 membered heterocyclyl ring); wherein said cycloalkyl or heterocyclyl are optionally substituted, especially by one or more of $C_{1-6}$alkyl, $C_{1-6}$haloalkyl, OH, ═O, and halo.

In one embodiment, X is —N($R^2$)—. In another embodiment, X is —O—. In a further embodiment, X is —C($R^{2a}$)$_2$—. In another embodiment, X is —CH($R^{2a}$)—.

In certain embodiments, $R^2$ is selected from the group consisting of: H, $C_{1-12}$alkyl and $C_{1-12}$haloalkyl; more especially $R^2$ is selected from the group consisting of: H, $C_{1-6}$alkyl and $C_{1-6}$haloalkyl; even more especially $R^2$ is selected from the group consisting of: H and methyl; most especially $R^2$ is H.

In one embodiment, $R^3$ is selected from the group consisting of: $R^4$, —CO—NH—$R^4$, —CO—$R^4$, CO C($R^{19a}R^{19b}$)$R^4$, —C($R^{19a}R^{19b}$)—CO—NH—$R^4$ and —CO—C($R^{19a}R^{19b}$)—CO—NH—$R^4$. In another embodiment, $R^3$ is selected from the group consisting of: $R^4$, —CO—NH—$R^4$, —CO—$R^4$, —C($R^{19a}R^{19b}$)$R^4$, —CO—C($R^{19a}R^{19b}$)$R^4$, —CO—C($R^{19a}R^{19b}$)—CO—NH—$R^4$ and H. In another embodiment, $R^3$ is selected from the group consisting of: $R^4$, —CO—NH—$R^4$, —CO—$R^4$ and —CO—C($R^{19a}R^{19b}$)—CO—NH—$R^4$. In one embodiment, $R^3$ is

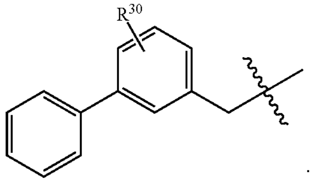

In another embodiment, $R^3$ is

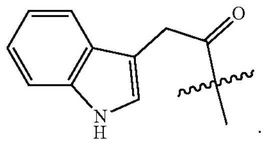

In a further embodiment, $R^3$ is

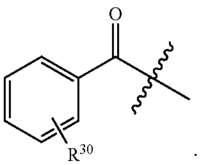

In one embodiment, $R^{19a}$ and $R^{19b}$ are each independently selected from the group consisting of: $C_{1-6}$alkyl and $C_{1-6}$haloalkyl; or $R^{19a}$ and $R^{19b}$ together with the carbon to which they are bonded form a cycloalkyl or heterocyclyl; wherein said cycloalkyl or heterocyclyl are optionally substituted (especially by one or more of $C_{1-6}$alkyl, $C_{1-6}$haloalkyl, OH, ═O, $NH_2$ and halo). In one embodiment, $R^{19a}$ and $R^{19b}$ together with the carbon to which they are bonded form a cycloalkyl or heterocyclyl; wherein said cycloalkyl or heterocyclyl are optionally substituted (especially by one or more of $C_{1-6}$alkyl, $C_{1-6}$haloalkyl, OH, ═O, $NH_2$ and halo). In a further embodiment, $R^{19a}$ and $R^{19b}$ together with the carbon to which they are bonded form

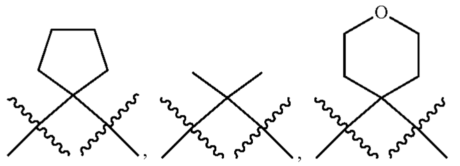

or

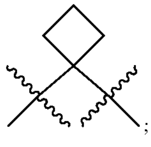

especially

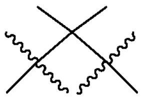

or

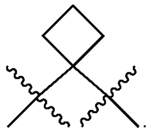

In a further embodiment, $R^{19a}$ and $R^{19b}$ are H.

In one embodiment, $R^4$ is selected from the group consisting of: heterocyclyl, heteroaryl, aryl, cycloalkyl, and $C_{1-12}$alkyl (especially $C_{1-6}$alkyl); wherein said heterocyclyl, heteroaryl, aryl, and cycloalkyl are optionally substituted. In another embodiment, $R^4$ is selected from the group consisting of: heterocyclyl, heteroaryl and aryl; wherein said heterocyclyl, heteroaryl and aryl are optionally substituted.

In one embodiment, $R^4$ is selected from the group consisting of: heterocyclyl, heteroaryl, aryl, cycloalkyl, and $C_{1-12}$alkyl; wherein said heterocyclyl, heteroaryl, aryl and cycloalkyl is optionally substituted by one or more $R^{30}$.

In one embodiment, $R^4$ is selected from the group consisting of: a monocyclic heterocyclyl, a bicyclic heterocyclyl, a monocyclic heteroaryl, a bicyclic heteroaryl, a monocyclic aryl, a bicyclic aryl, a monocyclic cycloalkyl, a bicyclic cycloalkyl and $C_{1-12}$alkyl; wherein said monocyclic heterocyclyl, bicyclic heterocyclyl, monocyclic heteroaryl, bicyclic heteroaryl, monocyclic aryl, bicyclic aryl, monocyclic cycloalkyl, bicyclic cycloalkyl and $C_{1-12}$alkyl are optionally substituted, especially by one or more $R^{30}$. In another embodiment, $R^4$ is selected from the group consisting of: a monocyclic heterocyclyl, a bicyclic heterocyclyl, a monocyclic heteroaryl, a bicyclic heteroaryl, a monocyclic aryl, a bicyclic aryl, a monocyclic cycloalkyl, and a bicyclic cycloalkyl; wherein said monocyclic heterocyclyl, bicyclic heterocyclyl, monocyclic heteroaryl, bicyclic heteroaryl, monocyclic aryl, bicyclic aryl, monocyclic cycloalkyl, and bicyclic cycloalkyl are optionally substituted, especially by one or more $R^{30}$.

In one embodiment, $R^4$ is selected from the group consisting of: quinolinyl, phenyl, $C_{1-12}$alkyl, pyridyl, pyrrolyl, indolyl, pyrrolidinyl, naphthyl, pyrimidinyl, pyrazinyl, imidazolyl, quinazolinyl, quinazolinone, pyrimidinone, benzimidazolyl, isoindolin-1,3-dione, pyrimidin-2,4-dione, pyridinone, piperazinyl, piperidinyl, piperazin-2,5-dione, benzodiazepinyl, benzo-1,4-diazepin-2,5-dione, imidazolidinyl, imidazoline-2,4-dione and triazolyl. In another embodiment, $R^4$ is selected from the group consisting of: quinolinyl, phenyl, pyridyl, pyrrolyl, indolyl, pyrrolidinyl, naphthyl, pyrimidinyl, pyrazinyl, imidazolyl, quinazolinyl, quinazolinone, pyrimidinone, benzimidazolyl, isoindolin-1,3-dione, pyrimidin-2,4-dione, pyridinone, piperazinyl, piperidinyl, piperazin-2,5-dione, benzodiazepinyl, benzo-1,4-diazepin-2,5-dione, imidazolidinyl, imidazoline-2,4-dione and triazolyl; especially selected from the group consisting of: quinolinyl, phenyl, $C_{1-12}$alkyl, pyridyl, pyrrolyl, indolyl, pyrrolidinyl, naphthyl, pyrimidinyl, pyrazinyl, imidazolyl, quinazolinyl, quinazolinone, pyrimidinone, benzimidazolyl, isoindolin-1,3-dione, pyrimidin-2,4-dione, pyridinone, piperazinyl, piperidinyl, piperazin-2,5-dione, benzodiazepinyl, benzo-1,4-diazepin-2,5-dione, imidazolidinyl, imidazoline-2,4-dione and triazolyl. In another embodiment, $R^4$ is selected from the group consisting of: quinolinyl, phenyl, pyridyl, pyrrolyl, indolyl, pyrrolidinyl, naphthyl, pyrimidinyl, pyrazinyl and imidazolyl. In an embodiment, the $R^4$ groups in this paragraph are optionally substituted, especially by one or more $R^{30}$.

In one embodiment, $R^4$ is selected from the group consisting of: $C_{1-12}$alkyl (especially $C_{1-6}$alkyl) which is optionally substituted by one or more $R^{30}$,

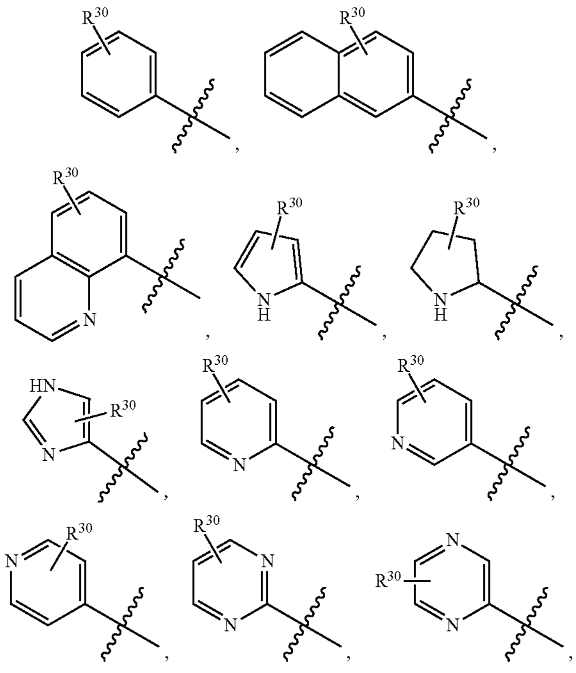

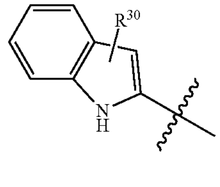

and

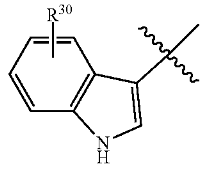

In a further embodiment, $R^4$ is selected from the group consisting of:

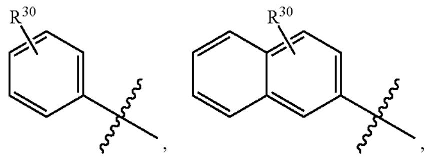

-continued

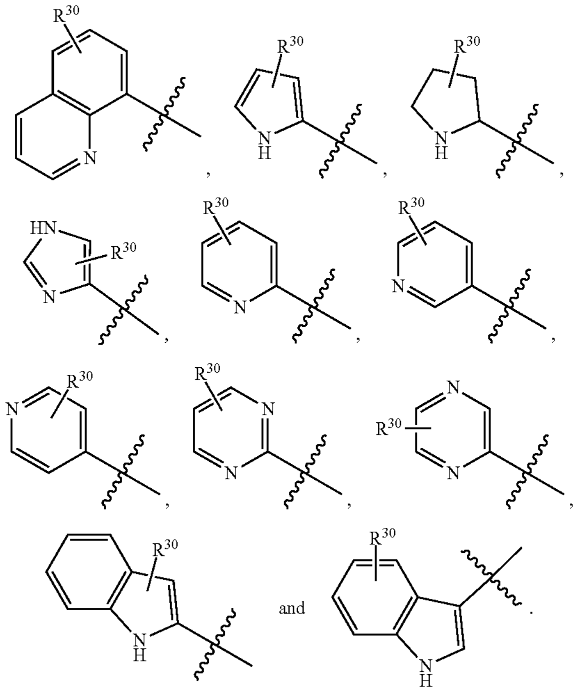

and

In another embodiment, $R^4$ is selected from the group consisting of: $C_{1-12}$alkyl(especially $C_{1-6}$alkyl) which is optionally substituted by one or more $R^{30}$,

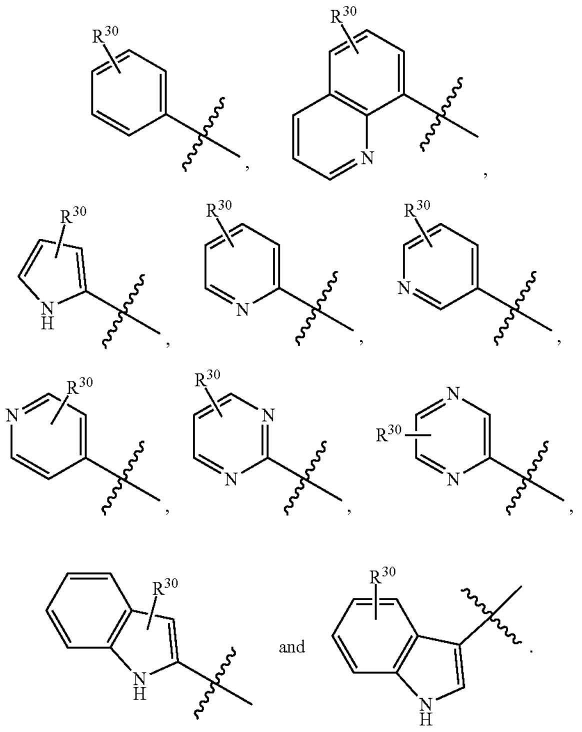

and

In a further embodiment, $R^4$ is selected from the group consisting of: $C_{1-12}$alkyl (especially $C_{1-6}$alkyl) which is optionally substituted by one or more $R^{30}$,

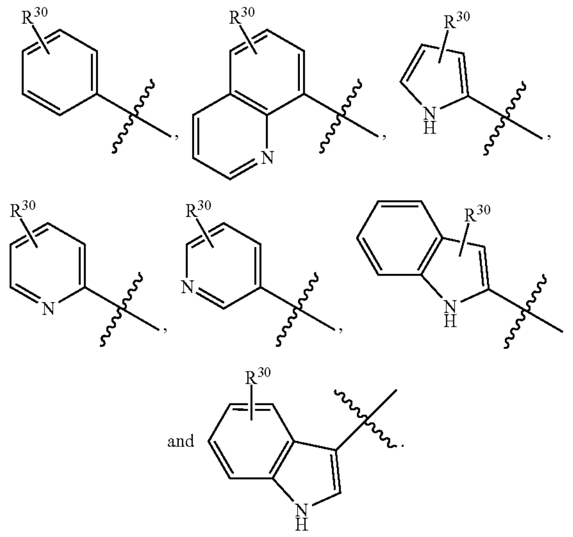

and

In one embodiment, $R^4$ is selected from the group consisting: of $C_{1-12}$alkyl(especially $C_{1-6}$alkyl),

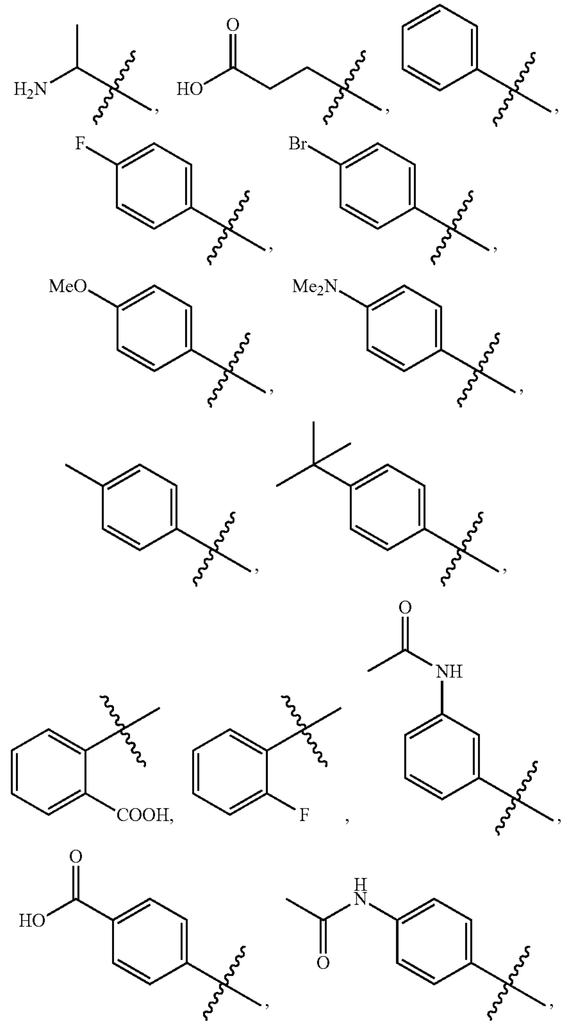

-continued
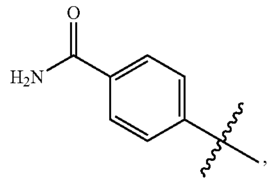,
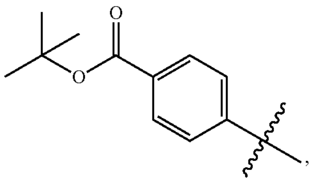,
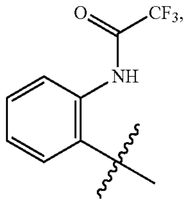,
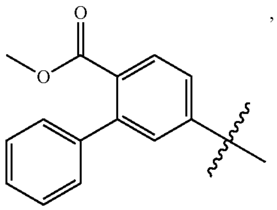,
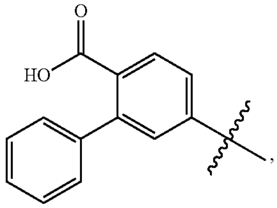,
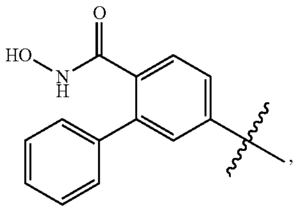,
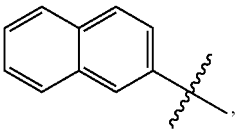,
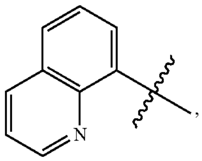,
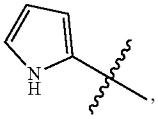,
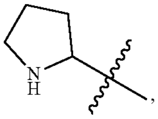,
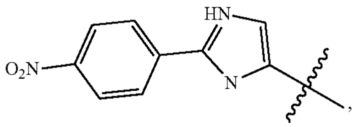,
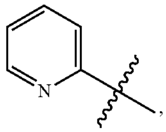,
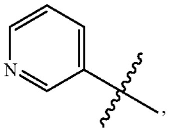,
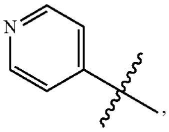,
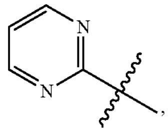,
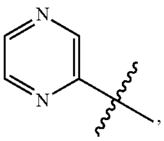,
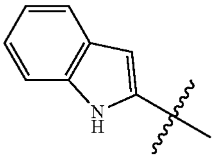 and
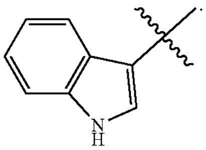.
In one embodiment, $R^4$ is selected from the group consisting: of $C_{1-12}$alkyl (especially $C_{1-6}$alkyl),
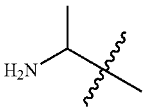,
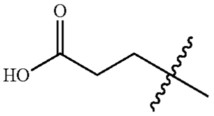,
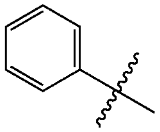,
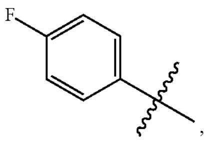,
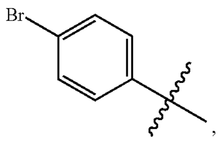,
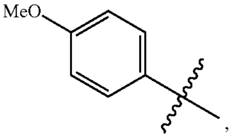,
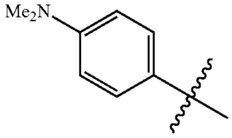,
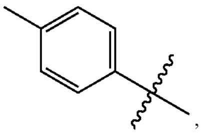,
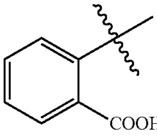,
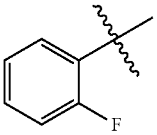,
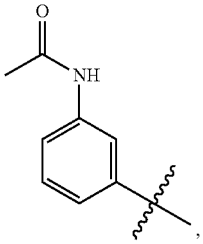,
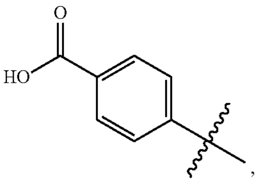,
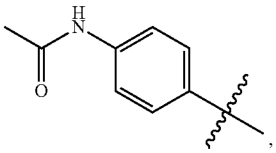,
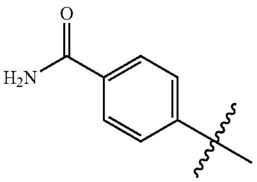,
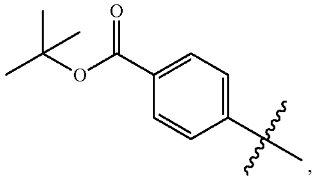,
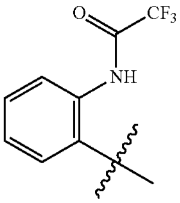,
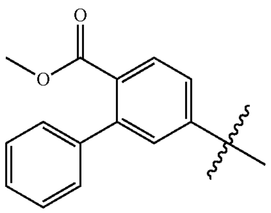,
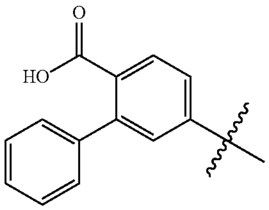, -continued
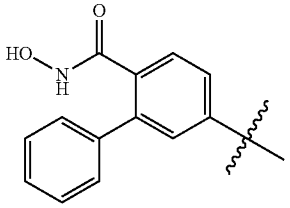
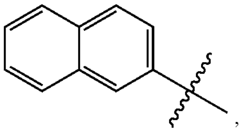
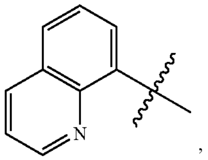
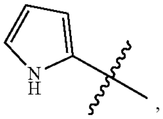
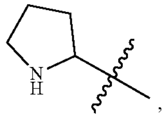
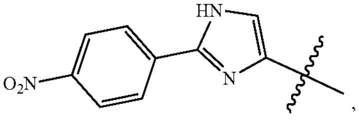
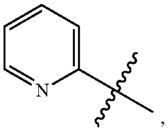
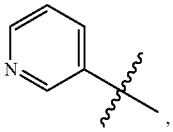
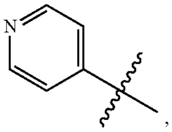
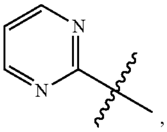
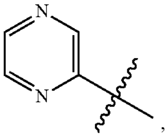
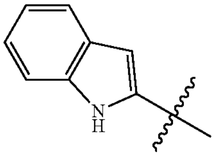
and
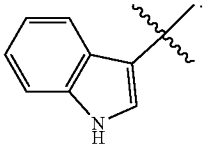
In another embodiment, $R^4$ is selected from the group consisting: of $C_{1-12}$alkyl (especially $C_{1-6}$alkyl),
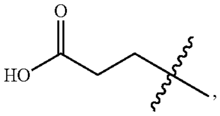
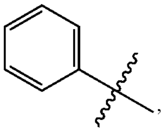
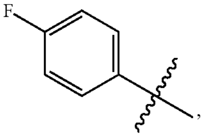
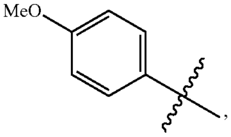
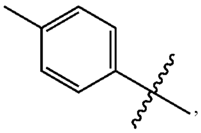
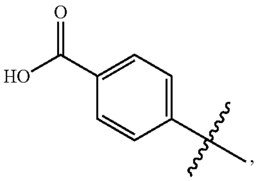
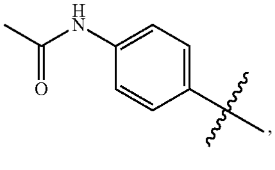
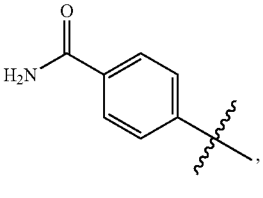
-continued
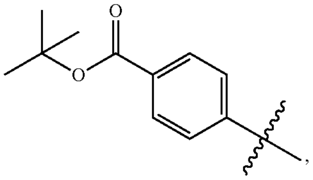
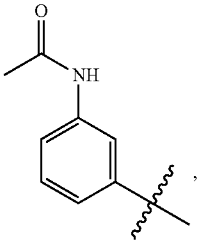
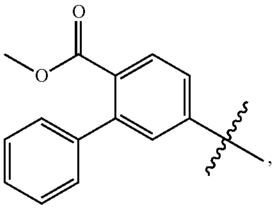
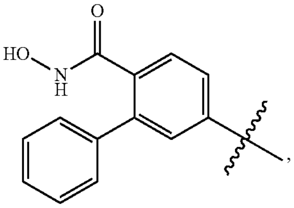
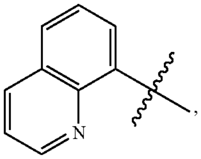
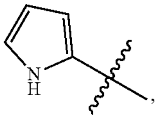
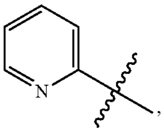
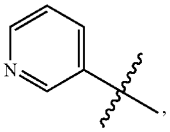
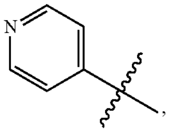
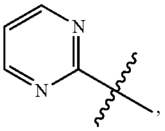
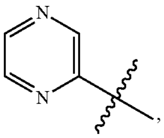
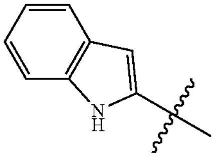
and
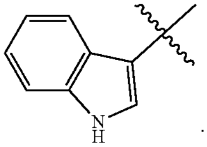
In a further embodiment, $R^4$ is selected from the group consisting: of $C_{1-12}$alkyl (especially $C_{1-6}$alkyl),
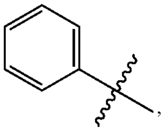
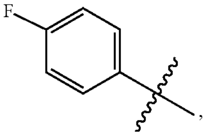
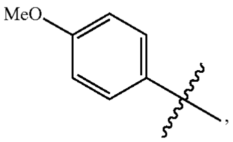
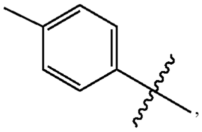
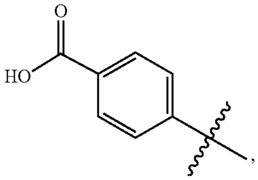

-continued

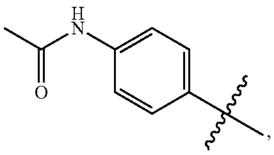

,

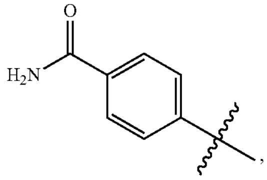

,

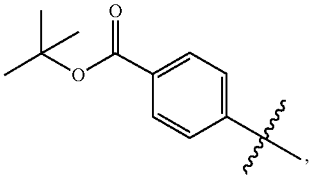

,

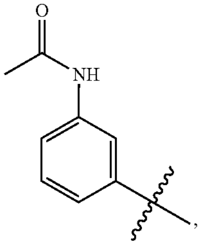

,

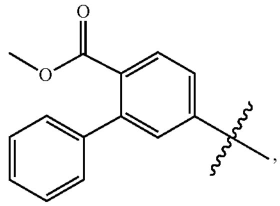

,

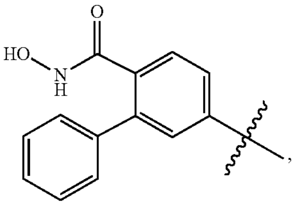

,

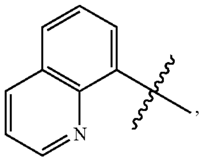

,

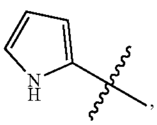

,

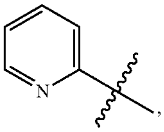

,

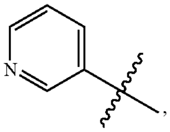

,

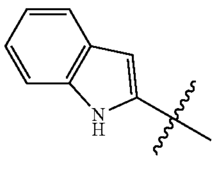

and

-continued

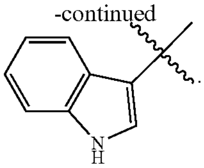

.

As used herein, the phrase "optionally substituted by one or more $R^{30}$" may refer to from 0-5 $R^{30}$ substituents, especially from 0-4, more especially from 0-3 or from 0-2, most especially 0 or 1 $R^{30}$ substituents.

In one embodiment, $R^{30}$ is selected from the group consisting of: —$R^{21}$-aryl, —$R^{21}$-heterocyclyl, —$R^{21}$-hetero aryl, —$R^{21}$-cycloalkyl, —$R^{21}$-cycloalkenyl, —$C_{1-6}$alkyl, —$C_{1-6}$haloalkyl, =O, halo, nitro, —$R^{21}$—$NR^{22}R^{23}$, —$R^{21}$—N($R^{22}$)—CO—$R^{23}$—$R^{21}$, —CO—$NR^{22}R^{23}$, —$R^{21}$—CO—$R^{24}$, —$R^{21}$, —O—$R^{24}$ and —$R^{21}$—N($R^{22}$)—CO—$R^{24}$; wherein $R^{21}$ is selected from the group consisting of: a bond, $C_{1-12}$alkylene, and -cycloalkylene; $R^{22}$ and $R^{23}$ are each independently selected from the group consisting of: H, $C_{1-6}$alkyl, $C_{1-6}$haloalkyl, and OH; $R^{24}$ is selected from the group consisting of: H, OH, $C_{1-6}$alkyl, $C_{1-6}$haloalkyl, —O—$C_{1-6}$alkyl, and —O—$C_{1-6}$haloalkyl. In another embodiment, $R^{30}$ is selected from the group consisting of: —$R^{21}$-aryl, —$C_{1-6}$alkyl, halo, =O, nitro, —$R^{21}$—$NR^{22}R^{23}$, —$R^{21}$—N($R^{22}$)—CO—$R^{23}$, —$R^{21}$—CO—$NR^{22}R^{23}$, —$R^{21}$—CO—$R^{24}$ and —$R^{21}$—O—$R^{24}$; wherein $R^{21}$ is a bond; $R^{22}$ and $R^{23}$ are each independently selected from the group consisting of: H, $C_{1-6}$alkyl, $C_{1-6}$haloalkyl, and OH; $R^{24}$ is selected from the group consisting of: OH, $C_{1-6}$alkyl, $C_{1-6}$haloalkyl and —O—$C_{1-6}$alkyl. In another embodiment, $R^{30}$ is selected from the group consisting of: —$R^{21}$-aryl, —$C_{1-6}$alkyl, halo, =O, —$R^{21}$—N($R^{22}$)—CO—$R^{23}$, —$R^{21}$—CO—$NR^{22}R^{23}$, —$R^{21}$—CO—$R^{24}$ and —$R^{21}$—O—$R^{24}$; wherein $R^{21}$ is a bond; $R^{22}$ and $R^{23}$ are each independently selected from the group consisting of: H, $C_{1-6}$alkyl and OH; $R^{24}$ is selected from the group consisting of: OH, $C_{1-6}$alkyl and —O—$C_{1-6}$alkyl. In a further embodiment, $R^{30}$ is selected from the group consisting of: —$R^{21}$-aryl, —$C_{1-6}$alkyl, halo, =O, —$R^{21}$—N($R^{22}$)—CO—$R^{23}$, —$R^{21}$—CO—$NR^{22}R^{23}$, —$R^{21}$—CO—$R^{24}$ and —$R^{21}$—O—$R^{24}$; wherein $R^{21}$ is a bond; $R^{22}$ and $R^{23}$ are each independently selected from the group consisting of: H, $C_{1-6}$alkyl and OH; $R^{24}$ is selected from the group consisting of: OH, $C_{1-6}$alkyl and —O—$C_{1-6}$alkyl.

In one embodiment:

$R^3$ is selected from the group consisting of: $R^4$, —CO—NH—$R^4$, —CO—$R^4$, —C($R^{19a}R^{19b}$)$R^4$, —CO—C($R^{19a}R^{19b}$)$R^4$, —C($R^{19a}R^{19b}$)—CO—NH—$R^4$, —CO—C($R^{19a}R^{19b}$)—CO—NH—$R^4$ and H;

$R^4$ is selected from the group consisting of: heterocyclyl, heteroaryl, aryl, cycloalkyl, cycloalkenyl, $C_{1-12}$alkyl, $C_{2-12}$alkenyl and $C_{2-12}$alkynyl; wherein said heterocyclyl, heteroaryl, aryl, cycloalkyl and cycloalkenyl is optionally substituted by one or more $R^{30}$; wherein $R^{30}$ is selected from the group consisting of: —$R^{21}$-aryl, —$R^{21}$-heterocyclyl, —$R^{21}$-heteroaryl, —$R^{21}$-cycloalkyl, —$R^{21}$— cycloalkenyl, —$C_{1-6}$alkyl, —$C_{1-6}$haloalkyl, =O, halo, nitro, —$R^{21}$—$NR^{22}R^{23}$, —$R^{21}$—N($R^{22}$)CO—$R^{23}$, $R^{21}$—CO—$NR^{22}R^{23}$, —$R^{21}$—CO—$R^{24}$; —$R^{21}$—O—$R^{24}$; and —$R^{21}$—N($R^{22}$)—CO—$R^{24}$; wherein $R^{21}$ is selected from the group consisting of: a bond, $C_{1-12}$alkylene, and -cycloalkylene; $R^{22}$ and $R^{23}$ are each independently selected from the group consisting of: H, $C_{1-6}$alkyl, $C_{1-6}$haloalkyl, and OH; $R^{24}$ is selected from the group consisting of: H, OH, $C_{1-6}$alkyl, $C_{1-6}$haloalkyl, —O—$C_{1-6}$alkyl, and —O—$C_{1-6}$haloalkyl; and $R^{19a}$ and $R^{19b}$ are each independently selected from the group consisting of: $C_{1-6}$alkyl, and $C_{1-6}$haloalkyl; or $R^{19a}$ and $R^{19b}$ together with the carbon to which they are bonded form a cycloalkyl, cycloalkenyl, or heterocyclyl; wherein said cycloalkyl, cycloalkenyl, or heterocyclyl are optionally substituted by one or more of $C_{1-6}$alkyl, $C_{1-6}$haloalkyl, OH, =O, $NH_2$, and halo.

In another embodiment, $R^2$ together with $R^3$ and the nitrogen to which they are bonded form a heterocyclyl or heteroaryl, wherein said heterocyclyl or heteroaryl is optionally substituted, especially by one or more $R^{25}$.

In one embodiment, $R^2$ together with $R^3$ and the nitrogen to which they are bonded form a monocyclic heterocyclyl, a bicyclic heterocyclyl, a monocyclic heteroaryl, or a bicyclic heteroaryl, wherein said monocyclic heterocyclyl, bicyclic heterocyclyl, monocyclic heteroaryl, or bicyclic heteroaryl is optionally substituted, especially by one or more $R^{25}$. The bicyclic heterocyclyl may be a spirane. In one embodiment, $R^2$ together with $R^3$ and the nitrogen to which they are bonded form a heterocyclyl or heteroaryl, wherein said heterocyclyl or heteroaryl has from 1 to 12 carbon atoms, and wherein said heterocyclyl or heteroaryl is optionally substituted, especially by one or more $R^{25}$.

In one embodiment, $R^2$ together with $R^3$ and the nitrogen to which they are bonded form a monocyclic heterocyclyl or a bicyclic heterocyclyl, wherein said monocyclic heterocyclyl or bicyclic heterocyclyl is optionally substituted, especially by one or more $R^{25}$. In one embodiment, $R^2$ together with $R^3$ and the nitrogen to which they are bonded form a heterocyclyl, wherein said heterocyclyl has from 1 to 12 carbon atoms, and wherein said heterocyclyl is optionally substituted, especially by one or more $R^{25}$.

In another embodiment, $R^2$ together with $R^3$ and the nitrogen to which they are bonded form a monocyclic heteroaryl or a bicyclic heteroaryl, wherein said monocyclic heteroaryl or bicyclic heteroaryl is optionally substituted, especially by one or more $R^{25}$. In one embodiment, $R^2$ together with $R^3$ and the nitrogen to which they are bonded form a heteroaryl, wherein said heteroaryl has from 1 to 12 carbon atoms, and wherein said heteroaryl is optionally substituted, especially by one or more $R^{25}$.

In one embodiment, $R^2$ together with $R^3$ and the nitrogen to which they are bonded form a heterocyclyl or heteroaryl selected from the group consisting of: quinolinyl, phenyl, pyridyl, pyrrolyl, indolyl, pyrrolidinyl, naphthyl, pyrimidinyl, pyrazinyl, imidazolyl, quinazolinyl, quinazolinone, pyrimidinone, benzimidazolyl, isoindolin-1-one, isoindolin-1,3-dione, benzo[d]isothiazol-3-one 1,1-dioxide, pyrrolidine-2,5-dione, pyrrolo[3,4-b]pyridine-5,7-dione, pyrrolo[3,4-c]pyridine-1,3-dione, pyrimidin-2,4-dione, pyridinone, piperazinyl, piperidinyl, piperazin-2,5-dione, benzodiazepinyl, benzo-1,4-diazepin-2,5-dione, 1,3-diazaspiro[4.4]nonane-2,4-dione, imidazolidinyl, imidazoline-2,4-dione and triazolyl. In another embodiment, $R^2$ together with $R^3$ and the nitrogen to which they are bonded form a heterocyclyl or heteroaryl selected from the group consisting of: quinolinyl, phenyl, pyridyl, pyrrolyl, indolyl, pyrrolidinyl, naphthyl, pyrimidinyl, pyrazinyl, imidazolyl, quinazolinyl, quinazolinone, pyrimidinone, benzimidazolyl, isoindolin-1-one, isoindolin-1,3-dione, benzo[d]isothiazol-3-one 1,1-dioxide, pyrimidin-2,4-dione, pyridinone, piperazinyl, piperidinyl, piperazin-2,5-dione, benzodiazepinyl, benzo-1,4-diazepin-2,5-dione, 1,3-diazaspiro[4.4]nonane-2,4-dione, imidazolidinyl, imidazoline-2,4-dione and triazolyl; especially selected from the group consisting of: quinazolinyl, quinazolinone, pyrimidinyl, pyrimidinone, benzimidazolyl, isoindolin-1-one, isoindolin-1,3-dione, benzo[d]isothiazol-3-one 1,1-dioxide, pyrimidin-2,4-dione, pyridinyl, pyridinone, piperazinyl, piperidinyl, piperazin-2,5-dione, benzodiazepinyl, benzo-1,4-diazepin-2,5-dione, 1,3-diazaspiro[4.4]nonane-2,4-dione, imidazolidinyl, imidazoline-2,4-dione and triazolyl. In an embodiment, the heterocyclyl or heteroaryl groups in this paragraph are optionally substituted, especially by one or more $R^{25}$. In one embodiment, $R^2$ together with $R^3$ and the nitrogen to which they are bonded form a quinazolinone, which is optionally substituted by one or more $R^{25}$.

In one embodiment, $R^2$ together with $R^3$ and the nitrogen to which they are bonded form a heterocyclyl or heteroaryl selected from the group consisting of:

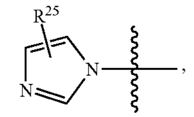

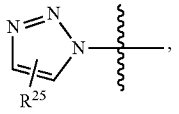

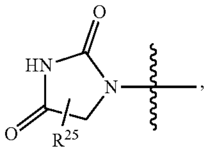

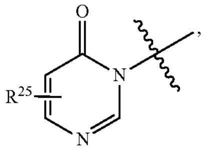

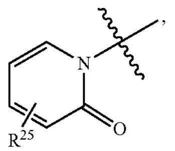

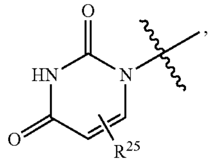

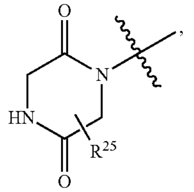

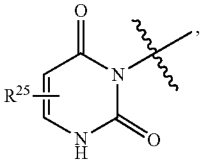

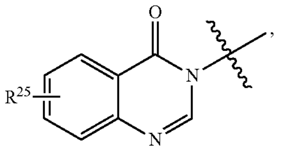

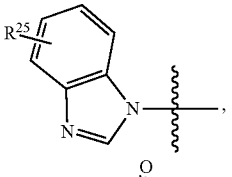

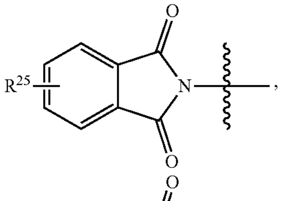

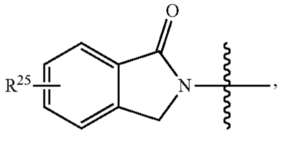

-continued

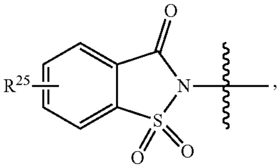,

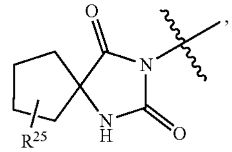,

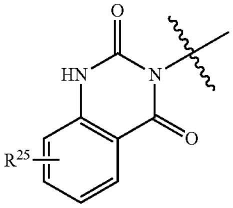 and

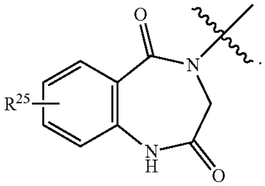.

In another embodiment, $R^2$ together with $R^3$ and the nitrogen to which they are bonded form a heterocyclyl or heteroaryl selected from the group consisting of:

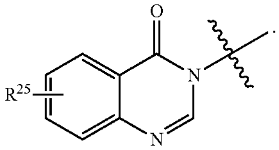.

In another embodiment, $R^2$ together with $R^3$ and the nitrogen to which they are bonded form a heteroaryl which is

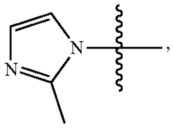, 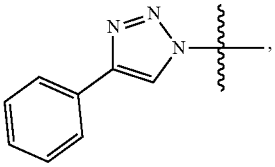,

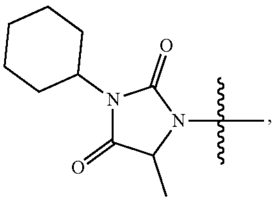, 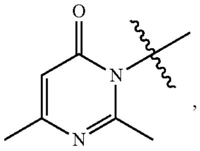,

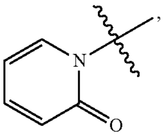, 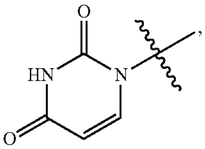,

-continued

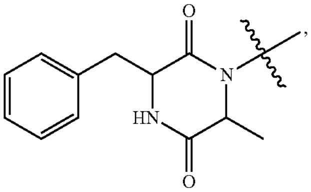, 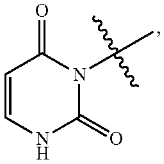,

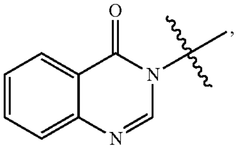, 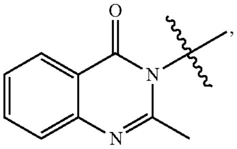,

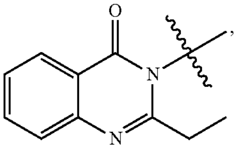, 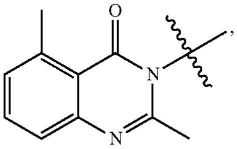,

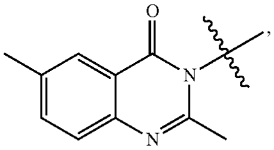, 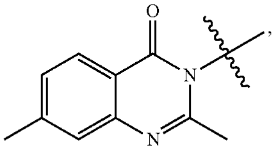,

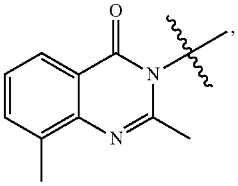, 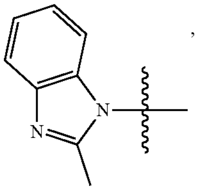,

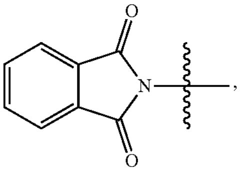, 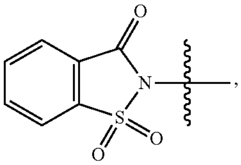,

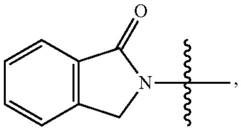, 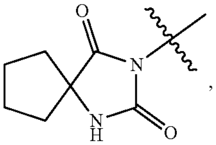,

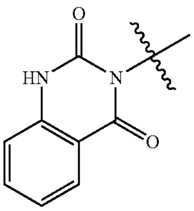 and 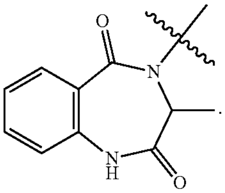.

In another embodiment, $R^2$ together with $R^3$ and the nitrogen to which they are bonded form a heteroaryl selected from the group consisting of:

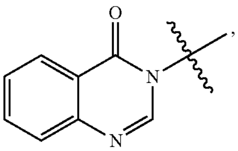, 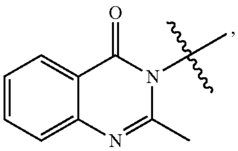,

-continued

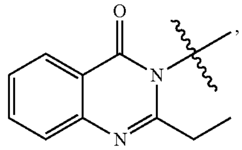
,
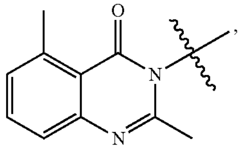
,
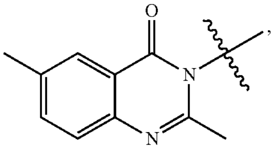
,
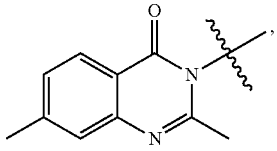
,
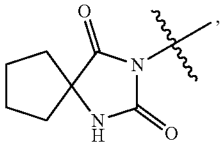
,
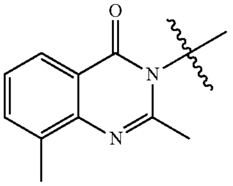
and
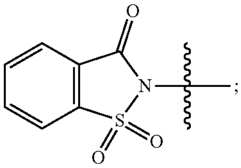
;

especially

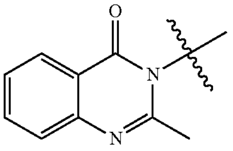
and
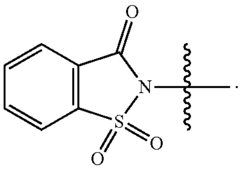
.

As used herein, the phrase "optionally substituted by one or more $R^{25}$" may refer to from 0-5 $R^{25}$ substituents, especially from 0-4, more especially from 0-3 or from 0-2, most especially 0 or 1 $R^{25}$ substituents.

In one embodiment, each $R^{25}$ is independently selected from the group consisting of: $R^{26}$-aryl, —$R^{26}$-heterocyclyl, —$R^{26}$-heteroaryl, —$R^{26}$-cycloalkyl, —$R^{26}$-cycloalkenyl, ═O, —$C_{1-12}$alkyl, —$C_{1-12}$haloalkyl, halo, —$R^{26}$—$NR^{27}R^{28}$, —$R^{26}$—N($R^{27}$)—CO—$R^{28}$, —$R^{26}$—CO—$NR^{27}R^{28}$, —$R^{26}$—CO—$R^{29}$, —$R^{26}$—O—$R^{29}$, —$R^{26}$—S—$R^{29}$, and —$R^{26}$—N($R^{27}$)—CO—$R^{29}$; wherein $R^{26}$ is selected from the group consisting of: a bond, $C_{1-12}$alkylene, and -cycloalkylene; $R^{27}$ and $R^{28}$ are each independently selected from the group consisting of: H, $C_{1-6}$ alkyl, $C_{1-6}$haloalkyl and OH; and $R^{29}$ is selected from the group consisting of: H, OH, $C_{1-6}$alkyl, $C_{1-6}$haloalkyl, —O—$C_{1-6}$alkyl, and —O—$C_{1-6}$haloalkyl. In another embodiment, each $R^{25}$ is independently selected from the group consisting of: —$R^{26}$-aryl, —$R^{26}$— cycloalkyl, ═O and —$C_{1-12}$alkyl (especially —$C_{1-16}$alkyl); wherein $R^{26}$ is selected from the group consisting of: a bond and $C_{1-12}$alkylene (especially $C_{1-6}$alkylene).

In another embodiment, one $R^{2a}$ together with $R^3$ and the carbon to which they are bonded form a heterocyclyl, heteroaryl, aryl, cycloalkyl or cycloalkenyl; wherein said heterocyclyl, heteroaryl, aryl, cycloalkyl or cycloalkenyl is optionally substituted, especially by one or more $R^{25}$.

In one embodiment, one $R^{2a}$ together with $R^3$ and the carbon to which they are bonded form a monocycle or a bicycle. In one embodiment, one $R^{2a}$ together with $R^3$ and the carbon to which they are bonded form an aryl, cycloalkyl or cycloalkenyl, wherein said aryl, cycloalkyl or cycloalkenyl has from 1 to 12 carbon atoms, and wherein said aryl, cycloalkyl or cycloalkenyl is optionally substituted, especially by one or more $R^{25}$.

In one embodiment, one $R^{2a}$ together with $R^3$ and the carbon to which they are bonded form a 2,3-dihydroindene or a indene-1,3-dione, which may be optionally substituted, especially by one or more $R^{25}$. In one embodiment, one $R^e$a together with $R^3$ and the carbon to which they are bonded form

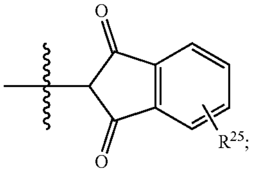
;

especially

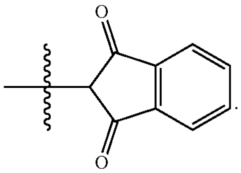 [SMILES: *C1C(=O)c2ccccc2C1=O]
.

In one embodiment, when $R^1$ is unsubstituted phenyl (or when $R^{1a}$, $R^{1b}$, $R^{1c}$, $R^{1d}$ and $R^{1e}$ are H), n is 1 and $R^5$ and $R^6$ are H, then $R^2$ together with $R^3$ and the nitrogen to which they are bonded do not form

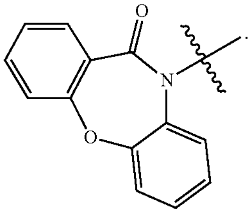 [SMILES: *N1C(=O)c2ccccc2Oc2ccccc21]
.

In this embodiment X may be —N($R^2$)—.

In another embodiment, when $R^1$ is unsubstituted phenyl (or when $R^{1a}$, $R^{1b}$, $R^{1c}$, $R^{1d}$ and $R^{1e}$ are H), n is 0, $R^2$ is H, $R^3$ is —C($R^{19a}R^{19b}$)$R^4$, and $R^{19a}$ and $R^{19b}$ are H, then $R^4$ is not phenyl. In this embodiment X may be —N($R^2$)—.

In a further embodiment, when $R^1$ is unsubstituted phenyl (or when $R^{1a}$, $R^{1b}$, $R^{1c}$, $R^{1d}$ and $R^{1e}$ are H), n is 0, and $R^2$ is H, then $R^3$ is not

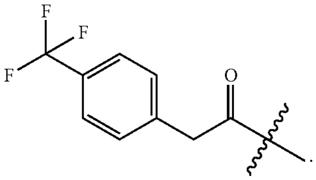 [SMILES: *C(=O)Cc1ccc(C(F)(F)F)cc1]
.

In this embodiment X may be —N($R^2$)—.

In one embodiment, the compound of Formula (I) is selected from the group consisting of:
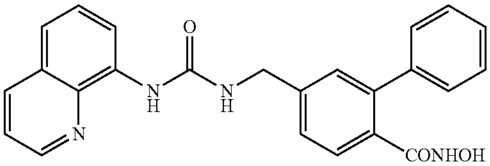,
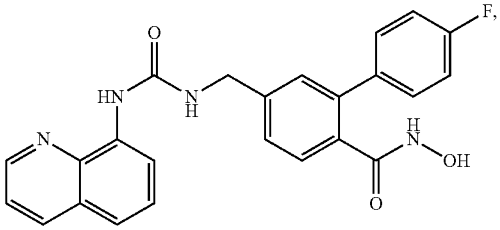
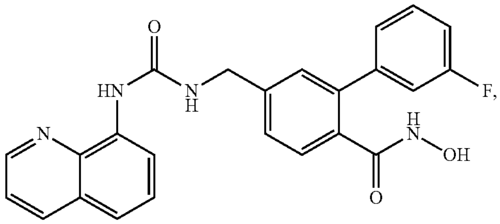
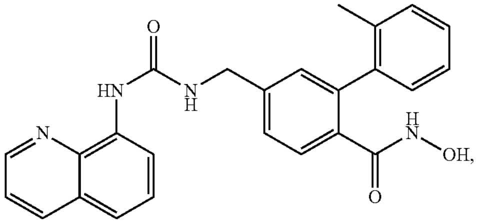
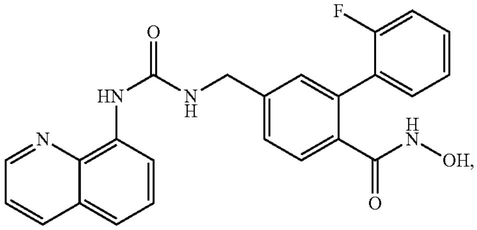
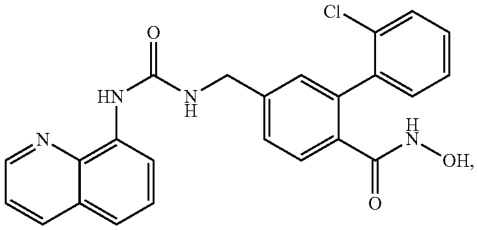
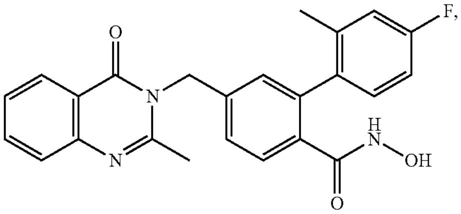
-continued
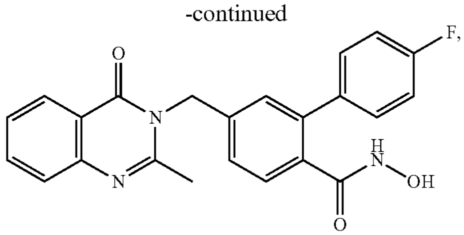
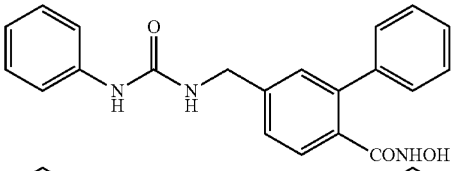,
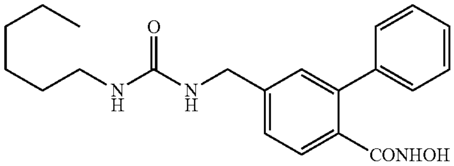,
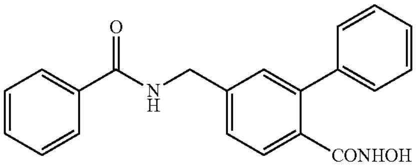,
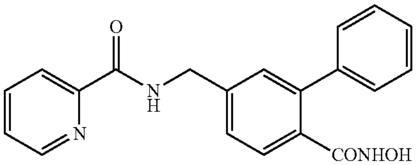,
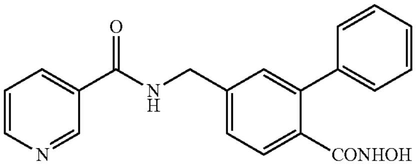,
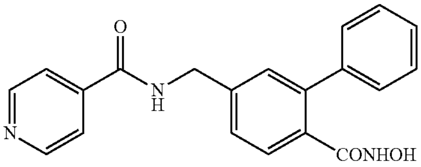,
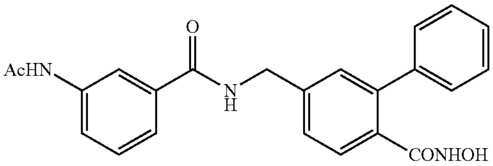,
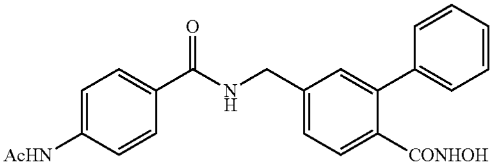,
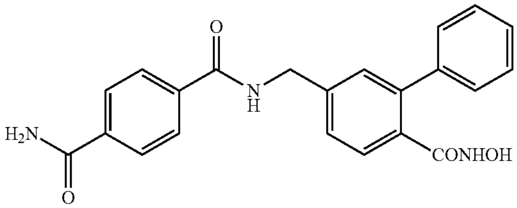, -continued
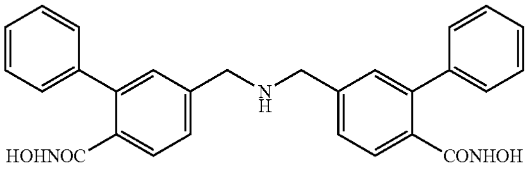
,
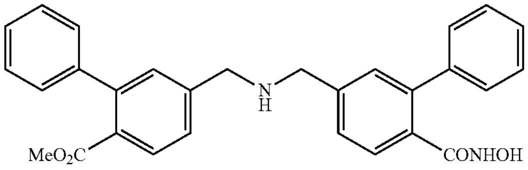
,
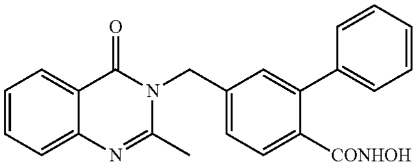
,
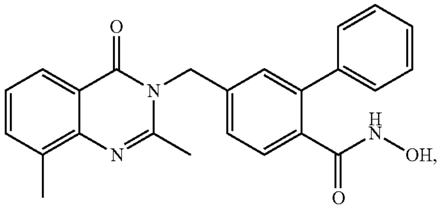
,
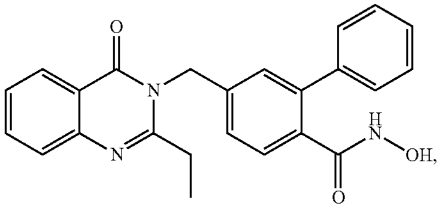
,
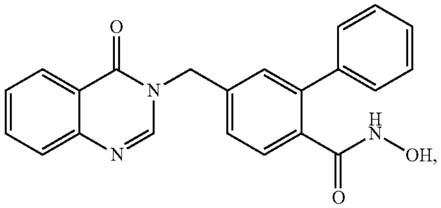
,
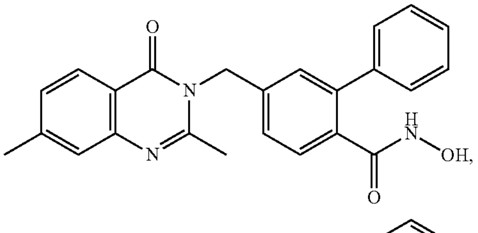
,
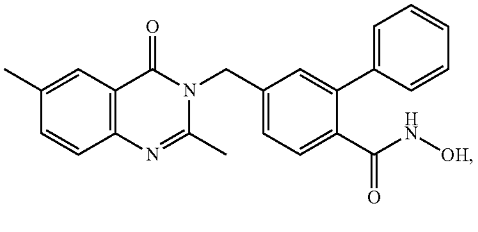
,
-continued
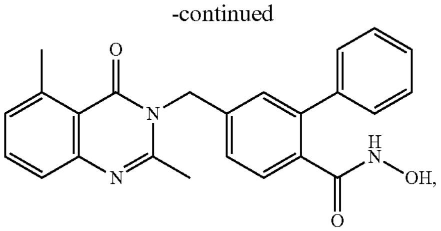
,
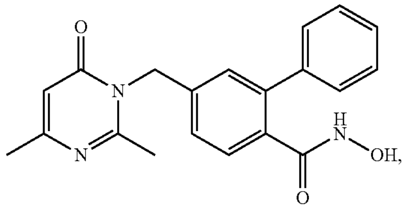
,
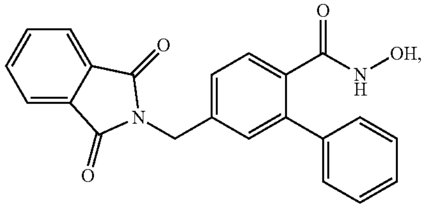
,
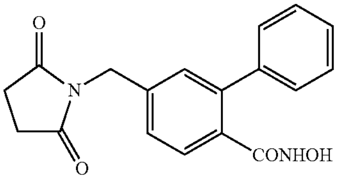
,
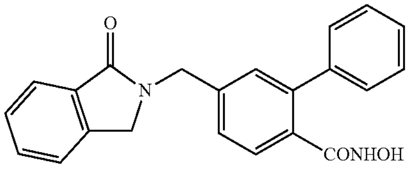
,
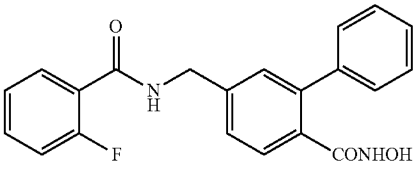
,
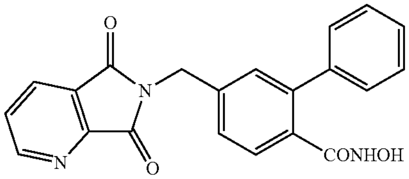
,
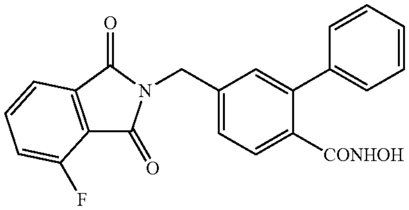
,
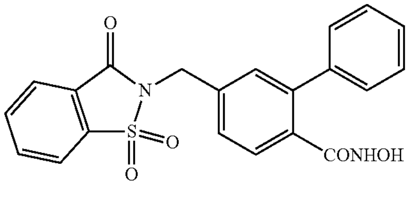
, -continued
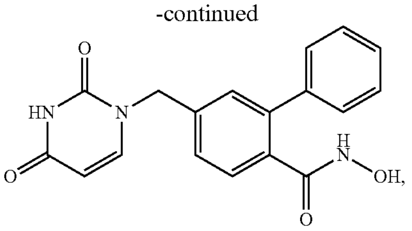
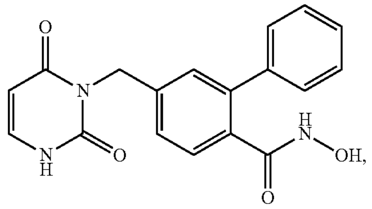
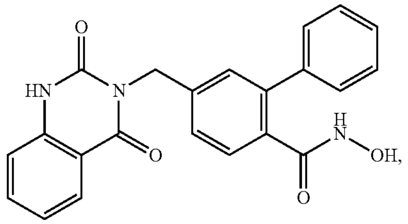
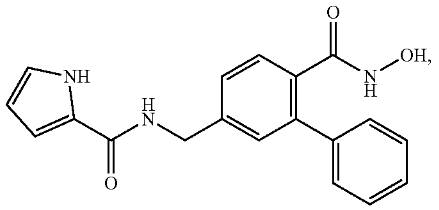
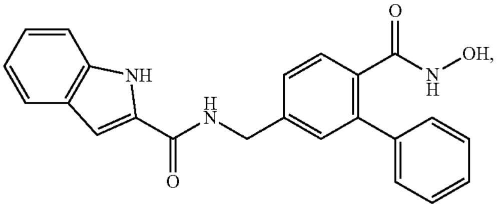
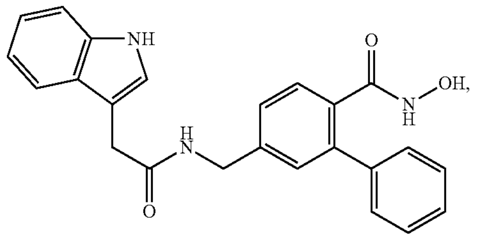
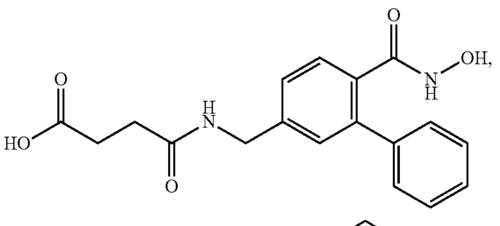
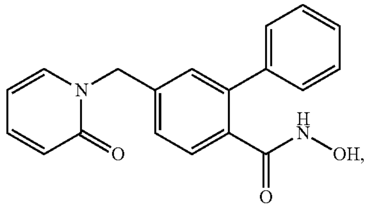
-continued
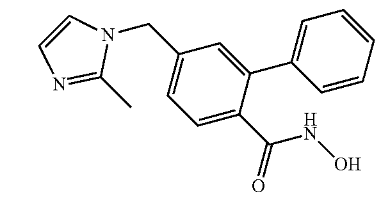
,
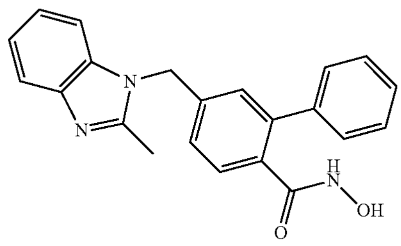
,
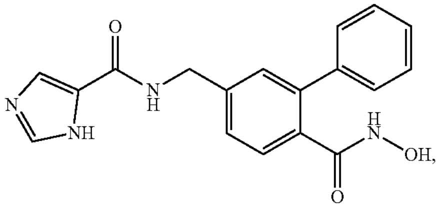
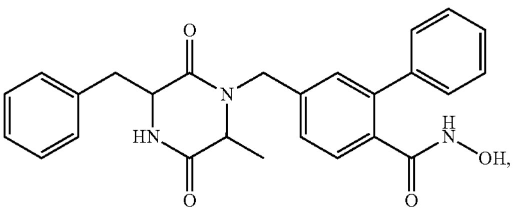
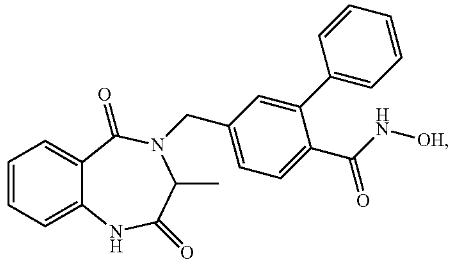
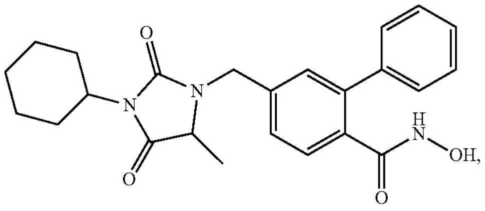
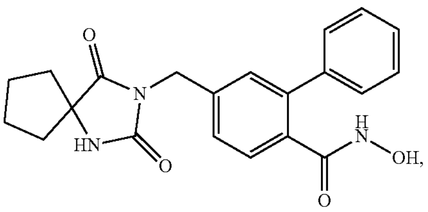

-continued
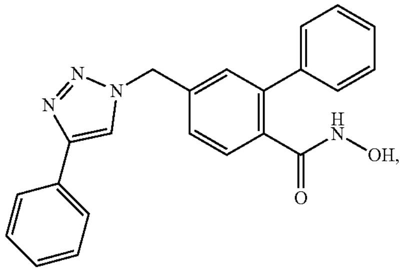
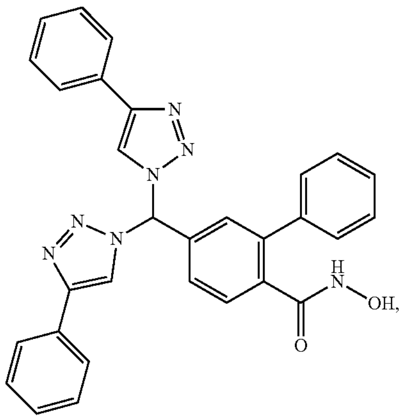
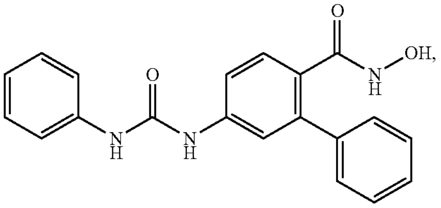
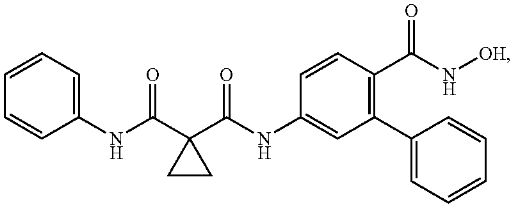
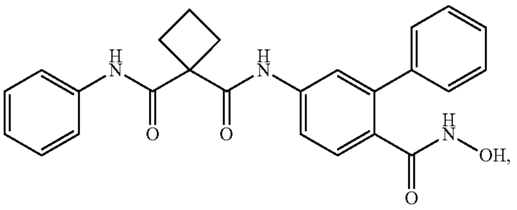
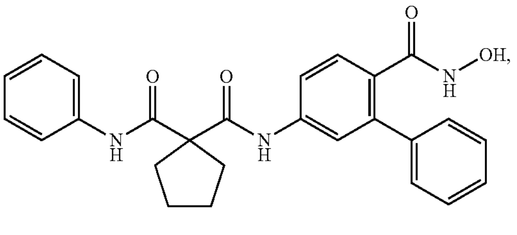
-continued
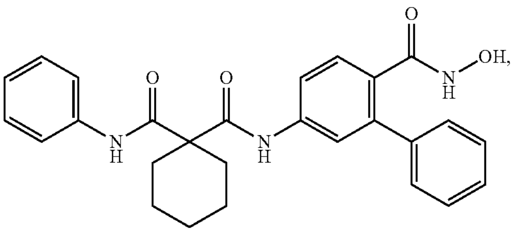
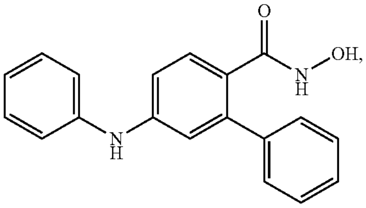
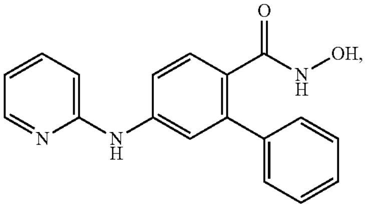
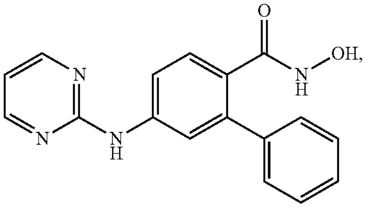
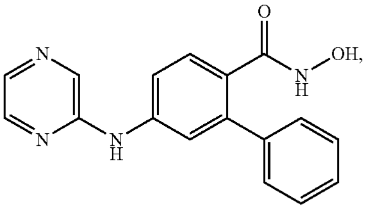
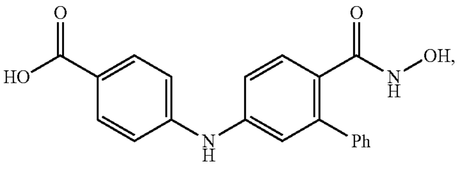
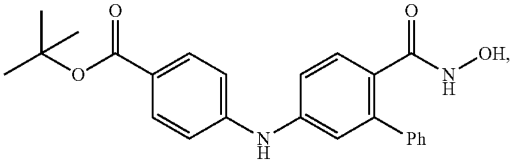
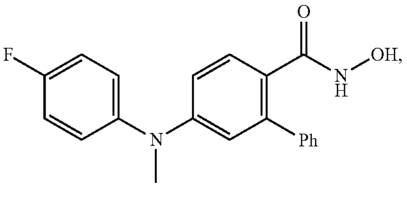

-continued
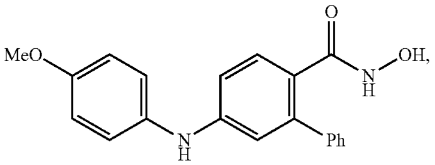
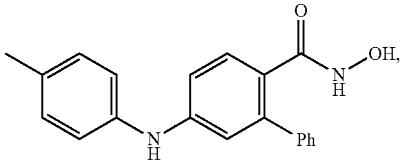
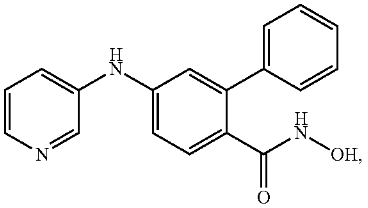
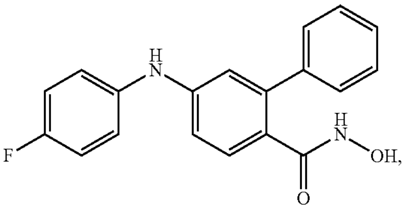
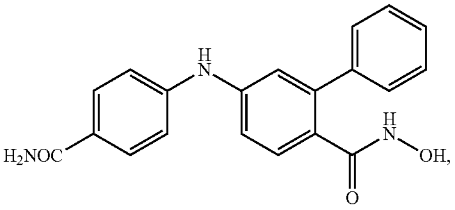
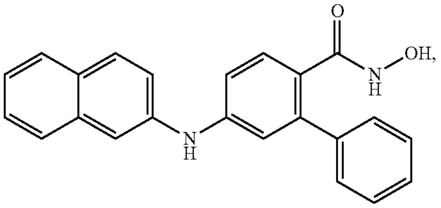
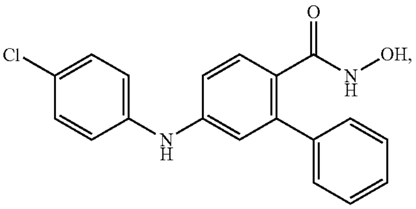
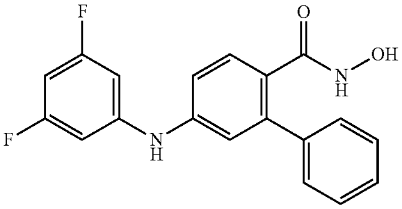
and
-continued
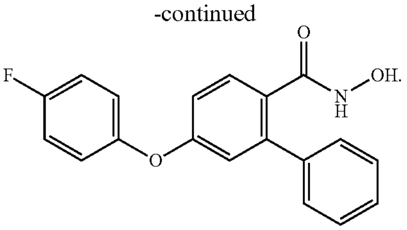
The compound of Formula (I) may also be selected from the group consisting of:
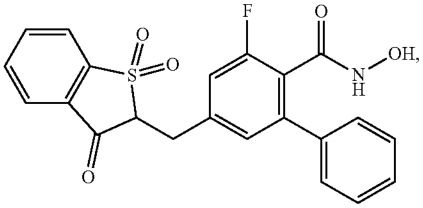
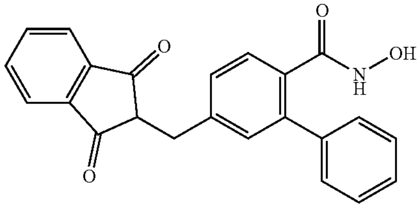
and
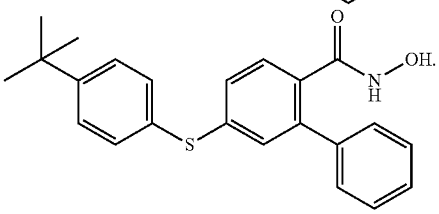
In another embodiment, the compound of Formula (I) is selected from the group consisting of:
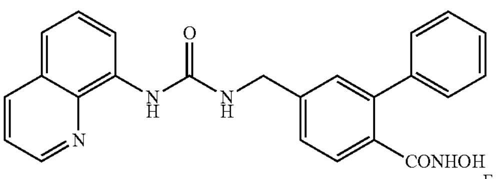
,
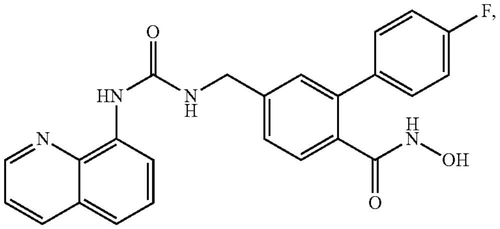
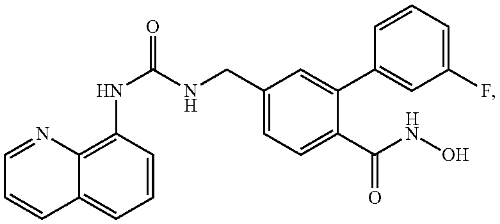

-continued
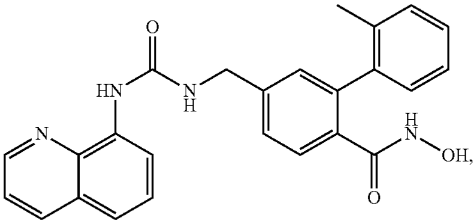
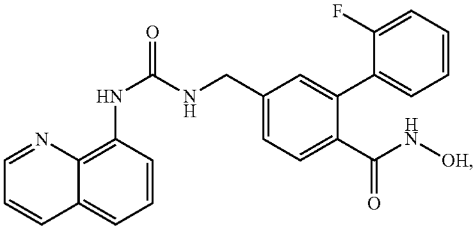
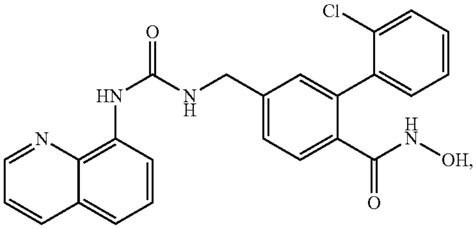
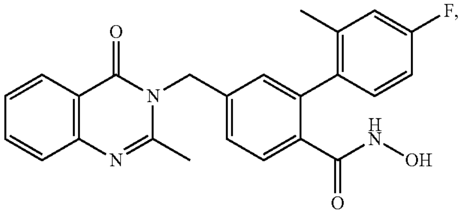
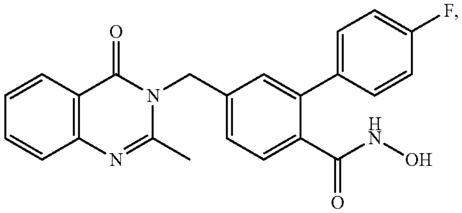
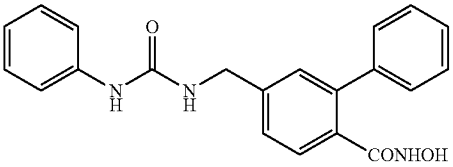
,
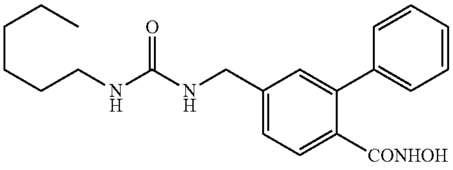
,
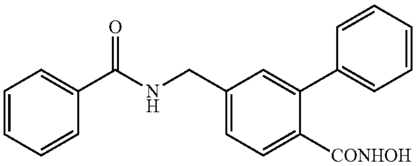
,
-continued
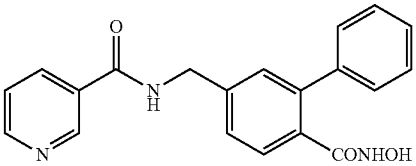
,
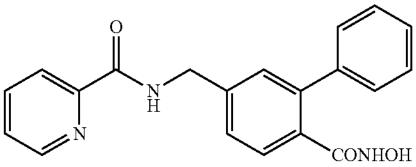
,
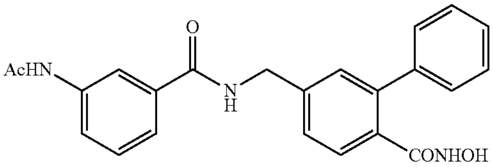
,
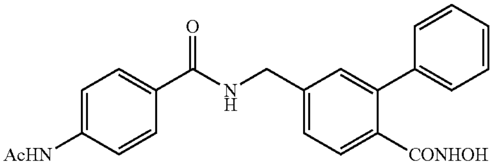
,
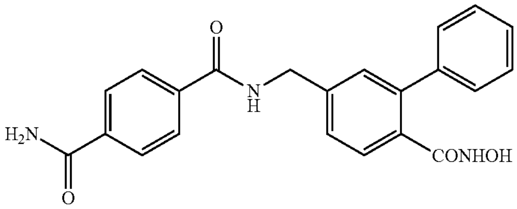
,
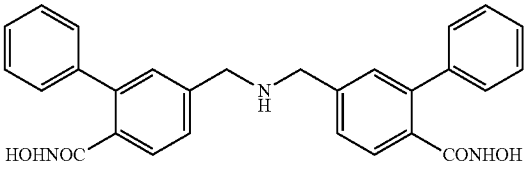
,
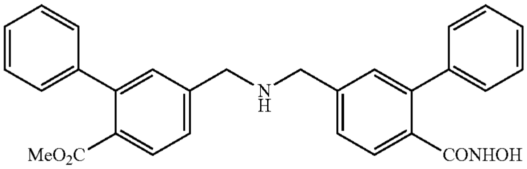
,
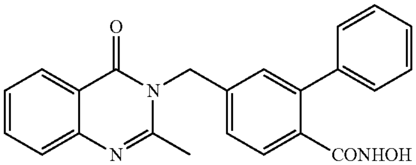
,
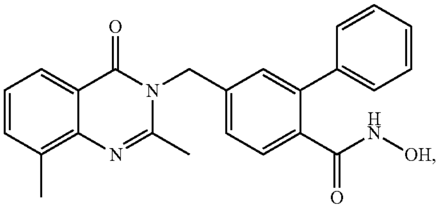

-continued
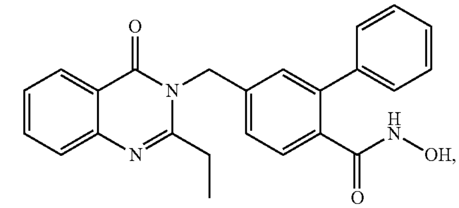
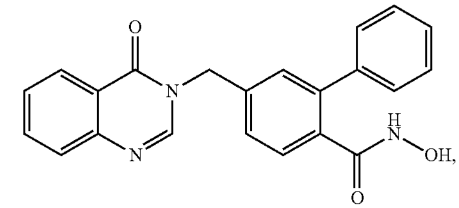
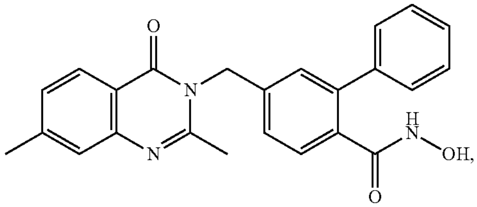
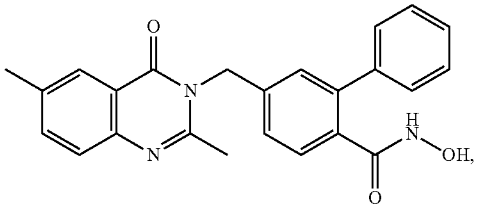
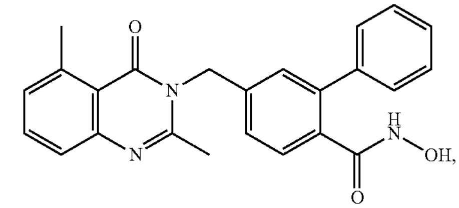
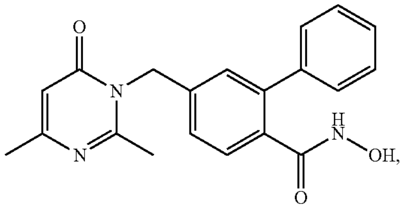
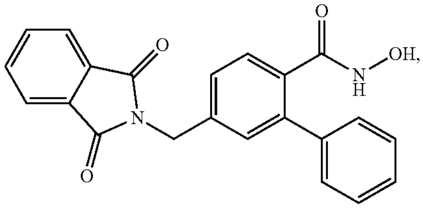
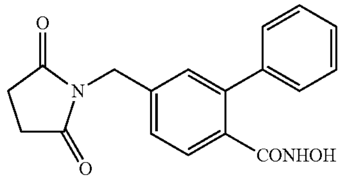
,
-continued
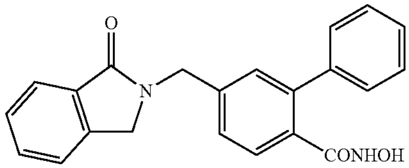
,
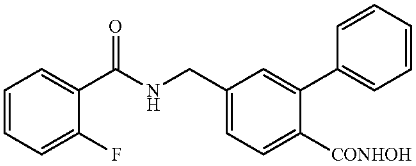
,
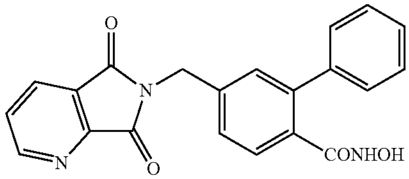
,
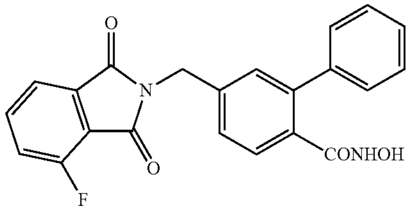
,
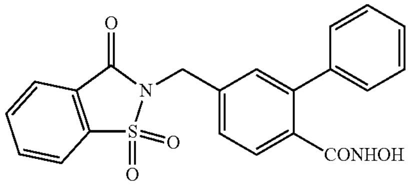
,
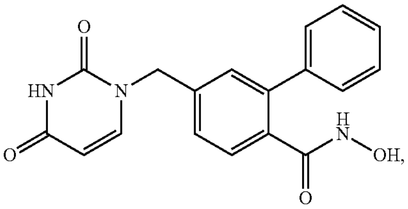
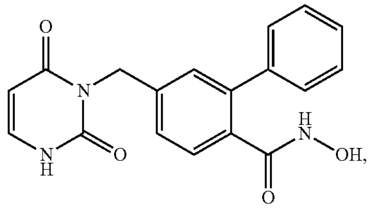
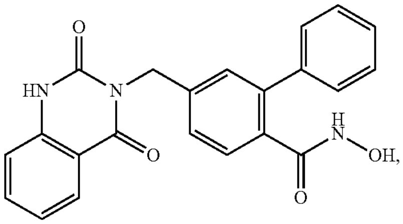

-continued
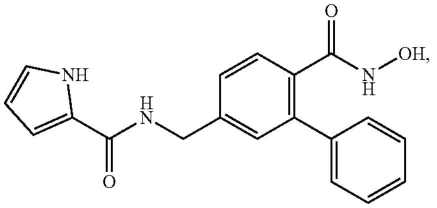
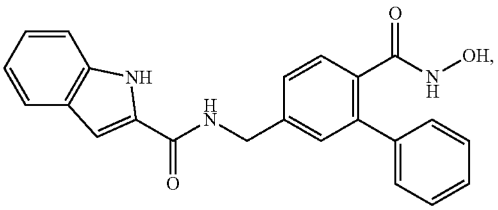
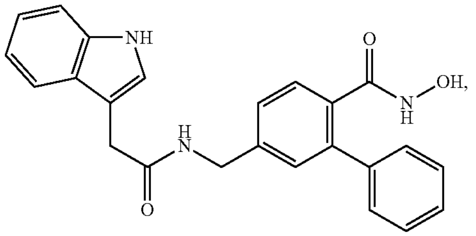
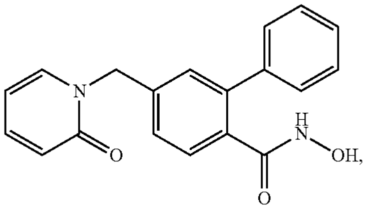
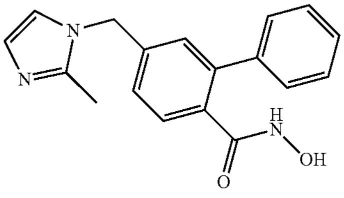
,
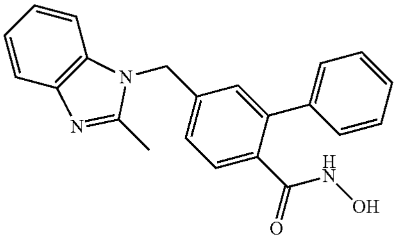
,
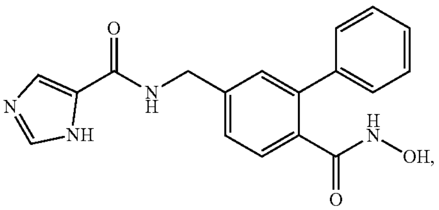
-continued
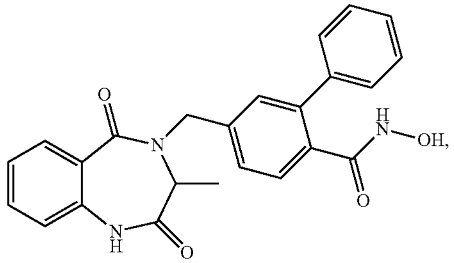
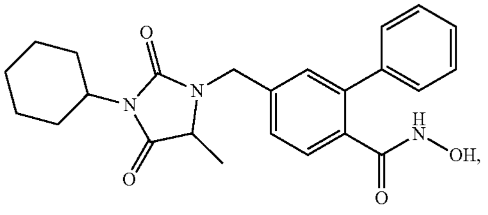
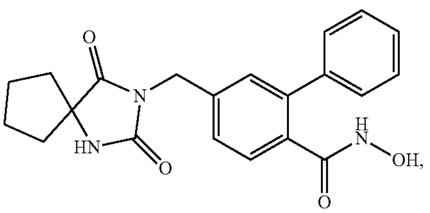
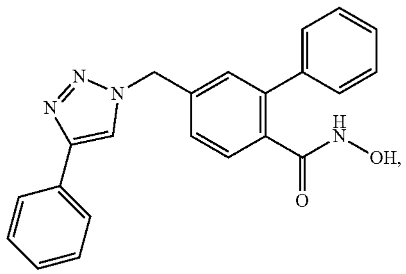
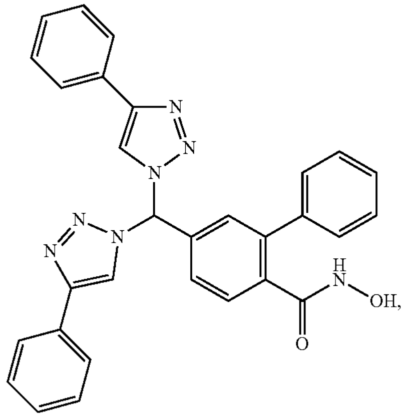
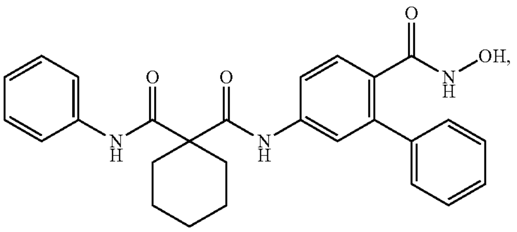

-continued
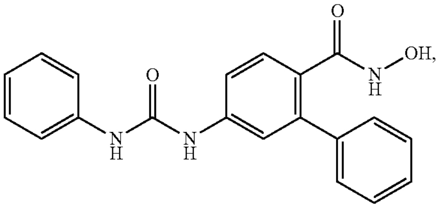
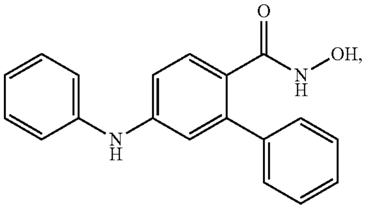
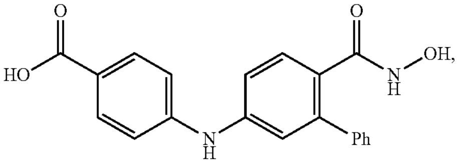
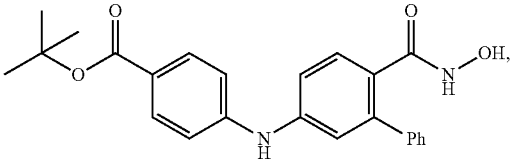
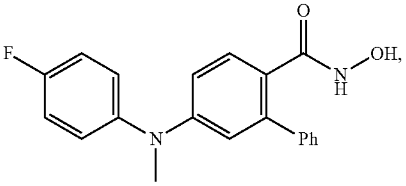
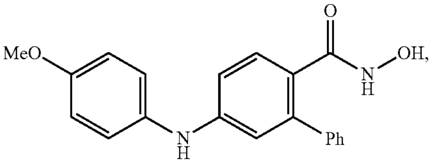
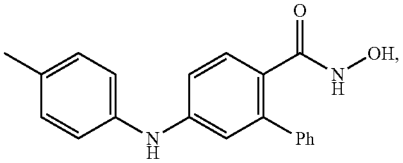
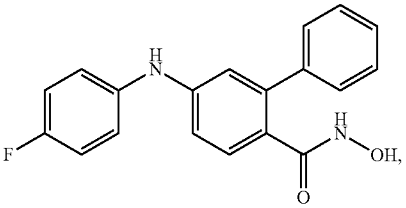
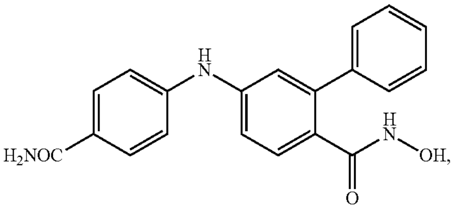
-continued
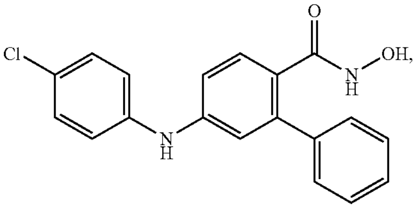
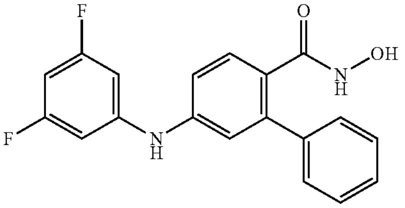
and
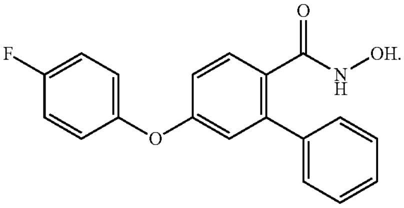
In another embodiment, the compound of Formula (I) is selected from the group consisting of:
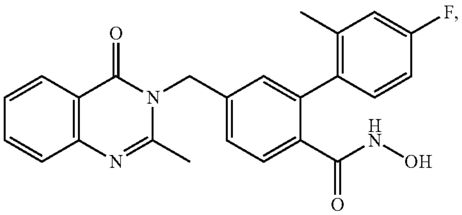
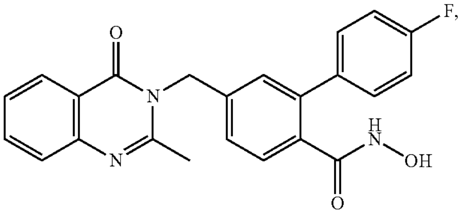
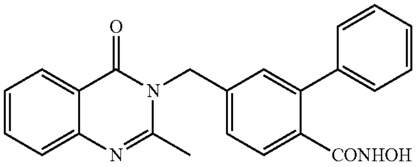
,
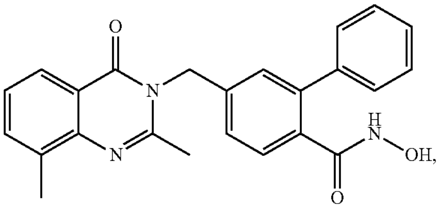

-continued
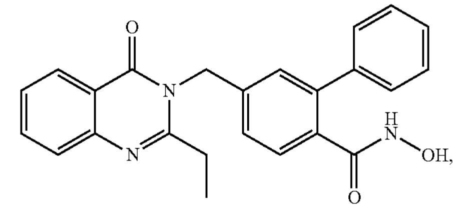
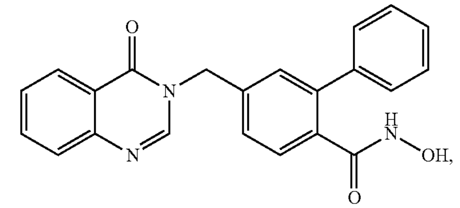
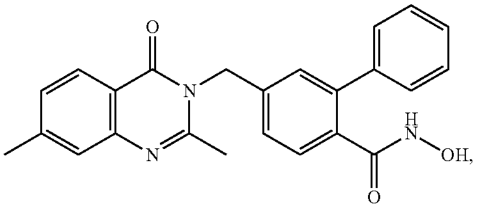
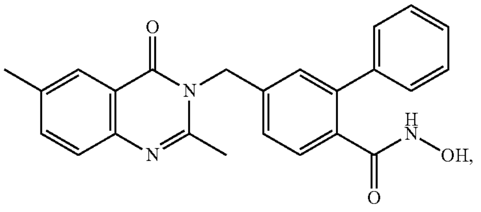
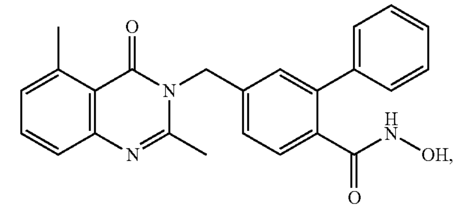
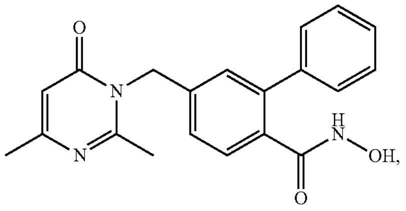
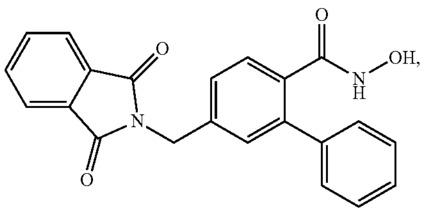
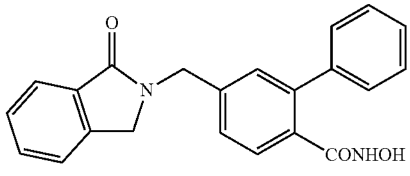
,
-continued
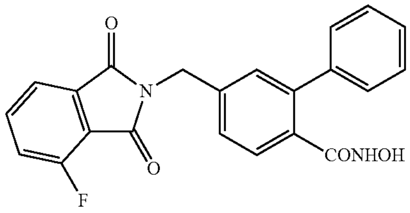
,
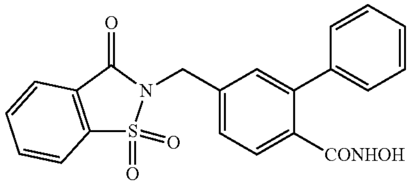
,
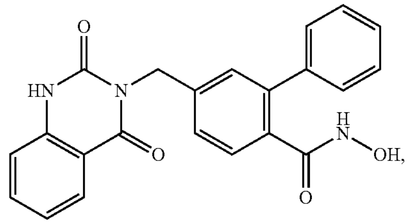
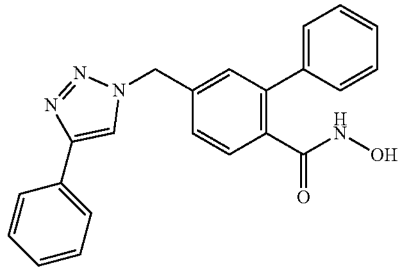
and
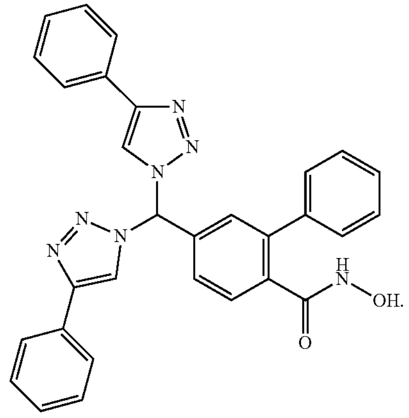
In another embodiment, the compound of Formula (I) is selected from the group consisting of:
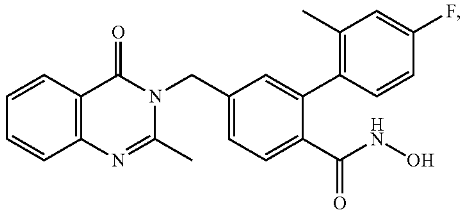

-continued
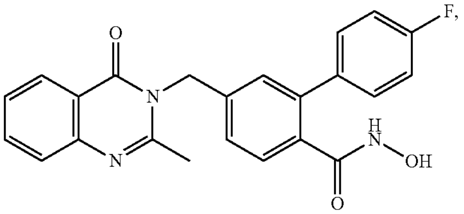
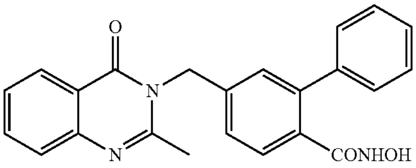
,
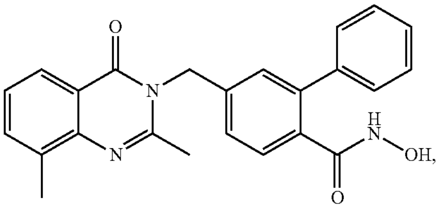
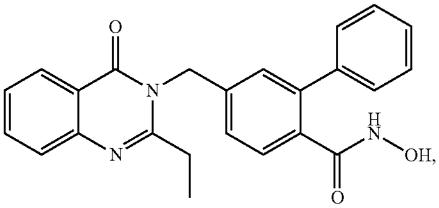
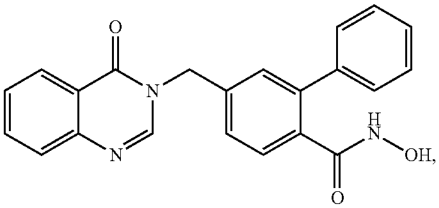
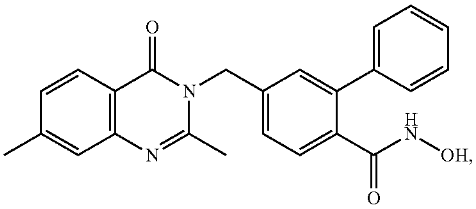
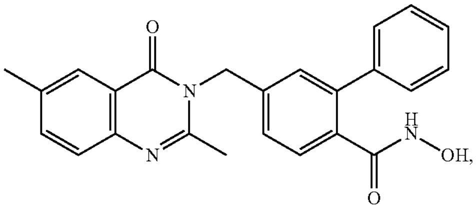
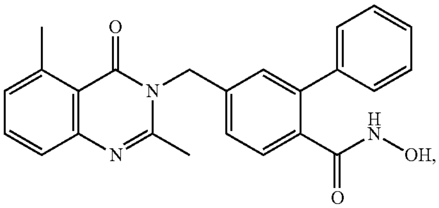
-continued
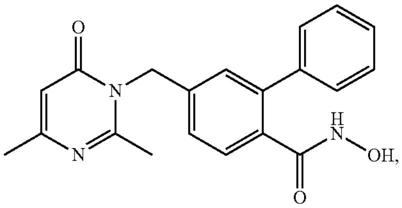
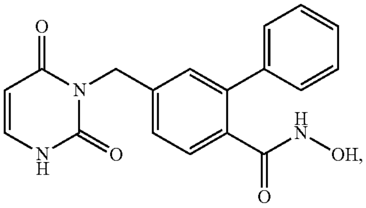
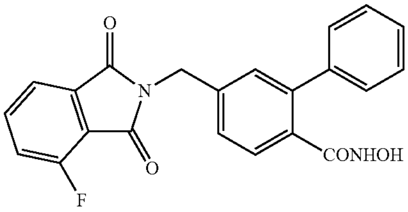
,
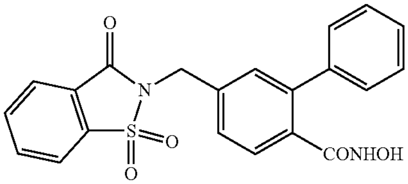
,
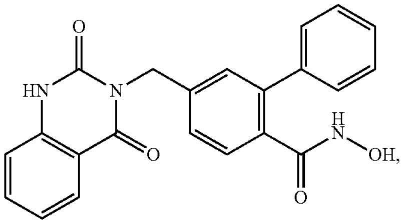
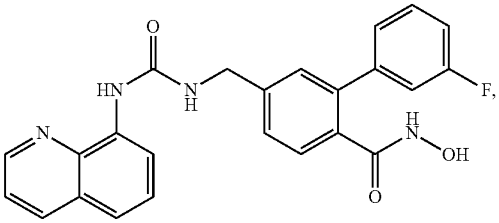
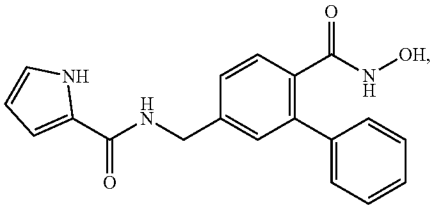
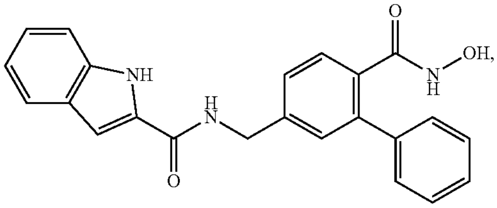

-continued
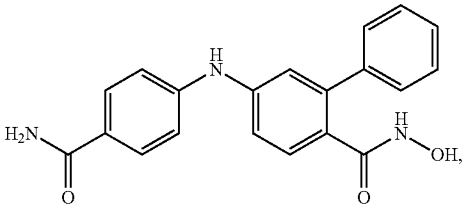
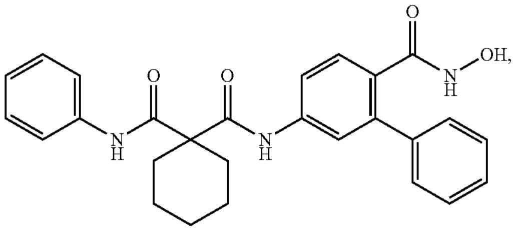
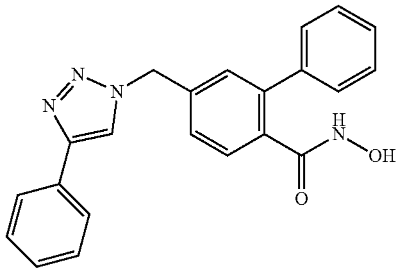
and
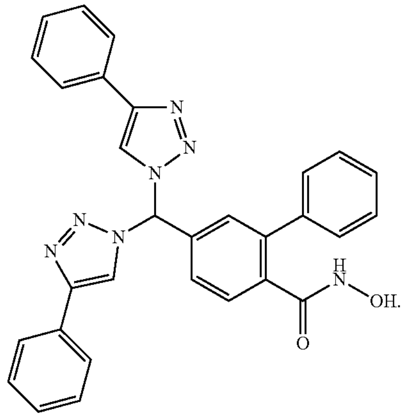
In another embodiment, the compound of Formula (I) is selected from the group consisting of:
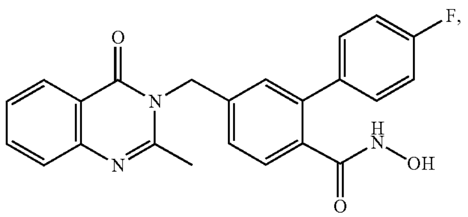
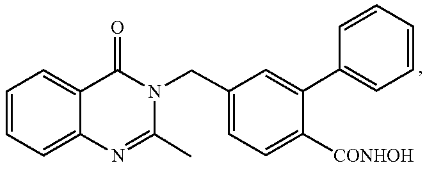
-continued
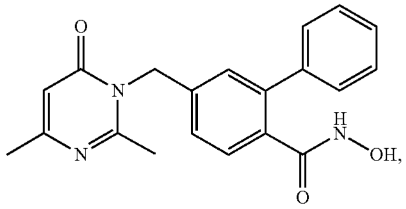
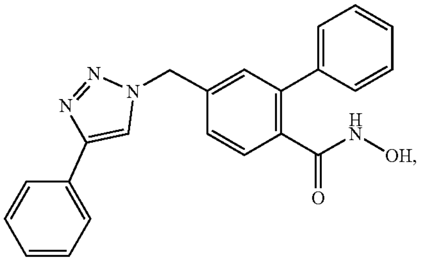
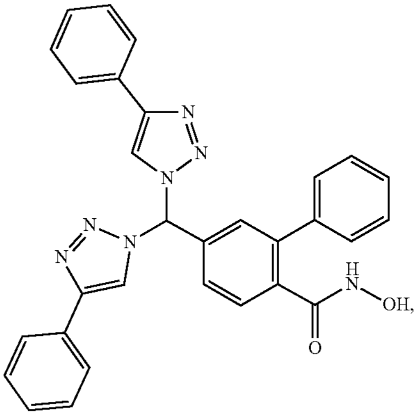
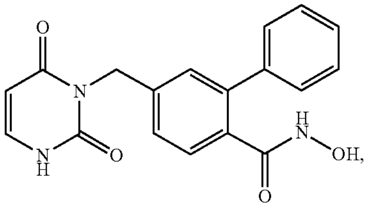
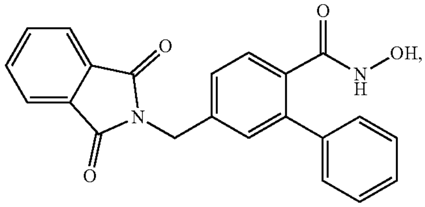
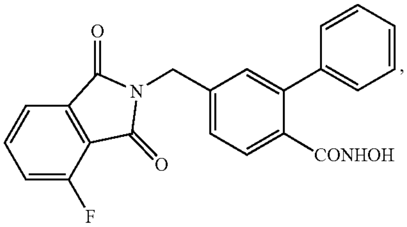
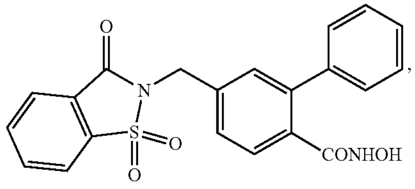

-continued

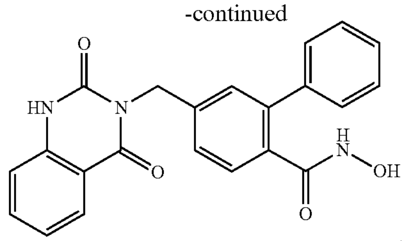

and

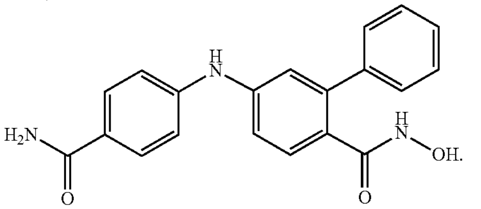

In a further embodiment, the compound of Formula (I) is selected from the group consisting of:

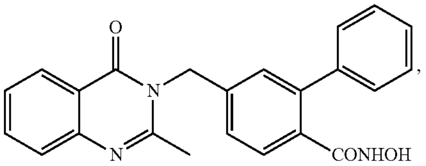

and

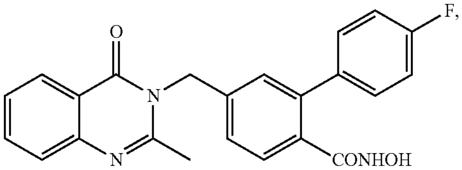

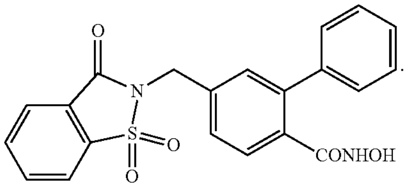

In a further embodiment, the compound of Formula (I) is:

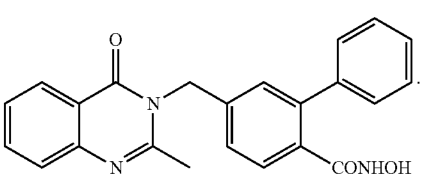

In one embodiment, the compound of the first aspect, or pharmaceutically acceptable salt or prodrug thereof, is an inhibitor of histone deacetylase (HDAC), especially an inhibitor of class IIa HDAC, more especially an inhibitor of HDAC7. Recognizing that inhibition (Ki, IC50) is related to Kd (dissociation constant), and that these terms all relate to affinity, the term inhibitor is taken to mean either inhibition of the enzymatic removal of the acetyl group or inhibition of the binding of a protein to the HDAC, given that occupation of the lysine-binding groove alone can potentially prevent proteins binding at that location to HDACs without any catalytic action occurring.

In one embodiment, the compound of the first aspect, or a pharmaceutically acceptable salt or prodrug thereof, is a selective inhibitor of class IIa HDAC, especially a selective inhibitor of class IIa HDAC over class I HDAC, more especially a selective inhibitor of HDAC7 over class I HDAC, most especially a selective inhibitor of HDAC7 over HDAC1. The compound of the first aspect, or a pharmaceutically acceptable salt or prodrug thereof, may have an $IC_{50}$ that is 50 times lower for a class IIa HDAC than a class I HDAC, especially 100 times lower, or 250 times lower, more especially 500 times lower, most especially 1,000 times lower. The compound of the first aspect, or a pharmaceutically acceptable salt or prodrug thereof, may have an $IC_{50}$ that is 50 times lower for HDAC7 than HDAC1, especially 100 times lower, or 250 times lower, more especially 500 times lower, most especially 1,000 times lower.

As used herein, terminology such as

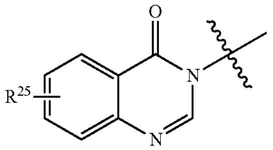

and

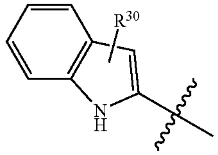

means that any number of $R^{25}$ or $R^{30}$ substituents may be appended to the cyclic system, and at any position, including at the NH in the indole example, or on either ring (for example in the quinazolinone, $R^{25}$ may be appended on the phenyl portion, or on the pyrimidin-one portion).

Unless defined otherwise, all technical and scientific terms used herein have the same meaning as would be commonly understood by those of ordinary skill in the art to which this invention belongs.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

The term "alkyl" refers to a straight-chain or branched alkyl substituent containing from, for example, 1 to about 12 carbon atoms, preferably 1 to about 8 carbon atoms, more preferably 1 to about 6 carbon atoms, even more preferably from 1 to about 4 carbon atoms. Examples of suitable alkyl groups include, but are not limited to, methyl, ethyl, propyl, isopropyl, n-butyl, sec-butyl, isobutyl, tert-butyl, pentyl, isoamyl, 2-methylbutyl, 3-methylbutyl, hexyl, heptyl, 2-methylpentyl, 3-methylpentyl, 4-methylpentyl, 2-ethylbutyl, 3-ethylbutyl, octyl, nonyl, decyl, undecyl, dodecyl and the like. The number of carbons referred to relates to the carbon backbone and carbon branching but does not include carbon atoms belonging to any substituents, for example the carbon atoms of an alkoxy substituent branching off the main carbon chain.

The term "alkenyl" refers to a straight-chain or branched alkenyl substituent containing from, for example, 2 to about 12 carbon atoms, preferably 2 to about 8 carbon atoms, more preferably 2 to about 6 carbon atoms. Examples of suitable alkenyl groups include, but are not limited to, ethenyl, propenyl, isopropenyl, butenyl, butadienyl, pentenyl, pentadienyl, hexenyl, hexadienyl, heptenyl, octenyl, nonenyl, decenyl, undecenyl, dodecenyl and the like. The number of carbons referred to relates to the carbon backbone and carbon branching but does not include carbon atoms belonging to any substituents, for example the carbon atoms of an alkoxy substituent branching off the main carbon chain.

The term "alkynyl" refers to a straight-chain or branched alkynyl substituent containing from, for example, 2 to about 12 carbon atoms, preferably 2 to about 8 carbon atoms, more preferably 2 to about 6 carbon atoms. Examples of suitable alkynyl groups include, but are not limited to, ethynyl, propynyl, butynyl, butadienyl, pentynyl, hexynyl, heptynyl, octynyl, nonynyl, decynyl, undecynyl, dodecynyl and the like. The number of carbons referred to relates to the carbon backbone and carbon branching but does not include carbon atoms belonging to any substituents, for example the carbon atoms of an alkoxy substituent branching off the main carbon chain.

The term "cycloalkyl" refers to a saturated non-aromatic cyclic hydrocarbon. The cycloalkyl ring may include a specified number of carbon atoms. For example, a 3 to 8 membered cycloalkyl group includes 3, 4, 5, 6, 7 or 8 carbon atoms. The cycloalkyl group may be monocyclic, bicyclic or tricyclic. When more than one ring is present the rings are fused together (for example, a bicyclic ring is fused if two atoms are common to both rings). Non-limiting examples may include cyclopropyl, cyclobutyl, cyclopentyl, cyclohexyl and the like.

The term "cycloalkenyl" refers to a cyclic hydrocarbon having at least one double bond, which is not aromatic. The cycloalkenyl ring may include a specified number of carbon atoms. For example, a 4 to 8 membered cycloalkenyl group includes 4, 5, 6, 7 or 8 carbon atoms. The cycloalkenyl group may be monocyclic, bicyclic or tricyclic. When more than one ring is present the rings are fused together (for example, a bicyclic ring is fused if two atoms are common to both rings). Non-limiting examples may include cyclopentenyl, cyclopenta-1,3-dienyl, cyclohexenyl, cyclohexen-1,3-dienyl and cyclohexen-1,4-dienyl and the like.

The term "aryl" refers to an aromatic carbocyclic substituent, as commonly understood in the art. It is understood that the term aryl applies to cyclic substituents that are planar and comprise $4n+2$ $\pi$ electrons, according to Bickel's Rule. Aryl groups may be monocyclic, bicyclic or tricyclic. Examples of aryl groups include, but are not limited to, phenyl and naphthyl. Aryl groups do not encompass cycloalkyl groups, and aryl groups have a ring system (for example monocyclic, bicyclic or tricyclic rings) in which all rings are aromatic. For example, a naphthyl group is an aryl group, a 1,2,3,4-tetrahydronaphthyl group would be a cycloalkenyl group. When more than one ring is present the rings are fused together (for example, a bicyclic ring is fused if two atoms are common to both rings).

The term "heterocyclic" or "heterocyclyl" as used herein, refers to a cycloalkyl or cycloalkenyl group in which one or more carbon atoms have been replaced by heteroatoms independently selected from N, S and O. For example, between 1 and 4 carbon atoms in each ring may be replaced by heteroatoms independently selected from N, S and O. The heterocyclyl group may be monocylic, bicyclic or tricyclic in which at least one ring includes a heteroatom. When more than one ring is present the rings are fused together (for example, a bicyclic ring is fused if two atoms are common to both rings). Each of the rings of a heterocyclyl group may include, for example, between 5 and 7 atoms. Examples of heterocyclyl groups include tetrahydrofuranyl, tetrahydrothiophenyl, pyrrolidinyl, pyrrolinyl, dithiolyl, 1,3-dioxanyl, dioxinyl, piperidinyl, piperazinyl, morpholinyl, thiomorpholinyl, pyranyl, 1,4-dithiane, and decahydroisoquinoline. In a bicyclic or tricyclic heterocyclyl group, one of the rings may be aromatic but not all rings are aromatic. In one embodiment, heterocyclyl may be optionally substituted by =O.

The term "heteroaryl", as used herein, refers to a monocyclic, bicyclic or tricyclic ring of up to 7 atoms in each ring, wherein all rings are aromatic and at least one ring contains from 1 to 4 heteroatoms selected from the group consisting of O, N and S. When more than one ring is present the rings are fused together (for example, a bicyclic ring is fused if two atoms are common to both rings). Consideration must be provided to tautomers of heteroatom containing ring systems containing carbonyl groups, for example, when determining if a ring is a heterocyclyl or heteroaryl ring. Heteroaryl includes, but is not limited to, 5-membered heteroaryls having one hetero atom (e.g., thiophenes, pyrroles, furans); 5 membered heteroaryls having two heteroatoms in 1,2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having four heteroatoms (e.g., tetrazoles); 6-membered heteroaryls with one heteroatom (e.g., pyridine, quinoline, isoquinoline); 6-membered heteroaryls with two heteroatoms (e.g., pyridazines, cinnolines, phthalazines, pyrazines, pyrimidines, quinazolines, quinoxalinone, quinazolinone); 6-membered heteroaryls with three heteroatoms (e.g., 1,3,5-triazine); and 6-membered heteroaryls with four heteroatoms. Examples of heteroaryl include thiophene, benzothiophene, benzofuran, benzimidazole, benzoxazole, benzothiazole, benzisothiazole, furan, pyrrole, imidazole, pyrazole, pyridine, pyrazine, pyrimidine, pyridazine, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, and phenoxazine. In one embodiment, heteroaryl may be optionally substituted by =O.

Whenever a range of the number of atoms in a structure is indicated (e.g., a $C_{1-12}$, $C_{1-6}$ alkyl, etc.), it is specifically contemplated that any sub-range or individual number of carbon atoms falling within the indicated range also can be used. Thus, for instance, the recitation of a range of 1-12 carbon atoms (e.g., $C_{1-12}$), 1-6 carbon atoms (e.g., $C_{1-6}$) as used with respect to any chemical group (e.g., alkyl, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

As used herein, "halo" refers to a halogen atom, especially F, Cl or Br; more especially F or Cl; most especially F.

As used herein, "haloalkyl" and the like refers to an alkyl group in which any number of the hydrogen atoms are replaced with a hydrogen atom. Thus, a haloalkyl group could be, for example, a monohaloalkyl group, a dihaloalkyl group or a perhaloalkyl group.

As used herein, the term "optionally substituted" means that any number of hydrogen atoms on the optionally substituted group are replaced with another moiety.

The term "pharmaceutically acceptable salt", as used herein, refers to salts which are toxicologically safe for systemic or localised administration such as salts prepared from pharmaceutically acceptable non-toxic bases or acids including inorganic or organic bases and inorganic or organic acids. The pharmaceutically acceptable salts may be selected from the group including alkali and alkali earth, ammonium, aluminium, iron, amine, glucosamine, chloride, sulphate, sulphonate, bisulphate, nitrate, citrate, tartrate, bitrate, phosphate, carbonate, bicarbonate, malate, maleate, napsylate, fumarate, succinate, acetate, benzoate, terephthalate, palmoate, piperazine, pectinate and S-methyl methionine salts and the like.

It will be appreciated by a person of skill in the art of synthetic chemistry that the COOH group is easily interchanged with a salt form or an ester protecting group, for example a methyl ester group, and so all such forms are considered to be disclosed herein with reference to the compounds listed above.

The prodrug form of the above compounds may be explicitly considered to include $C_1$-$C_{20}$ ester or ester comprising a cycloalkyl, or aryl moiety. The aryl moiety may include substituted phenyl or fused 2-3 cyclic aromatic rings.

According to a second aspect of the present invention, there is provided a pharmaceutical composition comprising an effective amount of the compound of the first aspect, or a pharmaceutically acceptable salt thereof. The composition may further comprise a pharmaceutically acceptable carrier, diluent and/or excipient.

While it is possible that the compound of Formula (I) (or a pharmaceutical salt or prodrug thereof) may be administered as a neat chemical, it also may be administered as part of a pharmaceutical composition which includes at least one carrier or excipient.

The type of pharmaceutical composition may depend upon the Absorption, Distribution, Metabolism and Excretion (ADME) profile of the compound of Formula (I) (or a pharmaceutical salt or prodrug thereof). For example, it may be most appropriate for compounds of Formula (I) (or a pharmaceutical salt or prodrug thereof) to be administered parenterally, especially intravenously, and consequently the pharmaceutical composition may be formulated for parenteral or intravenous administration. Nevertheless, if possible the pharmaceutical composition may include those suitable for oral or rectal administration, or for administration by non-intravenous routes.

Parenteral administration may include administration by one or more of the following routes: intravenously, intrathecally, cutaneously, subcutaneously, nasally, intramuscularly, intraocularly, transepithelially, vaginally, intraperitoneally and topically. Topical administration includes buccal, sub-lingual, dermal, ocular, rectal, nasal, as well as administration by inhalation or by aerosol means. For intravenous, cutaneous or subcutaneous injection, or injection at a site where treatment is desired, the active agent may be in the form of a parenterally acceptable aqueous solution which is pyrogen-free and has suitable pH, isotonicity and stability. Those of skill in the art would be able to prepare suitable solutions.

The nature of the pharmaceutical composition and the carrier or excipient will depend on the route of administration and the nature of the condition and the patient being treated. It is believed that the choice of a particular carrier, excipient or delivery system, and route of administration could be readily determined by a person skilled in the art. In some circumstances it may be necessary to protect the compound of Formula (I) (or a pharmaceutical salt or prodrug thereof) by means known in the art, for example, by micro encapsulation. The route of administration should also be chosen such that the active agent reaches its site of action. The pharmaceutical composition may include any suitable effective amount of the active agent commensurate with the intended dosage range to be employed.

The pharmaceutical composition may be in the form of a solid (including tablets, filled capsules, powders, cachets, capsules, troches, suppositories, wafers, dispersible granules and pessaries), or a liquid (including solutions, suspensions, syrups, emulsions, colloids, elixirs, creams, gels and foams). In one embodiment, the pharmaceutical composition may be in the form of a sterile injectable solution for parenteral use.

The pharmaceutically acceptable carrier(s) or excipient(s) must be acceptable in the sense of being compatible with the other components in the composition and not being deleterious to the patient. The pharmaceutically acceptable carrier or excipient may be either a solid or a liquid. The carrier or excipient may act as a diluent, buffer, stabiliser, isotonicising agent, flavouring agent, anti-oxidant, solubilizer, lubricant, suspending agent, binder, preservative, tablet disintegrating agent or an encapsulating material. Suitable carriers and excipients would be known to a skilled person. With regard to buffers, aqueous compositions may include buffers for maintaining the composition at close to physiological pH or at least within a range of about pH 6.0 to 9.0.

If the pharmaceutical composition is a powder, the active agent (the compound of Formula (I) or a pharmaceutically acceptable salt thereof) and a carrier or excipient may both be finely divided powders which are mixed together.

If the pharmaceutical composition is a tablet, the active agent may be mixed with a suitable amount of a carrier or excipient which has the necessary binding capacity before compaction into a tablet of the desired shape and size.

Powders or tablets may include any suitable amount of the active agent, and exemplary amounts of the active agent in the powder or tablet may range from about five or ten percent to about seventy percent. Exemplary carriers or excipients for powders and tablets may include, for example, magnesium carbonate, talc, sugar, lactose, pectin, dextrin, starch, gelatin, tragacanth, methylcellulose, a low melting wax, cocoa butter and the like.

Liquid form preparations may include, for example, water, saline, water-dextrose, water-propylene glycol, petroleum, or oil (including animal, vegetable mineral or synthetic oil) solutions. For example, parenteral injection liquid preparations may be formulated as solutions in aqueous polyethylene glycol solution. Such liquid form preparations may contain at least 0.1 wt % of the active compound.

Liquid pharmaceutical compositions may be formulated in unit dose form. For example, the compositions may be presented in ampoules, pre-filled syringes, small volume infusion or in multi-dose containers. Such compositions may include a preservative. The compositions may also include formulatory agents such as suspending, stabilising and/or dispersing agents. The composition may also be in powder form for constitution with a suitable vehicle (such as sterile water) before use. Liquid carriers and excipients may include colorants, flavours, stabilizers, buffers, artificial and natural sweeteners, dispersants, thickeners, solubilizing agents, suspending agents and the like.

Aqueous solutions for oral use may be prepared by dissolving the active agent in water and adding colourants, thickeners, flavours, and stabilizing agents, as necessary. Aqueous suspensions for oral use may be prepared by dispersing the active agent in water with viscous material, such as natural or synthetic gums, resins, methyl cellulose or other suspending agents.

For topical administration to the epidermis the compounds may be formulated as an ointment, cream or lotion, or as a transdermal patch.

The compositions may also be administered by inhalation in the form of an aerosol spray from a pressurised dispenser or container, which contains a propellant such as carbon dioxide gas, dichlorodifluoromethane, nitrogen, propane or other suitable gas or gas combination. The pharmaceutical composition may be in a form suitable for administration by inhalation or insufflation.

The pharmaceutical composition may be adapted to provide sustained release of the active agent.

The pharmaceutical composition may be in unit dosage form. In such form, the pharmaceutical composition may be prepared as unit doses containing appropriate quantities of the active agent. The unit dosage form may be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

According to a third aspect of the present invention, there is provided a method of treating or preventing a disease, disorder or condition associated with Class IIa histone deacetylase activity in a subject, the method comprising administering to the subject an effective amount of the compound of the first aspect or a pharmaceutically acceptable salt thereof, or the pharmaceutical composition of the second aspect.

As used herein, the term "histone deacetylase" may be interchanged with "lysine deacetylase".

According to a fourth aspect of the present invention, there is provided a method of treating or preventing one or more of: inflammatory diseases or disorders, immune disorders, cancer, fibrosis, kidney dysfunction (especially renal injury), cardiovascular diseases, neurodegenerative diseases, neuromuscular diseases and metabolic diseases in a subject; the method comprising administering to the subject an effective amount of the compound of the first aspect or a pharmaceutically acceptable salt or prodrug thereof, or the pharmaceutical composition of the second aspect.

According to a fifth aspect of the present invention, there is provided a use of the compound of the first aspect, or a pharmaceutically acceptable salt or prodrug thereof, in the manufacture of a medicament for the treatment or prevention of a disease, disorder or condition associated with Class IIa histone deacetylase activity in a subject.

According to a sixth aspect of the present invention, there is provided a use of the compound of the first aspect, or a pharmaceutically acceptable salt or prodrug thereof, in the manufacture of a medicament for the treatment or prevention of one or more of: inflammatory diseases or disorders, immune disorders, cancer, fibrosis, kidney dysfunction (especially renal injury), cardiovascular diseases, neurodegenerative diseases, neuromuscular diseases and metabolic diseases in a subject.

According to a seventh aspect of the present invention, there is provided the compound of the first aspect or a pharmaceutically acceptable salt or prodrug thereof, or the pharmaceutical composition of the second aspect, for use in the treatment or prevention of a disease, disorder or condition associated with Class IIa histone deacetylase activity.

According to an eighth aspect of the present invention, there is provided the compound of the first aspect or a pharmaceutically acceptable salt or prodrug thereof, or the pharmaceutical composition of the second aspect, for use in the treatment or prevention of one or more of: inflammatory diseases or disorders, immune disorders, cancer, fibrosis, kidney dysfunction (especially renal injury), cardiovascular diseases, neurodegenerative diseases, neuromuscular diseases and metabolic diseases.

The disease, disorder or condition associated with Class IIa histone deacetylase activity may be selected from one or more of the group consisting of: inflammatory diseases or disorders, immune disorders, cancer, fibrosis, kidney dysfunction (especially renal injury), cardiovascular diseases, neurodegenerative diseases, neuromuscular diseases and metabolic diseases; especially selected from the group consisting of: cancer, fibrosis, cardiovascular diseases, neurodegenerative diseases, and metabolic diseases. The compounds of the present invention may also be used to reduce oxidative stress is cardiomyocytes and promote cardiac tissue regeneration. In one embodiment, the disease, disorder or condition associated with Class IIa histone deacetylase activity is an inflammatory disease. The disease, disorder or condition associated with Class IIa histone deacetylase activity may be a disease, disorder or condition associated with HDAC7 activity.

Isoforms of class IIa HDACs are found highly expressed in diseases such as cancer, neurodegenerative diseases, immune disorders, and renal fibrosis/injury (Asfaha et al, Bioorg. Med. Chem. 2019; Wright et al, Am. J. Physiol. Heart. Circ. Physiol. 2016, 311 (1), H199-206; Clocchiatti et al, J. Cell. Mol. Med. 2011, 15 (9), 1833-1846; Martin et al, Int. J. Dev. Biol. 2009, 53 (2/3), 291-301; Oncogene 2007, 26 (37), 5450-5467; Xiong et al, FASEB J. 2019, 33 (7), 8249-8262; Okudela et al, Int. J. Clin. Exp. Pathol. 2014, 7 (1), 213-220; Ma et al, J. Pineal. Res. 2019, 67 (2), e12587; Gil et al, Dis. Models Mech. 2016, 9 (12), 1483-1495). Inhibition of class IIa HDACs through either knockdown or inhibition are found to be beneficial in the treatment of cancer (Guerriero et al, Nature 2017, 543 (7645), 428-432; Li et al, Cold Spring Harbor Perspect. Med. 2016, 6 (10), a026831/1-a026831/35), renal fibrosis/injury (Xiong et al, FASEB J. 2019, 33 (7), 8249-8262), muscle and heart development (Nebbioso et al, Embo Rep. 2009, 10 (7), 776-782; Vega et al, Cell 2004, 119 (4), 555-566), cardiovascular diseases (Kim et al, J. Hypertens. 2016, 34 (11), 2206-2219; Usui et al, Hypertension 2014, 63 (2), 397-403) and metabolic diseases (Wang et al, Kidney Int. 2014, 86 (4), 712-725; Mihaylova et al, Cell 2011, 145 (4), 607-621; Wang et al, Cell 2011, 145 (4), 596-606).

Advantageously, class IIa HDACs are much more tissue or organ specific than class I HDACs. Consequently, selective targeting of class IIa HDACs is expected to provide significantly fewer side effects than targeting class I HDACs. Differing from class I and IIb enzymes, class IIa HDACs have very inefficient protein-deacetylase activity. Lahm et al, Proc. Natl. Acad. Sci. 2007, 104 (44), 17335-17340, shows this is due to a tyrosine-to-histidine mutation in the catalytic site (Tyr976His in HDAC4). The tyrosine-to-histidine mutation in the catalytic site induced a distinct sub-pocket adjacent to the conventional zinc-binding site, differentiating class IIa HDACs from other HDACs, (reviews: Asfaha, Y., et al., Bioorg. Med. Chem., 2019, 27, 115087; Wright, L. H. and D. R. Menick, Am. J. Physiol. Heart Circ. Physiol., 2016. 311 (1), H199-206; Di Giorgio et al, Cell. Mol. Life Sci., 2015. 72(1), 73-86) therefore assisting to provide the selectivity of the compounds of Formula (I).

In the present specification and claims, the word 'comprising' and its derivatives including 'comprises' and 'comprise' include each of the stated integers but does not exclude the inclusion of one or more further integers.

As used herein, the terms "treatment" (or "treating") and "prevention" (or "preventing") are to be considered in their broadest contexts. For example, the term "treatment" does not necessarily imply that a patient is treated until full recovery. The term "treatment" includes amelioration of the symptoms of a disease, disorder or condition, or reducing the severity of a disease, disorder or condition. Similarly, "prevention" does not necessarily imply that a subject will never contract a disease, disorder or condition. "Prevention" may be considered as reducing the likelihood of onset of a disease, disorder or condition, or preventing or otherwise reducing the risk of developing a disease, disorder or condition.

As used herein, the terms "subject" or "individual" or "patient" may refer to any subject, particularly a vertebrate subject, and even more particularly a mammalian subject, for whom therapy is desired. Suitable vertebrate animals include, but are not restricted to, primates, avians, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes). A preferred subject is a human.

As used herein, "effective amount" refers to the administration of an amount of the relevant active agent sufficient to at least partially attain the desired response, or to prevent the occurrence of symptoms of the disease, disorder or condition being treated, or to bring about a halt in the worsening of symptoms or to treat and alleviate or at least reduce the severity of the symptoms. The amount may vary depending on factors such as: the health and physical condition of the individual to whom the compound is administered, the taxonomic group of the individual to whom the compound is administered, the extent of treatment/prevention desired, the formulation of the composition, and the assessment of the medical situation. It is expected that the "effective amount" will fall within a broad range that can be determined through routine trials. An effective amount in relation to a human patient, for example, may lie in the range of about 0.1 ng per kg of body weight to 1 g per kg of body weight per dosage, or in the range of about 100 ng to 100 mg per kg of body weight per dosage. Dosage regimes may be adjusted to provide the optimum therapeutic response. For example, several doses may be administered daily, bi-weekly or weekly, or at other suitable time intervals, or the dose may be proportionally reduced as indicated by the circumstances. Decisions on dosage and the like would be within the skill of the medical practitioner or veterinarian responsible for the care of the patient.

The compound of Formula (I) (or a pharmaceutically acceptable salt or prodrug thereof) may be administered with a further active agent. For example, if the disease, disorder or condition being treated or prevented is cancer, then the compound of Formula (I) can be administered with other cancer drugs (such as docetaxel, 5-fluorouracil and the like).

Features of the second to eighth aspects of the present invention may be as described for the first aspect of the present invention. The medicament of the fifth and sixth aspects of the present invention may be a pharmaceutical composition, as described above.

Any of the features described herein can be combined in any combination with any one or more of the other features described herein within the scope of the invention.

BRIEF DESCRIPTION OF DRAWINGS

Examples of the invention will now be described by way of example with reference to the accompanying Figures, in which.

Figure 1:
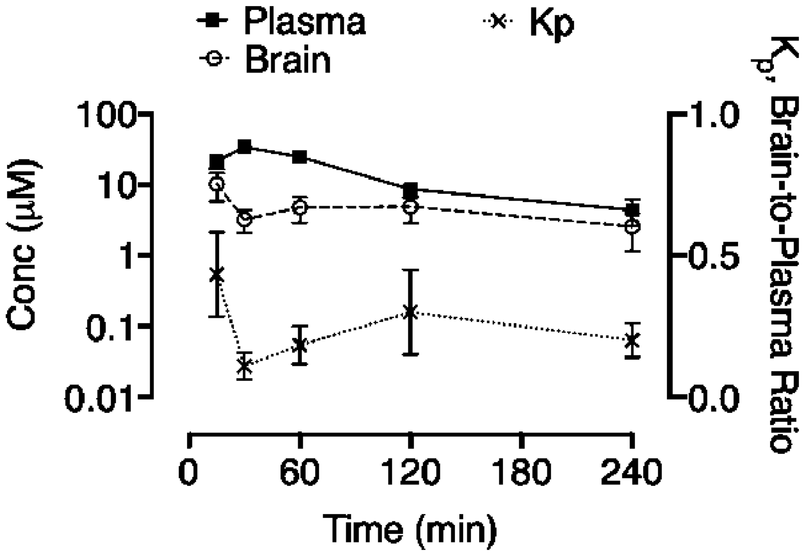
FIG. 1 is a graph illustrating the concentration of compound 12 in plasma and brain of Dark Agouti rats.

Preferred features, embodiments and variations of the invention may be discerned from the following Examples which provides sufficient information for those skilled in the art to perform the invention. The following Examples are not to be regarded as limiting the scope of the preceding Summary of the Invention in any way.

EXAMPLES

Examples of the present invention will now be described with reference to FIGS. 1 to 4.

Compound Synthesis

General Methods:

Anhydrous dichloromethane and tetrahydrofuran were dispensed from an Innovative Technology PureSolv solvent purification system. Anhydrous toluene was prepared by distillation from sodium/benzophenone under argon. Anhydrous pyridine was prepared by distillation over calcium hydride. All other chemicals were purchased without further purification. Reactions were monitored by TLC with Merck Silica gel 60 F254 aluminium backed sheets and LCMS analysis on a Shimadzu LCMS-2020 mass spectrometer. TLC was visualized using 5% sulfuric acid in ethanol or 5% ceric ammonium molybdate in ethanol. Analytical UPLC/MS was performed on a Shimadzu LCMS-2020 system equipped with a Phenomenex Aeris PEPTIDE 1.7 micron XB-C18 50×2.1 mm column (P/No OOB-4506-AN) and a SPD-M20A diode array detector. The flow rate was 0.5 mL/min with a linear gradient: 0% to 100% solvent B over 5 min followed by 1 min at 100% solvent B. Solvent A: 0.1% formic acid in MilliQ water, solvent B: 0.1% formic acid in acetonitrile-MilliQ water (90:10). Electrospray ionization high-resolution mass spectra (ESI-HRMS) measurements were obtained on a Bruker microTOF mass spectrometer in positive ion mode by direct infusion in water at 100 μL/h using sodium formate clusters as an internal calibrant. Compounds were purified by flash chromatography (SNAP cartridge filled with Merck silica gel 70-230 or 230-400 mesh) on a Biotage Isolera Flash Purification System or on a Shimadzu LC-20APP prominence HPLC equipped with a Phenomenex Luna 10 μm, C18(2), preparative scale—250×30 mm and semi-prep scale—250×21.2 mm columns (P/No 00G-4253-U0 and 00G-4253-P0, respectively) and a SPD-M20A diode array detector. The following were used as preparative HPLC mobile phases, solvent A: 1% TFA in MilliQ water, solvent B: 1% TFA in acetonitrile-MilliQ water (90:10). Flow rate: 40 and 20 mL/min for preparative and semi-preparative scales, respectively. $^1H$ and $^{13}C$ NMR spectra were recorded on Bruker Avance 600 spectrometers at 298 K in the solvents indicated and referenced to tetramethylsilane or residual solvent signals in DMSO-$d_6$ ($^1H/^{13}C$: δ 2.50/39.52).

Methods for Preparing Compounds of the General Formula (I) and/or Comparative Examples.

The following examples are representative of the present invention, and provide detailed methods for preparing exemplary compounds of the present invention.

Example 1 (Comparative Example)

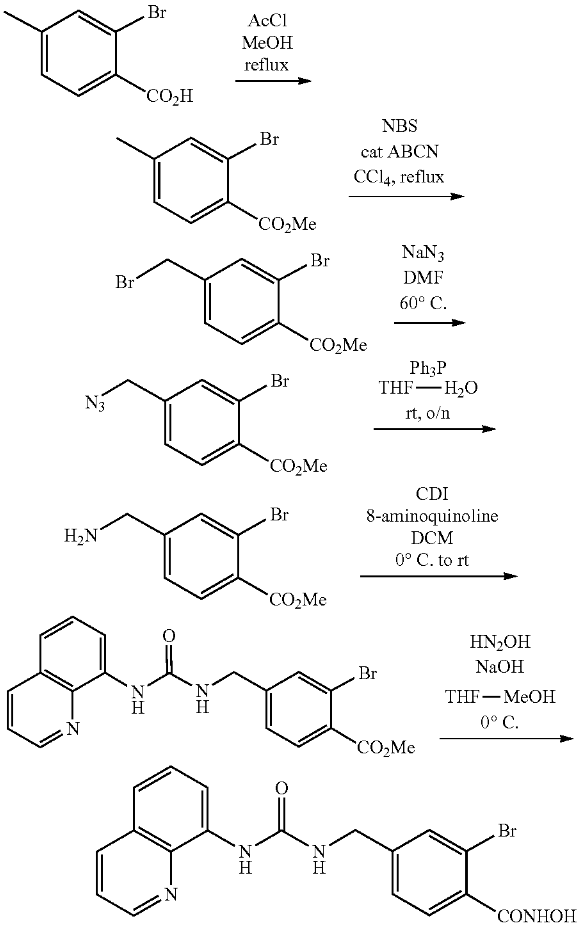

Step a. In an oven-dry round-bottomed flask (RBF) (500 mL) was loaded anhydrous MeOH (200 mL). The flask was cooled in an ice-water bath while acetyl chloride (20 mL) was added dropwise within 5 min. The mixture was stirred at 0° C. for 5 min. The powdered 2-bromo-4-methylbenzoic acid (40.0 g, 0.186 mol) was added in one portion. The mixture was stirred under reflux for 9 h. The clear solution was concentrated to dryness on rotary evaporator. The residue was dissolved in ethyl acetate (100 mL). After chilled at 0° C., the ethyl acetate solution was basified by slow addition of saturated aqueous $NaHCO_3$ solution (80 mL), separated and washed with brine (40 mL×3), dried over anhydrous $MgSO_4$. Filtration and evaporation to dryness to give methyl 2-bromo-4-methylbenzoate as a light-yellow oil (40.21 g, 94%).

Step b. To a two-necked RBF (500 mL) was loaded the above methyl ester from step a (7.64 g, 32.9 mmol), NBS (6.21 g (34.9 mmol, 1.06 eq) and $CCl_4$ (250 mL). The mixture was stirred under reflux (external temperature 92° C.) under nitrogen atmosphere, while a solution of 1,1'-azobis(cyclohexane carbonitrile) (ABCN, 129 mg, 0.526 mmol, 0.016 eq) in $CCl_4$ (5 mL) was added in portions (1 mL each loading) over a period of 80 min. After addition, the mixture was stirred under reflux for 5 h, cooled, and concentrated to dryness on rotary evaporator. The residue was extracted with ethyl acetate (100 mL) and water (100 mL). The ethyl acetate phase was separated, washed with brine (50 mL), and dried over anhydrous $MgSO_4$. Filtration and evaporation to dryness to give the crude methyl 2-bromo-4-bromomethylbenzoate as a light-yellow liquid (10.95 g). UPLCMS analysis indicated a mixture of the desired bromide methyl 2-bromo-4-bromomethylbenzoate, the starting material methyl 2-bromo-4-methylbenzoate, and bis-brominated methyl 2-bromo-4-dibromomethylbenzoate in a ratio of 61:12:27). The crude was used without further purification.

Step c. The crude bromide from step b (10.95 g) was dissolved in DMF (60 mL). The solution was treated with $NaN_3$ (2.57 g, 39.5 mmol, 1.2 eq) and stirred at 60° C. (external temperature) for 1 h. The mixture was cooled and concentrated to dryness on rotary evaporator. The residue was extracted with ethyl acetate (100 mL) and water (100 mL). The ethyl acetate phase was separated, washed with brine (50 mL), and dried over anhydrous $MgSO_4$. Filtration and evaporation to dryness gave the crude, which was purified using silica gel column chromatography (230-400 mesh, gradient elution with ethyl acetate-petroleum ether, 0% to 10%). After checking TLC and UPLCMS, the product fractions were combined and evaporated to give the isolated pure product. Fraction 1 was the recovered methyl 2-bromo-4-methylbenzoate (light-yellow liquid, 1.53 g). Fraction 2 was a mixture of methyl 2-bromo-4-azidomethylbenzoate and methyl 2-bromo-4-(bisazido)methylbenzoate as a colourless liquid (7.24 g), in a ratio of 79:21 as confirmed by both UPLCMS and $^1H$ NMR.

Step d. The above crude azide (6.09 g, 22.1 mmol based on an average MW275.9 for mono-: bis-azide in a ratio of 79:21) was dissolved in THE (63 mL). Water (0.812 mL, 45.1 mmol) was added. The mixture was stirred at 0° C., while a solution of Ph3P (8.87 g, 33.8 mmol) was added in portions over a period of 30 min. After stirring at 0° C. for 1 h, the mixture was allowed to warm up to room temperature and stirred at rt overnight. The mixture was concentrated on rotary evaporator. The residue was suspended in $Et_2O$ (100 mL), chilled at 0° C., and extracted with chilled 0.5M HCl aqueous solution (150 mL×3). The combined aqueous HCl phases were washed with $Et_2O$ (50 mL×2), pumped on rotary evaporator to remove residual volatile organic solvents, and freeze-dried to the crude HCl salt of methyl 2-bromo-4-aminomethylbenzoate as a white powder (4.65 g, 75%). ES-MS: m/z 244 (100%) and 246 (100%), $[M+H]^+$.

Step e. In an oven-dried RBF was loaded CDI (1.115 g, 6.87 mmol) and anhydrous DCM (80 mL). The mixture was stirred at 0° C. while a solution of 8-aminoquinoline (0.991 g, 6.87 mmol) in anhydrous DCM (10 mL) was added slowly using a syringe pump over 2 h. The mixture was stirred at 0° C. for another 2 h. In the meantime, the amine HCl salt from step d (1.929 g, 6.87 mmol) was suspended in anhydrous DCM (18 mL) and treated with diisopropylethylamine (2.4 mL, 13.7 mmol, 2 eq). The slightly milky suspension was added into the above CDI-activated 8-aminoquinoline reaction mixture. The mixture was stirred at rt overnight, diluted with DCM (60 mL), washed with water (100 mL×3) and brine (50 mL). The DCM phase was evaporated to small volume and purified using silica gel column chromatography (100 g, 70-230 mesh, gradient elution with ethyl acetate-DCM, 0% to 25%). The combined product fractions were concentrated on rotary evaporator to dryness and the residue (yellow syrup) was crystallised from $Et_2O$ (15 mL) to the urea product as yellow solid (0.478 g, 17%). ES-MS: m/z 414 (100%) and 416 (100%) $[M+H]^+$.

Step f. The urea product from step e, methyl 2-bromo-4-((3-(quinolin-8-yl)ureido)methyl)benzoate (80 mg, 0.19 mmol), was dissolved in THE-MeOH (1:1 v/v, 5.8 mL). The mixture was stirred at 0° C. and treated with a chilled stock $HN_2OH$/NaOH solution (0.49 mL, total bases including NaOH and $HN_2OH$: 9.61 mmol), freshly prepared by dissolving NaOH (139.5 mg, 3.49 mmol) in aqueous $HN_2OH$ (50% w/w, 1.05 mL, i.e. 3.32 M NaOH and 16.3 M $HN_2OH$). After completion (0° C., 40 min), the mixture was neutralised with conc. HCl (0.577 mL, 5.77 mmol, 0.6 eq based on the total bases) at 0° C., and concentrated to dryness on rotary evaporator. The residue was dissolved in MeCN—$H_2O$ (4 mL, 9:1 v/v containing 0.1% TFA), MeOH (6 mL) and TFA (0.1 mL), and purified using preparative rpHPLC (a linear gradient 0% B to 75% B over 30 min). The product fractions were confirmed using UPLCMS, pooled and lyophilised. Fraction 1 (10.1-12.6 min) gave the desired hydroxamic acid, 2-bromo-N-hydroxy-4-((3-(quinolin-8-yl)ureido)methyl)benzamide, as amorphous pale-yellow powder (8.3 mg, 10%. UPLCMS: $t_R$=2.68 min, ES-MS: m/z 415 (100%) and 417 (100%) $[M+H]^+$). Fraction 2 (15.3-19.1 min) gave the corresponding carboxylic acid, 2-bromo-4-((3-(quinolin-8-yl)ureido)methyl)benzoic acid, as amorphous yellow powder (2.6 mg, 3.4%. UPLCMS: $t_R$=3.15 min, ES-MS: m/z 400 (100%) and 402 (100%) $[M+H]^+$). Fraction 3 (22.7-24.8 min) gave the recovered starting material as amorphous yellow powder (6.0 mg, 7.5%. UPLCMS: $t_R$=3.70 min, ES-MS: m/z 414 (100%) and 416 (100%) $[M+H]^+$.

Example 2

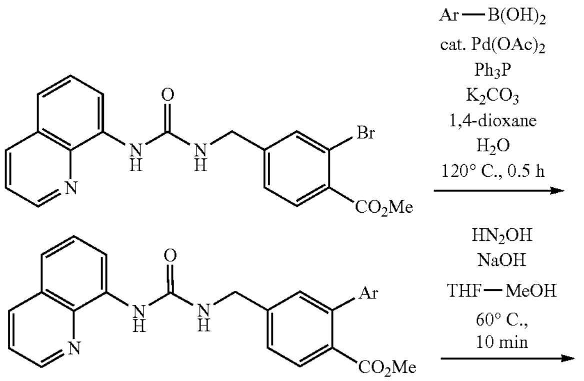

-continued

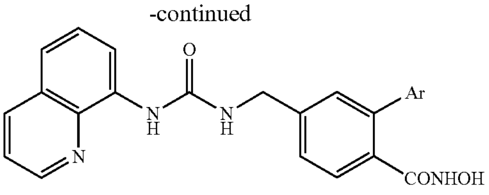

Step a. In a microwave vial was loaded methyl 2-bromo-4-((3-(quinolin-8-yl)ureido)methyl)benzoate (100 mg, 0.241 mmol, 1 eq), arylboronic acid (0.266 mmol, 1.1 eq), $Pd(OAc)_2$ (5.4 mg, 0.024 mmol, 0.1 eq), $Ph_3P$ (25.3 mg, 0.0964 mmol, 0.4 eq), $K_2CO_3$ (66.6 mg, 0.482 mmol, 2 eq), 1,4-dioxane (0.3 mL) and water (0.2 mL). The mixture was purged with argon. The vial was crimp sealed and irradiated in microwave reactor at 120° C. for 30 min. After cooled, the mixture was poured into a separating funnel, diluted with ethyl acetate (40 mL) and washed with brine (40 mL). The aqueous phase was extracted with ethyl acetate (20 mL×2). The combined ethyl acetate phases were concentrated. The residue was purified using silica gel column chromatography (10 g, 70-230 mesh, gradient elution with ethyl acetate-DCM, 0% to 5%) to give methyl 2-aryl-4-((3-(quinolin-8-yl)ureido)methyl)benzoate product.

Step b. The corresponding methyl ester (0.184 mmol) was dissolved in THE-MeOH (1:1 v/v, 5.4 mL). The mixture was stirred at rt and treated with a freshly prepared solution of NaOH (58.9 mg, 1.47 mmol, 8 eq) in aqueous $HN_2OH$ (50% w/w, 452 μL, 7.36 mmol, 40 eq) aqueous solution (total bases: 8.83 mmol). The mixture was stirred at elevated temperature (varying from 40 to 60° C.) for 10 to 30 min, while the progress of the reaction was monitored using UPLCMS. After the completion of the reaction, the mixture was cooled to 0° C. and neutralised with conc. HCl (530 μL, 5.30 mmol, 0.6 eq based on the total bases) at 0° C. The mixture was concentrated to dryness on rotary evaporator. The residue was dissolved in MeCN—$H_2O$ (9.5 mL, 1:1 v/v containing 0.1% TFA), and purified using preparative rpHPLC. The product fractions were confirmed using UPLCMS, pooled and lyophilised. Apart from the desired hydroxamic acid product, the corresponding carboxylic acid was often isolated as a by-product.

Example 3 (Comparative Example)

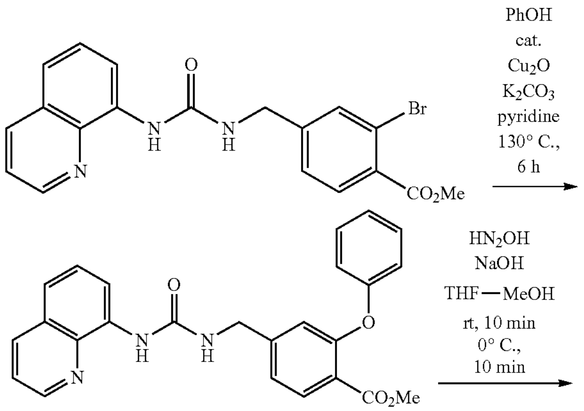

-continued

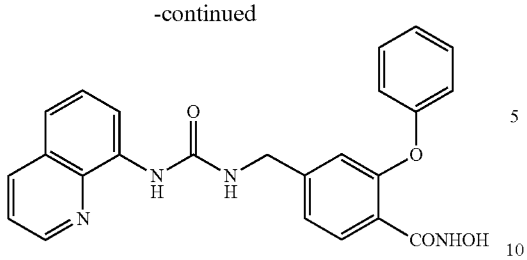

Step a. In a RBF (5 mL) was loaded methyl 2-bromo-4-((3-(quinolin-8-yl)ureido)methyl)benzoate (163 mg, 0.393 mmol), phenol (39 mg, 0.413 mmol, 1.05 eq), $K_2CO_3$ (109 mg, 0.786 mmol, 2 eq), $Cu_2O$ (5.6 mg, 0.039 mmol, 0.1 eq) and pyridine (1.0 mL). The mixture was purged with nitrogen for 1 min, then stirred under nitrogen atmosphere at 130° C. (external heating block) for 6 h. The mixture was cooled to rt, diluted with ethyl acetate (40 mL), and washed with brine (60 mL). The aqueous phase was extracted with ethyl acetate (30 mL×2). The combined ethyl acetate phases were washed with brine (40 mL×2) and concentrated to dryness on rotary evaporator, purified using silica gel column chromatography (10 g, 70-230 mesh, gradient elution with ethyl acetate-DCM, 0% to 6%) to give the product as a light-brownish gum (57 mg). Further purification using semi-preparative rpHPLC (linear gradient from 5% B to 80% B over 30 min) separated the de-bromination by-product (white powder 11 mg, 8%. UPLCMS: $t_R$=3.45 min, ES-MS: m/z 336 $[M+H]^+$) from the desired ortho-phenoxy product (beige powder, 38 mg, 23%. UPLCMS: $t_R$=3.96 min, ES-MS: m/z 428 $[M+H]^+$).

Step b. The ortho-phenoxy benzoate product from step a, methyl 2-phenoxy-4-((3-(quinolin-8-yl)ureido)methyl)benzoate (37 mg, 0.087 mmol), was dissolved in THE-MeOH (1:1 v/v, 2.6 mL). The mixture was stirred at rt and treated with a freshly prepared solution of NaOH (27.8 mg, 0.696 mmol, 8 eq) in aqueous $HN_2OH$ (50% w/w, 213 μL, 3.48 mmol, 40 eq) aqueous solution (total bases: 4.18 mmol). The mixture was stirred at rt for 10 min, 0° C. for another 10 min, and neutralised with conc. HCl (251 μL, 2.51 mmol, 0.6 eq based on the total bases) at 0° C. The mixture was concentrated to dryness on rotary evaporator. The residue was dissolved in MeCN—$H_2O$ (4.5 mL, 1:1 v/v containing 0.1% TFA), and purified using semi-preparative rpHPLC (a linear gradient 0% B to 60% B over 30 min, 60% B to 80% B for 1 min, 80% B for 4 min). The product fractions were confirmed using UPLCMS, pooled and lyophilised. Fraction 1 (21.7-23.7 min) gave the desired hydroxamic acid, 2-phenoxy-N-hydroxy-4-((3-(quinolin-8-yl)ureido)methyl)benzamide, as amorphous pale-yellow powder (22.6 mg, 61%. UPLCMS: $t_R$=3.11 min, ES-MS: m/z 429 (pos mode) $[M+H]^+$ and 427 (neg mode) $[M-H]^-$). Fraction 2 (26.4-26.9 min) gave the corresponding carboxylic acid, 2-phenoxy-4-((3-(quinolin-8-yl)ureido)methyl)benzoic acid, as amorphous pale-yellow powder (0.7 mg, 1.9%. UPLCMS: $t_R$=3.46 min, ES-MS: m/z 414 (pos mode) $[M+H]^+$ and 412 (neg mode) $[M-H]^-$). Fraction 3 (33.0-33.5 min) gave the recovered starting material as amorphous pale-yellow powder (0.6 mg, 1.6%. UPLCMS: $t_R$=3.94 min, ES-MS: m/z 428 $[M+H]^+$).

Example 4

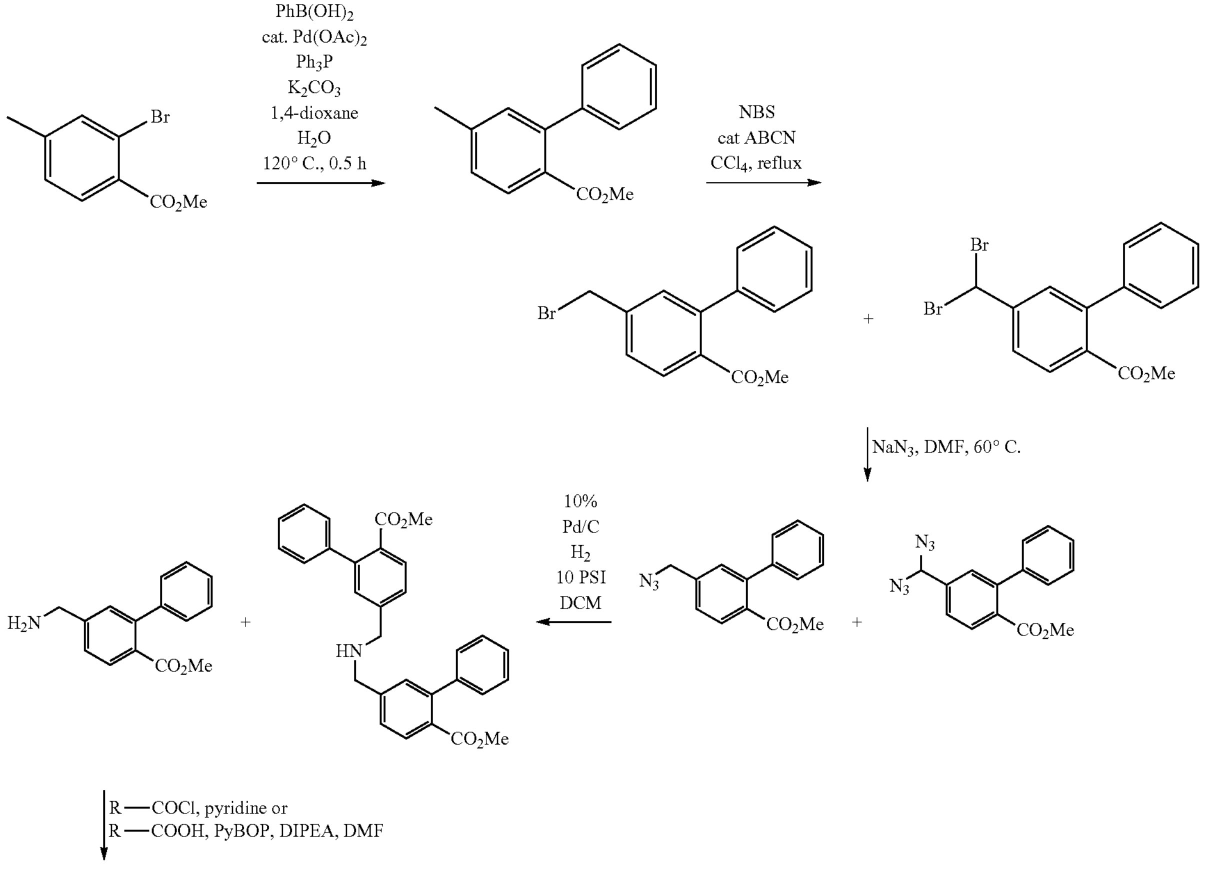

-continued

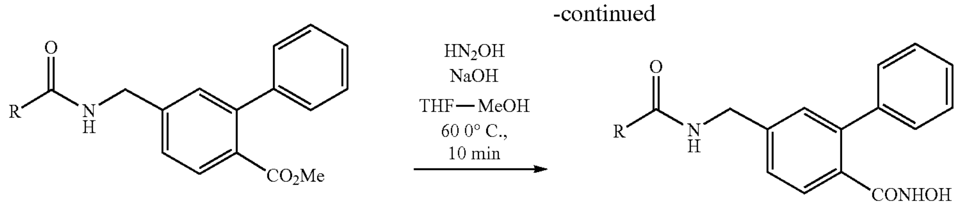

Step a. In a microwave vial was loaded methyl 2-bromo-4-methylbenzoate (1.83 g, 7.98 mmol, 1 eq), phenylboronic acid (1.07 g, 8.76 mmol, 1.1 eq), $Pd(OAc)_2$ (179 mg, 0.798 mmol, 0.1 eq), $Ph_3P$ (837 mg, 3.19 mmol, 0.4 eq), $K_2CO_3$ (2.21 g, 16.0 mmol, 2 eq), 1,4-dioxane (9 mL) and water (6 mL). The mixture was purged with argon. The vial was crimp sealed and irradiated in microwave reactor at 120° C. for 30 min. The above reaction was repeated at the same scale twice. After cooled, the combined reaction mixture from three runs was pooled and concentrated on rotary evaporator. The residue was dissolved in ethyl acetate (80 mL) and washed with brine (40 mL). Ethyl acetate phase were concentrated. The residue was purified using silica gel column chromatography (100 g, 230-400 mesh, gradient elution with ethyl acetate-petroleum ether, 0% to 5%) to give methyl 4-methyl-2-phenylbenzoate as colourless oil (5.01 g, 92%). ES-MS: m/z 227 $[M+H]^+$.

Step b. To a two-necked RBF was loaded methyl 4-methyl-2-phenylbenzoate from step a (5.00 g, 22.1 mmol), NBS (4.13 g, 23.2 mmol, 1.05 eq) and $CCl_4$ (170 mL). The mixture was stirred under reflux (external temperature 92° C.) under nitrogen atmosphere, while a solution of 1,1'-azobis(cyclohexane carbonitrile) (ABCN, 86 mg, 0.354 mmol, 0.016 eq) in $CCl_4$ (3 mL) was added in portions (1 mL each loading) over a period of 1 h. After addition, the mixture was stirred under reflux for 3 h, cooled, and concentrated to dryness on rotary evaporator. The residue was extracted with ethyl acetate (150 mL) and water (80 mL). The ethyl acetate phase was separated, washed with brine (50 mL), and dried over anhydrous $MgSO_4$. Filtration and evaporation to dryness to give the crude product as a light-yellow oil (7.28 g). UPLCMS indicated a mixture of methyl 4-bromomethyl-2-phenyl benzoate ($t_R$=4.10 min, ES-MS: m/z 305 and 307 (1:1) $[M+H]^+$) and methyl 4-dibromomethyl-2-phenylbenzoate ($t_R$=4.37 min, ES-MS: m/z 383/385/387 (1:2:1) $[M+H]^+$) in a ratio of 80:20. The crude was used directly without further purification.

Step c. The crude bromide from step b (7.28 g) was dissolved in DMF (40 mL). The solution was treated with $NaN_3$ (1.72 g, 26.5 mmol, 1.2 eq) and stirred at 60° C. (external temperature) for 1 h. The mixture was cooled and concentrated to dryness on rotary evaporator. The residue was extracted with DCM (150 mL) and water (100 mL). The DCM phase was separated, washed with brine (50 mL), and dried over anhydrous $MgSO_4$. Filtration and evaporation to dryness gave the crude product. UPLCMS indicated a mixture of methyl 4-azidomethyl-2-phenyl benzoate ($t_R$=3.91 min, ES-MS: m/z 268 $[M+H]^+$) and methyl 4-bisazidomethyl-2-phenylbenzoate ($t_R$=4.19 min, ES-MS: m/z 309 $[M+H]^+$) in a ratio of 80:20. The crude was used directly without further purification.

Step d. The crude azide from step c was dissolved in DCM (10 mL). 10% Pb/C (135 mg) was added. The mixture was shaken on Parr Hydrogenator at 10 PSI of hydrogen atmosphere for 2 h. UPLCMS indicated complete conversion to give a mixture of methyl 4-aminomethyl-2-phenyl benzoate, bis(3-phenyl-4-methoxycarbonylbenzyl)amine, and methyl 4-methyl-2-phenyl benzoate (the carry-on product from step a) in a ratio of 47:36:17. The mixture was transferred into an Eppendorf tube (15 mL) and centrifuged at 4000 RPM for 5 min. The top clear solution was decanted into a RBF. The black residue was rinsed with DCM (5 mL×3). Each time the mixture was vortexed, centrifuged and the top clear solution were combined. The combined reaction solution and rinses were concentrated on rotary evaporator. The residue was purified using silica gel column chromatography (50 g, 230-400 mesh, gradient elution with ethyl acetate-petroleum ether, 0% to 10%) to recover methyl 4-methyl-2-phenyl benzoate (colourless oil, 0.600 g, 12%. UPLCMS: $t_R$=4.04 min, ES-MS: m/z 227 $[M+H]^+$). Further elution with ethyl acetate-petroleum ether (10% to 50% then 50%) gave bis (3-phenyl-4-methoxycarbonylbenzyl)amine (yellow syrup, 1.79 g, 35%. UPLCMS: $t_R$=3.10 min, ES-MS: m/z 466 $[M+H]^+$). Further elution with 10% MeOH In DCM containing 0.2% triethylamine gave the desired product methyl 4-aminomethyl-2-phenyl benzoate (colourless oil, 2.65 g, 50%. UPLCMS: $t_R$=2.24 min, ES-MS: m/z 242 $[M+H]^+$).

Step e. Method A—The carboxylic acid (0.268 mol, 1 eq), PyBOP (167 mg, 0.321 mmol, 1.2 eq) was dissolved in DMF (0.4 mL). To the mixture was added DIPEA (140 μL, 0.804 mmol, 3 eq) and 0.2 M stock solution of methyl 4-aminomethyl-2-phenyl benzoate in DCM (1.34 mL, 1 eq). The mixture was stirred at rt overnight and evaporated to dryness. The residue was dissolved in MeCN—$H_2O$ (1:1, 9 mL) containing 0.1% TFA and purified using preparative rpHPLC to give the coupled amide product. Method B—To a mixture of the carboxylic acid chloride (0.382 mmol, 1 eq) in DCM (2 mL)-TEA (106.5 μL, 0.764 mmol, 2 eq) or pyridine (0.5 mL) was added 0.2 M stock solution of methyl 4-aminomethyl-2-phenyl benzoate (1.91 mL, 0.382 mmol, 1 eq). The mixture was stirred at rt overnight. Workup as Method A gave the pure amide coupling product.

Step f. The corresponding methyl ester (0.184 mmol) was dissolved in THE-MeOH (1:1 v/v, 5.4 mL). The mixture was stirred at rt and treated with a freshly prepared solution of NaOH (58.9 mg, 1.47 mmol, 8 eq) in aqueous $HN_2OH$ (50% w/w, 452 μL, 7.36 mmol, 40 eq) aqueous solution (total bases: 8.83 mmol). The mixture was stirred at elevated temperature (varying from 40 to 60° C.) for 10 to 30 min, while the progress of the reaction was monitored using UPLCMS. After the completion of the reaction, the mixture was cooled to 0° C. and neutralised with conc. HCl (530 μL, 5.30 mmol, 0.6 eq based on the total bases) at 0° C. The mixture was concentrated to dryness on rotary evaporator. The residue was dissolved in MeCN—$H_2O$ (9.5 mL, 1:1 v/v containing 0.1% TFA), and purified using preparative rpHPLC. The product fractions were confirmed using UPLCMS, pooled and lyophilised. Apart from the desired hydroxamic acid product, the corresponding carboxylic acid was often isolated as a by-product.

Example 5

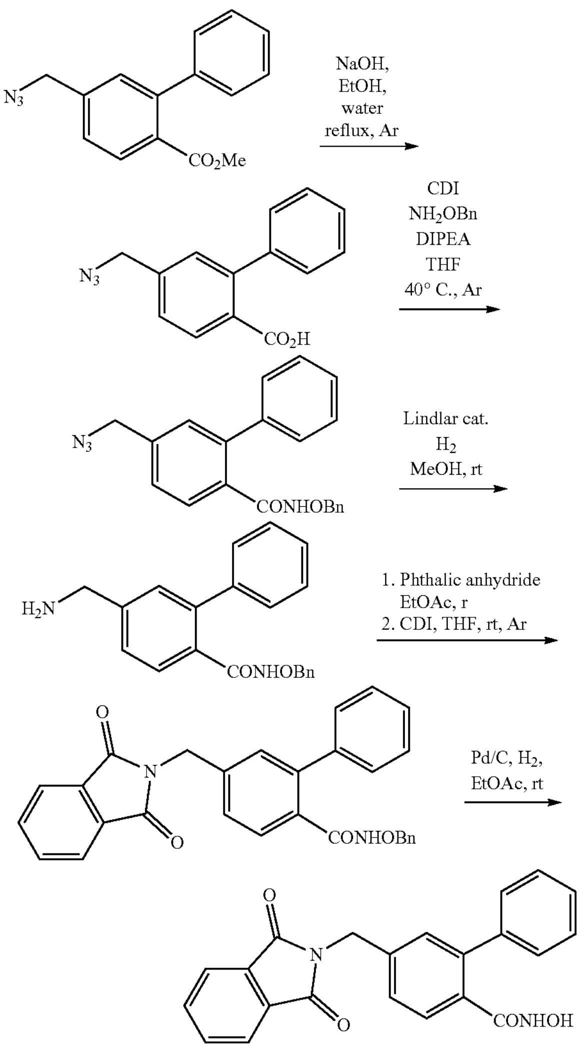

Step a. To a solution of the starting methyl ester (180 mg, 0.673 mmol) in ethanol (2.5 mL) was added water (0.675 mL) and sodium hydroxide aqueous solution (5 M, 0.675 mL). The mixture was refluxed under argon for 1.5 h, at which point LCMS indicated complete consumption of starting material. The mixture was concentrated in vacuo to remove the ethanol, diluted with water, and then adjusted to pH 1 with concentrated hydrochloric acid. The mixture was extracted with ethyl acetate (×3). The combined extracts were washed with brine, dried over magnesium sulfate, then concentrated in vacuo to give the corresponding carboxylic acid product (173 mg, 0.683 mmol, quant.), which was used without further purification.

Step b. To the starting carboxylic acid (173 mg, 0.683 mmol) and carbonyldiimidazole (167 mg, 1.03 mmol) was added tetrahydrofuran (anhydrous, 1.7 mL). The reaction was stirred at 40° C. under argon for 30 min. After adding O-Benzylhydroxylamine hydrochloride (164 mg, 1.03 mmol) and N,N-diisopropylethylamine (0.206 mL, 1.18 mmol), the mixture was stirred overnight at 45° C. LCMS indicated approximately 80% conversion to the product. The mixture was acidified with aqueous hydrochloric acid (1 M), then extracted with ethyl acetate (×3). The combined extracts were washed with saturated sodium bicarbonate aqueous solution, brine, dried over magnesium sulfate, then concentrated in vacuo. Purification by column chromatography (silica, 25% ethyl acetate/petroleum spirit) gave the protected hydroxamate product (95 mg, 0.27 mmol).

Step c. A mixture of the starting azide (62 mg, 0.17 mmol), Lindlar's catalyst (5.5 mg) and methanol (1.73 mL) was stirred under a hydrogen atmosphere (1 atm) at room temperature overnight, at which point LCMS indicated complete consumption of starting material. The mixture was carefully filtered through celite under nitrogen, eluting with methanol. The filtrate was concentrated in vacuo, and then twice co-evaporated with ethyl acetate to give the corresponding amine product as a white foam, which was used in the next step without further purification.

Step d. To a solution of the above crude product in ethyl acetate (0.87 mL) was added phthalic anhydride (34 mg, 0.216 mmol) under argon. Tetrahydrofuran (anhydrous, 0.87 mL) was added to achieve complete dissolution. When starting material was completely consumed, as indicated by LCMS (approximately 15 min), the solvent was evaporated in vacuo. The residue was taken up in tetrahydrofuran (anhydrous, 1.1 mL), and then carbonyldiimidazole (42 mg, 0.26 mmol) was added under argon. After stirring at room temperature for 1 h, the mixture was diluted with water, and then extracted with ethyl acetate (×3). The extracts were washed with brine, dried over magnesium sulfate, then concentrated in vacuo. The crude product was purified by chromatography (silica, 25 to 40% ethyl acetate/petroleum spirit) to give the phthalimide product (56 mg, 0.12 mmol, 70% over 3 steps) that solidified upon standing overnight.

Step e. To a solution of the starting benzyl protected hydroxamate (56 mg, 0.12 mmol) in ethyl acetate (1.2 mL) was added palladium on charcoal (10%, 4 mg) under argon. Tetrahydrofuran (1.2 mL) was added to achieve complete dissolution. The mixture was stirred at room temperature under a hydrogen atmosphere (1 atm) overnight, at which point LCMS indicated complete consumption of starting material. The mixture was filtered with celite, eluting with methanol, concentrated in vacuo, then purified by rpHPLC (20 to 100% solvent B over 25 min). Lyophilisation gave the desired product.

Example 6

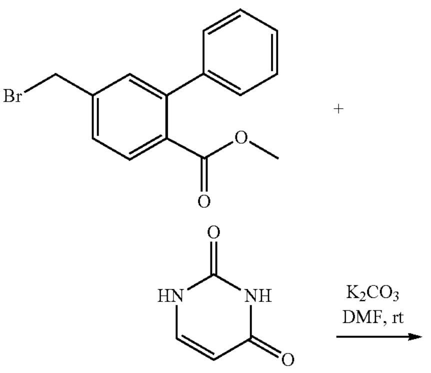

-continued

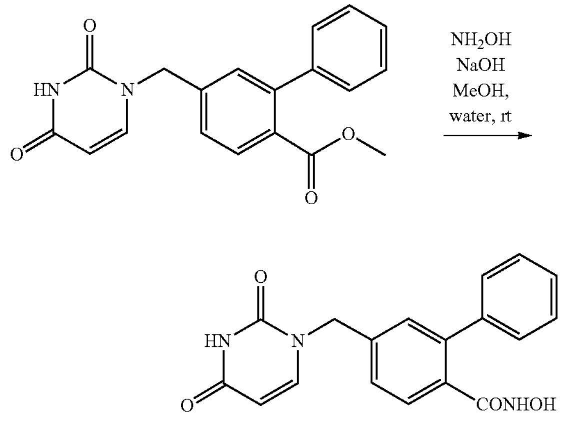

Step a. To a solution of the starting bromide (56 mg, 0.184 mmol) in N,N-dimethylformamide (0.73 mL) was added uracil (31 mg, 0.277 mmol, 1.5 eq) and then potassium carbonate (38 mg, 0.275 mmol, 1.5 eq). The reaction was stirred at room temperature overnight, at which point LCMS indicated complete consumption of starting material. After acidifying with hydrochloric acid (1 M), the mixture was extracted with ethyl acetate (×3). The combined extracts were washed with brine, dried over magnesium sulfate, then concentrated in vacuo. The residue was purified by chromatography (silica, 50 to 100% ethyl acetate/petroleum spirit) to give the desired adduct (59 mg).

Step b. Sodium hydroxide (0.20 g, 5.0 mmol) was dissolved in methanol (1.8 mL) and aqueous hydroxylamine (50% w/w, 0.600 mL). A portion of this solution (1.8 mL) was used to dissolve the starting uracil substituted methyl ester (59 mg, 0.175 mmol), adding tetrahydrofuran to achieve complete dissolution as necessary. The reaction mixture was stirred at room temperature for 1 h, at which point LCMS indicated complete consumption of starting material. Concentrated hydrochloric acid was added to the mixture to pH 1, and then the organic solvents were removed in vacuo. The mixture was dissolved in acetonitrile and water then purified by preparative rpHPLC. Identification of the product peak(s) by LCMS, followed by lyophilisation gave the desired hydroxamic acid product.

Example 7

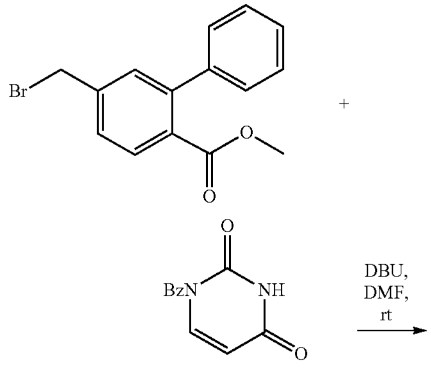

-continued

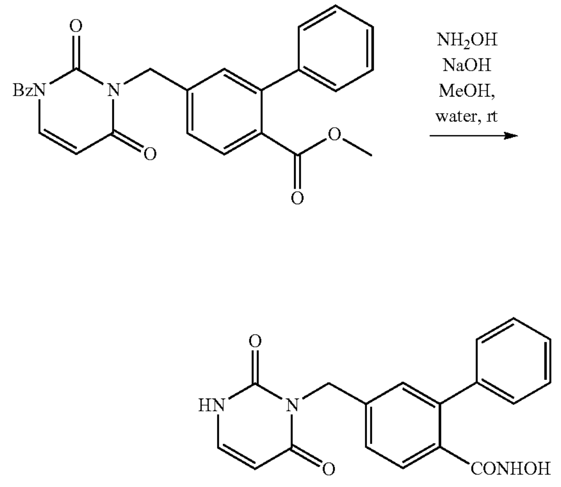

Step a. To a solution of the protected uracil analogue (41 mg, 190 mmol) and the starting bromide (56 mg, 0.184 mmol) in N,N-dimethylformamide (1 mL) was added 1,8-diazabicyclo(5.4.0)undec-7-ene (DBU, 0.028 mL, 0.190 mmol). The mixture was stirred overnight at room temperature, at which point LCMS indicated complete consumption of starting material. After adding saturated ammonium chloride aqueous solution, the mixture was extracted with ethyl acetate (×3). The combined extracts were washed with brine, dried over magnesium sulfate, then concentrated in vacuo. The residue was purified by chromatography (silica, 10 to 80% ethyl acetate/petroleum spirit) to give the desired adduct.

Step b. The methyl ester was then converted to the corresponding hydroxamate according to Example 6.

Example 8

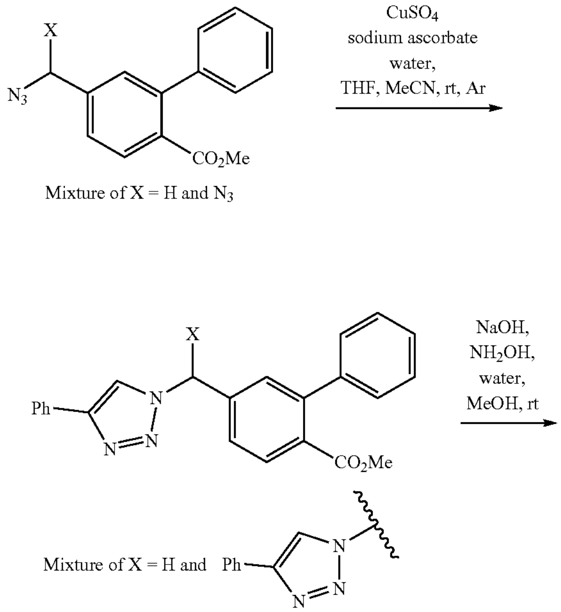

-continued

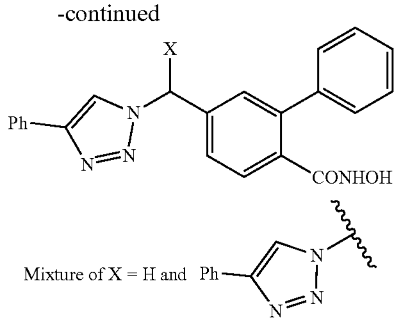

Step a. To a degassed solution of the starting azide (60 mg, 0.225 mmol, containing approximately 30% diazide), phenylacetylene (30 µL, 0.270 mmol), sodium ascorbate (18 mg, 0.090 mmol) in tetrahydrofuran (0.8 mL), water (0.4 mL) and acetonitrile (0.4 mL) was added copper(II) sulfate pentahydrate (11 mg, 0.045 mmol). The mixture was stirred under argon at room temperature for 1.5 h, at which point TLC indicated complete consumption of the starting material. After adding saturated ammonium chloride solution, the mixture was extracted with dichloromethane (×3). The extracts were washed with saturated sodium bicarbonate solution, dried over magnesium sulfate, then concentrated in vacuo. The crude product was purified by chromatography (silica gel, 10 to 25% ethyl acetate/petroleum spirit) to give the triazole adducts as a colourless oil (84 mg, 0.228 mmol, quant.).

Step b. The methyl ester was then converted to the corresponding hydroxamate according to Example 6. Upon reaction completion as indicated by TLC, concentrated hydrochloric acid was added to pH 1. The mixture was extracted with ethyl acetate (×3). The extracts were concentrated in vacuo, then purified on preparative rpHPLC (20 to 100% B over 40 minutes) to give both products with baseline separation.

Example 9

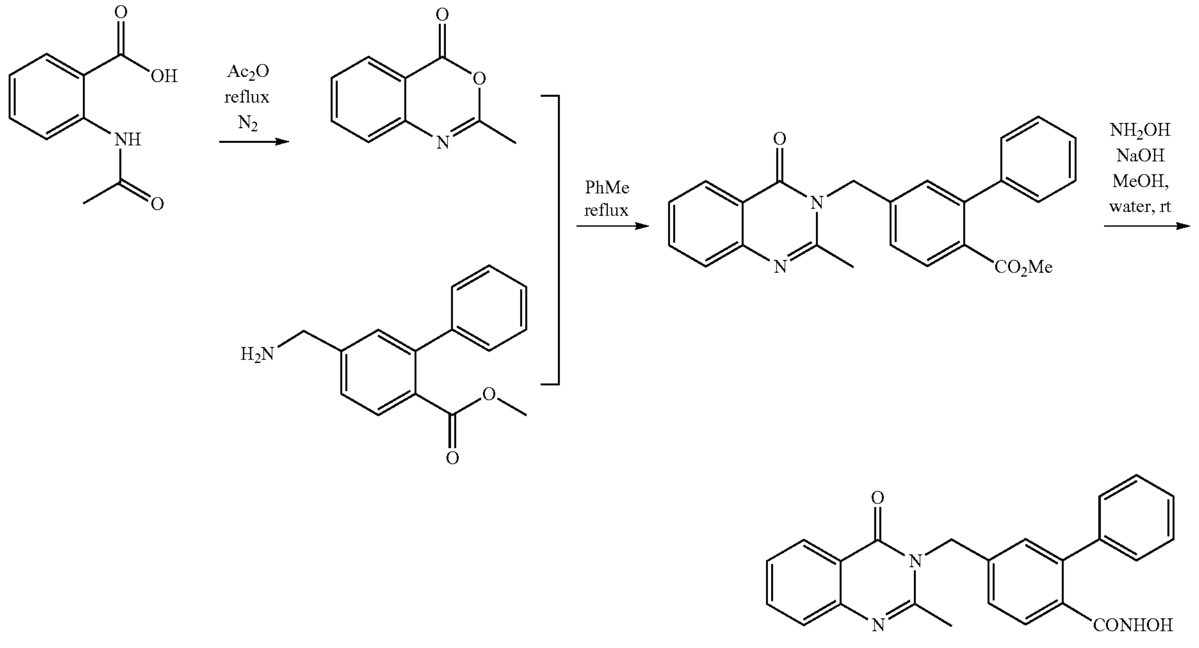

Step a. A mixture of 2-acetamidobenzoic acid (9.02 g, 50.3 mmol) and acetic anhydride (40 mL) was refluxed for 2 h, then stirred at room temperature overnight under nitrogen. Excess acetic anhydride was removed in vacuo. The solid residue was filtered and washed with 10% ethyl acetate/petroleum spirit (30 mL) to give acetanthranil as a light brown solid (6.59 g, 40.9 mmol, 81%).

Step b. A mixture of acetanthranil (272 mg, 1.69 mmol) and the starting amine (340 mg, 1.40 mmol) was refluxed in toluene (4.7 mL) for 4 h. After removing the solvent in vacuo, the residue was purified by chromatography (silica, 20 to 50% ethyl acetate/petroleum spirit) to give a mixture of the desired product and the corresponding hydrate (560 mg, 1.45 mmol, quant.).

Step c. The methyl ester was then converted to the corresponding hydroxamate according to Example 6.

Example 10

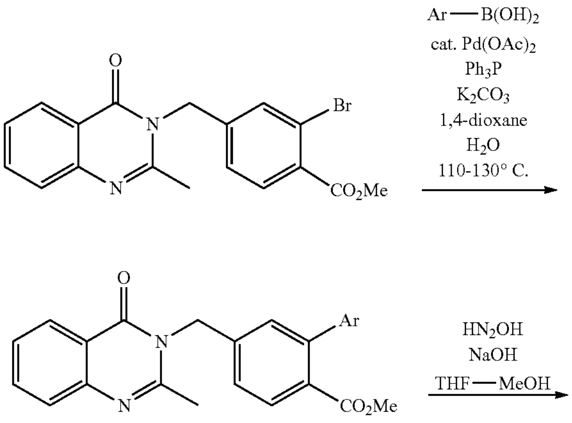

-continued

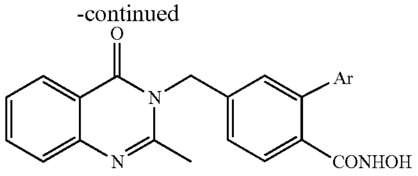

Step a. In a microwave vial was loaded the aryl bromide (1 eq), arylboronic acid (1.1 eq), $Pd(OAc)_2$ (0.1 eq), $Ph_3P$ (0.4 eq), $K_2CO_3$ (2 eq), 1,4-dioxane and water (3:2, v/v). The mixture was purged with argon. The vial was crimp sealed and irradiated in microwave reactor at 110-130° C. until UPLCMS indicated the completion of the reaction. After cooled, the mixture was poured into a separating funnel, diluted with ethyl acetate and washed with brine. The aqueous phase was extracted twice with ethyl acetate. The combined ethyl acetate phases were concentrated. The residue was purified using silica gel column chromatography to give the aryl-coupled product.

Step b. The corresponding methyl ester (1 eq) was dissolved in THE-MeOH (1:1 v/v). The mixture was stirred at rt and treated with a freshly prepared solution of NaOH (8 eq) in aqueous $HN_2OH$ (50% w/w, 40 eq) aqueous solution. The mixture was stirred at elevated temperature (varying from rt to 60° C.) until the completion of the reaction. The mixture was cooled to 0° C., neutralised with conc. HCl, and concentrated to dryness on rotary evaporator. The residue was dissolved in MeCN—$H_2O$ (1:1 v/v, containing 0.1% TFA), and purified using preparative rpHPLC. The product fractions were confirmed using UPLCMS, pooled and lyophilised to give the hydroxamic acid product.

Example 11

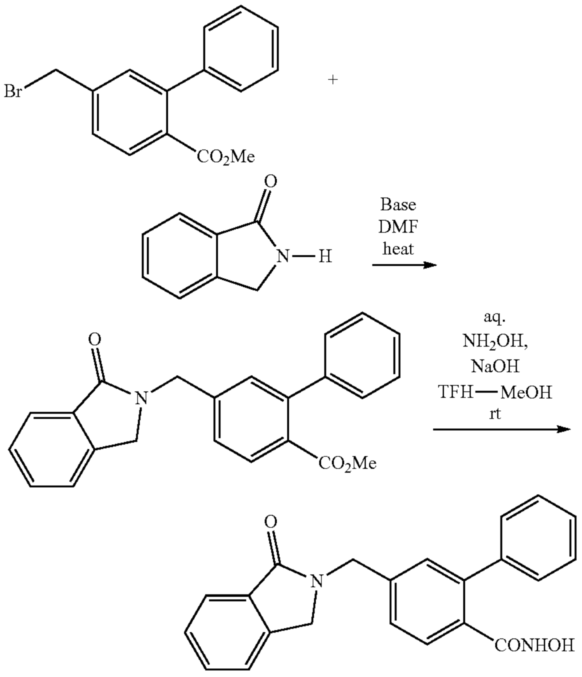

Step a. To a solution of isoindolin-1-one (30 mg, 0.23 mmol) in DMF (0.4 mL) was added sodium hydride (60% w/w, 10 mg, 0.25 mmol) under argon. The mixture was stirred under argon at 40° C. for 30 min, at which point the bromide was added in one portion. After stirring for 20 min at the same temperature, TLC (10% ethyl acetate/petroleum spirit) indicated complete consumption of starting material. The mixture was cooled to rt, then diluted with saturated ammonium chloride solution (1 mL) and water (4 mL). The mixture was extracted with ethyl acetate (×3). The combined extracts were washed with brine, dried over magnesium sulfate, and then concentrated in vacuo. Purification by column chromatography (silica gel, 25 to 60% ethyl acetate/petroleum spirit) gave the N-alkylated isoindolin-1-one intermediate as a yellow oil (17 mg, 0.048 mmol, 21%).

Step b. A mixture of sodium hydroxide (200 mg, 5.00 mmol), aq hydroxylamine solution (50%, 0.9 mL), and methanol (1.8 mL) was stirred at rt in a scintillation vial under the sodium hydroxide was completely dissolved. A small amount of this solution (0.5 mL) was used to dissolve the methyl ester from step a (17 mg, 0.048 mmol) at rt, adding THE (0.5 mL) to effect complete dissolution. The mixture was stirred at rt for 30 minutes, at which point LCMS or TLC indicated complete consumption of starting material. Hydrochloric acid (2 M) was added to pH 1, and then the organic solvents were removed in vacuo. The resultant mixture was dissolved in water and a minimum amount of acetonitrile, purified by preparative. The product fractions were pooled and lyophilised to give the hydroxamic acid product as a white powder (13 mg, 0.036 mmol, 75%).

Example 12

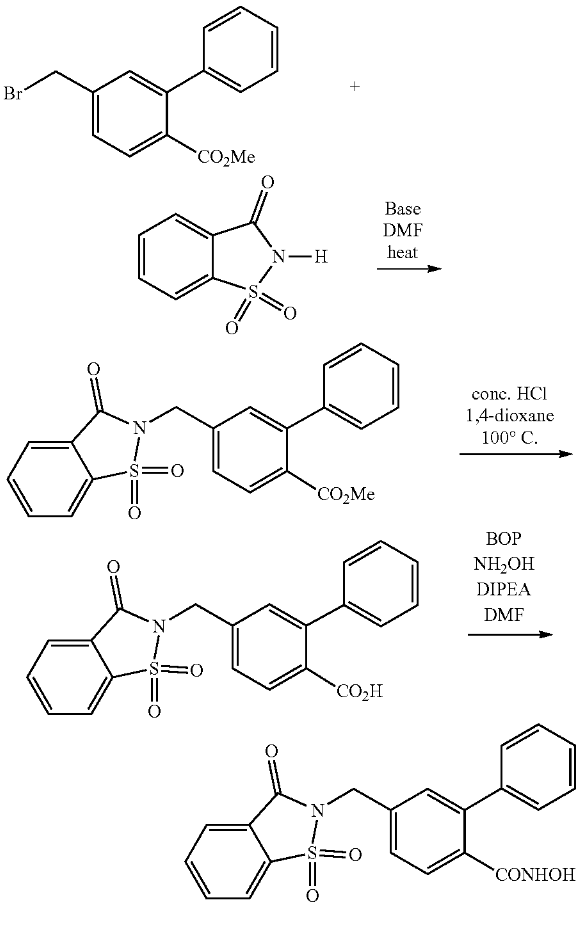

Step a. A mixture of the bromide (214 mg, 0.702 mmol), saccharin (154 mg, 0.842 mmol), potassium carbonate (139 mg, 1.01 mmol) and DMF (1.2 mL) was stirred at 110° C. under argon for 1.5 h, at which point UPLC indicated complete consumption of starting material. The mixture was diluted with hydrochloric acid solution (0.5 M, 20 mL), and then extracted with ethyl acetate (×3). The combined extracts were washed with brine, dried over magnesium sulfate, and then concentrated in vacuo. The residue was dissolved in DCM and then adsorbed onto silica gel. Purification by column chromatography (silica gel, 25 to 30% ethyl acetate/petroleum spirit) gave N-alkylated saccharin intermediate as a light yellow oil that solidified on standing (125 mg, 0.307 mmol, 44%).

Step b. A mixture of the above methyl ester product (62 mg, 0.152 mmol), concentrated hydrochloric acid (32% aq solution, 2 mL), and 1,4-dioxane (2 mL) was heated to 100° C. for 10 h, at which point UPLC indicated complete consumption of starting material. The mixture was cooled, diluted with water, and then extracted with ethyl acetate (×3). The combined extracts were washed with brine, dried over magnesium sulfate, and then concentrated in vacuo to give crude carboxylic acid product. The residue (64 mg, quant.) was used in the next step without further purification. ESMS: m/z 394.1 $[M+H]^+$, 391.7 $[M-H]^-$.

Step c. To a solution of the above crude carboxylic acid (64 mg, 0.15 mmol, assumed quantitative conversion from previous step) in DMF (0.5 mL) was added BOP (67 mg, 0.15 mmol) and N,N-diisopropylethylamine (53 mL, 0.30 mmol) under argon at rt. After stirring the mixture for 15 min, hydroxylamine hydrochloride (10.7 mg, 0.152 mmol) was added. UPLC indicated no further conversion to the product after 1 h, at which point the mixture was diluted with aq hydrochloric acid (1 M, 5 mL). The mixture was extracted with ethyl acetate (×3). The combined extracts were evaporated in vacuo without further drying to give a residue that was purified by rpHPLC (25 to 100% solvent B over 60 min), then lyophilised to give the product as a white powder (29 mg, 0.071 mmol, 47% over 2 steps).

Example 12a

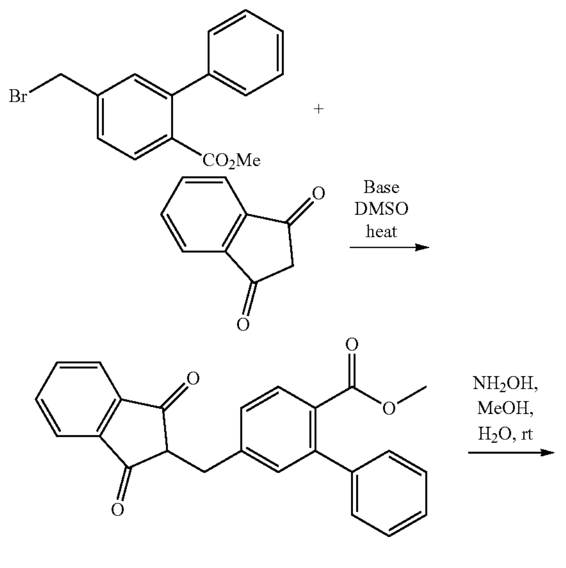

-continued

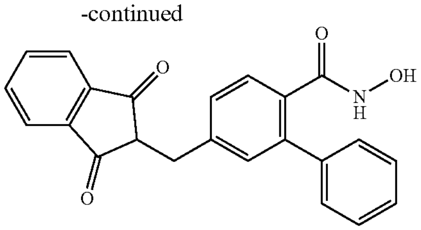

Step a. A mixture of the bromide (50 mg, 0.164 mmol), 1H-indene-1,3(2H)-dione (31 mg, 0.213 mmol), cesium carbonate (107 mg, 0.328 mmol) and DMSO (0.5 mL) was stirred at 80° C. under argon for 8 h, at which point UPLC indicated complete consumption of starting material. The mixture was diluted with water (10 mL), and then extracted with ethyl acetate (×3). The combined extracts were washed with brine, dried over magnesium sulfate, and then concentrated in vacuo. Purification by column chromatography (silica gel, 20 to 50% ethyl acetate/petroleum spirit) gave the C-alkylated intermediate as a light yellow semi-solid (11 mg, 0.030 mmol, 18%).

Step b. A mixture of sodium hydroxide (200 mg, 5.00 mmol), aq hydroxylamine solution (50%, 0.9 mL), and methanol (1.8 mL) was stirred at room temperature in a scintillation vial until the sodium hydroxide was completely dissolved. A small amount of this solution (0.9 mL) was used to dissolve the methyl ester from step a (11 mg, 0.030 mmol) at room temperature. The mixture was stirred at room temperature for 30 minutes, at which point UPLC indicated complete consumption of starting material. Hydrochloric acid (2 M) was added to pH 1, and then the organic solvents were removed in vacuo. The resultant mixture was dissolved in water and a minimum amount of acetonitrile, purified by preparative rpHPLC (20 to 100% solvent B over 40 min). The product fractions were pooled and concentrated in vacuo to give the hydroxamic acid product as a white solid (75%).

Example 13

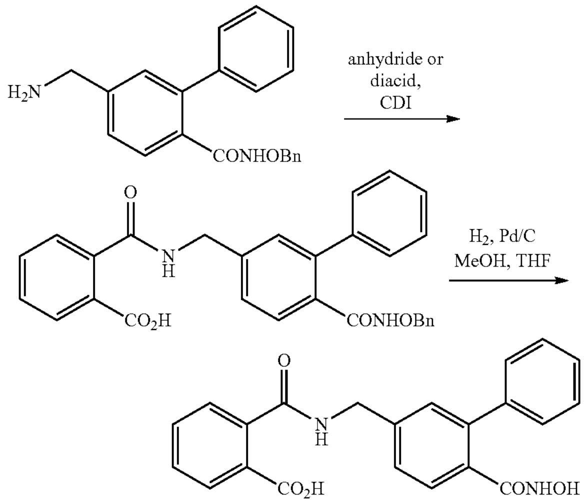

Step a. To a solution of the respective amine (1.0 eq) in THF (0.4 M) was added the corresponding anhydride (1.16 eq). The mixture was stirred at rt. Complete consumption of starting material was monitored by LCMS (typically 30-90 min), at which point, the solvent was removed in vacuo to give the corresponding amide product. The product was purified by column chromatography, or used in the next step without further purification.

Step b. To a mixture of the benzyl protected hydroxamic acid (1.0 eq) and palladium on carbon (10% w/w, 56 mg/mmol) under argon was added ethyl acetate (5.6 mL/mmol). THF can be added to effect complete dissolution. The reaction vessel was evacuated under house vacuum and then filled with hydrogen from a balloon. After repeating the process four times, the mixture was stirred at rt for 16 hours, at which point TLC indicated complete consumption of starting material. The mixture was filtered, concentrated in vacuo. Purification by preparative HPLC gave the respective hydroxamic acid final products.

Example 14

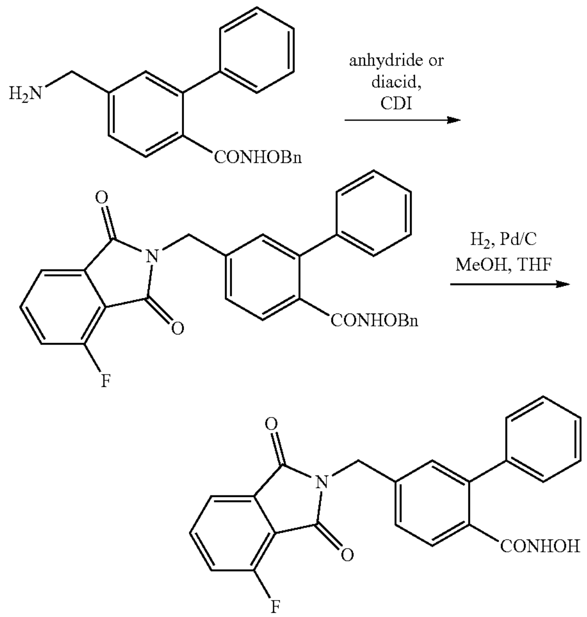

Step a. To a solution of the respective amine (1.0 eq) in THF (0.4 M) was added the corresponding anhydride (1.16 eq). The mixture was stirred at rt. Complete consumption of starting material was monitored by LCMS (typically 30-90 min), at which point, the solvent was removed in vacuo to give the corresponding amide product. The product could be purified by column chromatography, or used in the next step without further purification. To a solution of the above crude amide product in THF (0.4 M) was added 1,1'-carbonyldiimidazole (1.1 eq). The mixture was stirred at rt. Further aliquots of 1,1'-carbonyldiimidazole was added as necessary to drive the reaction to completion. Complete consumption of starting material was monitored by LCMS (typically 1 h), at which point the mixture was diluted with water. The mixture was extracted with ethyl acetate (×3). The combined extracts were washed with brine, dried over magnesium sulfate, and then concentrated in vacuo. Purification by column chromatography gave the desired phthalimide products.

Step b. To a mixture of the benzyl protected hydroxamic acid (1.0 eq) and palladium on carbon (10% w/w, 56 mg/mmol) under argon was added ethyl acetate (5.6 mL/mmol). THF can be added to effect complete dissolution. The reaction vessel was evacuated under house vacuum and then filled with hydrogen from a balloon. After repeating the process four times, the mixture was stirred at rt for 16 hours, at which point TLC indicated complete consumption of starting material. The mixture was filtered, concentrated in vacuo. Purification by preparative HPLC gave the respective hydroxamic acid final product.

Example 15

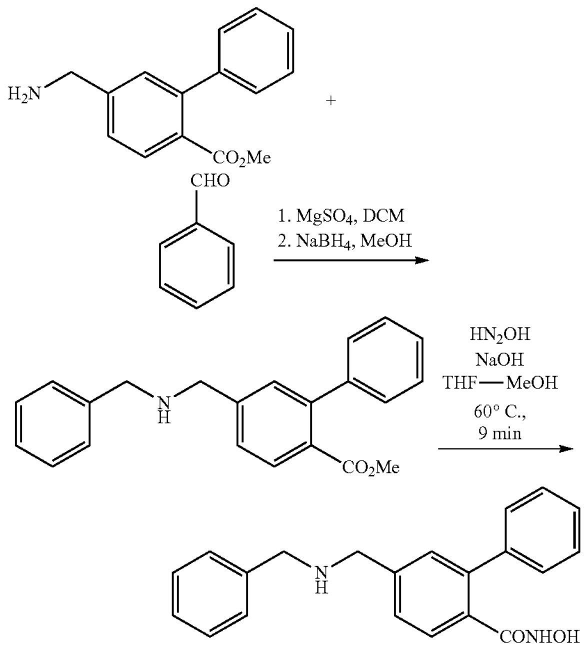

Step a. To a solution of methyl 4-aminomethyl-2-phenyl benzoate in DCM (0.2 M, 1.0 mL, 0.20 mmol, 1 eq) was added anhydrous $MgSO_4$ (30 mg, 0.25 mmol, 1.25 eq). The mixture was stirred at rt overnight and evaporated to dryness. The residue was suspended in anhydrous MeOH (1.5 mL), chilled at 0° C., and treated with $NaBH_4$ (13 mg, 0.34 mmol, 1.7 eq). The mixture was stirred at 0° C. for 30 min, then rt for another 30 min, treated with MeCN (3.5 mL) and two drops of TFA. The suspension was transferred into an Eppendorf tube, vortexed, and centrifuged at 4000 RPM for 5 min. The top clear solution was decanted, diluted with 0.1% TFA in $H_2O$ (4.8 mL), and filtered through a 45 μm syringe filter. The filtrate was purified using preparative rpHPLC (linear gradient 0% B to 55% B over 20 min, then 55% for 5 min) to give the secondary amine product methyl 4-((benzylamino)methyl)-2-phenyl benzoate as a gummy white solid (55 mg, TFA salt, 62%) after lyophilisation. UPLCMS: $t_R$=2.85 min, ES-MS: m/z 332 $[M+H]^+$).

Step b. To a microwave vial was added methyl 4-benzylaminomethyl-2-phenyl benzoate (55 mg as TFA salt from step a, 0.123 mmol) and THE-MeOH (1:1 v/v, 3.8 mL). The mixture was stirred at rt and treated with a freshly prepared solution of NaOH (39.5 mg, 0.988 mmol, 8 eq) in aqueous $HN_2OH$ (50% w/w, 312 μL, 5.09 mmol, 41 eq) aqueous solution (total bases: 6.08 mmol). The vial was crimp sealed and irradiated in microwave reactor at 60° C. for 9 min. UPLCMS indicated a mixture of the desired hydroxamic acid, the corresponding carboxylic acid by-product, and the starting material in a ratio of 24:65:11. The mixture was cooled to 0° C. and neutralised with conc. HCl (364 μL, 3.64 mmol, 0.6 eq based on the total bases) at 0° C. The mixture was concentrated to dryness on rotary evaporator. The residue was dissolved in MeCN—$H_2O$ (9.5 mL, 1:1 v/v containing 0.1% TFA), and purified using preparative rpHPLC (linear gradient 0% B to 55% B over 40 min). The product fractions were confirmed using UPLCMS, pooled and lyophilised. Fraction 1 (23.9-25.0 min) gave the desired hydroxamic acid, 5-((benzylamino)methyl)-N-hydroxy-[1,1'-biphenyl]-2-carboxamide (white powder, 9.9 mg, as TFA salt, 18%. UPLCMS: $t_R$=2.24 min, ES-MS: m/z 333 $[M+H]^+$). Fraction 2 (28.9-30.8 min) gave the carboxylic acid, 5-((benzylamino)methyl)-[1,1'-biphenyl]-2-carboxylic acid (white powder, 27.0 mg, as TFA salt, 51%. UPLCMS: $t_R$=2.53 min, ES-MS: m/z 318 $[M+H]^+$). Fraction 3 (35.6-37.0 min) gave the recovered starting material methyl 4-benzylaminomethyl-2-phenyl benzoate as TFA salt (white powder, 4.4 mg, 8%. UPLCMS: $t_R$=2.99 min, ES-MS: m/z 332 $[M+H]^+$).

Example 16

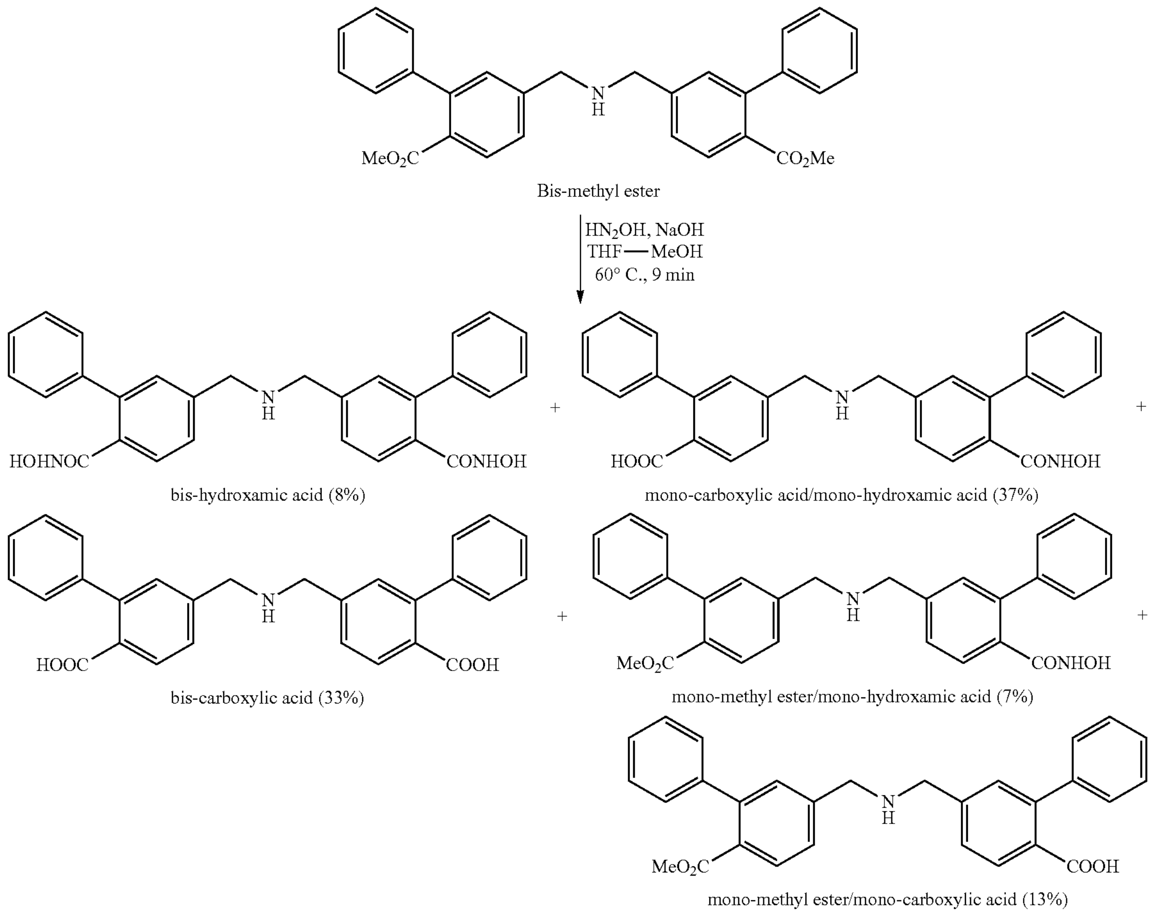

Bis-methyl ester bis-hydroxamic acid (8%)
+
mono-carboxylic acid/mono-hydroxamic acid (37%)
+
bis-carboxylic acid (33%)
+
mono-methyl ester/mono-hydroxamic acid (7%)
+
mono-methyl ester/mono-carboxylic acid (13%)

To a microwave vial was added bis(3-phenyl-4-methoxycarbonylbenzyl)amine (95 mg, 0.204 mmol) and THE-MeOH (1:1 v/v, 6.0 mL). The mixture was stirred at rt and treated with a freshly prepared solution of NaOH (65 mg, 1.63 mmol, 8 eq) in aqueous $HN_2OH$ (50% w/w, 514 μL, 8.38 mmol, 41 eq) aqueous solution (total bases 10.0 mmol). The vial was crimp sealed and irradiated in microwave reactor at 60° C. for 9 min. UPLCMS indicated a mixture of bis-hydroxamic acid, mono-carboxylic acid/mono-hydroxamic acid, bis-carboxylic acid, mono-methyl ester/mono-hydroxamic acid, mono-methyl ester/mono-carboxylic acid, and the starting material bis-methyl ester in a ratio of 8:37:33:7:13:1. The mixture was cooled to 0° C. and neutralised with conc. HCl (601 μL, 6.01 mmol, 0.6 eq based on the total bases) at 0° C. The mixture was concentrated to dryness on rotary evaporator. The residue was dissolved in MeCN—$H_2O$ (9.5 mL, 1:1 v/v containing 0.1% TFA), and purified using preparative rpHPLC (linear gradient 0% B to 60% B over 40 min). The product fractions were confirmed using UPLCMS, pooled and lyophilised. Fraction 1 (19.5-21.7 min) gave the bis-hydroxamic acid, bis(4-hydroxyaminocarbonyl-3-phenylbenzyl)amine (white powder, 9.5 mg, 4%). UPLCMS: $t_R$=2.15 min, ES-MS: m/z 468 $[M+H]^+$). Fraction 2 (22.4-25.6 min) gave the mono-carboxylic acid/mono-hydroxamic acid, N-(4-hydroxyaminocarbonyl-3-phenylbenzyl)-N-(4-hydroxycarbonyl-3-phenylbenzyl) amine (white powder, 31.8 mg, 14%). UPLCMS: $t_R$=2.34 min, ES-MS: m/z 453 $[M+H]^+$). Fraction 3 (25.8-28.2 min) gave bis-carboxylic acid, bis(4-hydroxycarbonyl-3-phenylbenzyl)amine (white powder, 28.9 mg, 13%). UPLCMS: $t_R$=2.58 min, ES-MS: m/z 438 $[M+H]^+$). Fraction 4 (29.8-30.7 min) gave the mono-methyl ester/mono-hydroxamic acid, N-(4-hydroxyaminocarbonyl-3-phenylbenzyl)-N-(4- methoxycarbonyl-3-phenylbenzyl)amine (white powder, 5.1 mg, 2%). UPLCMS: $t_R$=2.71 min, ES-MS: m/z 467 [M+H]$^+$). Fraction 5 (33.3-34.7 min) gave mono-methyl ester/mono-carboxylic acid, N-(4-hydroxycarbonyl-3-phenylbenzyl)-N-(4-methoxycarbonyl-3-phenylbenzyl)amine (white powder, 11.3 mg, 2%). UPLCMS: $t_R$=2.96 min, ES-MS: m/z 452 [M+H]$^+$).

Example 17

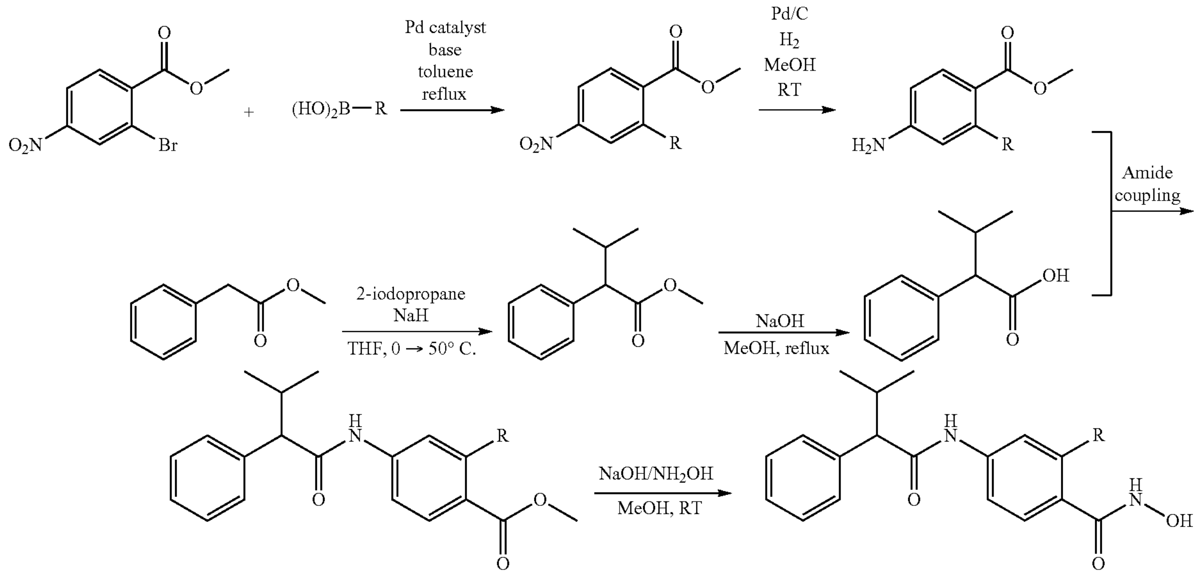

Preparation of the Amine:

Step a. Methyl 2-bromo-4-nitrobenzene (5.0 g, 19.2 mmol, 1.0 equiv.), arylboronic acid (28.8 mmol, 1.5 equiv.) and cesium carbonate (18.8 g, 57.7 mmol, 3.0 equiv.) in toluene (50 mL) were treated with nitrogen gas at RT for 15 min. $Pd(PPh_3)_4$ (2.2 g, 10 mol %) was then added. The mixture was stirred and refluxed for 22 h. The mixture was diluted saturated $NaHCO_3$ solution. The organic layer was separated while the aqueous layer was further extracted with EtOAc (3×). The combined organic layers were washed with brine, dried over $MgSO_4$, and concentrated in vacuo. A brown oil was purified by flash column chromatography to give methyl 2-aryl-4-nitrobenzoate as a pale yellow solid (~70%).

Step b. The solution of methyl 2-aryl-4-nitrobenzoate (7.4 mmol, 1 equiv.) in MeOH (25 mL) was treated with Pd/C and $H_2$ at RT for 3 h. The mixture was filtered through a cake of celite, washed with MeOH. The filtrate was then filtered through a 0.45 μm cartridge, concentrated in vacuo. Methyl 5-amino-2-arylbenzoate was obtained as a yellow solid (~90%).

Preparation of the Carboxylic Acid:

Step a. Methyl phenylacetate (5.05 g, 33.6 mmol) was dissolved in dry THE (35 mL) and cooled to 0° C. under $N_2$. NaH (60% dispersion in mineral oil, 1.61 g, 40.3 mmol, 1.2 equiv.) was added in portions over 5 min then 2-iodopropane (4 mL, 40.8 mmol, 1.2 equiv.). The mixture was stirred at room temperature under nitrogen for 17 h. The mixture was acidified with 2M HCl and extracted with diethyl ether (3×). The combined ether extracts were washed with $NaHCO_3$, sodium thiosulfate, brine, dried over $MgSO_4$ and concentrated in vacuo. The residual oil was kugelrohr distilled giving the ester as a colourless liquid (b.p. 100-110° C./1 mbar, 5.80 g, 90%).

Step b. The corresponding ester (5.50 g, 28.6 mmol) was dissolved in a 1:1 mixture of THE/MeOH (30 mL) then a solution of NaOH (2.29 g, 57 mmol, 2 equiv.) in water 20 mL was added and the mixture was stirred and refluxed for 6 h. The mixture was diluted with water. Solvents were removed in vacuo and the aqueous layer was washed with diethyl ether (2×). The aqueous layer was acidified to pH 1 with conc. HCl and extracted with diethyl ether (3×). The extracts were washed with brine, dried over $MgSO_4$ and evaporated to give the acid as a colourless oil (4.64 g, 91%). The product crystallised after several days.

Amide Coupling and Preparation of Final Hydroxamic Acid:

Step c. The acid (0.11 g, 0.60 mmol, 1 equiv.) in dry DCM (5 mL) at 0° C. under $N_2$ was treated with thionyl chloride (0.14 mL, 1.85 mmol, 1 equiv.). The mixture was stirred at 0° C. for 3 h. The initially insoluble acid fully dissolved in the solvent giving a clear solution upon completion of reaction. Excess $SOCl_2$ was removed under a stream of $N_2$ gas. The crude acid chloride was dissolved in dry DCM (5 mL), cooled to 0° C. A solution of amine (0.66 mmol, 1.1 equiv.) in dry DCM (1 mL) was added dropwise. Triethylamine (0.26 mL, 1.85 mmol, 3.0 equiv.) was added. The mixture was then stirred at RT for 16 h. The mixture was diluted with DCM. The organic layer was washed with water. The organic layer was separated while the aqueous layer was further extracted with DCM (2×). The combined organic layers were washed with brine, dried over $MgSO_4$, and concentrated in vacuo. Yellow oil was purified by flash column chromatography to give pure amide coupling product.

Step d. To a stirred solution of the resulting methyl ester in MeOH, was added a solution of NaOH/$NH_2$OH (1 mL; pre-dissolving 0.2 g of NaOH in 0.7 mL of 50% $NH_2$OH in water). The mixture was stirred at RT for 1 h. The mixture was neutralised with 2M HCl. Solvents were removed in vacuo. The residue was taken up in 80% MeCN/water, purified by preparative rpHPLC. The product fractions were confirmed using UPLCMS, pooled and lyophilised. Apart from the desired hydroxamic acid product, the corresponding carboxylic acid was often isolated as a by-product.

Example 18

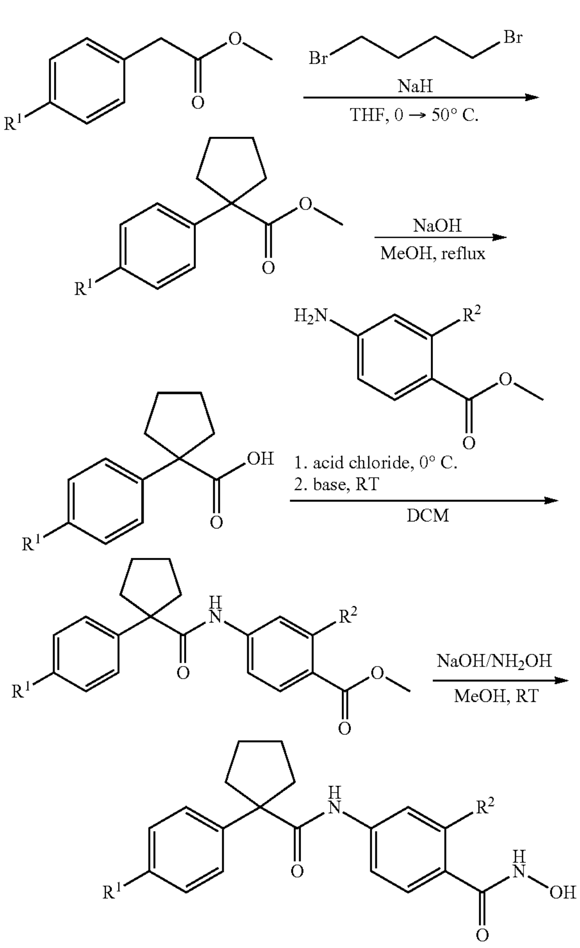

Step a. Methyl 4-substituted phenylacetate (2.9 g, 19.3 mmol, 1.0 equiv.) was dissolved in dry THE (20 mL) and cooled to 0° C. under $N_2$. NaH (60% dispersion in mineral oil, 0.89 g, 23.2 mmol, 1.2 equiv.) was added in portions over 30 min then 1,4-dibromobutane (2.75 mL, 23.2 mmol, 1.2 equiv.) was added and the mixture was stirred and refluxed under nitrogen overnight. The mixture was acidified with 2M HCl solution and extracted with diethyl ether (3×). The combined organic layers were washed with $NaHCO_3$, sodium thiosulfate, brine, dried over $MgSO_4$, and concentrated in vacuo. The residual oil was purified by flash column chromatography (1:45 EtOAc/petrol, $R_f$ 0.35) to give the ester as a clear colourless oil (2.1 g, 72%).

Step b. The corresponding ester (1.8 g, 8.8 mmol, 1 equiv.) in a 1:1 mixture of MeOH/water (20 mL) was treated with NaOH (1.1 g). The mixture was stirred and refluxed for 3 h. The mixture was diluted with water. Solvents were removed in vacuo and the aqueous layer was washed with diethyl ether (2×). The aqueous layer was then acidified to pH 1 with conc. HCl and extracted with DCM (3×). The combined organic layers were washed with brine, dried over $MgSO_4$ and evaporated to give the acid as a white solid (1.2 g, 67%).

Step c. The acid (180 mg, 0.95 mmol) in dry DCM (3 mL) at 0° C. under $N_2$ was treated with thionyl chloride (0.2 mL, 2.84 mmol, 3.0 equiv.). The initially insoluble acid fully dissolved in the solvent giving a clear solution upon completion of reaction. Excess thionyl chloride was removed under a stream of $N_2$. The residue was dissolved in dry DCM (20 mL), cooled to 0° C. The coupling amine (1.09 mmol, 1.2 equiv.) and triethylamine (0.2 mL, 2.84 mmol, 3.0 equiv.) were added. The mixture was then stirred at room temperature for 2 h. The mixture was diluted with DCM. The organic layer was washed with water. The organic layer was separated while the aqueous layer was further extracted with DCM (2×). The combined organic layers were washed with brine, dried over $MgSO_4$, and concentrated in vacuo. Yellow oil was purified by flash chromatography to give the ester as a yellow solid (150 mg, 86%, $R_f$ 0.2 petrol/EtOAc 1:7).

Step d. To a stirred solution of the resulting methyl ester in MeOH, was added a solution of $NaOH/NH_2OH$ (1 mL; pre-dissolving 0.2 g of NaOH in 0.7 mL of 50% $NH_2OH$ in water). The mixture was stirred at RT for 1 h. The mixture was neutralised with 2M HCl. Solvents were removed in vacuo. The residue was taken up in 80% MeCN/water, purified by preparative rpHPLC. The product fractions were confirmed using UPLCMS, pooled and lyophilised. Apart from the desired hydroxamic acid product, the corresponding carboxylic acid was often isolated as a by-product.

Example 19

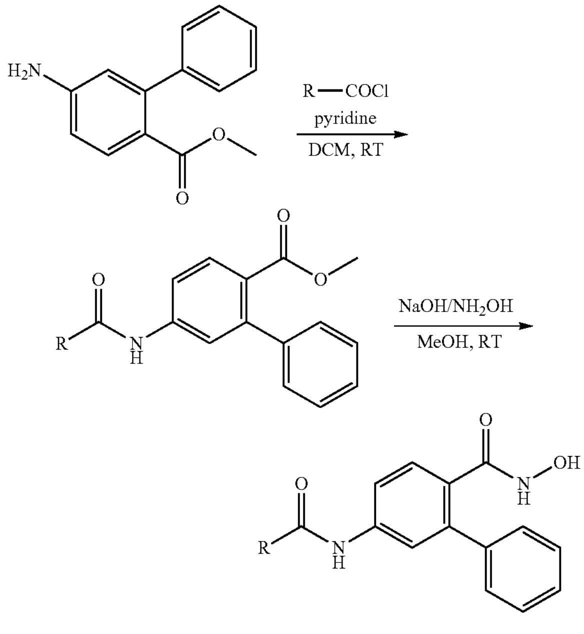

Step a. To a stirred solution of acyl chloride (0.15 mmol, 1.1 equiv.) in dry DCM (2 mL) under $N_2$, was added methyl 5-amino-[1,1'-biphenyl]-2-carboxylate (30 mg, 0.13 mmol, 1.0 equiv.) and pyridine (32 μL, 0.40 mM, 3.0 equiv.). The mixture was stirred at RT for 5 min. The mixture was diluted with DCM. The organic layer was washed with water. The organic layer was separated while the aqueous layer was further extracted with DCM (2×). The combined organic layers were washed with brine, dried over $MgSO_4$, and concentrated in vacuo. The crude yellow oil (residual pyridine present) was used in the next step without further purification.

Step b. To a stirred solution of the resulting methyl ester in MeOH, was added a solution of NaOH/$NH_2OH$ (1 mL; pre-dissolving 0.2 g of NaOH in 0.7 mL of 50% $NH_2OH$ in water). The mixture was stirred at RT for 1 h. The mixture was neutralised with 2M HCl. Solvents were removed in vacuo. The residue was taken up in 80% MeCN/water, purified by preparative rpHPLC. The product fractions were confirmed using UPLCMS, pooled and lyophilised.

Example 20

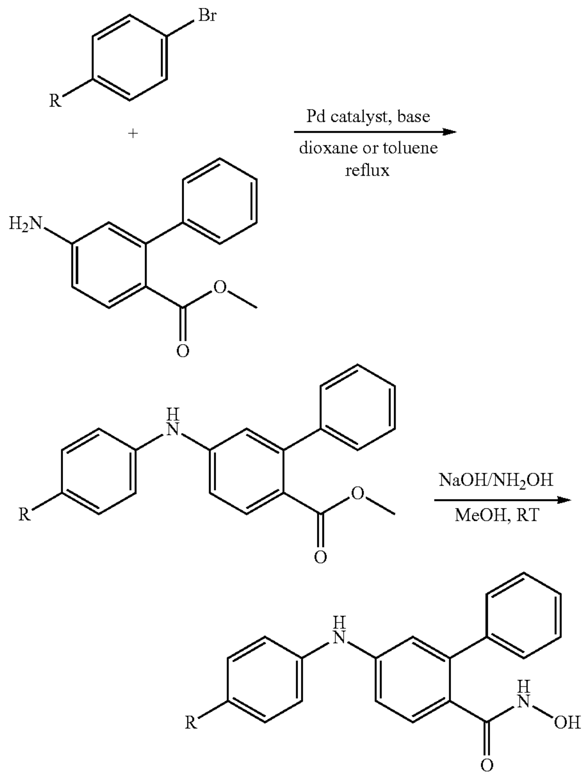

Step a. Bromobenzene (15 μL, 0.15 mM, 1.1 equiv.), methyl 5-amino-[1,1'-biphenyl]-2-carboxylate (30 mg, 0.13 mmol, 1.0 equiv.) and potassium carbonate (22 mg, 0.40 mmol, 3.0 equiv.) in dioxane (2 mL) were treated with nitrogen gas at RT for 15 min. $Pd(PPh_3)_4$ (15 mg, 0.013 mmol, 10 mol %) was added. The mixture was stirred and refluxed at 150° C. for 17 h. The mixture was diluted with saturated $NaHCO_3$. The aqueous layer was extracted with EtOAc (3×). The combined organic layers were washed with brine, dried over $MgSO_4$, and concentrated in vacuo. A yellow oil was purified by flash column chromatography to give the product as a yellow oil (30 mg, 75%, $R_f$ 0.5 petrol/EtOAc 6:1).

Step b. To a stirred solution of the resulting methyl ester in MeOH, was added a solution of NaOH/$NH_2OH$ (1 mL; pre-dissolving 0.2 g of NaOH in 0.7 mL of 50% $NH_2OH$ in water). The mixture was stirred at RT for 1 h. The mixture was neutralised with 2M HCl. Solvents were removed in vacuo. The residue was taken up in 80% MeCN/water, purified by preparative rpHPLC. The product fractions were confirmed using UPLCMS, pooled and lyophilised. Apart from the desired hydroxamic acid product, the corresponding carboxylic acid was often isolated as a by-product.

Example 21

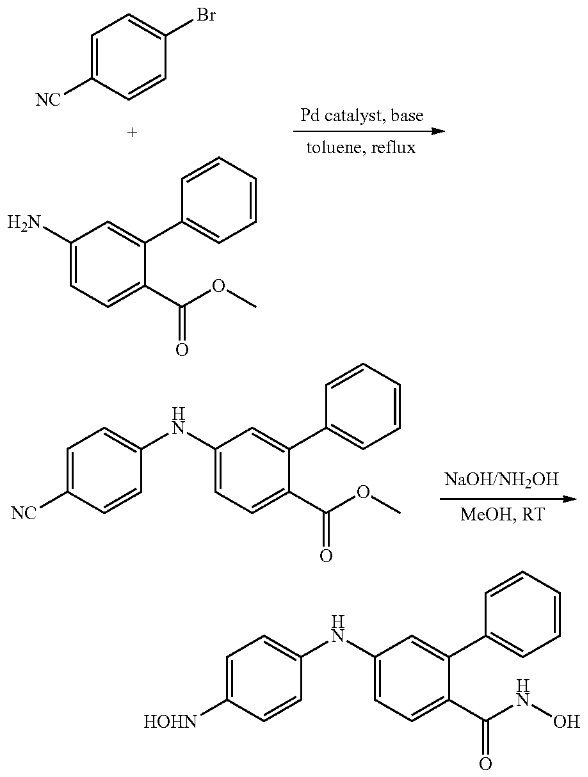

Step a. 4-Bromobenzonitrile (60 mg, 0.33 mmol, 1.5 equiv.), methyl 5-amino-[1,1'-biphenyl]-2-carboxylate (50 mg, 0.22 mmol, 1.0 equiv.), and $Cs_2CO_3$ (220 mg, 0.66 mmol. 3.0 equiv.) in toluene (2 mL) were treated with $N_2$ at RT for 15 min. Pd. xPhos G1 (3 mg, 2 mol %) was then added. The mixture was stirred and refluxed for 11 h. The mixture was diluted with saturated $NaHCO_3$. The aqueous layer was extracted with EtOAc (3×). The combined organic layers were washed with brine, dried over $MgSO_4$, and concentrated in vacuo. A yellow oil was purified by flash column chromatography to give the ester as a yellow solid (50 mg, 69%, $R_f$ 0.69 petrol/EtOAc 3:1).

Step b. To a stirred solution of the resulting ester (50 mg, 0.15 mmol, 1 equiv.) in MeOH (5 mL), was added a solution of NaOH/$NH_2OH$ (1 mL; pre-dissolving 0.2 g of NaOH in 0.7 mL of 50% $NH_2OH$ in water). The mixture was stirred at RT for 1 h. The mixture was neutralised with 2M HCl. Solvents were removed in vacuo. The residue was taken up in 80% MeCN/water, purified by preparative rpHPLC. The product fractions were confirmed using UPLCMS, pooled and lyophilised. Apart from the desired hydroxamic acid product, the corresponding carboxylic acid was often isolated as a by-product.

Example 22

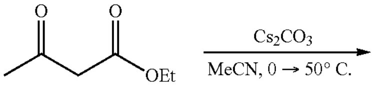

-continued

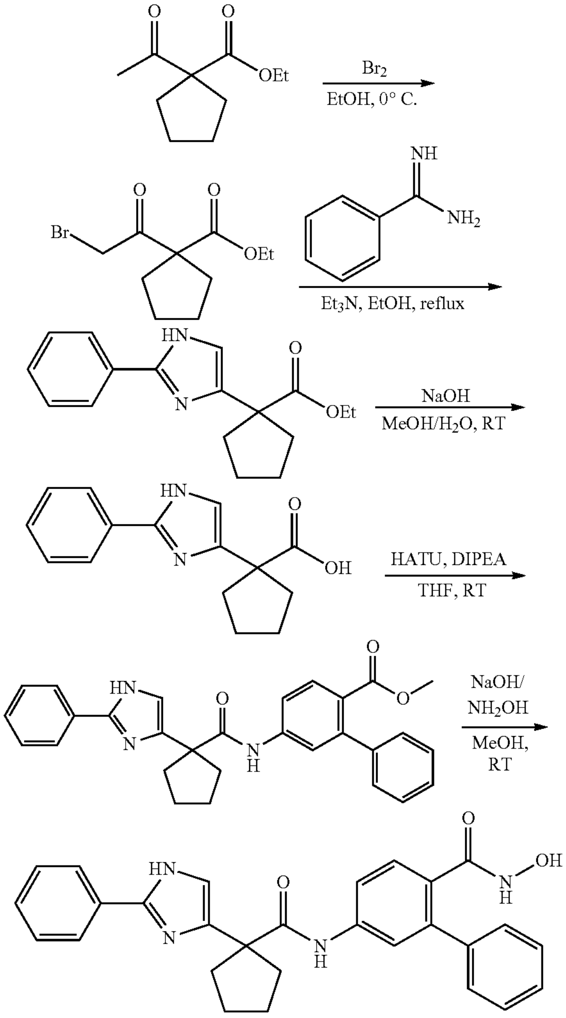

Step a. To a stirred solution of ethyl acetoacetate (4.9 mL, 38 mmol) in MeCN (20 mL), was added $Cs_2CO_3$ (25 g, 77 mmol, 2 equiv.) in three portions at a 10-min interval. The mixture was stirred at 0° C. until no effervescence was observed when the reaction was slowly warmed to RT. 1,4-Bromobutane (5.5 mL, 46 mmol, 1.2 equiv.) was added dropwise at 0° C. The mixture was stirred at 0° C. for 10 min and then, slowly warmed to RT. Stirring was continued at 50° C. for 19 h. The reaction mixture was quenched with $H_2O$. The aqueous layer was extracted with EtOAc (3×). The combined organic layers were washed with brine, dried over $MgSO_4$ and concentrated in vacuo. The residue was purified by flash column chromatography (petrol/EtOAc 20:1) to give the product as a clear colourless oil (4.9 g, 70%, $R_f$ 0.52 petrol/EtOAc 10:1).

Step b. Ethyl 1-(2-bromoacetyl)cyclopentane-1-carboxylate was generated in situ by treating ethyl 1-acetylcyclopentene-1-carboxylate (1 g, 5.4 mmol) in EtOH (5 mL) at 0° C. with $Br_2$ (0.3 mL, 6.0 mmol, 1.1 equiv.), added dropwise. The mixture was stirred at 0° C. for 30 min.

Step c. Benzamidine hydrochloride hydrate (1.02 g, 6.5 mmol, 1.2 equiv.) and $Et_3N$ (2.3 mL, 16.5 mmol, 3 equiv.) were added. The resulting mixture was stirred and refluxed for 5 h. Solvent was removed in vacuo and the residue was partitioned between $H_2O$ and EtOAc. The organic layer was separated while the $H_2O$ layer was further extracted with EtOAc. The combined organic layers were washed with brine, dried over $MgSO_4$ and concentrated in vacuo. The residue was purified by flash column chromatography (petrol/EtOAc 1:1) to give the ester as a yellow oil (0.36 g, 23%, $R_f$ 0.58 petrol/EtOAc 1:1).

Step d. The starting ester (0.27 g, 0.82 mmol, 1 equiv.) in a 1:1 mixture of MeOH/water (5 mL) was treated with NaOH (98 mg, 2.5 mmol, 3 equiv.). The mixture was stirred and refluxed for 16 h. Solvents were removed in vacuo and the residue was taken up in water. The aqueous layer was washed with $Et_2O$ (2×). The aqueous layer was then acidified to pH 1 with 2 M HCl, extracted with EtOAc (3×). The combined organic layers were washed with brine, dried over $MgSO_4$, and concentrated in vacuo to give the acid as a yellow solid (0.18 g, 73%).

Step e. To a stirred solution of the starting acid (30 mg, 0.01 mmol, 1.0 equiv.) in dry THE (3 mL), was added HATU (76 mg, 0.2 mmol, 2.0 equiv.) and DIPEA (52 μL, 0.3 mmol, 3.0 equiv.). The mixture was stirred at RT for 45 min before methyl 5-amino-[1,1'-biphenyl]-2-carboxylate (25 mg, 0.11 mmol, 1.1 equiv.) was added. The mixture was stirred at RT for 29 h. The mixture was diluted with water and EtOAc. The organic layer was separated while the aqueous layer was further extracted with EtOAc (2×). The combined organic layers were washed with brine, dried over $MgSO_4$, and concentrated in vacuo. A yellow oil was purified by flash column chromatography to give the ester as a yellow oil (50 mg, quantitative).

Step f. To a stirred solution of the corresponding ethyl ester (50 mg, 0.01 mmol, 1 equiv.) in MeOH (1 mL), was added a freshly prepared solution of $NaOH/NH_2OH$ (0.5 mL, dissolving 0.2 g of NaOH in 0.67 mL of aqueous $HN_2OH$ (50% w/w)). The mixture was stirred at RT for 1 h. The mixture was neutralised with 2M HCl. Solvents were removed in vacuo. The residue was taken up in 80% MeCN/water, purified by preparative rpHPLC. The product fractions were confirmed using UPLCMS, pooled and lyophilised. Apart from the desired hydroxamic acid product, the corresponding carboxylic acid was often isolated as a by-product.

Example 23

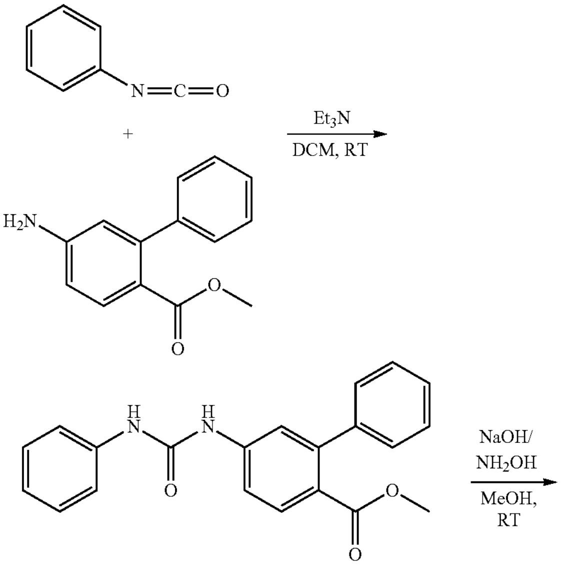

-continued

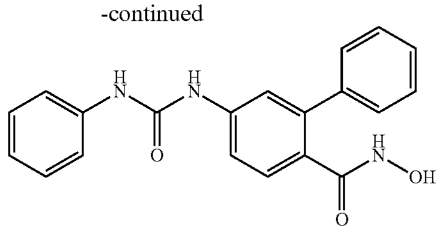

Step a. To a stirred solution of methyl 5-amino-[1,1'-biphenyl]-2-carboxylate (53 mg, 0.23 mmol, 1.0 equiv.) in DCM (1 mL), was added $Et_3N$ (0.1 mL, 0.72 mmol, 3.0 equiv.). The mixture was stirred at RT for 5 min before phenyl isocyanate (18 μL, 0.23 mmol, 1.0 equiv.) was added. The mixture was then stirred at RT for 1 h. The mixture was diluted with DCM, washed with water. The organic layer was separated while the aqueous layer was further extracted with DCM (2×). The combined organic layers were washed with brine, dried over $MgSO_4$, and concentrated in vacuo. A yellow oil was purified by flash column chromatography to give the product as a white solid (50 mg, 62%, $R_f$ 0.24 petrol/EtOAc 3:1).

Step b. To a stirred solution of the resulting methyl ester in MeOH, was added a solution of $NaOH/NH_2OH$ (1 mL; pre-dissolving 0.2 g of NaOH in 0.7 mL of 50% $NH_2OH$ in water). The mixture was stirred at RT for 1 h. The mixture was neutralised with 2M HCl. Solvents were removed in vacuo. The residue was taken up in 80% MeCN/water, purified by preparative rpHPLC. The product fractions were confirmed using UPLCMS, pooled and lyophilised. Apart from the desired hydroxamic acid product, the corresponding carboxylic acid was often isolated as a by-product.

Example 24

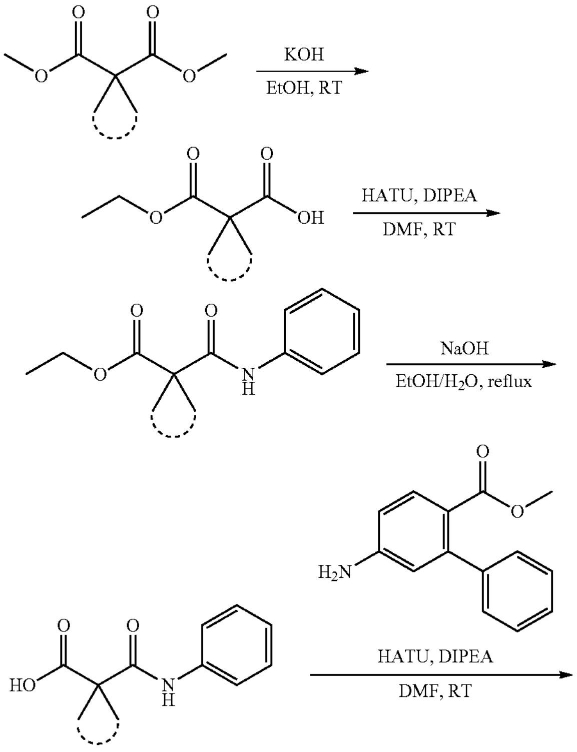

-continued

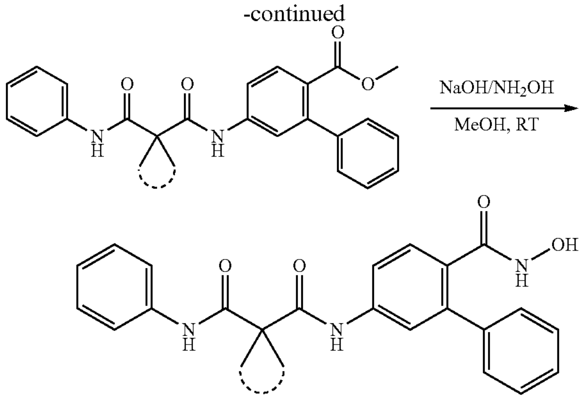

Step a. The commercially available dimethyl cyclopropane-1,1-dicarboxylate (0.5 g, 3.2 mmol, 1 equiv.) in EtOH (35 mL) was treated with potassium hydroxide (0.18 g, 3.2 mmol, 1 equiv.). The mixture was stirred at RT for 17 h. Solvents were removed in vacuo and the residue was taken up in 5% $NaHCO_3$. The aqueous layer was washed with DCM, acidified to pH 1 with concentrated HCl. The aqueous layer was then extracted with DCM (3×). The combined organic layers were washed with brine, dried over $MgSO_4$, and concentrated in vacuo to give the product as a clear colourless oil (0.50 g, quantitative).

Step b. To a stirred solution of the starting acid (0.22 g, 1.4 mmol, 1.0 equiv.) in DMF (10 mL), was added HATU (1.2 g, 3.2 mmol, 2.5 equiv.) and DIPEA (1.4 mL, 7.9 mmol, 5.7 equiv.). The mixture was stirred at RT for 30 min before aniline (0.29 mL, 3.2 mM, 2.5 equiv.) was added. The mixture was stirred at RT for 2 h. The mixture was diluted water and diethyl ether. The aqueous layer was separated while the organic layer was further washed with water (2×). The organic layer was washed with brine, dried over $MgSO_4$, and concentrated in vacuo. A yellow oil was purified by flash column chromatography to give the ester as a white solid (0.26 g, 80%, $R_f$ 0.49 petrol/EtOAc 10:1).

Step c. The corresponding ester (0.26 g, 1.1 mmol, 1 equiv.) in a 1:1 mixture of MeOH/water (10 mL) was treated with NaOH (0.2 g, 5.0 mmol, 4.5 equiv.). The mixture was stirred and refluxed for 1 h. Solvents were removed in vacuo and the residue was taken up in water. The water layer was washed with diethyl ether (2×), acidified to pH 1 with 2 M HCl. The aqueous layer was then extracted with EtOAc (3×). The combined organic layers were washed with brine, dried over $MgSO_4$, and concentrated in vacuo to give the acid as a white solid (0.23 g, quantitative).

Step d. To a stirred solution of the acid (70 mg, 0.34 mmol, 1 equiv.) in DMF (5 mL). was added HATU (0.26 g, 0.68 mmol, 2 equiv.) and DIPEA (0.18 mL, 1.0 mmol, 3 equiv.). The mixture was stirred at RT for 30 min before methyl 5-amino-[1,1'-biphenyl]-2-carboxylate (77 mg, 0.34 mmol, 1 equiv.) was added. The mixture was stirred at RT for 2 h. The mixture was diluted with water and EtOAc. The organic layer was separated while the aqueous layer was further extracted with EtOAc (2×). The combined organic layers were washed with brine, dried over $MgSO_4$, and concentrated in vacuo. Yellow oil was purified by flash column chromatography to give the ester as a yellow oil (60 mg, 42%, $R_f$ 0.07 petrol/EtOAc 5:1).

Step e. To a stirred solution of the corresponding methyl ester (60 mg, 0.14 mmol, 1 equiv.) in MeOH (2 mL), was added a freshly prepared solution of $NaOH/NH_2OH$ (0.5 mL, dissolving 0.2 g of NaOH in 0.67 mL of aqueous $HN_2OH$ (50% w/w)). The mixture was stirred at RT for 1 h. The mixture was neutralised with 2M HCl. Solvents were removed in vacuo. The residue was taken up in 80% MeCN/water, purified by preparative rpHPLC. The product fractions were confirmed using UPLCMS, pooled and lyophilised. Apart from the desired hydroxamic acid product, the corresponding carboxylic acid was often isolated as a by-product.

Example 25

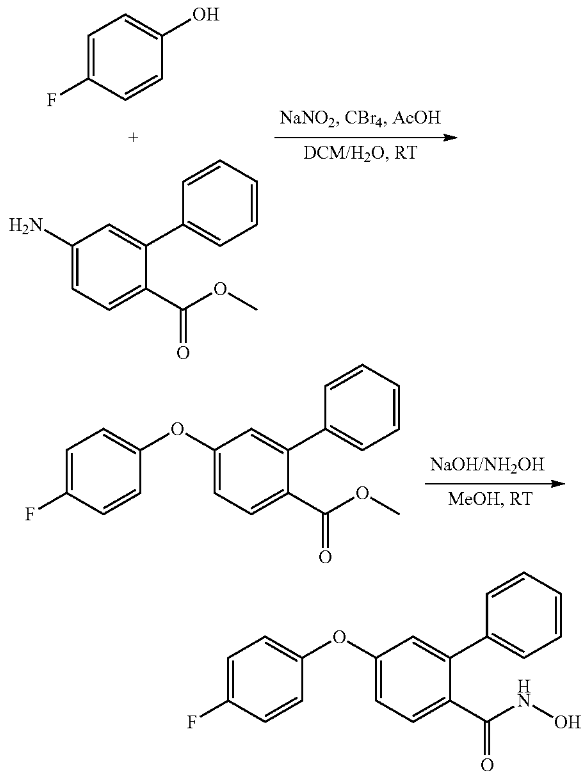

Step a. To a stirred solution of methyl 5-amino-[1,1'-biphenyl]-2-carboxylate (30 mg, 0.1 mmol, 1.0 equiv.) in dioxane (2 mL), was added 4-fluorophenyl (29 mg, 0.26 mmol, 2.5 equiv.), $Cs_2CO_3$ (110 mg, 0.34 mmol, 3.3 equiv.), and N,N-dimethylglycine (9 mg, 0.06 mmol, 0.6 equiv.). The mixture was stirred and refluxed for 5 h. The mixture was diluted with water and EtOAc. The organic layer was separated while the aqueous layer was further extracted with EtOAc (2×). The combined organic layers were washed with brine, dried over $MgSO_4$, and concentrated in vacuo. Brown oil was purified by flash column chromatography to give the ester as a white solid (10 mg, 30%, $R_f$ 0.68 petrol/EtOAc 6:1).

Step b. To a stirred solution of the resulting methyl ester in MeOH, was added a solution of $NaOH/NH_2OH$ (1 mL; pre-dissolving 0.2 g of NaOH in 0.7 mL of 50% $NH_2OH$ in water). The mixture was stirred at RT for 1 h. The mixture was neutralised with 2M HCl. Solvents were removed in vacuo. The residue was taken up in 80% MeCN/water, purified by preparative rpHPLC. The product fractions were confirmed using UPLCMS, pooled and lyophilised. Apart from the desired hydroxamic acid product, the corresponding carboxylic acid was often isolated as a by-product.

Example 26

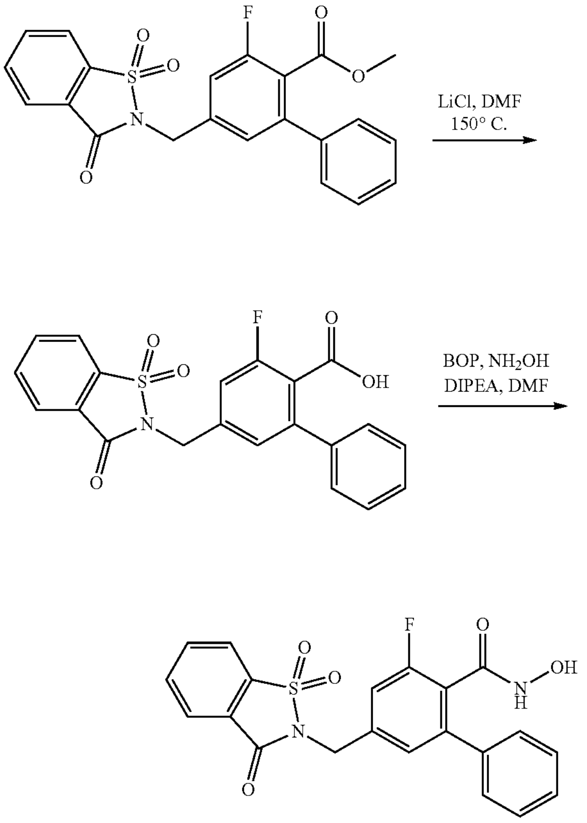

Step a: A mixture of the starting ester (83 mg, 0.20 mmol), lithium chloride (42 mg, 1.0 mmol) and DMF (1 mL) were heated at 150° C. for 2 h, at which point LCMS indicated complete consumption of starting material. The mixture was cooled to room temperature, diluted with aqueous HCl (2M, 10 mL), and then extracted with ethyl acetate (×3). The combined extracts were washed with brine, dried over magnesium sulfate, and then concentrated in vacuo to give the corresponding carboxylic acid as a pale yellow oil (55 mg, 0.14 mmol, 70%).

Step b: A mixture of the starting carboxylic acid (55 mg, 0.14 mmol), BOP (71 mg, 0.16 mmol), DIPEA (0.070 mL, 0.40 mmol) and DMF (0.5 mL) was stirred at room temperature for 15 min, at which point LCMS indicated complete consumption of starting material. Hydroxylamine hydrochloride (11 mg, 0.16 mmol) was added in one portion. After stirring the mixture for a further 1 h, LCMS indicated complete conversion to the product. The mixture was diluted with aqueous HCl (2 M, 5 mL) and brine (5 mL), and then extracted with ethyl acetate (×3). The combined extracts were evaporated in vacuo, and then purified by preparative rpHPLC (20 to 100% solvent B over 40 min). Concentration in vacuo and lyophilisation gave the pure product (17 mg, 0.040 mmol, 20% over 2 steps).

Compounds Synthesised According to the Above Methods

Compounds were synthesised according to the above methods. Table 1 provides structures and characterisation data for compounds of the Formula X.

Formula X

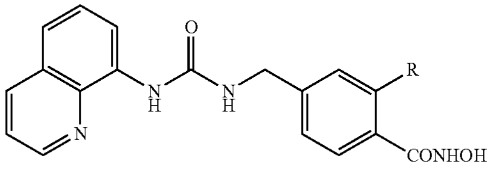

TABLE 1

Structures and characterisation data for compounds of the Formula X.

| Cmpd No. | R | Characterisation data |
|---|---|---|
| 1 | Br (Comparative Example) | $^1$H NMR (600 MHz, DMSO-$d_6$): δ 10.91 (s, 1H), 10.10 (s, 1H), 9.50 (s, 1H), 8.88 (dd, J = 4.0, 1.5 Hz, 1H), 8.49 (dd, J = 6.5, 2.5 Hz, 1H), 8.36 (dd, J = 8.2, 1.5 Hz, 1H), 8.00 (t, J = 5.9 Hz, 1H), 7.62-7.59 (m, 2H), 7.52-7.48 (m, 2H), 7.37 (d, J = 7.8 Hz, 1H), 7.34 (d, J = 7.8 Hz, 1H), 4.38 (d, J = 5.8 Hz, 2H). $^{13}$C NMR (150 MHz, DMSO-$d_6$): δ 164.1, 155.1, 148.1, 144.0, 137.6, 136.5, 136.4, 135.0, 131.1, 129.4, 127.9, 127.2, 126.1, 121.9, 119.7, 119.2, 114.0, 41.9. ESI-MS: m/z 415 and 417 (1:1) $[M + H]^+$ |
| 2 | 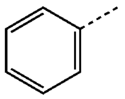 | $^1$H NMR (600 MHz, DMSO-$d_6$): δ 10.75 (br s, 1H), 9.48 (s, 1H), 8.86 (dd, J = 4.1, 1.5 Hz, 1H), 8.50 (dd, J = 7.1, 1.8 Hz, 1H), 8.35 (dd, J = 8.2, 1.5 Hz, 1H), 7.98 (t, J = 5.6 Hz, 1H), 7.59 (dd, J = 8.3, 4.2 Hz, 1H), 7.51-7.46 (m, 2H), 7.42-7.32 (m, 8H), 4.44 (d, J = 5.4 Hz, 2H). $^{13}$C NMR (150 MHz, DMSO-$d_6$): δ 166.0, 155.2, 148.1, 141.9, 140.2, 139.8, 137.6, 136.6, 136.4, 132.9, 128.8, 128.5, 128.4, 128.2, 127.9, 127.2(2), 127.2(0), 125.7, 121.9, 119.2, 114.0, 42.5. ESI-MS: m/z 413 $[M + H]^+$ (pos mode), 411 $[M - H]^-$ (neg mode). |
| 3 | 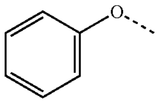 (Comparative Example) | $^1$H NMR (600 MHz, DMSO-$d_6$): δ 10.78 (br s, 1H), 9.41 (s, 1H), 8.86 (dd, J = 4.1, 1.5 Hz, 1H), 8.45 (dd, J = 6.5, 2.5 Hz, 1H), 8.35 (dd, J = 8.3, 1.5 Hz, 1H), 7.91 (t, J = 5.6 Hz, 1H), 7.59 (dd, J = 8.3, 4.2 Hz, 1H), 7.46-7.52 (m, 3H), 7.32 (t, J = 7.6 Hz, 2H), 7.17 (d, J = 7.9 Hz, 1H), 7.06 (t, J = 7.4 Hz, 1H), 7.00 (d, J = 8.3 Hz, 2H), 6.86 (s, 1H), 4.31 (d, J = 5.5 Hz, 2H). $^{13}$C NMR (150 MHz, DMSO-$d_6$): δ 162.9, 156.6, 155.1, 153.7, 148.1, 144.5, 137.6, 136.6, 136.4, 129.8(8), 129.8(5), 127.9, 127.2, 125.1, 123.4, 122.1, 121.9, 119.2, 118.6, 117.3, 114.1, 42.3. ESI-MS: m/z 429 $[M + H]^+$ (pos mode), 427 $[M - H]^-$ (neg mode). |
| 4 | 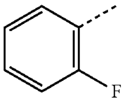 | $^1$H NMR (600 MHz, DMSO-$d_6$): δ 10.82 (s, 1H), 9.48 (s, 1H), 8.86 (dd, J = 4.1 Hz, 1.4 Hz, 1H), 8.50 (dd, J = 6.9 Hz, 1.7 Hz, 1H), 8.35 (dd, J = 8.2 Hz, 1.4 Hz, 1H), 7.98 (t, J = 5.9 Hz, 1H), 7.59 (dd, J = 8.3 Hz, 4.2 Hz, 1H), 7.51-7.31 (m, 7H), 7.23-7.18 (m, 2H), 4.43 (d, J = 5.8 Hz, 2H). $^{13}$C NMR (150 MHz, DMSO-$d_6$): δ 165.5, 159.0(d, J = 224.9 Hz), 155.2, 148.1, 142.0, 137.6, 136.5, 136.4, 134.2, 133.3, 131.2 (d, J = 3 Hz), 129.6, 129.4 (d, J = 8.0 Hz), 128.2, 128.0 (d, J = 15.6 Hz), 127.9, 127.2, 126.3, 124.1 (d, J = 3.0 Hz), 121.9, 119.2, 115.3 (d, J = 22.1 Hz), 114.1, 42.3. ESI-MS: m/z 431 $[M + H]^+$ |
| 5 | 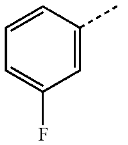 | $^1$H NMR (600 MHz, DMSO-$d_6$): δ 10.79 (s, 1H), 9.48 (s, 1H), 8.87 (dd, J = 4.1 Hz, 1.6 Hz, 1H), 8.49 (dd, J = 7.0 Hz, 2.1 Hz, 1H), 8.35 (dd, J = 8.3 Hz, 1.7 Hz, 1H), 7.98 (t, J = 5.7 Hz, 1H), 7.60 (dd, J = 8.3 Hz, 4.2 Hz, 1H), 7.51-7.47 (m, 2H), 7.46-7.38 (m, 4H), 7.24-7.17 (m, 3H), 4.44 (d, J = 5.58, 2H). $^{13}$C NMR (150 MHz, DMSO-$d_6$): δ 166.2, 162.3 (d, J = 243.2 Hz), 155.6, 148.6, 143.0 (d, J = 7.9 Hz), 142.6, 138.8, 138.0, 137.0, 136.9, 133.4, 130.7 (d, J = 8.5 Hz), 129.2, 129.0, 128.4, 127.7, 126.7, 125.0 (J = 2.0 Hz), 122.4, 119.6, 115.6 (d, J = 21.9 Hz), 114.5 (d, J = 20.8 Hz), 114.5, 42.9. ESI-MS: m/z 431 $[M + H]^+$ |
| 6 | 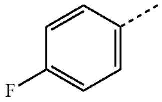 | $^1$H NMR (600 MHz, DMSO-$d_6$): δ 10.75 (s, 1H), 10.09 (s, 1H), 9.47 (s, 1H), 8.84 (dd, J = 4.1 Hz, 1.6 Hz, 1H), 8.49 (dd, J = 7.0 Hz, 2.0 Hz, 1H), 8.35 (dd, J = 8.3 Hz, 1.6 Hz, 1H), 7.98 (t, J = 5.8 Hz, 1H), 7.60 (dd, J = 8.3 Hz, 4.2 Hz, 1H), 7.51-7.47 (m, 2H), 7.43-7.41 (m, 2H), 7.38-7.35 (m, 3H), 7.23 (t, J = 8.9 Hz, 2H), 4.43 (d, J = 5.6 Hz, 2H). $^{13}$C NMR (150 MHz, DMSO-$d_6$): δ 166.3, 162.1 (d, J = 243.8 Hz), 155.6, 148.6, 142.5, 139.2, 138.0, 137.0, 136.9, 133.4, 130.7 (d, J = 8.3 Hz), 129.2, 128.9, 128.4, 127.7, 126.3, 122.4, 119.6, 155.5 (d, J = 21.3 Hz), 114.5, 42.9. ESI-MS: m/z 431 $[M + H]^+$ |

TABLE 1-continued

Structures and characterisation data for compounds of the Formula X.

| Cmpd No. | R | Characterisation data |
|---|---|---|
| 7 | 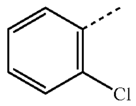 | $^{1}$H NMR (600 MHz, $CDCl_3$): δ 10.81 (s, 1H), 9.48 (s, 1H), 8.86 (dd, J = 4.17 Hz, 1.65 Hz, 1H), 8.49 (dd, J = 7.0 Hz, 2.0 Hz, 1H), 8.35 (dd, J = 8.3 Hz, 1.6 Hz, 1H), 7.97 (t, 5.9 Hz, 1H), 7.59 (dd, J = 8.3 Hz, 4.2 Hz, 1H), 7.51-7.45 (m, 4H), 7.41 (dd, J = 7.9 Hz, 1.3 Hz, 1H), 7.34-7.28 (m, 3H), 7.23 (s, 1H), 4.44 (d, J = 5.8 Hz, 2H). $^{13}$C NMR (150 MHz, DMSO-$d_6$): δ 165.7, 155.6, 148.6, 142.3, 139.8, 138.4, 138.1, 136.98, 136.90, 133.4, 132.4, 131.7, 129.8, 129.4, 129.3, 128.4, 128.3, 127.7, 127.1, 126.7, 122.4, 119.6, 114.5, 42.7. ESI-MS: m/z 447 $[M + H]^+$ |
| 8 | 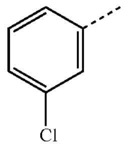 | $^{1}$H NMR (600 MHz, DMSO-$d_6$): δ 10.79 (s, 1H), 9.48 (s, 1H), 8.87 (dd, J = 4.20 Hz, 1.68 Hz, 1H), 8.49 (dd, J = 6.92 Hz, 2.08 Hz, 1H), 8.35 (dd, J = 8.23 Hz, 1.63 Hz, 1H), 7.98 (t, J = 5.86 Hz, 1H), 7.60 (dd, J = 8.3 Hz, 4.2 Hz, 1H), 7.51-7.32 (m, 9H), 4.44 (d, J = 5.79 Hz, 2H). ESI-MS: m/z 447 $[M + H]^+$ |
| 9 | 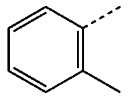 | $^{1}$H NMR (600 MHz, DMSO-$d_6$): δ 10.65 (s, 1H), 9.47 (s, 1H), 8.86 (dd, J = 4.2 Hz, 1.7 Hz, 1H), 8.49 (dd, J = 7.1 Hz, 2.0 Hz, 1H), 8.35 (dd, J = 8.3 Hz, 1.7 Hz, 1H), 7.95 (t, J = 5.9 Hz, 1H), 7.59 (dd, J = 8.3 Hz, 4.2 Hz, 1H), 7.51-7.47 (m, 2H), 7.40 (d, J = 7.9 Hz, 1H), 7.36 (dd, J = 7.9 Hz, 1.5 Hz, 1H), 7.20-7.14 (m, 4H), 7.09 (d, J = 7.3 Hz, 1H), 4.42 (d, J = 5.9 Hz, 2H), 2.07 (s, 3H). $^{13}$C NMR (150 MHz, DMSO-$d_6$): δ 166.1, 155.6, 148.6, 142.0, 140.7, 140.5, 138.1, 137.0, 135.9, 133.6, 130.0, 129.7, 129.4, 128.4, 128.3, 127.7, 127.6, 126.0, 125.6, 122.3, 119.6, 114.4, 110.0, 42.8, 20.6. ESI-MS: m/z 427 $[M + H]^+$ |
| 10 | 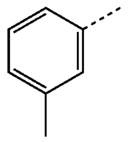 | $^{1}$H NMR (600 MHz, DMSO-$d_6$): δ 10.71 (s, 1H), 9.48 (s, 1H), 8.86 (dd, J = 4.14 Hz, 1.62 Hz, 1H), 8.49 (dd, J = 6.99 Hz, 2.01 Hz, 1H), 8.35 (dd, J = 8.31 Hz, 1.65 Hz, 1H), 7.97 (t, J = 5.75 Hz, 1H), 7.59 (dd, J = 8.28 Hz, 4.20 Hz, 1H), 7.51-7/47 (m, 2H), 7.35-7.33 (m, 3H), 7.26 (t, J = 7.56 Hz, 1H), 7.22 (s, 1H), 7.18 (d, J = 7.56 Hz, 1H), 7.14 (d, J = 7.56 Hz, 1H), 4.43 (d, J = 5.58 Hz, 2H), 2.33 (s, 3H). $^{13}$C NMR (150 MHz, DMSO-$d_6$): δ 155.6, 148.6, 142.3, 140.6, 140.3, 138.1, 137.7, 136.99, 136.91, 133.4, 129.5, 129.2, 128.9, 128.5, 128.4, 128.3, 127.7, 126.0, 125.98, 122.4, 119.6, 114.5, 110.0, 42.9, 21.6. ESI-MS: m/z 427 $[M + H]^+$ |
| 11 | 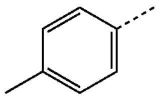 | $^{1}$H NMR (600 MHz, DMSO-$d_6$): δ 10.70 (s, 1H), 9.47 (s, 1H), 8.86 (dd, J = 4.2 Hz, 1.7 Hz, 1H), 8.50 (dd, J = 7.1 Hz, 1.9 Hz, 1H), 8.35 (dd, J = 8.3 Hz, 1.7 Hz, 1H), 7.97 (t, J = 5.9 Hz, 1H), 7.59 (dd, J = 8.3 Hz, 4.2 Hz, 1H), 7.51-7.47 ( m, 2H), 7.34-7.33 (m, 3H), 7.30 (d, J = 8.0 Hz, 2H), 7.19 (d, J = 8.0 Hz, 2H), 4.42 (d, J = 5.8 Hz, 2H), 2.32 (s, 3H). $^{13}$C NMR (150 MHz, DMSO-$d_6$): δ 166.6, 155.6, 148.6, 142.3, 140.1, 138.4, 138.0, 137.7, 136.99, 136.90, 133.4, 129.3, 129.1, 128.9, 128.7, 128.4, 127.7, 125.9, 122.4, 119.6, 114.4, 42.9, 21.2. ESI-MS: m/z 427 $[M + H]^+$ |

Formula XI

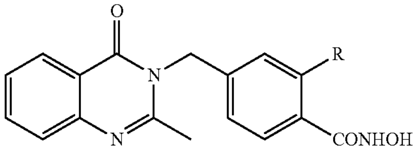

TABLE 2

Structures and characterisation data for compounds of the Formula XI.

| Cmpd No. | R | Characterisation data |
|---|---|---|
| 12 | 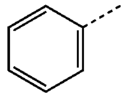 | $^1$H NMR (600 MHz, DMSO-$d_6$): δ 10.77 (br s, 1H), 8.16 (dd, J = 7.9, 1.0 Hz, 1H), 7.86 (ddd, J = 8.0, 7.2, 1.4 Hz, 1H), 7.65 (d, J = 8.0 Hz, 1H), 7.55 (t, J = 7.5 Hz, 1H), 7.40-7.31 (m, 7H), 7.20 (d, J = 7.9 Hz, 1H), 5.45 (s, 2H), 2.58 (s, 3H). $^{13}$C NMR (150 MHz, DMSO-$d_6$): δ 165.8, 161.2, 156.0, 145.9, 140.1, 139.8, 137.9, 134.9, 133.6, 129.0, 128.4, 128.3(3), 128.2(9), 127.4, 126.9, 126.6, 125.8, 124.8, 119.7, 46.5, 22.7. ESI-MS: m/z 386 $[M + H]^+$ |
| 13 | 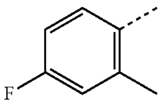 | $^1$H NMR (600 MHz, DMSO-$d_6$): δ 10.70 (s, 1H), 8.15 (d, J = 7.9 Hz, 1H), 7.84 (ddd, J = 8.0 Hz, 7.1 Hz, 1.5 Hz, 1H), 7.63 (d, J = 8.1 Hz, 1H), 7.53 (d, J = 8.0 Hz, 7.1 Hz, 1.0 Hz, 1H), 7.40 (d, J = 7.9 Hz, 1H), 7.23 (dd, 8.0 Hz, 1.4 Hz, 1H), 7.10-7.04 (m, 3H), 6.97 (ddd, J = 8.5 Hz, 8.5 Hz, 2.4 Hz, 1H), 5.43 (s, 2H), 2.53 (s, 3H), 2.03 (s, 3H). $^{13}$C NMR (150 MHz, DMSO-$d_6$): δ 165.7, 161.8, 161.8 (d, J = 242.8 Hz), 155.95, 146.9, 139.7, 138.8 (d, J = 8.0 Hz), 138.2, 136.5 (d, J = 2.5 Hz), 135.2, 134.5, 131.4 (d, J = 8.4 Hz), 129.1, 128.8, 127.2, 127.0, 126.6, 125.5, 120.2, 116.5 (d, J = 21 Hz), 112.3 (d, J = 20.9 Hz), 46.7, 23.3, 20.5. ESI-MS: m/z 418 $[M + H]^+$ |
| 14 | 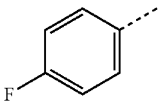 | $^1$H NMR (600 MHz, DMSO-$d_6$): δ 10.78 (s, 1H), 8.15 (dd, J = 8.0 Hz, 1.2 Hz, 1H), 7.85 (ddd, J = 8.0 Hz, 7.3 Hz, 1.5 Hz, 1H), 7.64 (d, J = 8.10 Hz, 1H), 7.54 (ddd, J = 8.0 Hz, 7.3 Hz, 1.5 Hz, 1H), 7.40 (ddt, J = 8.7 Hz, 5.5 Hz, 2.1 Hz, 2H), 7.36 (d, J = 7.92 Hz, 1H), 7.30 (d, J = 1.20 Hz, 1H), 7.22 (tt, J = 8.9 Hz, 2.0 Hz, 2H), 5.44 (s, 2H), 2.56 (s, 3H). $^{13}$C NMR (150 MHz, DMSO-$d_6$): δ 166.1, 162.2 (d, J = 244.2 Hz), 161.8, 156.1, 146.8, 139.5, 138.5, 136.6 (d, J = 2.9 Hz), 135.3, 134.0, 130.8 (d, J = 8.2 Hz), 129.4, 128.7, 127.2, 127.0, 126.5, 125.3, 120.2, 115.6 (d, J = 21.4 Hz), 46.9, 23.3. ESI-MS: m/z 404 $[M + H]^+$ |

Table 3 provides structures and characterisation data for compounds of the Formula XII.

Formula XII

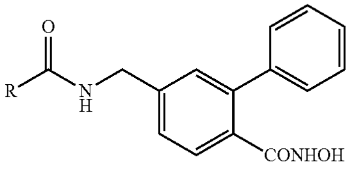

TABLE 3

Structures and characterisation data for compounds of the Formula XII.

| Cmpd No. | R | Characterisation data |
|---|---|---|
| 15 | 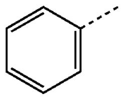 | $^1$H NMR (600 MHz, DMSO-$d_6$): δ 10.73 (s, 1H), 9.11 (t, J = 5.8 Hz, 1H), 7.88 (br d, J = 7.5 Hz, 2H), 7.55-7.52 (m, 1H), 7.48-7.46 (m, 2H), 7.41-7.37 (m, 4H), 7.35-7.33 (m, 4H), 4.54 (d, J = 5.83 Hz, 2H). ESI-MS: m/z 347 $[M + H]^+$ |
| 16 | 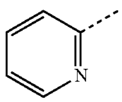 | $^1$H NMR (600 MHz, DMSO-$d_6$): δ 10.73 (br s, 1H), 9.45 (t, J = 6.4 Hz, 1H), 8.65 (d, J = 4.5 Hz, 1H), 8.04 (d, J = 7.7 Hz, 1H), 8.00 (td, J = 7.6, 1.6 Hz), 7.61 (ddd, J = 7.1, 4.9, 1.0 Hz), 7.40-7.31 (m, 8H), 4.55 (d, J = 6.4 Hz, 2H). $^{13}$C NMR (150 MHz, DMSO-$d_6$): δ 166.0, 164.0, 149.9, 148.5, 141.2, 140.1, 139.6, 137.9, 132.9, 129.2, 128.4, 128.3, 128.2, 127.2, 126.6, 126.0, 122.0, 42.2. ESI-MS: m/z 348 $[M + H]^+$ |
| 17 | 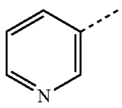 | $^1$H NMR (600 MHz, DMSO-$d_6$): δ 10.75 (br s, 1H), 9.38 (t, J = 6.0 Hz, 1H), 9.09 (d, J = 1.6 Hz, 1H), 8.78 (dd, J = 5.0, 1.6 Hz, 1H), 8.36 (dt, J = 8.0, 1.8 Hz, 1H), 7.64 (dd, J = 7.9, 5.0 Hz, 1H), 7.41-7.32 (m, 8H), 4.57 (d, J = 5.8 Hz, 2H). $^{13}$C NMR (150 MHz, DMSO-$d_6$): δ 166.0, 164.3, 150.6, 147.2, 140.8, 140.1, 139.7, 136.7, 133.1, 130.3, 129.1, 128.5, 128.3(3), 128.2(6), 127.2, 125.9, 124.2, 42.5. ESI-MS: m/z 348 $[M + H]^+$ |

TABLE 3-continued

Structures and characterisation data for compounds of the Formula XII.

| Cmpd No. | R | Characterisation data |
|---|---|---|
| 18 | 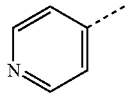 | $^{1}$H NMR (600 MHz, DMSO-$d_6$): δ 10.75 (br s, 1H), 9.50 (t, J = 5.8 Hz, 1H), 8.81 (dd, J = 4.7, 1.4 Hz, 2H), 7.92 (dd, J = 4.7, 1.4 Hz, 2H), 7.41-7.32 (m, 8H), 4.57 (d, J = 5.9 Hz, 2H). $^{13}$C NMR (150 MHz, DMSO-$d_6$): δ 166.0, 164.3, 148.8, 142.8, 140.6, 140.0, 139.8, 133.1, 129.2, 128.5, 128.3(3), 128.2(6), 127.2, 125.9, 122.1, 42.6. ESI-MS: m/z 348 $[M + H]^+$ |
| 19 | 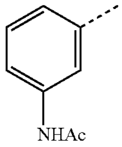 | $^{1}$H NMR (600 MHz, DMSO-$d_6$): δ 10.74 (br s, 1H), 10.07 (s, 1H), 9.07 (t, J = 5.9 Hz, 1H), 8.04 (s, 1H), 7.74 (dd, J = 8.1, 1.2 Hz, 1H), 7.53 (d, J = 7.7 Hz, 1H), 7.41-7.32 (m, 9H), 4.52 (d, J = 5.9 Hz, 2H), 2.05 (s, 3H). $^{13}$C NMR (150 MHz, DMSO-$d_6$): δ 168.5, 166.3, 166.0, 141.4, 140.1, 139.7, 139.4, 135.0, 132.9, 129.1, 128.7, 128.4, 128.3, 128.2, 127.2, 125.8, 121.7, 121.4, 118.3, 42.4, 24.0. ESI-MS: m/z 404 $[M + H]^+$ |
| 20 | 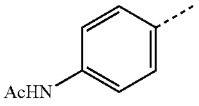 | $^{1}$H NMR (600 MHz, DMSO-$d_6$): δ 10.74 (br s, 1H), 10.16 (s, 1H), 8.98 (t, J = 5.9, 1H), 7.83 (d, J = 8.7 Hz, 2H), 7.65 (d, J = 8.7 Hz, 2H), 8.41-7.31 (m, 8H), 4.51 (d, J = 5.9 Hz, 2H), 2.06 (s, 3H). $^{13}$C NMR (150 MHz, DMSO-$d_6$): δ 168.7, 166.0, 165.8, 142.0, 141.5, 140.1, 139.6, 132.9, 129.0, 128.5, 128.4, 128.3, 128.2, 128.1, 127.2, 125.8, 118.1, 42.4, 24.1. ESI-MS: m/z 404 $[M + H]^+$ |
| 21 | 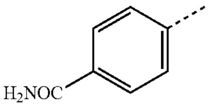 | $^{1}$H NMR (600 MHz, DMSO-$d_6$): δ 10.74 (s, 1H), 9.21 (t, J = 5.9 Hz, 1H), 8.94 (s, 1H), 8.07 (s, 1H), 7.96-7.92 (m, 4H), 7.49 (s, 1H), 7.41-7.29 (m, 8H), 4.55 (d, J = 5.9 Hz, 2H). ESI-MS: m/z 390 $[M + H]^+$ |
| 22 | 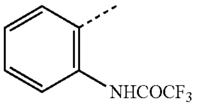 | |
| 23 | 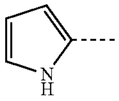 | $^{1}$H NMR (600 MHz, DMSO-$d_6$): δ 10.72 (s, 1H), 8.59 (t, J = 6.2 Hz, 1H), 7.41-7.31 (m, 8H), 6.85 (m, 1H), 6.80 (m, 1H), 6.08 (dt, J = 3.6 Hz, 2.4 Hz, 1H), 4.48 (d, J = 6.1 Hz, 2H), $^{13}$C NMR (150 MHz, DMSO-$d_6$): δ 166.5, 161.2, 142.3, 140.6, 140.1, 133.3, 129.4, 128.8, 128.8, 128.7, 127.6, 126.5, 126.2, 122.0, 110.5, 109.1, 42.1. ESI-MS: m/z 336 $[M + H]^+$ |
| 24 | 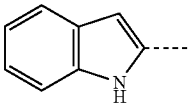 | $^{1}$H NMR (600 MHz, DMSO-$d_6$): δ 10.74 (s, 1H), 9.10 (t, J = 6.14 Hz, 1H), 7.61 (d, J = 8.0 Hz, 1H), 7.42-7.32 (m, 9H), 7.19-7.16 (m, 2H), 7.03 (ddd, J = 7.8 Hz, 7.2 Hz, 0.7 Hz, 1H), 4.57 (d, J = 6.0 Hz, 2H). $^{13}$C NMR (150 MHz, DMSO-$d_6$): δ 166.5, 161.7, 141.8, 140.6, 140.2, 136.9, 133.4, 132.0, 129.5, 128.9, 128.8, 128.7, 127.7, 127.5, 126.3, 123.8, 122.0, 120.2, 112.8, 103.1, 42.4. ESI-MS: m/z 386 $[M + H]^+$ |
| 25 | 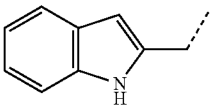 | $^{1}$H NMR (600 MHz, DMSO-$d_6$): δ 10.88 (s, 1H), 10.71 (s, 1H), 8.46 (t, J = 5.9 Hz, 1H), 7.54 (d, J = 7.9 Hz, 1H), 7.39-7.19 (m, 10H), 7.06 (t, J = 7.4 Hz, 1H), 6.91 (t, J = 7.4 Hz, 1H), 4.33 (d, J = 5.9 Hz, 2H), 3.57 (s, 2H). $^{13}$C NMR (150 MHz, DMSO-$d_6$): δ 171.3, 166.5, 141.9, 140.5, 140.1, 136.6, 133.3, 129.2, 128.7, 128.7, 127.6, 127.6, 126.2, 124.3, 121.4, 119.1, 118.8, 111.8, 109.2, 42.3, 33.2. ESI-MS: m/z 400 $[M + H]^+$ |
| 26 | 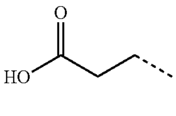 | $^{1}$H NMR (600 MHz, DMSO-$d_6$): δ 10.73 (s, 1H), 8.36 (t, J = 5.9 Hz, 1H), 7.40-7.27 (m, 9H), 7.00 (t, J = 6.0 Hz, 1H), 4.34 (d, J = 6.0 Hz, 2H), 3.55 (d, J = 5.8 Hz, ?H), 1.37 (s, ?H). $^{13}$C NMR (150 MHz, DMSO-$d_6$): δ 170.0, 166.5, 156.3, 141.7, 140.5, 140.1, 133.3, 129.3, 128.8, 128.7, 128.6, 127.6, 126.2, 78.5, 43.9, 42.2, 28.6. ESI-MS: m/z 343 $[M + H]^+$ |
| 27 | 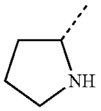 | $^{1}$H NMR (600 MHz, DMSO-$d_6$): δ 10.75 (bs, 1H), 9.33 (bs, 0.5H), 9.08 (t, J = 5.9 Hz), 8.59 (bs, 0.5H), 7.41-7.30 (m, 8H), 4.47-4.39 (m, 2H), 4.21 (quint, 1H), 3.28-3.17 (m, 2H), 2.34-2.29 (m, 1H), 1.94-1.82 (m, 3H). $^{13}$C NMR (150 MHz, DMSO-$d_6$): δ 168.2, 165.9, 140.2, 140.0, 139.8, 133.2, 129.0, 128.5, 128.3, 128.3, 127.3, 125.8, 59.2, 45.6, 42.1, 29.4, 23.5. ESI-MS: m/z 340 $[M + H]^+$ |

TABLE 3-continued

| Structures and characterisation data for compounds of the Formula XII. | | |
|---|---|---|
| Cmpd No. | R | Characterisation data |
| 28 | 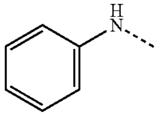 | $^{1}$H NMR (600 MHz, DMSO-$d_6$): δ 10.73 (s, 1H), 8.58 (s, 1H), 7.41-7.38 (m, 6H), 7.36-7.31 (m, 4H), 7.21 (t, J = 7.6 Hz, 2H), 6.89 (t, J = 7.4 Hz, 1H), 6.70 (t, J = 6.1 Hz, 1H), 4.36 (d, J = 6.0 Hz, 2H). ESI-MS: m/z 362 $[M + H]^+$ |
| 29 | 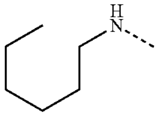 | $^{1}$H NMR (600 MHz, DMSO-$d_6$): δ 10.72 (s, 1H), 7.40-7.24 (m, 8H), 6.35 (s, 1H), 5.94 (s, 1H), 4.25 (s, 2H), 2.98 (t, J = 6.8 Hz, 2H), 1.37-1.32 (m, 2H), 1.27-1.21 (m, 6H), 0.85 (t, J = 6.3 Hz, 3H). ESI-MS: m/z 370 $[M + H]^+$ |

Table 4 provides structures and characterisation data for compounds of the Formula XIII.

Formula XIII

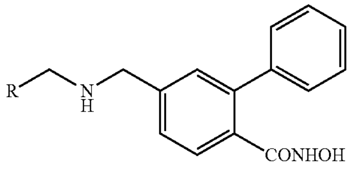

Table 5 provides structures and characterisation data for compounds of the Formula XIV.

Formula XIV

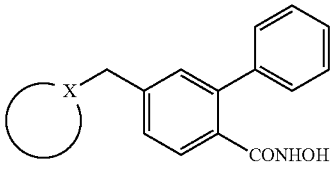

TABLE 4

| Structures and characterisation data for compounds of the Formula XIII. | | |
|---|---|---|
| Cmpd No. | R | Characterisation data |
| 30 | 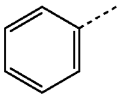 | TFA salt. $^{1}$H NMR (600 MHz, DMSO-$d_6$): δ 10.85 (s, 1H), 9.44 (s, 2H), 9.04 (br s, 1H), 7.57 (d, J = 1.5 Hz, 1H), 7.51-7.35 (m, 12H), 4.27 (s, 2H), 4.22 (s, 2H). $^{13}$C NMR (150 MHz, DMSO-$d_6$): δ 165.5, 139.8, 139.5, 134.7, 133.3, 131.8, 130.0, 129.0, 128.7, 128.6, 128.5, 128.3(1), 128.2(6), 127.5, 50.3, 49.7. ESI-MS: m/z 333 $[M + H]^+$ |
| 31 | 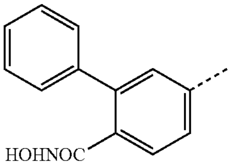 | TFA salt. $^{1}$H NMR (600 MHz, DMSO-$d_6$): δ 10.84 (s, 2H), 9.45 (br s, 2H), 9.04 (br s, 2H), 7.57 (d, J = 1.2 Hz, 2H), 7.51 (dd, J = 7.9, 1.4 Hz, 2H), 7.46-7.35 (m, 12H), 4.31 (s, 4H). $^{13}$C NMR (150 MHz, DMSO-$d_6$): δ 165.6, 139.9, 139.5, 134.8, 133.3, 131.8, 128.7, 128.6, 128.3(4), 128.3(0), 127.5, 49.89. ESI-MS: m/z 468 $[M + H]^+$ |
| 32 | 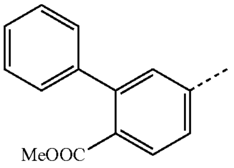 | TFA salt. $^{1}$H NMR (600 MHz, DMSO-$d_6$): δ 10.84 (s, 1H), 9.49 (s, 2H), 9.08 (br s, 1H), 7.81 (d, J = 8.0 Hz, 1H), 7.62 (d, J = 1.3 Hz, 1H), 7.60 (dd, J = 8.0, 1.5 Hz, 1H), 7.57 (d, J = 1.5 Hz, 1H), 7.51 (dd, J = 7.8, 1.5 Hz, 1H), 7.46-7.35 (m, 9H), 7.32-7.30 (m, 2H), 4.34 (s, 2H), 4.32 (s, 2H), 3.60 (s, 3H). $^{13}$C NMR (150 MHz, DMSO-$d_6$): δ 168.2, 165.5, 141.3, 139.8(9), 139.8(8), 139.5, 135.2, 134.8, 133.3, 132.2, 131.8, 131.2, 129.6, 128.9, 128.7, 128.6, 128.3(4)(2 × C), 128.2(9), 128.1, 127.6, 127.5, 52.1, 49.9, 49.8. ESI-MS: m/z 467 $[M + H]^+$ |
| 33 | 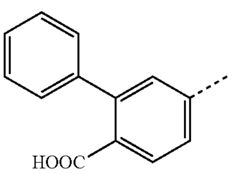 | TFA salt. $^{1}$H NMR (600 MHz, DMSO-$d_6$): δ 12.97 (br s, 1H), 10.85 (s, 1H), 9.51 (s, 2H), 9.05 (br, 1H), 7.78 (d, J = 8.6, 1H), 7.58-7.55 (m, 3H), 7.51 (dd, J = 8.0, 1.6 Hz, 1H), 7.45-7.34 (m, 11H), 4.32 (s, 4H). $^{13}$C NMR (150 MHz, DMSO-$d_6$): δ 169.3, 165.6, 141.1, 140.3, 139.9, 139.6, 134.8, 134.5, 133.3, 132.8, 132.2, 131.8, 129.4, 128.8, 128.7, 128.6, 128.4, 128.3(0), 128.2(7), 128.2(0), 127.4(9), 127.4(8), 49.9, 49.8. ESI-MS: m/z 453 $[M + H]^+$ |

TABLE 5

Structures and characterisation data for compounds of the Formula XIV.

| Cmpd No. |  | Characterisation data |
| --- | --- | --- |
| 34 | 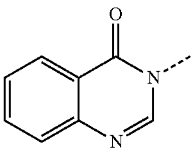 | $^{1}$H NMR (600 MHz, DMSO-$d_6$): δ 10.74 (s, 1H), 8.66 (s, 1H), 8.15 7 (dd, J = 7.9 Hz, 1.2 Hz, 1H), 7.84 (ddd, J = 8.0 Hz, 7.3 Hz, 1.5 Hz, 1H), 7.70 (d, J = 8.0 Hz, 1H), 7.56 (ddd, J = 8.0 Hz, 7.1 Hz, 0.9 Hz, 1H), 7.45 (d, J = 1.3 Hz, 1H), 7.40-7.34 (m, 7H), 5.27 (s, 2). $^{13}$C NMR (150 MHz, DMSO-$d_6$): δ 166.2, 160.6, 148.5, 148.3, 140.4, 140.2, 138.8, 135.0, 134.3, 130.1, 129.2, 128.8, 128.7, 127.8, 127.8, 127.7, 126.8, 126.6, 122.1, 49.2. ESI-MS: m/z 372 $[M + H]^+$ |
| 35 | 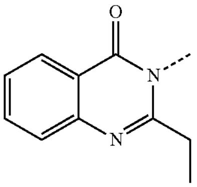 | $^{1}$H NMR (600 MHz, DMSO-$d_6$): δ 10.76 (s, 1H), 8.16 (dd, J = 8.0 Hz, 1.2 Hz, 1H), 7.84 (ddd, J = 8.0 Hz, 7.3 Hz, 1.6 Hz, 1H), 7.67 (d, J = 7.9 Hz, 1H), 7.53 (ddd, J = 8.0 Hz, 7.1 Hz, 1.0 Hz, 1H), 7.40-7.29 (m, 7H), 7.13 (dd, 7.9 Hz, 1.5 Hz, 1H), 5.46 (s, 2H), 2.83 (q, J = 7.2 Hz, 2H), 1.23 (t, J = 7.2 Hz, 3H). $^{13}$C NMR (150 MHz, DMSO-$d_6$): δ 166.2, 162.0, 158.7, 147.1, 140.5, 140.2, 138.7, 135.1, 133.9, 129.4, 128.8, 128.8, 128.6, 127.8, 127.2, 127.1, 126.9, 125.00, 120.2, 45.9, 27.8, 11.2. ESI-MS: m/z 400 $[M + H]^+$ |
| 36 | 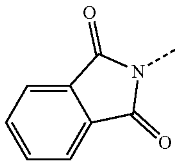 | $^{1}$H NMR (600 MHz, DMSO-$d_6$): δ 10.74 (s, 1H), 7.91-7.85 (m, 4H), 7.41-7.31 (m, 8H), 4.85 (s, 2H). $^{13}$C NMR (150 MHz, DMSO-$d_6$): δ 167.7, 165.8, 139.9, 139.8, 138.2, 134.6, 133.6, 131.6, 129.2, 128.7, 128.32, 128.27, 127.3, 125.9, 123.3, 40.6. HRMS: m/z calcd for $C_{22}H_{16}N_2O_4Na^+$: 395.1002 $[M + Na]^+$; found: 395.1007. |
| 37 | 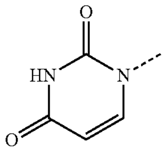 | $^{1}$H NMR (600 MHz, DMSO-$d_6$): δ 11.33 (s, 1H), 10.76 (s, 1H), 7.83 (d, J = 7.9 Hz, 1H), 7.42-7.31 (m, 8H), 5.61 (dd, J = 7.8 Hz, 2.1 Hz, 1H), 4.93 (s, 2H). ESI-MS: m/z 338 $[M + H]^+$ |
| 38 | 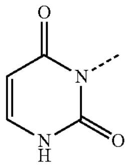 | $^{1}$H NMR (600 MHz, DMSO-$d_6$): δ 11.24 (d, J = 5.4 Hz, 1H), 10.73 (s, 1H), 7.48 (dd, J = 7.5 Hz, 5.8 Hz, 1H), 7.41-7.38 (m, 2H), 7.37-7.32 (m, 4H), 7.29-7.26 (m, 2H), 5.64 (dd, J = 7.7 Hz, 1.5 Hz, 1H), 5.00 (s, 2H). ESI-MS: m/z 338 $[M + H]^+$ |
| 39 | 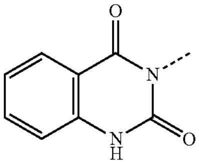 | $^{1}$H NMR (DMSO-$d_6$, 600 MHz): δ 11.55 (s, 1H), 10.73 (s, 1H), 7.94 (d, J = 8.2 Hz, 1H), 7.67 (m, 1H), 7.41-7.32 (m, 8H), 7.23-7.20 (m, 2H), 5.15 (s, 2H).<br>$^{13}$C NMR (DMSO-$d_6$, 150 MHz): δ 165.9, 162.0, 150.2, 139.9, 139.7, 139.5, 139.0, 135.2, 133.3, 129.3, 128.5, 128.31, 128.26, 127.5, 127.3, 126.0, 122.7, 115.3, 113.7, 43.0.<br>ESI-MS: m/z 388 $[M + H]^+$ |
| 40 | 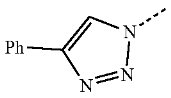 | $^{1}$H NMR (DMSO-$d_6$, 600 MHz): δ 10.77 (s, 1H), 8.70 (s, 1H), 7.84 (d, J = 7.2 Hz, 2H), 7.46-7.31 (m, 11H), 5.73 (s, 2H).<br>$^{13}$C NMR (DMSO-$d_6$, 150 MHz): δ 165.6, 146.7, 140.1, 139.6, 137.5, 134.2, 130.6, 129.7, 128.9, 128.34, 128.30, 127.9, 127.4, 126.5, 125.2, 121.7, 52.6.<br>ESI-MS: m/z 371 $[M + H]^+$ |
| 41 | 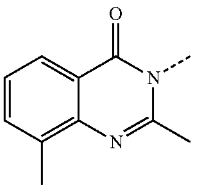 | $^{1}$H NMR (600 MHz, DMSO-$d_6$): δ 10.76 (s, 1H), 7.98 (dd, J = 8.0 Hz, 0.8 Hz, 1H), 7.68 (d, J = 7.26, 1H), 7.41-7.32 (m, 7H), 7.29 (d, J = 1.50 Hz, 1H), 7.16 (dd, J = 7.9 Hz, 1.6 Hz, 1H), 5.44 (s, 2H), 2.56 (s, 3H), 2.53 (s, 3H). $^{13}$C NMR (150 MHz, DMSO-$d_6$): δ 166.2, 162.2, 154.5, 145.9, 140.6, 140.2, 138.7, 135.4, 135.2, 133.9609, 129.4, 128.8, 128.7, 128.7, 127.8, 126.5, 125.1, 124.6, 120.2, 46.8, 23.8, 17.4. ESI-MS: m/z 400 $[M + H]^+$ |

TABLE 5-continued

Structures and characterisation data for compounds of the Formula XIV.

| Cmpd No. |  | Characterisation data |
|---|---|---|
| 42 | 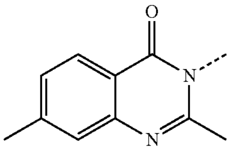 | $^1$H NMR (600 MHz, DMSO-$d_6$): δ 10.76 (s, 1H), 8.04 (d, J = 8.0 Hz, 1H), 7.43-7.16 (m, 11H), 5.43 (s, 2H), 2.54 (s, 3H), 2.46 (s, 3H). $^{13}$C NMR (150 MHz, DMSO-$d_6$): δ 166.2, 161.6, 156.2, 146.8, 145.9, 140.6, 140.2, 138.5, 134.0, 129.4, 128.8, 128.7, 128.7, 128.7, 127.8, 126.9, 126.0, 125.2, 117.8, 46.7, 23.3, 21.9. ESI-MS: m/z 400 [M + H]$^+$ |
| 43 | 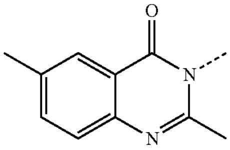 | $^1$H NMR (600 MHz, DMSO-$d_6$): δ 10.76 (s, 1H), 7.96 (s, 1H), 7.67 (dd, J = 8.3 Hz, 2.0 Hz, 1H), 7.55 (d, J = 8.3 Hz, 1H), 7.40-7.32 (m, 6H), 7.29 (s, 1H), 5.44 (s, 2H), 2.55 (s, 3H), 2.45 (s, 3H). $^{13}$C NMR (150 MHz, DMSO-$d_6$): δ 166.2, 161.6, 155.5, 144.3, 140.6, 140.2, 138.4, 137.1, 136.6, 134.0, 129.4, 128.8, 128.7, 128.7, 127.8, 126.3, 126.1, 125.2, 119.9, 46.8, 23.0, 21.3. ESI-MS: m/z 400 [M + H]$^+$ |
| 44 | 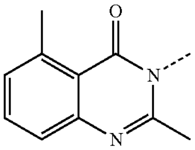 | $^1$H NMR (600 MHz, DMSO-$d_6$): δ 10.78 (s, 1H), 7.69 (t, J = 7.8 Hz, 1H), 7.47 (d, J = 8.0 Hz, 1H), 7.39-7.32 (m, 8H), 7.20 (d, J = 7.9 Hz, 1H), 5.40 (s, 2H), 2.77 (s, 3H), 2.56 (s, 3H). $^{13}$C NMR (150 MHz, DMSO-$d_6$): δ 166.2, 161.9, 156.5, 147.2, 140.9, 140.5, 140.2, 138.4, 134.5, 134.0, 129.8, 129.4, 128.8, 128.7, 128.7, 127.8, 125.1, 123.9, 118.5, 46.9, 23.1, 22.8. ESI-MS: m/z 400 [M + H]$^+$ |
| 45 | 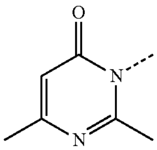 | $^1$H NMR (600 MHz, DMSO-$d_6$): δ 10.76 (s, 1H), 7.41-7.34 (m, 6H), 7.24 (d, J = 1.6 Hz, 1H), 7.15 (dd, J = 7.8 Hz, 1.4 Hz, 1H), 6.30 (s, 1H), 5.32 (s, 2H), 2.45 (s, 3H), 2.19 (s, 3H). $^{13}$C NMR (150 MHz, DMSO-$d_6$): δ 166.2, 162.1, 161.7, 160.3, 140.5, 140.2, 138.0, 134.1, 129.4, 128.8, 128.8, 127.8, 125.3, 110.0, 46.3, 23.0, 22.8. ESI-MS: m/z 350 [M + H]$^+$ |
| 46 | 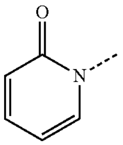 | $^1$H NMR (600 MHz, DMSO-$d_6$): δ 10.76 (s, 1H), 7.87 (dd, J = 6.84 Hz, 1.74 Hz, 1H), 7.44-7.31 (m, 9H), 6.41 (d, J = 9.06 Hz, 1H), 6.24 (td, J = 10.0 Hz, 1.32 Hz, $^1$H ), 5.15 (s, 2H). $^{13}$C NMR (150 MHz, DMSO-$d_6$): δ 166.3, 161.9, 140.7, 140.3, 139.7, 139.5, 134.1, 130.0, 129.1, 128.8, 128.76, 127.8, 126.8, 120.4, 106.1, 51.4. ESI-MS: m/z 321 [M + H]$^+$ |
| 47 | 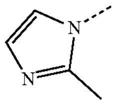 | $^1$H NMR (600 MHz, DMSO-$d_6$): δ 10.83 (s, 1H), 7.74 (d, J = 2.1 Hz, 1H), 7.61 (d, J = 2.1 Hz, 1H), 7.43-7.33 (m, 9H), 5.45 (s, 2H), 2.63 (s, 3H). $^{13}$C NMR (150 MHz, DMSO-$d_6$): δ 166.0, 152.6, 140.64, 139.95, 136.70, 134.69, 132.67, 132.67, 129.62, 129.48, 128.83, 128.79, 127.95, 126.09, 125.96, 125.63, 115.17, 113.03, 47.46, 12.65. ESI-MS: m/z 358 [M + H]$^+$ |
| 48 | 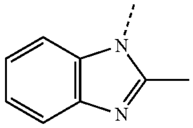 | $^1$H NMR (600 MHz, DMSO-$d_6$): δ 10.81 (s, 1H), 7.83~7.80 (m, 2H), 7.54~7.25 (m, 10H), 5.78 (s, 2H), 2.87 (s, 3H). $^{13}$C NMR (150 MHz, DMSO-$d_6$): δ 166.0, 152.6, 140.6, 139.9, 136.7, 134.7, 132.7, 132.67, 129.6, 129.5, 128.8, 128.8, 127.9, 126.1, 125.9, 125.6, 115.2, 113.0, 47.5, 12.7. ESI-MS: m/z 358 [M + H]$^+$ |
| 49 | 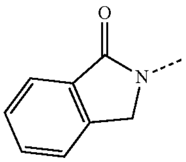 | $^1$H NMR (600 MHz, DMSO-$d_6$): δ 10.75 (s, 1H), 7.72 (d, J = 7.5 Hz, 1H), 7.61-7.56 (m, 2H), 7.50 (m, 1H), 7.40-7.29 (m, 8H), 4.80 (s, 2H), 4.43 (s, 2H). $^{13}$C NMR (150 MHz, DMSO-$d_6$): δ 167.4, 165.8, 141.8, 140.0, 139.9, 139.2, 133.5, 131.9, 131.5, 129.4, 128.8, 128.3, 128.0, 127.3, 126.2, 123.6, 122.9, 49.4, 45.1. HRMS: m/z calcd for $C_{22}H_{18}N_2O_3Na^+$: 381.1210 [M + Na]$^+$; found: 381.1220 |
| 50 | 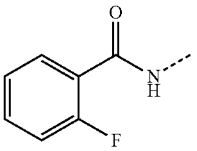 | $^1$H NMR (600 MHz, DMSO-$d_6$): δ 10.76, (s, 1H), 8.96 (t, J = 5.9 Hz, 1H), 7.63 (td, J = 7.6, 1.8 Hz, 1H), 7.54 (m, 1H), 7.42-7.27 (m, 10H), 4.53 (d, J = 6.1 Hz, 2H). $^{13}$C NMR (150 MHz, DMSO-$d_6$): δ 166.0, 163.8, 159.1 (d, J = 245.8 Hz), 141.0, 140.1, 139.7, 133.0, 132.5 (d, J = 8.6 Hz), 130.0 (d, J = 2.8 Hz), 128.9, 128.4, 128.3, 128.2, 127.2, 125.7, 124.6 (d, J = 2.9 Hz), 123.98 (d, J = 14.2 Hz), 116.2 (d, J = 22.0 Hz), 42.4. HRMS: m/z calcd for $C_{21}H_{17}FN_2O_3Na^+$: 387.1115 [M + Na]$^+$; found: 387.1128. |

TABLE 5-continued

Structures and characterisation data for compounds of the Formula XIV.

| Cmpd No. | 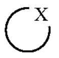 | Characterisation data |
|---|---|---|
| 51 | 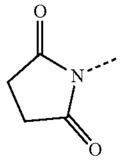 | $^{1}H$ NMR (600 MHz, $CDCl_3$): δ 7.76 (s, 1H), 7.54 (br d, J = 8.0 Hz, 1H), 7.44-7.36 (m, 7H), 7.29-7.26 (m, 3H), 7.13-7.11 (m, 2H), 4.71 (s, 2H), 4.68 (s, 2H), 2.70 (s, 4H). This compound (22 mg, 0.053 mmol) was subjected to General Procedure 7 to give 24 (19 mg, 0.059 mmol, quant.). $^{1}H$ NMR (600 MHz, DMSO-$d_6$): δ 10.76 (s, 1H), 7.41-7.26 (m, 8H), 4.61 (s, 2H), 2.69 (s, 4H). $^{13}C$ NMR (150 MHz, DMSO-$d_6$): δ 177.7, 165.8, 139.81, 139.79, 137.9, 133.6, 129.4, 128.5, 128.33, 128.27, 127.3, 126.1, 41.0, 28.2. HRMS: m/z calcd for $C_{18}H_{16}N_2O_4Na^+$: 347.1002 [M + Na]$^+$; found: 347.1012. |
| 52 | 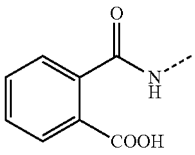 | $^{1}H$ NMR (600 MHz, DMSO-$d_6$): δ 10.75 (s, 1H), 8.91 (t, J = 5.9 Hz, 1H), 7.77 (dd, J = 7.7, 1.1 Hz, 1H), 7.59 (td, J = 7.5, 1.3 Hz, 1H), 7.52 (td, J = 7.5, 1.3 Hz, 1H), 7.46 (dd, J = 7.6, 1.1 Hz, 1H), 7.44-7.38 (m, 6H), 7.35-7.32 (m, 2H), 4.50 (d, J = 6.0 Hz, 2H). $^{13}C$ NMR (150 MHz, DMSO-$d_6$): δ 168.6, 168.0, 166.1, 141.2, 140.1, 139.6, 138.2, 132.8, 131.2, 130.9, 129.3, 129.2, 128.9, 128.39, 128.37, 128.2, 127.6, 127.2, 125.8, 42.3. HRMS: m/z calcd for $C_{22}H_{18}N_2O_5Na^+$: 413.1108 [M + Na]$^+$; found: 413.1118. |
| 53 | 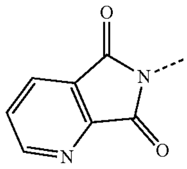 | $^{1}H$ NMR (600 MHz, DMSO-$d_6$): δ 10.76 (br s, 1H), 8.98 (dd, J = 5.0, 1.5 Hz, 1H), 8.32 (dd, J = 7.7, 1.5 Hz, 1H), 7.79 (dd, J = 7.7, 4.9 Hz, 1H), 7.39-7.33 (m, 8H), 4.88 (s, 2H). $^{13}C$ NMR (150 MHz, DMSO-$d_6$): δ 166.3, 166.2, 165.8, 154.9, 151.5, 139.9, 139.8, 138.0, 133.6, 131.4, 129.2, 128.6, 128.4, 128.2, 127.9, 127.4, 127.3, 126.0, 40.7. HRMS: m/z calcd for $C_{21}H_{16}N_3O_4^+$: 374.1135 [M + H]$^+$; found: 374.1139. |
| 54 | 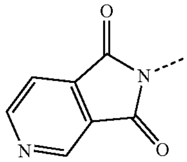 | $^{1}H$ NMR (600 MHz, DMSO-$d_6$): δ 10.76 (br s, 1H), 9.14 (d, J = 1.1 Hz, 1H), 9.10 (d, J = 4.8 Hz, 1H), 7.91 (dd, J = 4.7, 1.0 Hz, 1H), 7.41-7.32 (m, 8H), 4.86 (s, 2H). $^{13}C$ NMR (150 MHz, DMSO-$d_6$): δ 167.2, 166.8, 165.8, 155.9, 144.1, 140.0, 139.8, 139.4, 137.8, 133.7, 129.3, 128.6, 128.4, 128.2, 127.3, 126.0, 125.9, 117.0, 40.9. HRMS: m/z calcd for $C_{21}H_{16}N_3O_4^+$: 374.1135 [M + H]$^+$; found: 374.1131. |
| 55 | 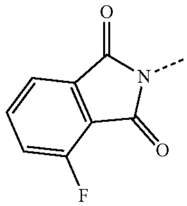 | $^{1}H$ NMR (600 MHz, $CDCl_3$): δ 7.73 (br s, 1H), 7.71 (dd, J = 8.3, 4.3 Hz, 1H), 7.66 (d, J = 7.4 Hz, 1H), 7.56 (d, J = 8.0 Hz, 1H), 7.45 (dd, J = 7.9, 1.4 Hz, 1H), 7.42-7.35 (m, 7H), 7.28-7.24 (m, 3H), 7.10 (m, 2H), 4.86 (s, 2H), 4.70 (s, 2H). This compound (33 mg, 0.069 mmol) was subjected to General Procedure 7 to give 28 (25 mg, 0.064 mmol, 93%). $^{1}H$ NMR (600 MHz, DMSO-$d_6$): δ 10.75 (s, 1H), 7.90 (m, 1H), 7.74 (d, J = 7.5 Hz, 1H), 7.68 (t, J = 9.0 Hz, 1H), 7.41-7.32 (m, 8H), 4.82 (s, 2H). $^{13}C$ NMR (150 MHz, DMSO-$d_6$): δ 166.8, 165.8, 164.6, 156.7 (d, J = 262.1 Hz), 139.9, 139.8, 138.0, 137.6 (d, J = 7.5 Hz), 133.9, 133.6, 129.2, 128.7, 128.4, 128.3, 127.3, 126.0, 122.6 (d, J = 19.8 Hz), 119.8 (d, J = 2.0 Hz), 117.5 (d, J = 12.8 Hz), 40.7. HRMS: m/z calcd for $C_{22}H_{15}FN_2O_4Na^+$: 413.0908 [M + Na]$^+$; found: 413.0912. |

TABLE 5-continued

Structures and characterisation data for compounds of the Formula XIV.

| Cmpd No. | 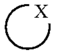 | Characterisation data |
|---|---|---|
| 56 | 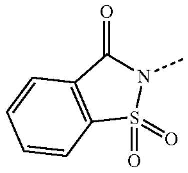 | $^1$H NMR (600 MHz, DMSO-$d_6$): δ 10.80 (s, 1H), 8.35 (d, J = 7.9 Hz, 1H), 8.13 (d, J = 7.6 Hz, 1H), 8.07 (t, J = 7.6 Hz, 1H), 8.01 (t, J = 7.6 Hz, 1H), 7.48 (br s, 1H), 7.46-7.44 (m, 1H), 7.42-7.33 (m, 6H), 5.01 (s, 2H). $^{13}$C NMR (150 MHz, DMSO-$d_6$): δ 165.7, 158.7, 139.8, 139.7, 136.8, 136.7, 136.0, 135.4, 133.9, 129.6, 128.6, 128.3, 127.4, 126.4, 126.2, 125.3, 121.7, 41.3 (18 carbons signals). HRMS: m/z calcd for $C_{21}H_{16}N_2O_5SNa^+$: 431.0672 [M + Na]$^+$; found: 431.0677. |
| 57 | 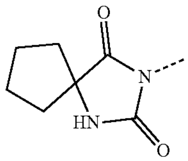 | $^1$H NMR (DMSO-$d_6$, 600 MHz) δ 10.77 (s, 1H), 8.97 (s, 1H), 8.61 (s, 1H), 7.44-7.39 (m, 2H), 7.38-7.32 (m, 4H), 7.26-7.21 (m, 2H), 4.61 (s, 2H), 1.98-1.91 (m, 2H), 1.80-1.68 (m, 6H). $^{13}$C NMR (151 MHz, DMSO) δ 165.8, 155.4, 139.8, 139.8, 138.4, 133.5, 128.9, 128.7, 128.3, 128.2, 127.3, 125.7, 67.3, 40.7, 37.2, 24.6. HRMS (ESI+) m/z calcd for $C_{21}H_{22}N_3O_4^+$ ([M + H]+): 380.1605, found: 380.1630. |
| 57a | 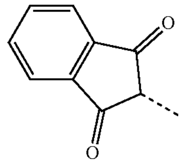 | Major ketone tautomer shown (~33% enol tautomer) $^1$H NMR (600 MHz, DMSO-$d_6$): δ 10.71 (s, 1H), 8.90 (s, 1H), 7.93 (s, 2H + 2H), 7.39-7.17 (m, 8H), 3.88 (t, J = 5.6 Hz, 1H), 3.25 (d, J = 5.6 Hz, 2H). $^{13}$C NMR (150 MHz, DMSO-$d_6$): 8199.8, 165.9, 141.9, 140.0, 139.9, 139.4, 136.1, 132.4, 130.9, 128.3, 128.22, 128.21, 127.7, 127.2, 122.8, 54.4, 30.7. ESI-MS m/z 372 [M + H]$^+$. |

Compound 57b of the structure

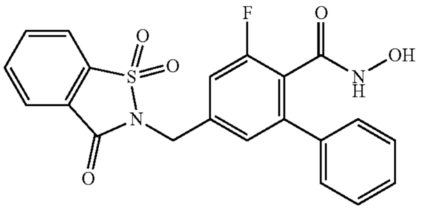 [SMILES: O=C(NO)c1c(F)cc(CN2C(=O)c3ccccc3S2(=O)=O)cc1-c1ccccc1]

was also prepared. This compound had the following characterisation data: 1H NMR (600 MHz, DMSO-d6: δ 10.94 (s, 1H), 8.35 (dt, J=7.8, 0.8 Hz, 1H), 8.13 (dt, J=7.6, 0.9 Hz, 1H), 8.01 (td, J=7.5, 1.1 Hz, 1H), 8.01 (td, J=7.7, 0.9 Hz, 1H), 7.46-7.32 (m, 7H), 5.03 (s, 2H). 13C NMR (150 MHz, DMSO-d6): δ 160.1 (d, J=34 Hz), 158.7, 158.3, 141.7, 138.6 (d, J=9 Hz), 138.5, 136.8, 135.9, 135.4, 128.4 (d, J=22 Hz), 128.0, 126.3, 125.3, 125.0, 122.1 (d, J=19 Hz), 121.7, 113.5 (d, J=24 Hz), 40.8.

Table 6 provides structures and characterisation data for compounds of the Formula XV.

Formula XV

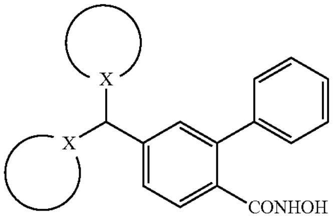

TABLE 6

Structures and characterisation data for compounds of the Formula XV.

| Cmpd No. | Structure | Characterisation data |
|---|---|---|
| 58 | 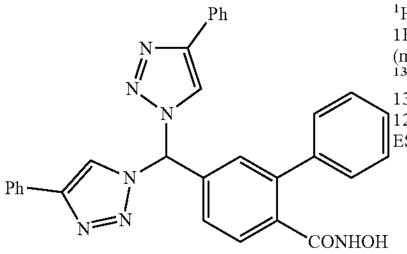 | $^1$H NMR (DMSO-$d_6$, 600 MHz): δ 10.88 (s, 1H), 9.04 (s, 1H), 8.95 (s, 2H), 7.92 (d, J = 7.1 Hz, 4H), 7.55-7.35 (m, 14H). $^{13}$C NMR (DMSO-$d_6$, 150 MHz): δ 165.2, 147.1, 140.4, 139.2, 135.8, 135.1, 129.9, 129.3, 129.1, 129.0, 128.4, 128.3, 127.7, 126.2, 125.5, 121.6, 73.3. ESI-MS: m/z 514 [M + H]$^+$ |

Table 7 provides structures and characterisation data for compounds of the Formula XVI.

Formula XVI

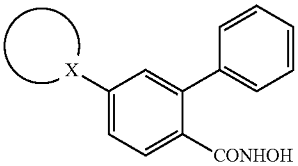

TABLE 7

| Structures and data for compounds of the Formula XVI. | | |
|---|---|---|
| Cmpd No. | 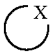 | Characterisation data |
| 59 | 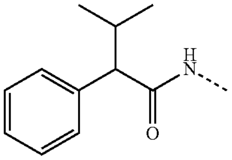 | $^1$H NMR (600 MHz, DMSO-$d_6$): δ 10.66 (s, 1H), 10.29 (s, 1H), 7.65 (m, 1H), 7.57-7.58 (d, 1H), 7.38-7.40 (m, 4H), 7.30-7.35 (m, 6H), 7.23-7.26 (m, 1H), 3.24 (d, J = 10.7 Hz), 2.30-2.37 (m, 1H), 1.01 (d, J = 6.5 Hz, 3H) , 0.67 (d, J = 6.7 Hz, 3H). HRMS m/z calculated for $C_{24}H_{25}N_2O_3^+$ 389.1860 found 389.1862. |
| 60 | 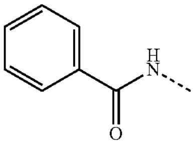 | $^1$H NMR (600 MHz, DMSO-$d_6$): δ 10.74 (s, 1H), 10.42 (s, 1H), 7.97-7.98 (m, 2H), 7.84-7.85 (m, 2H), 7.60-7.62 (m, 1H), 7.53-7.56 (m, 2H), 7.42-7.44 (m, 4H), 7.34-7.39 (m, 2H). ESI-MS m/z 333 [M + H]$^+$. |
| 61 | 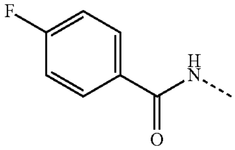 | $^1$H NMR (600 MHz, DMSO-$d_6$): δ 10.74 (s, 1H), 10.43 (s, 1H), 8.05-8.07 (m, 2H), 7.82-7.84 (m, 2H), 7.35-7.43 (m, 8H). ESI-MS m/z 351 [M + H]$^+$. |
| 62 | 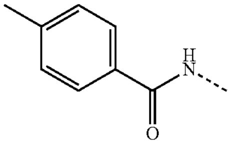 | $^1$H NMR (600 MHz, DMSO-$d_6$): δ 10.73 (s, 1H), 10.32 (s, 1H), 7.89-7.90 (m, 2H), 7.84-7.86 (m, 2H), 7.34-7.43 (m, 8H), 2.39 (s, 3H). ESI-MS m/z 347 [M + H]$^+$. |
| 63 | 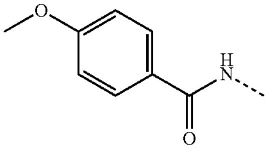 | $^1$H NMR (600 MHz, DMSO-$d_6$): δ 10.73 (s, 1H), 10.25 (s, 1H), 7.97-7.99 (m, 2H), 7.83-7.85 (m, 2H), 7.30-7.43 (m, 6H), 7.06-7.08 (m, 2H), 3.84 (s, 3H). ESI-MS m/z 363 [M + H]$^+$. |
| 64 | 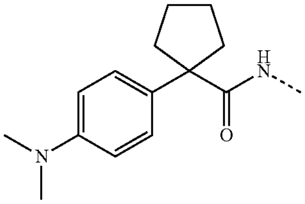 | $^1$H NMR (600 MHz, DMSO-$d_6$): δ 10.64 (s, 1H), 9.24 (s, 1H), 7.65-7.67 (m, 1H), 7.62 (m, 1H), 7.37-7.38 (m, 2H), 7.33-7.34 (m, 3H), 7.27-7.28 (m, 3H), 6.84 (br, s, 1H), 2.90 (s, 6H), 2.56-2.58 (m, 2H), 1.89-1.90 (m, 2H), 1.60-1.66 (m, 4H). HRMS m/z calculated for $C_{27}H_{30}N_3O_3^+$ 444.2282 found 444.2286. |
| 65 | 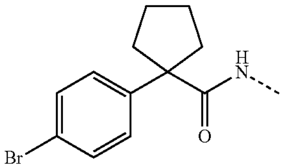 | $^1$H NMR (600 MHz, DMSO-$d_6$): δ 10.65 (s, 1H), 9.38 (s, 1H), 7.63-7.65 (m, 1H), 7.60 (m, 1H), 7.52-7.54 (m, 2H), 7.37-7.38 (m, 2H), 7.33-7.35 (m, 5H), 7.28-7.29 (m, 1H), 2.59-2.62 (m, 2H), 1.88-1.92 (m, 2H), 1.63-1.69 (m, 4H). HRMS m/z calculated for $C_{25}H_{24}BrN_3O_2^+$ 479.0965 found 479.0968. |

TABLE 7-continued

Structures and data for compounds of the Formula XVI.

| Cmpd No. |  | Characterisation data |
|---|---|---|
| 66 | 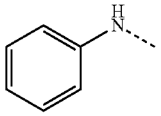 | $^1$H NMR (600 MHz, DMSO-$d_6$): δ 10.61 (s, 1H), 8.46 (br, s, 1H), 7.36-7.39 (m, 4H), 7.30-7.33 (m, 1H), 7.25-7.29 (m, 3H), 7.13-7.15 (m, 2H), 7.03-7.05 (m, 1H), 6.97 (m, 1H), 6.89-6.91 (m, 1H). HRMS m/z calculated for $C_{19}H_{17}N_2O_2^+$ 305.1285 found 305.1300. |
| 67 | 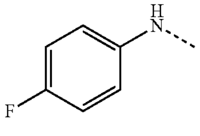 | $^1$H NMR (600 MHz, DMSO-$d_6$): δ 10.59 (s, 1H), 8.41 (br, s, 1H), 7.35-7.38 (m, 4H), 7.30-7.33 (m, 1H), 7.24-7.25 (m, 1H), 7.11-7.17 (m, 4H), 6.95-6.97 (m, 1H), 6.89-6.90 (m, 1H). ESI-MS m/z 323 [M + H]$^+$. |
| 68 | 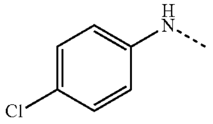 | $^1$H NMR (600 MHz, DMSO-$d_6$): δ 10.63 (s, 1H), 8.59 (s, 1H), 7.36-7.39 (m, 4H), 7.27-7.35 (m, 4H), 7.12-7.15 (m, 2H), 7.04-7.06 (m, 1H), 6.97 (m, 1H). ESI-MS m/z 339 [M + H]$^+$. |
| 69 | 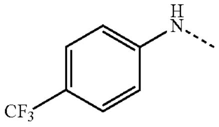 | $^1$H NMR (600 MHz, DMSO-$d_6$): δ 10.69 (s, 1H), 8.96 (s, 1H), 7.57-7.58 ( m, 2H), 7.38-7.41 (m, 4H), 7.33-7.35 (m, 2H), 7.23-7.24 (m, 2H), 7.17-7.19 (m, 1H), 7.09-7.10 (m, 1H). ESI-MS m/z 373 [M + H]$^+$. |
| 70 | 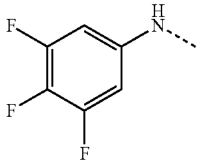 | $^1$H NMR (600 MHz, DMSO-$d_6$): δ 10.66 (s, 1H), 8.79 (s, 1H), 7.38-7.39 (m, 4H), 7.31-7.35 (m, 2H), 7.13-7.14 (m, 1H), 7.00 (m, 1H), 6.90-6.93 (m, 4H). ESI-MS m/z 359 [M + H]$^+$. |
| 71 | 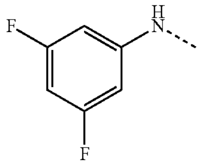 | $^1$H NMR (600 MHz, DMSO-$d_6$): δ 10.68 (s, 1H), 8.92 (s, 1H), 7.38-7.41 (m, 4H), 7.33-7.36 (m, 2H), 7.17-7.18 (m, 1H), 7.03-7.04 (m, 1H), 6.70-6.72 (m, 2H), 6.60-6.63 (m, 1H). ESI-MS m/z 341 [M + H]$^+$. |
| 72 | 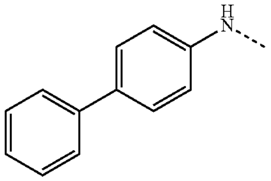 | $^1$H NMR (600 MHz, DMSO-$d_6$): δ 10.63 (s, 1H), 8.62 (s, 1H), 7.60-7.63 (m, 4H), 7.41-7.44 (m, 2H), 7.38-7.39 (m, 4H), 7.31-7.35 (m, 1H), 7.28-7.30 (m, 2H), 7.22-7.23 (m, 2H), 7.10-7.11 (m, 1H), 7.03 (m, 1H). ESI-MS m/z 381 [M + H]$^+$. |
| 73 | 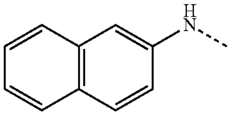 | $^1$H NMR (600 MHz, DMSO-$d_6$): δ 10.65 (s, 1H), 8.71 (br, s, 1H), 7.82-7.84 (m, 1H), 7.77-7.79 (m, 1H), 7.73-7.75 (m, 1H), 7.56 (s, 1H), 7.37-7.42 (m, 5H), 7.29-7.34 (m, 4H), 7.19-7.21 (m, 1H), 7.08 (s, 1H). ESI-MS m/z 355 [M + H]$^+$. |
| 74 | 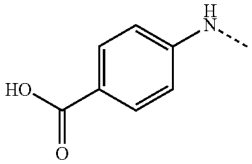 | $^1$H NMR (600 MHz, DMSO-$d_6$): δ 12.39 (br, s, 1H), 10.69 (s, 1H), 8.97 (s, 1H), 7.82-7.84 (m, 2H), 7.38-7.41 (m, 4H), 7.31-7.36 (m, 2H), 7.18-7.20 (m, 1H), 7.14-7.15 (m, 2H), 7.10 (m, 1H). ESI-MS m/z 349 [M + H]$^+$. |

TABLE 7-continued

Structures and data for compounds of the Formula XVI.

| Cmpd No. |  | Characterisation data |
|---|---|---|
| 75 | 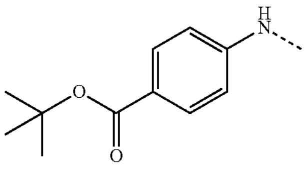 | H NMR (600 MHz, DMSO-$d_6$): δ 10.69 (s, 1H), 8.98 (s, 1H), 7.79-7.80 (m, 2H), 7.38-7.41 (m, 4H), 7.32-7.35 (m, 2H), 7.16-7.18 (m, 2H), 7.14-7.15 (m, 2H), 7.09-7.10 (m, 1H), 1.52 (s, 9H). ESI-MS m/z 405 $[M + H]^+$. |
| 76 | 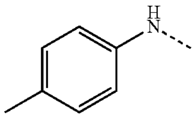 | $^1$H NMR (600 MHz, DMSO-$d_6$): δ 10.57 (s, 1H), 8.32 (s, 1H), 7.30-7.38 (m, 5H), 7.22-7.24 (m, 1H), 7.09-7.11 (m, 2H), 7.04-7.05 (m, 2H), 6.95-6.97 (m, 1H), 6.90 (m, 1H), 2.24 (s, 3H). ESI-MS m/z 319 $[M + H]^+$. |
| 77 | 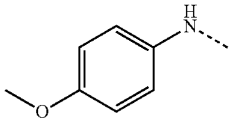 | $^1$H NMR (600 MHz, DMSO-$d_6$): δ 10.54 (s, 1H), 8.17 (br, s, 1H), 7.27-7.37 (m, 5H), 7.20-7.23 (m, 1H), 7.08-7.15 (m, 2H), 6.89-6.94 (m, 2H), 6.84-6.94 (m, 2H), 6.84-6.86 (m, 1H), 6.79-6.81 (m, 2H), 3.72 (s, 3H). ESI-MS m/z 335 $[M + H]^+$. |
| 78 | 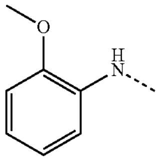 | $^1$H NMR (600 MHz, DMSO-$d_6$): δ 10.57 (s, 1H), 7.74 (br, s, 1H), 7.29-7.38 (m, 5H), 7.26-7.27 (m, 1H), 7.20-7.22 (m, 1H), 7.04-7.05 (m, 1H), 6.97-6.99 (m, 1H), 6.89-6.94 (m, 3H), 3.81 (s, 3H). ESI-MS m/z 335 $[M + H]^+$. |
| 79 | 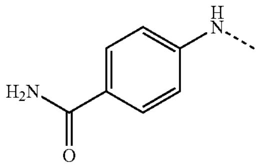 | $^1$H NMR (600 MHz, DMSO-$d_6$): δ 10.66 (s, 1H), 8.81 (s, 1H), 7.78-7.80 (m, 2H), 7.73 (br, s, 1H), 7.39 (m, 4H), 7.31-7.35 (m, 2H), 7.127.17 (m, 4H), 7.09 (br, s, 1H), 7.06 (m, 1H). ESI-MS m/z 348 $[M + H]^+$. |
| 80 | 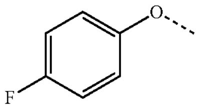 | $^1$H NMR (600 MHz, DMSO-$d_6$): δ 10.76 (s, 1H), 8.97 (br, s, 1H), 7.37-7.40 (m, 5H), 7.33-7.35 (m, 1H), 7.26-7.30 (m, 2H), 7.16-7.18 (m, 2H), 6.93-6.97 (m, 2H). ESI-MS m/z 324 $[M + H]^+$. |
| 81 | 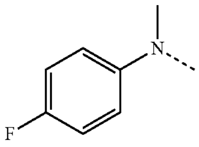 | $^1$H NMR (600 MHz, DMSO-$d_6$): δ 10.60 (s, 1H), 7.30-7.36 (m, 5H), 7.23-7.25 (m, 5H), 6.75 (dd, J = 2.4, 8.6 Hz, 1H), 6.68-6.69 (m, 1H), 3.28 (s, 3H). ESI-MS m/z 337 $[M + H]^+$. |
| 82 | 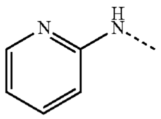 | $^1$H NMR (600 MHz, DMSO-$d_6$): δ 10.69 (s, 1H), 10.11 (br, s, 1H), 9.07 (m, 1H), 8.47-8.48 (m, 1H), 8.20-8.21 (m, 1H), 7.84-7.86 (m, 1H), 7.57-7.59 (m, 1H), 7.38-7.41 (m, 4H), 7.32-7.36 (m, 2H), 7.16-7.18 (m, 1H), 7.09-7.10 (m, 1H). HRMS m/z calculated for $C_{18}H_{16}N_3O_2^+$ 306.1237 found 306.1245. |
| 83 | 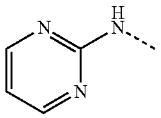 | $^1$H NMR (600 MHz, DMSO-$d_6$): δ 10.66 (s, 1H), 9.86 (s, 1H), 8.51 (d, J = 4.74 Hz, 2H), 7.83-7.85 (m, 1H), 7.77-7.78 (m, 1H), 7.38-7.41 (m, 4H), 7.31-7.35 (m, 2H), 6.88 (t, J = 4.7 Hz, 1H). HRMS m/z calculated for $C_7H_{15}N_4O_2^+$ 307.1190 found 307.1189. |
| 84 | 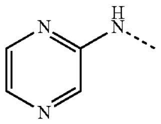 | $^1$H NMR (600 MHz, DMSO-$d_6$): δ 10.67 (s, 1H), 9.74 (s, 1H), 8.26 (m, 1H), 8.15-8.16 (m, 1H), 7.96 (d, J = 2.8 Hz, 1H), 7.75 (dd, J = 2.4, 8.6 Hz, 1H), 7.71 (m, 1H), 7.39-7.42 (m, 4H), 7.33-7.36 (m, 2H). HRMS m/z calculated for $C_{17}H_{15}N_4O_2^+$ 307.1190 found 307.1191. |

TABLE 7-continued

Structures and data for compounds of the Formula XVI.

| Cmpd No. | 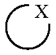 | Characterisation data |
|---|---|---|
| 85 | 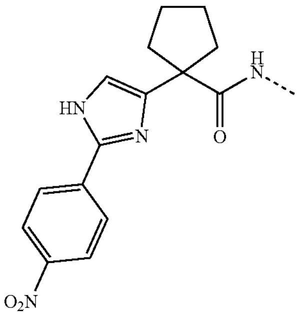 | $^{1}$H NMR (600 MHz, DMSO-$d_6$): δ 10.67 (s, 1H), 10.09 (s, 1H), 9.59 (s, 1H), 8.38-8.40 (m, 2H), 8.22-8.23 (m, 2H), 7.64 (m, 2H), 7.31-7.40 (m, 6H), 2.41-2.43 (m, 2H), 2.22-2.24 (m, 2H), 1.67-1.70 (m, 4H). ESI-MS m/z 512 $[M + H]^+$. |
| 86 | 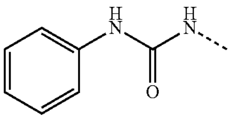 | $^{1}$H NMR (600 MHz, DMSO-$d_6$): δ 10.68 (s, 1H), 8.92 (s, 1H), 8.76 (s, 1H), 7.54 (m, 1H), 7.45-7.46 (m, 2H), 7.38-7.43 (m, 5H), 7.33-7.6 (m, 1H), 7.27-7.32 (m, 3H), 6.96-6.99 (m, 1H). HRMS m/z calculated for $C_{20}H_{18}N_3O_3^+$ 348.1343 found 348.1344. |
| 87 | 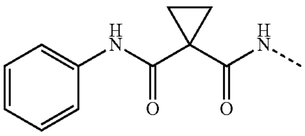 | $^{1}$H NMR (600 MHz, DMSO-$d_6$): δ 10.70 (s, 1H), 10.20 (s, 1H), 10.00 (s, 1H), 7.69-7.70 (m, 1H), 7.64-7.65 (m, 1H), 7.60-7.61 (m, 2H), 7.36-7.41 (m, 4H), 7.32-7.35 (m, 2H), 7.28-7.31 (m, 2H), 7.05-7.07 (m, 1H), 1.47 (s, 4H). HRMS m/z calculated for $C_{24}H_{22}N_3O_4^+$ 416.1605 found 416.1605. |
| 88 | 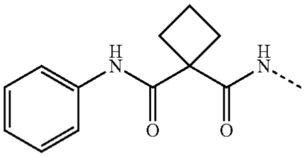 | $^{1}$H NMR (600 MHz, DMSO-$d_6$): δ 10.69 (s, 1H), 9.79 (s, 1H), 9.58 (s, 1H), 7.71-7.73 (m, 2H), 7.65-7.66 (m, 2H), 7.28-7.41 (m, 8H), 7.04-7.07 (m, 1H), 2.66 (t, J = 7.8 Hz, 4H), 1.84 (quintuplet, J = 7.8 Hz, 2H). HRMS m/z calculated for $C_{25}H_{24}N_3O_4^+$ 430.1761 found 430.1783. |
| 89 | 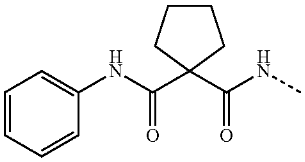 | $^{1}$H NMR (600 MHz, DMSO-$d_6$): δ 10.68 (s, 1H), 9.67 (s, 1H), 9.46 (s, 1H), 7.74 (m, 1H), 7.69-7.71 (m, 1H), 7.62-7.64 (m, 2H), 7.26-7.41 (m, 8H), 7.02-7.05 (m, 1H), 2.29-2.32 (m, 4H), 1.64-1.65 (m, 4H). ESI-MS m/z 444 $[M + H]^+$. |
| 90 | 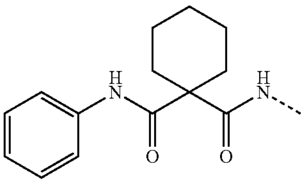 | $^{1}$H NMR (600 MHz, DMSO-$d_6$): δ 10.68 (s, 1H), 9.52 (s, 1H), 9.32 (s, 1H), 7.71-7.74 (m, 2H), 7.62-7.64 (m, 2H), 7.27-7.41 (m, 8H), 7.04-7.06 (m, 1H), 2.16-2.17 (m, 4H), 1.50-1.54 (m, 4H), 1.42-1.45 (m, 2H). ESI-MS m/z 458 $[M + H]^+$. |
| 91 | 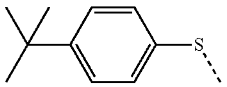 | 1H NMR (600 MHz, DMSO-$d_6$): δ 10.76 (s, 1H), 8.98 (br, 1H), 7.47 (d, J = 8.3 Hz, 2H), 7.41 (d, J = 8.3 Hz, 2H), 7.39-7.33 (m, 6H), 7.20-7.19 (m, 2H), 1.28 (s, 9H).<br>13C NMR (150 MHz, DMSO-$d_6$): δ 165.5, 151.3, 140.6, 139.3, 138.6, 132.6, 132.5, 129.8, 129.4, 129.2, 128.31, 128.25, 127.5, 127.1, 126.8, 34.4, 31.0.<br>ESI-MS m/z 378 [M + H]+ |

Table 7a provides structures and characterisation data for further compounds.

TABLE 7a

Structures and characterisation data for further compounds.

| Cmpd No. | 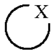 | Characterisation data |
|---|---|---|
| 92 | 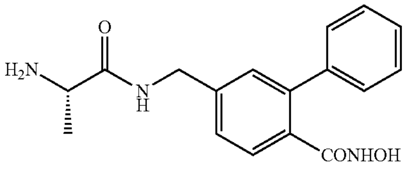 | $^1$H NMR (600 MHz, DMSO-$d_6$: δ 10.76 (br s, 1H), 8.96 (t, J = 6.0 Hz, 1H), 8.12 (br s, 1H), 7.43-7.34 (m, 6H), 7.31-7.30 (m, 2H), 4.42 (m, 2H), 3.90 (m, 1H), 2.79 (d, J = 6.0 Hz, 3H). |
| 93 | 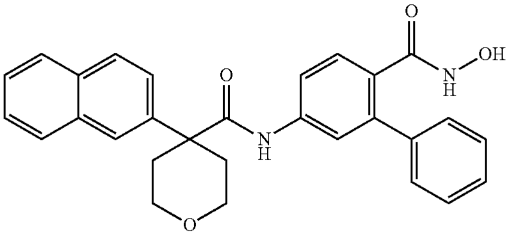 [SMILES: O=C(NO)c1ccc(NC(=O)C2(c3ccc4ccccc4c3)CCOCC2)cc1-c1ccccc1] | $^1$H NMR (600 MHz, DMSO-$d_6$): δ 10.65 (s, 1H), 9.38 (s, 1H), 7.63-7.65 (m, 1H), 7.60 (m, 1H), 7.52-7.54 (m, 2H), 7.37-7.38 (m, 2H), 7.33-7.35 (m, 5H), 7.28-7.29 (m, 1H), 2.59-2.62 (m, 2H), 1.88-1.92 (m, 2H), 1.63-1.69 (m, 4H). $^{13}$C NMR (150 MHz, DMSO-$d_6$): δ 173.4, 165.8, 143.2, 140.3, 140.2, 140.1, 131.2, 129.1, 129.0, 128.7, 128.2, 128.1, 127.2, 121.3, 119.7, 118.0, 59.9, 35.6, 23.2. |
| 94 | 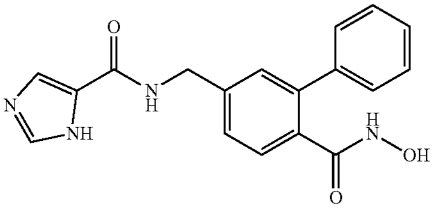 [SMILES: O=C(NCc1ccc(C(=O)NO)c(-c2ccccc2)c1)c1cnc[nH]1] | 1H NMR (600 MHz, DMSO-d6): 10.74 (s, 1H), 9.13 (d, J = 6.3 Hz, 1H), 8.64 (s, 1H), 7.98 (s, 1H), 7.43-7.32 (m, 8H), 4.54 (s, 2H). 13C NMR (150 MHz, DMSO-d6): δ 165.9, 158.9, 140.8, 140.0, 139.7, 135.9, 133.1, 129.1, 128.4, 128.3, 128.2, 127.2, 125.9, 120.2, 41.8. HRMS (ESI+) m/z calcd for C18H17N4O3+ [M + H]+): 337.1295, found: 337.1717. |
| 95 | 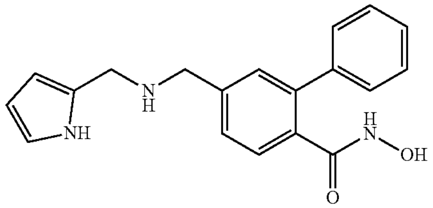 [SMILES: O=C(NO)c1ccc(CNCc2ccc[nH]2)cc1-c1ccccc1] | 1H NMR (600 MHz, DMSO-d6) δ 10.92 (s, 1H), 10.82 (s, 1H), 9.24-9.19 (m, 2H), 7.52 (d, J = 1.7 Hz, 1H), 7.46-7.29 (m, 6H), 6.81 (td, J = 2.7, 1.5 Hz, 1H), 6.20 (p, J = 1.7 Hz, 1H), 6.04 (q, J = 2.8 Hz, 1H), 4.14 (dt, J = 29.4, 5.5 Hz, 4H). 13C NMR (400 MHz, DMSO-d6) δ 165.5, 139.9, 139.5, 134.7, 133.3, 131.8, 128.7, 128.5, 128.3, 128.3, 127.5, 121.3, 119.2, 110.0, 108.2, 49.0, 43.0. ESI-MS m/z ([M + H]+): 322. |
| 96 | 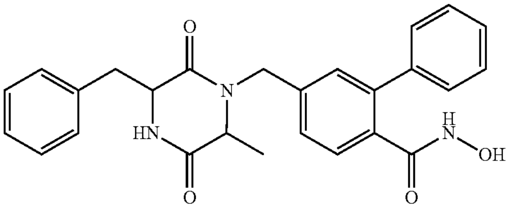 [SMILES: CC1C(=O)NC(Cc2ccccc2)C(=O)N1Cc1ccc(C(=O)NO)c(-c2ccccc2)c1] | 1H NMR (600 MHz, DMSO-d6) (mixture of diastereomers) δ 10.75 (s, 1H), 8.35 (d, J = 2.8 Hz, 1H), 7.44-7.27 (m, 9H), 7.25-7.16 (m, 5H), 7.15-7.06 (m, 3H), 5.06 (d, J = 15.2 Hz, 0.3H), 4.84 (d, J = 15.2 Hz, 1H), 4.50 (t, J = 4.3 Hz, 0.3H), 4.34 (td, J = 4.5, 2.7 Hz, 1H), 4.20 (d, J = 15.2 Hz, 1H), 4.08 (d, J = 15.2 Hz, 0.3H), 3.58 (q, J = 7.0 Hz, 1H), 3.35 (q, J = 6.9 Hz, 0.3H), 3.28 (dd, J = 13.8, 3.7 Hz, 0.3H), 3.17 (dd, J = 13.4, 4.2 Hz, 1H), 2.94 (dd, J = 13.8, 4.9 Hz, 0.3H), 2.90 (dd, J = 13.4, 4.9 Hz, 1H), 1.34 (d, J = 6.9 Hz, 1H), 0.46 (d, J = 7.0 Hz, 3H). 13C NMR (600 MHz, DMSO-d6) (mixture of diastereomers) δ 166.9, 165.8, 165.0, 139.9, 139.7, 138.6, 135.9, 133.4, 130.3, 130.2, 129.6, 128.5, 128.3, 128.2, 128.2, 127.8, 127.3, 126.8, 126.3, 55.7, 54.8, 46.5, 39.9, 39.8, 39.6, 39.5, 39.4, 39.2, 39.1, 17.9. ESI-MS m/z ([M + H]+): 444. |

TABLE 7a-continued

| Structures and characterisation data for further compounds. | | |
|---|---|---|
| Cmpd No. |  | Characterisation data |
| 97 | 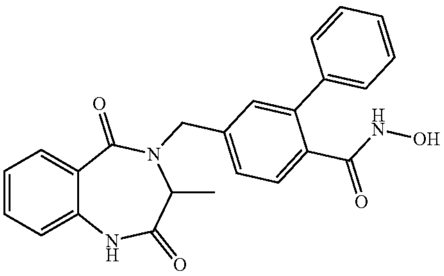 [SMILES: CC1C(=O)Nc2ccccc2C(=O)N1Cc1ccc(C(=O)NO)c(-c2ccccc2)c1] | 1H NMR (600 MHz, DMSO-d6) δ 10.79 (s, 1H), 10.57 (s, 1H), 7.79 (d, J = 7.8 Hz, 1H), 7.53 (td, J = 7.7, 1.6 Hz, 1H), 7.40 (d, J = 4.4 Hz, 4H), 7.38-7.20 (m, 5H), 7.12 (dd, J = 8.2, 1.1 Hz, 1H), 4.94 (d, J = 16.3 Hz, 1H), 4.67 (d, J = 16.7 Hz, 1H), 4.36 (d, J = 7.0 Hz, 1H), 1.32 (d, J = 6.9 Hz, 3H). 13C NMR (600 MHz, DMSO-d6) δ 171.1, 168.0, 166.0, 140.0, 139.8, 139.6, 136.8, 132.8, 132.1, 130.8, 128.4, 128.3, 128.2, 127.2, 125.2, 123.9, 120.6, 51.0, 44.8, 12.3. HRMS (ESI+) m/z calcd for C24H22N3O4 + ([M + H]+): 416.1605, found: 416.1591. |
| 98 | 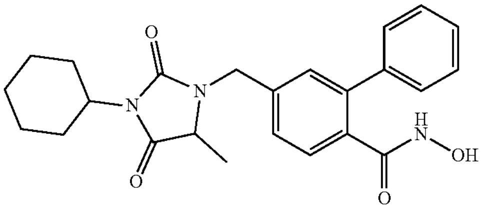 [SMILES: CC1C(=O)N(C2CCCCC2)C(=O)N1Cc1ccc(C(=O)NO)c(-c2ccccc2)c1] | 1H NMR (600 MHz, DMSO-d6) δ 10.77 (s, 1H), 7.40 (d, J = 4.3 Hz, 4H), 7.37-7.29 (m, 4H), 4.67 (d, J = 15.9 Hz, 1H), 4.45 (d, J = 15.9 Hz, 1H), 3.97 (q, J = 6.9 Hz, 1H), 3.77 (tt, J = 12.3, 3.8 Hz, 1H), 2.06-1.95 (m, 2H), 1.79-1.73 (m, 2H), 1.64-1.57 (m, 3H), 1.32-1.21 (m, 5H), 1.15-1.05 (m, 1H).13C NMR (600 MHz, DMSO-d6) δ 173.2, 165.8, 155.8, 139.9, 139.8, 138.7, 133.5, 129.3, 128.69, 128.3, 128.2, 127.3, 126.1, 54.8, 50.6, 43.8, 39.9, 39.7, 39.6, 39.5, 39.3, 39.2, 39.1, 29.0, 25.3, 24.8, 15.2. HRMS (ESI+) m/z calcd for C24H28N3O4+. ([M + H]+): 422.2074, found: 422.2109. |
| 99 | 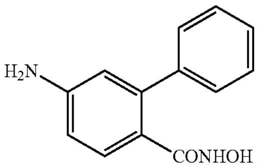 | $^{1}$H NMR (600 MHz, DMSO-$d_6$: δ 10.52 (br s, 1H), 7.39-7.31 (m, 5H), 7.17 (d, J = 6.0 Hz, 1H), 6.70-6.66 (m, 2H). $^{13}$C NMR (150 MHz, DMSO-$d_6$): δ 166.6, 146.9, 141.2, 140.8, 129.7, 128.2, 128.1, 127.0, 123.8, 116.9, 113.5. |
| 100 | 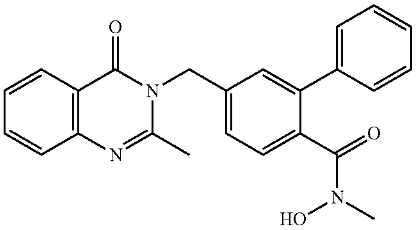 [SMILES: Cc1nc2ccccc2c(=O)n1Cc1ccc(C(=O)N(C)O)c(-c2ccccc2)c1] (Comparative Example) | $^{1}$H NMR (600 MHz, DMSO-$d_6$): δ 11.30 (s, 1H), 8.14-8.16 (m, 1H), 7.82-7.85 (m, 1H), 7.62-7.64 (m, 1H), 7.51-7.54 (m, 1H), 7.34-7.41 (m, 6H), 7.31 (m, 1H), 7.19-7.21 (m, 1H), 5.45 (s, 2H), 3.45 (s, 3H), 2.54 (s, 3H). $^{13}$C NMR (150 MHz, DMSO-$d_6$): δ 165.3, 161.4, 155.3, 146.8, 140.2, 139.5, 138.4, 134.7, 132.9, 128.8, 128.3, 128.2, 128.0, 127.5, 126.6, 126.4, 124.8, 119.8, 62.6, 46.3, 22.9. HRMS m/z calculated for $C_{24}H_{22}N_3O_3^+$ 400.1656, found 400.1663. |
| 101 | 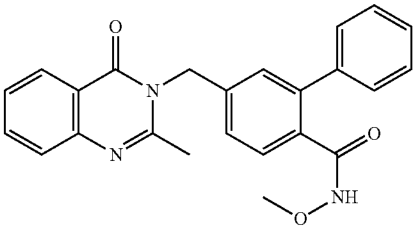 [SMILES: CONC(=O)c1ccc(Cn2c(C)nc3ccccc3c2=O)cc1-c1ccccc1] (Comparative Example) | $^{1}$H NMR (600 MHz, DMSO-$d_6$): δ 9.88 (br, s, 1H), 8.15-8.16 (m, 1H), 7.83-7.85 (m, 1H), 7.63-7.64 (m, 1H), 7.53-7.55 (m, 1H), 7.31-7.31 (m, 6H), 7.287-7.293 (m, 1H), 7.16-7.17 (m, 1H), 5.44 (s, 2H), 3.09 (s, 2H), 2.57 (s, 3H). $^{13}$C NMR (150 MHz, DMSO-$d_6$): δ 169.8, 161.4, 155.5, 146.5, 140.0, 139.1, 137.0, 135.0, 134.7, 128.3, 128.0, 127.7, 127.4, 127.3, 126.6, 126.5, 126.2, 124.4, 119.7, 46.4, 35.9, 22.9. HRMS m/z calculated for $C_{24}H_{22}N_3O_3^+$ 400.1656, found 400.1664. |

TABLE 7a-continued

Structures and characterisation data for further compounds.

| Cmpd No. |  | Characterisation data |
|---|---|---|
| 102 | 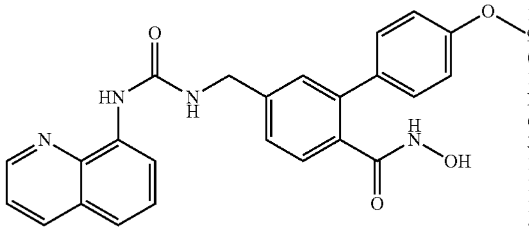 (Comparative Example) | 1H NMR (600 MHz, DMSO-d6): δ 10.69 (s, 1H), 9.47 (s, 1H), 8.87 (dd, J = 4.1, 1.7 Hz, 1H), 8.50 (dd, J = 7.0, 2.0 Hz, 1H), 8.35 (dd, J = 8.3, 1.7 Hz, 1H), 7.97 (t, J = 5.8 Hz, 1H), 7.60 (dd, J = 8.3, 4.2 Hz, 1H), 7.51-7.47 (m, 2H), 7.34-7.32 (m, 5H), 6.95 (d, J = 8.7 Hz, 2H), 4.42 (d, J = 5.6 Hz, 2H), 3.77 (s, 3H). 13C NMR (150 MHz, DMSO-d6): δ 166.7, 159.1, 155.6, 148.6, 142.3, 139.8, 138.0, 137.0, 136.9, 133.3, 132.9, 130.0, 129.0, 128.9, 128.4, 127.7, 125.7, 122.3, 119.6, 114.5, 114.2, 55.6, 42.9. HRMS (ESI+) m/z calcd for C25H23N4O4+ ([M + H]+): 443.1714, found: 443.1741. |
| 103 | 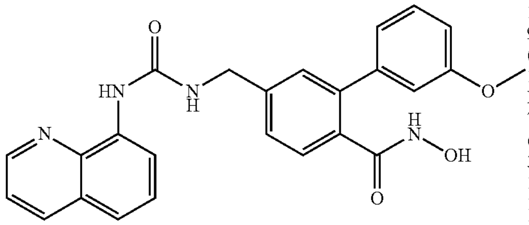 (Comparative Example) | 1H NMR (600 MHz, DMSO-d6): δ 10.73 (s, 1H), 9.48 (s, 1H), 8.86 (dd, J = 4.2, 1.7 Hz, 1H), 8.49 (dd, J = 7.0, 2.1 Hz, 1H), 8.35 (dd, J = 8.4, 1.7 Hz, 1H), 7.97 (t, J = 5.7 Hz, 1H), 7.60 (dd, J = 8.3, 4.2 Hz, 1H), 7.51-7.47 (m, 2H), 7.36-7.34 (m, 3H), 7.30 (t, J = 7.9 Hz, 1H), 6.97-6.96 (m, 2H), 6.91-6.89 (m, 1H), 4.43 (d, J = 5.7 Hz, 2H), 3.75 (s, 3H). 13C NMR (150 MHz, DMSO-d6): δ 166.5, 159.4, 155.6, 148.6, 142.3, 142.0, 140.0, 138.0, 137.0, 136.9, 133.5, 129.8, 129.1, 128.9, 128.4, 127.7, 126.2, 122.3, 121.1, 119.6, 114.5, 113.2, 55.4, 42.9. HRMS (ESI+) m/z calcd for C25H23N4O4+ ([M + H]+): 443.1714, found: 443.1736. |
| 104 | 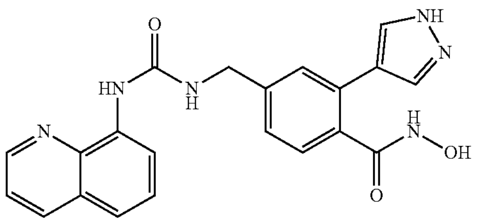 [SMILES: O=C(NCc1ccc(C(=O)NO)c(-c2cn[nH]c2)c1)Nc1cccc2cccnc12] (Comparative Example) | 1H NMR (600 MHz, DMSO-d6): δ 10.79 (s, 1H), 10.09 (s, 0.1H), 9.47 (s, 1H), 8.87 (dd, J = 4.2, 1.7 Hz, 1H), 8.50 (dd, J = 8.2, 1.9 Hz, 1H), 8.35 (dd, J = 8.3, 1.7 Hz, 1H), 7.95 (t, J = 5.7 Hz, 1H), 7.83 (s, 2H), 7.60 (dd, J = 8.3, 4.2 Hz, 1H), 7.53-7.47 (m, 4H), 7.24-7.21 (m, 2H), 4.39 (d, J = 5.6 Hz, 2H). 13C NMR (150 MHz, DMSO-d6): δ 167.0, 155.6, 148.6, 142.0, 138.1, 136.99, 136.95, 132.2, 131.2, 128.7, 128.4, 127.7, 127.3, 124.9, 122.3, 119.6, 119.47, 114.5, 110.0, 43.0. HRMS (ESI+) m/z calcd for C21H19N6O3+ ([M + H]+): 403.1513, found: 403.1529. |
| 105 | 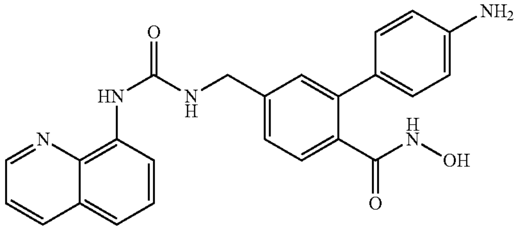 [SMILES: Nc1ccc(-c2cc(CNC(=O)Nc3cccc4cccnc34)ccc2C(=O)NO)cc1] (Comparative Example) | 1H NMR (600 MHz, DMSO-d6): δ 10.17 (s, 1H), 9.47 (s, 1H), 8.86 (dd, J = 4.2, 1.7 Hz, 1H), 8.49 (dd, J = 6.8, 2.1 Hz, 1H), 8.35 (dd, J = 8.2, 1.6 Hz, 1H), 7.98 (d, J = 5.7 Hz, 1H), 7.60 (dd, J = 8.3, 4.2 Hz, 1H), 7.51-7.47 (m, 2H), 7.39-7.33 (m, 5H), 7.14-7.13 (m, 2H), 4.42 (d, J = 5.8 Hz, 2H). 13C NMR (150 MHz, DMSO-d6): δ 166.5, 155.6, 148. 6, 142.4, 139.5,138.0, 137.0, 136.9, 133.2, 130.0, 129.0, 128.97, 128.4, 127.7, 126.1, 122.4, 119.6, 114.5, 42.9. HRMS (ESI+) m/z calcd for C24H22N5O3+ ([M + H]+): 428.1717, found: 428.1736. |
| 106 | 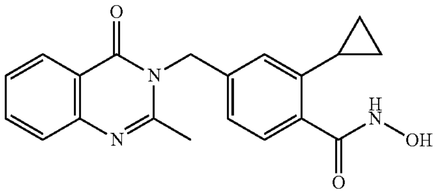 [SMILES: Cc1nc2ccccc2c(=O)n1Cc1ccc(C(=O)NO)c(C2CC2)c1] (Comparative Example) | 1H NMR (600 MHz, DMSO-d6) δ 10.84 (s, 1H), 8.16 (dd, J = 8.0, 1.5 Hz, 1H), 7.85 (ddd, J = 8.5, 7.2, 1.5 Hz, 1H), 7.66-7.62 (m, 1H), 7.55 (ddd, J = 8.1, 7.1, 1.1 Hz, 1H), 7.17 (d, J = 8.3 Hz, 1H), 6.90-6.85 (m, 2H), 5.34 (s, 2H), 2.50 (s, 7H), 2.17 (tt, J = 8.5, 5.2 Hz, 1H), 0.96-0.87 (m, 2H), 0.66-0.60 (m, 2H). 13C NMR (600 MHz, DMSO-d6) δ 165.9, 161.2, 158.4, 158.1, 155.7, 146.1, 142.1, 137.9, 134.8, 134.4, 127.7, 126.7, 126.5, 125.9, 122.3, 122.2, 119.6, 46.4, 39.9, 39.7, 39.6, 39.4, 39.3, 39.2, 39.0, 22.6, 12.1, 9.3. HRMS (ESI+) m/z calcd for C20H20N3O3+. ([M + H]+): 350.1499, found: 350.1530. |

Assay Example Methods

Assay Example 1: Inhibition of Class I HDACs—Human HDAC1 Enzyme Assay

The inhibitory effect of compounds on HDAC1 activity was assessed in vitro using an optimised assay performed in black/flat black wall 384-well plate (Corning Inc.). All reagents and compounds were prepared in HDAC1 assay buffer (25 mM Tris-HCl, 137 mM NaCl, 2.7 mM KCl, 1 mM $MgCl_2 \cdot H_2O$ and 0.1 mg/mL bovine serum albumin; pH 8). Various concentrations of inhibitor were pre-incubated with 50 ng/mL human HDAC1 enzyme (BPS Bioscience) for 30 min at room temperature on a plate shaker. Substrate (Leu (Ac)-Gly-Lys(Ac)-AMC, 12 μM) were then added and incubated for 90 min at 37° C. in the dark. The enzymatic reaction was then incubated with the developer solution (1 mg/mL trypsin and 25 μM SAHA) for 15-20 min at room temperature. Fluorescence intensity was measured using PHERAstar plate reader (BMG Labtech) at 350 nm excitation and 460 nm emission.

Data analysis: Triplicate measurements were made for each data point and error bars represent mean±SEM of three independent experiments. All data were plotted and analysed using GraphPad Prism Version 6.0d for Mac OS X (GraphPad Software). Dose Response Curves plotted using 4 parameters logistic model.

Assay Example 2: Inhibition of Class IIa HDACs—Human HDAC7 Enzyme Assay

The inhibitory effect of compounds on HDAC7 activity was assessed in vitro using an optimised assay performed in black/flat black wall 384-well plate (Corning Inc.). All reagents and compounds were prepared in HDAC7 assay buffer (25 mM Tris-HCl, 137 mM NaCl, 2.7 mM KCl, 1 mM $MgCl_2 \cdot H_2O$ and 0.1 mg/mL bovine serum albumin; pH 8). Various concentrations of inhibitor were pre-incubated with 5 pg/μl human HDAC7 enzyme (Reaction Biology Corp.) for 15 min at room temperature on a plate shaker. Substrate (Ac-Leu-Gly-Lys(trifluroAc)-AMC, 20 μM) were then added and incubated for 60 min at 37° C. in the dark. The enzymatic reaction was then incubated with the developer solution (1 mg/mL trypsin and 10 μM SAHA) for 15-20 min at room temperature. Fluorescence intensity was measured using PHERAstar plate reader (BMG Labtech) at 350 nm excitation and 460 nm emission.

Assay Example 3: Inhibition of Class IIb HDACs—Human HDAC6 Enzyme Assay

The inhibitory effect of compounds on HDAC6 activity was assessed in vitro using an optimised assay performed in black/flat black wall 384-well plate (Corning Inc.). All reagents and compounds were prepared in HDAC assay buffer (25 mM Tris-HCl, 137 mM NaCl, 2.7 mM KCl, 1 mM $MgCl_2 \cdot H_2O$ and 0.1 mg/mL bovine serum albumin; pH 8). Various concentrations of inhibitor were pre-incubated with 100 ng/ml human HDAC6 enzyme (Cayman Chemical) for 15 min at room temperature on a plate shaker. Substrate (Boc-Lys(Ac)-AMC, 25 μM) were then added and incubated for 60 min at 37° C. in the dark. The enzymatic reaction was then incubated with the developer solution (1 mg/mL trypsin and 10 μM SAHA) for 15-20 min at room temperature. Fluorescence intensity was measured using PHERAstar plate reader (BMG Labtech) at 350 nm excitation and 460 nm emission.

Data analysis: Triplicate measurements were made for each data point and error bars represent mean±SEM of three independent experiments. All data were plotted and analysed using GraphPad Prism Version 6.0d for Mac OS X (GraphPad Software). Dose Response Curves plotted using 4 parameters logistic model.

Assay Results

Table 8 provides data for the inhibitor potency of selected compounds against recombinant human HDAC1 versus recombinant human HDAC7. While this specific data measures inhibition of the enzymatic processing of acetylated lysine substrates indicated below, it is appreciated that this is also a measure of the affinity of the compound for the indicated HDAC protein. Thus the compounds with low $IC_{50}$ have higher affinity for the indicated HDAC protein and serve as inhibitors of both HDAC deacetylase activity and HDAC binding affinity to a peptide or protein bearing a lysine that binds to the HDAC at the zinc-occupying site. The comparative examples provide rationale for modifications which are detrimental for either inhibitor affinity, potency or selectivity, in particular (1) the ortho-substituent on the central benzene ring is a halogen, phenoxy, $sp^3$-alkyl/cycloalkyl; (2) the size of substituents on the ortho-phenyl ring is limited; (3) at least some other heteroaromatics are not tolerated as replacements for the ortho-phenyl ring. Table 9 provides data for isoform selectivity of selected compounds binding to and inhibiting representative class I, class IIa, and class IIb recombinant human HDACs.

TABLE 8

Inhibitor potency of some representative compounds ($IC_{50}$, nM) against HDAC1 versus HDAC7

| Cmpd No. | Structure | $IC_{50}$ (nM) (HDAC1) | $IC_{50}$ (nM) (HDAC7) |
|---|---|---|---|
| 2 | 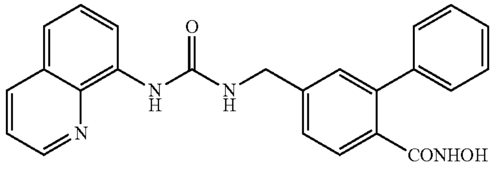 | 2361 ± 452 | 214 ± 54 |

TABLE 8-continued
Inhibitor potency of some representative compounds ($IC_{50}$, nM) against HDAC1 versus HDAC7
| | Structure | $IC_{50}$ (nM) (HDAC1) | $IC_{50}$ (nM) (HDAC7) |
|---|---|---|---|
| 4 | 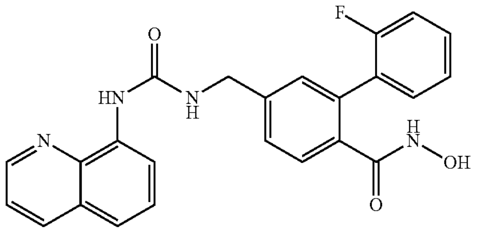 [SMILES: O=C(NCc1ccc(C(=O)NO)c(-c2ccccc2F)c1)Nc1cccc2cccnc12] | | 152 ± 40 |
| 5 | 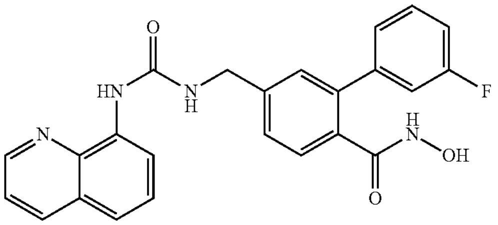 [SMILES: O=C(NCc1ccc(C(=O)NO)c(-c2cccc(F)c2)c1)Nc1cccc2cccnc12] | | 64 ± 12 |
| 6 | 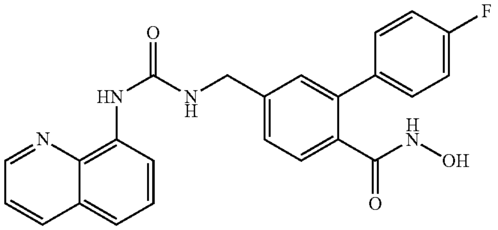 [SMILES: O=C(NCc1ccc(C(=O)NO)c(-c2ccc(F)cc2)c1)Nc1cccc2cccnc12] | | 118 ± 21 |
| 7 | 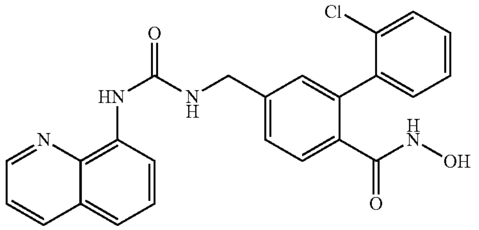 [SMILES: O=C(NCc1ccc(C(=O)NO)c(-c2ccccc2Cl)c1)Nc1cccc2cccnc12] | | 178 ± 47 |
| 8 | 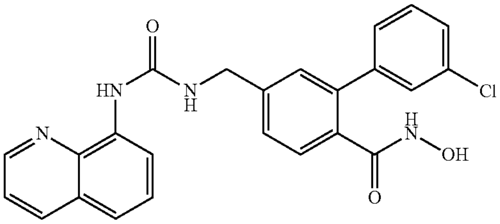 [SMILES: O=C(NCc1ccc(C(=O)NO)c(-c2cccc(Cl)c2)c1)Nc1cccc2cccnc12] | | 886 ± 192 |
| 9 | 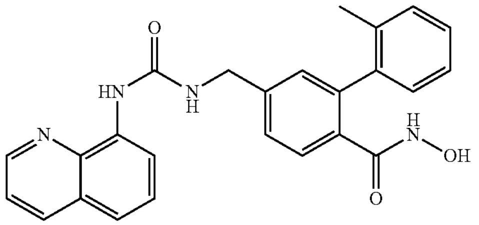 [SMILES: Cc1ccccc1-c1cc(CNC(=O)Nc2cccc3cccnc23)ccc1C(=O)NO] | | 125 ± 26 |

TABLE 8-continued
Inhibitor potency of some representative compounds ($IC_{50}$, nM) against HDAC1 versus HDAC7
| | Structure | $IC_{50}$ (nM) (HDAC1) | $IC_{50}$ (nM) (HDAC7) |
|---|---|---|---|
| 10 | 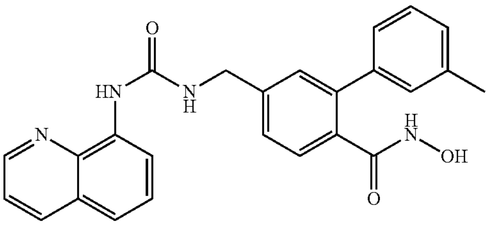 [SMILES: Cc1cccc(-c2cc(CNC(=O)Nc3cccc4cccnc34)ccc2C(=O)NO)c1] | | >10,000 |
| 11 | 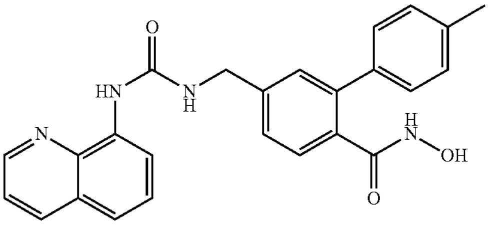 [SMILES: Cc1ccc(-c2cc(CNC(=O)Nc3cccc4cccnc34)ccc2C(=O)NO)cc1] | | 1893 ± 431 |
| 12 | 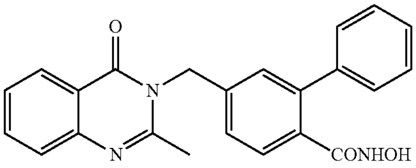 | 2,200 ± 1,200 | 7.3 ± 1.2 |
| 13 | 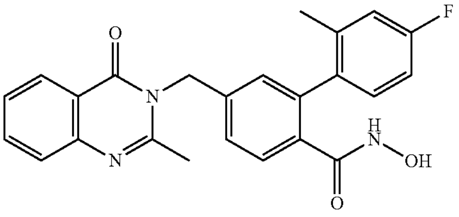 [SMILES: Cc1cc(F)ccc1-c1cc(Cn2c(C)nc3ccccc3c2=O)ccc1C(=O)NO] | 4210 ± 1760 | 12 ± 1.2 |
| 14 | 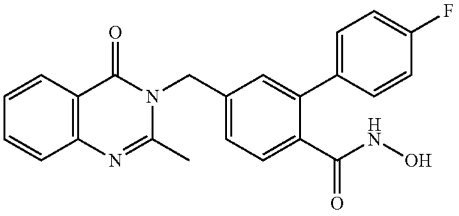 [SMILES: Cc1nc2ccccc2c(=O)n1Cc1ccc(C(=O)NO)c(-c2ccc(F)cc2)c1] | 3,200 ± 800 | 6.4 ± 0.8 |
| 15 | 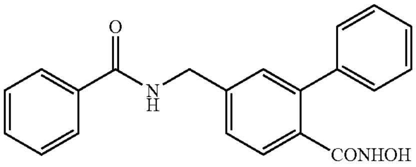 | | 123 ± 39 |
| 16 | 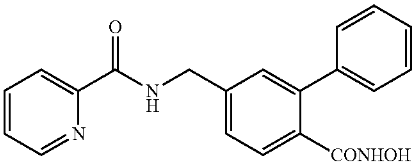 | | 108 ± 34 |

TABLE 8-continued
Inhibitor potency of some representative compounds ($IC_{50}$, nM) against HDAC1 versus HDAC7
| | Structure | $IC_{50}$ (nM) (HDAC1) | $IC_{50}$ (nM) (HDAC7) |
|---|---|---|---|
| 17 | 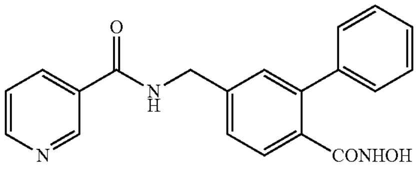 | | 151 ± 52 |
| 18 | 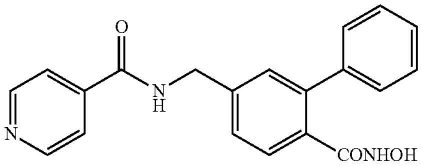 | | 205 ± 47 |
| 19 | 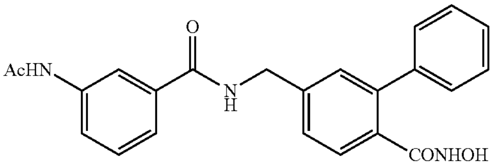 | | 78 ± 21 |
| 20 | 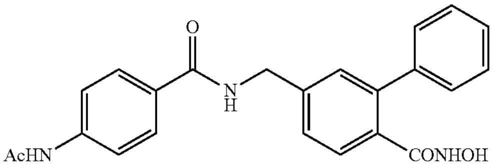 | | 101 ± 26 |
| 21 | 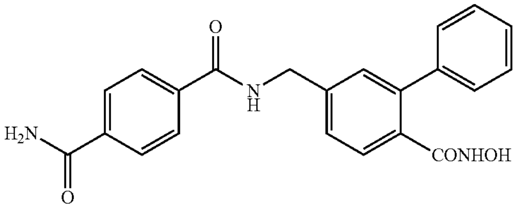 | | 116 ± 27 |
| 22 | 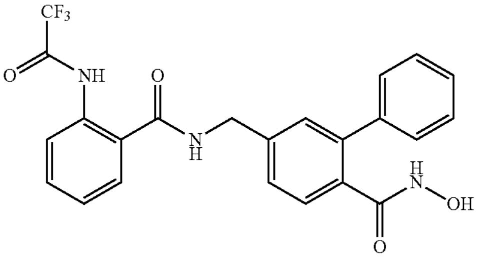 [SMILES: O=C(NCc1ccc(C(=O)NO)c(-c2ccccc2)c1)c1ccccc1NC(=O)C(F)(F)F] | | 925 ± 865 |
| 23 | 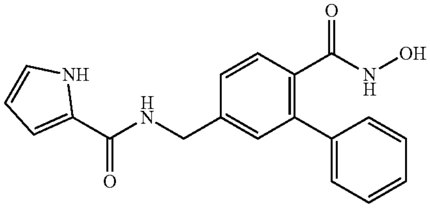 [SMILES: O=C(NCc1ccc(C(=O)NO)c(-c2ccccc2)c1)c1ccc[nH]1] | >10,000 | 81 ± 14 |

TABLE 8-continued
| Inhibitor potency of some representative compounds ($IC_{50}$, nM) against HDAC1 versus HDAC7 | | | |
|---|---|---|---|
| | Structure | $IC_{50}$ (nM) (HDAC1) | $IC_{50}$ (nM) (HDAC7) |
| 24 | 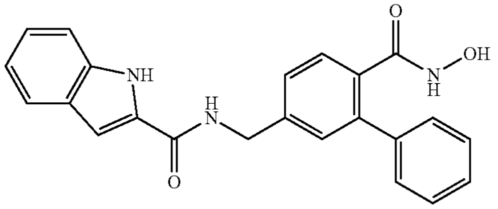 [SMILES: O=C(NCc1ccc(C(=O)NO)c(-c2ccccc2)c1)c1cc2ccccc2[nH]1] | >10,000 | 59 ± 10 |
| 25 | 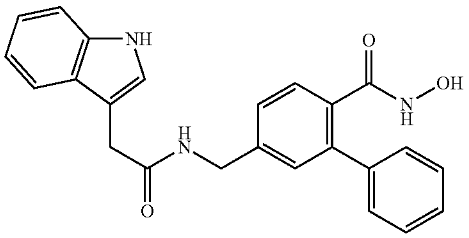 [SMILES: O=C(Cc1c[nH]c2ccccc12)NCc1ccc(C(=O)NO)c(-c2ccccc2)c1] | | 238 ± 86 |
| 26 | 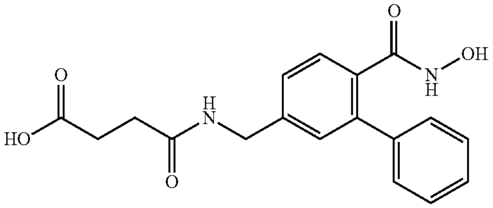 [SMILES: O=C(O)CCC(=O)NCc1ccc(C(=O)NO)c(-c2ccccc2)c1] | | 403 ± 339 |
| 27 | 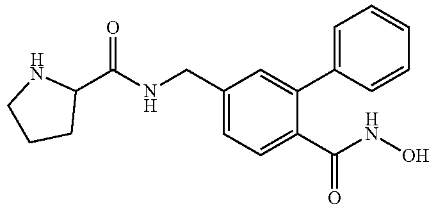 [SMILES: O=C(NO)c1ccc(CNC(=O)C2CCCN2)cc1-c1ccccc1] | | 960 ± 225 |
| 28 | 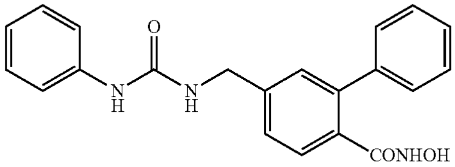 | | 104 ± 21 |
| 29 | 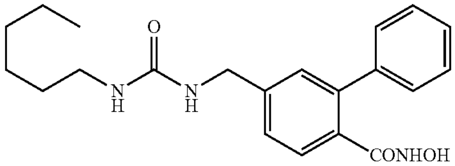 | | 196 ± 66 |
| 30 | 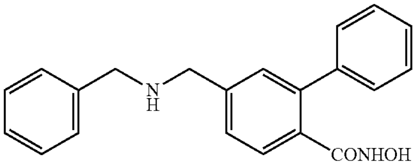 | | 1465 ± 426 |

TABLE 8-continued
| Inhibitor potency of some representative compounds ($IC_{50}$, nM) against HDAC1 versus HDAC7 | | | |
|---|---|---|---|
| | Structure | $IC_{50}$ (nM) (HDAC1) | $IC_{50}$ (nM) (HDAC7) |
| 31 | 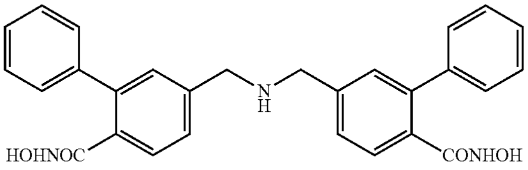 | | 125 ± 22 |
| 32 | 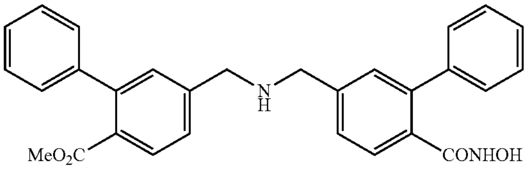 | | 137 ± 30 |
| 33 | 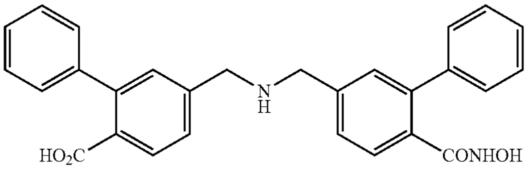 | | 658 ± 208 |
| 34 | 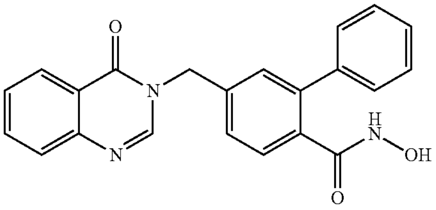 [SMILES: O=C(NO)c1ccc(Cn2cnc3ccccc3c2=O)cc1-c1ccccc1] | 3193 ± 816 | 36 ± 6 |
| 35 | 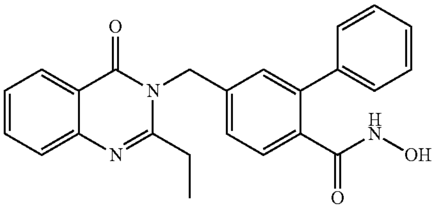 [SMILES: CCc1nc2ccccc2c(=O)n1Cc1ccc(C(=O)NO)c(-c2ccccc2)c1] | 5276 ± 3488 | 7.3 ± 1.3 |
| 36 | 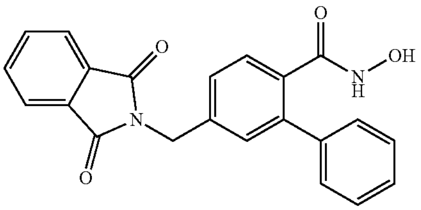 [SMILES: O=C(NO)c1ccc(CN2C(=O)c3ccccc3C2=O)cc1-c1ccccc1] | 32,000 ± 18,000 | 11 ± 2 |
| 37 | 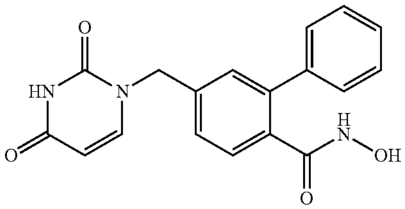 [SMILES: O=C(NO)c1ccc(Cn2ccc(=O)[nH]c2=O)cc1-c1ccccc1] | | 85 ± 30 |

TABLE 8-continued
Inhibitor potency of some representative compounds ($IC_{50}$, nM) against HDAC1 versus HDAC7
| | Structure | $IC_{50}$ (nM) (HDAC1) | $IC_{50}$ (nM) (HDAC7) |
|---|---|---|---|
| 38 | 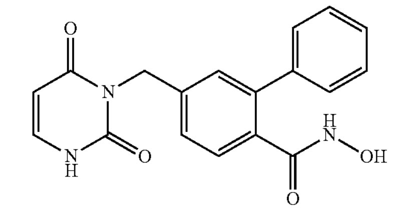 [SMILES: O=C(NO)c1ccc(Cn2c(=O)cc[nH]c2=O)cc1-c1ccccc1] | >10,000 | 22 ± 3 |
| 39 | 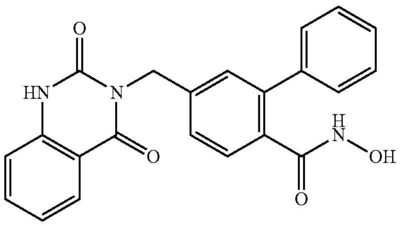 [SMILES: O=C(NO)c1ccc(Cn2c(=O)[nH]c3ccccc3c2=O)cc1-c1ccccc1] | | 10 ± 1 |
| 40 | 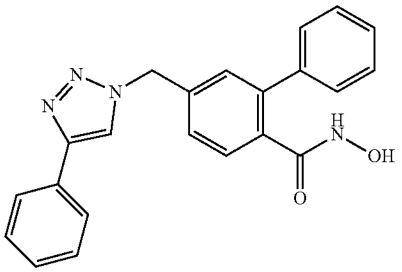 [SMILES: O=C(NO)c1ccc(Cn2cc(-c3ccccc3)nn2)cc1-c1ccccc1] | | 19 ± 3 |
| 41 | 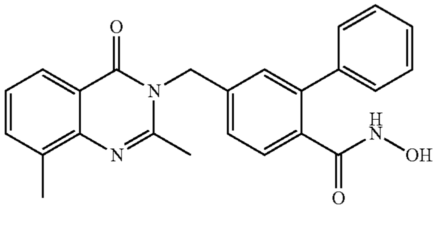 [SMILES: Cc1cccc2c(=O)n(Cc3ccc(C(=O)NO)c(-c4ccccc4)c3)c(C)nc12] | | 8.8 ± 2.6 |
| 42 | 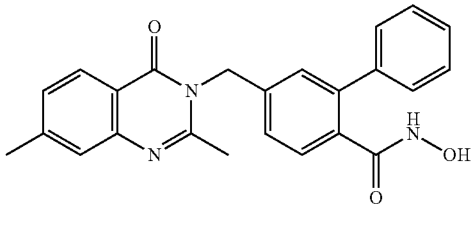 [SMILES: Cc1ccc2c(=O)n(Cc3ccc(C(=O)NO)c(-c4ccccc4)c3)c(C)nc2c1] | | 6.3 ± 2.3 |
| 43 | 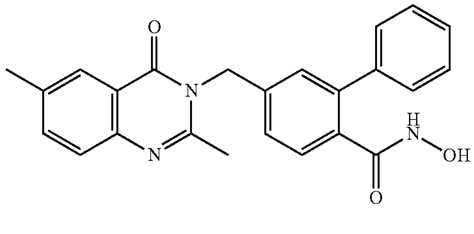 [SMILES: Cc1ccc2nc(C)n(Cc3ccc(C(=O)NO)c(-c4ccccc4)c3)c(=O)c2c1] | | 7.1 ± 1.0 |

TABLE 8-continued
Inhibitor potency of some representative compounds ($IC_{50}$, nM) against HDAC1 versus HDAC7
| | Structure | $IC_{50}$ (nM) (HDAC1) | $IC_{50}$ (nM) (HDAC7) |
|---|---|---|---|
| 44 | 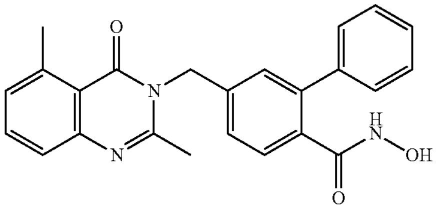 [SMILES: Cc1cccc2nc(C)n(Cc3ccc(C(=O)NO)c(-c4ccccc4)c3)c(=O)c12] | | 7.7 ± 0.8 |
| 45 | 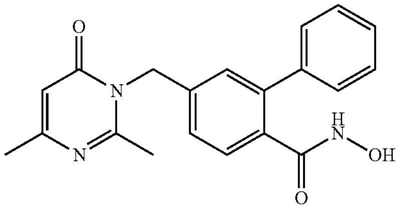 [SMILES: Cc1cc(=O)n(Cc2ccc(C(=O)NO)c(-c3ccccc3)c2)c(C)n1] | >10,000 | 27 ± 5 |
| 46 | 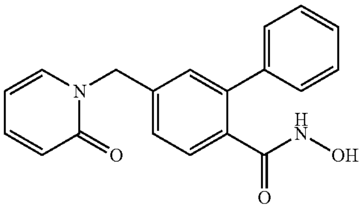 [SMILES: O=C(NO)c1ccc(Cn2ccccc2=O)cc1-c1ccccc1] | | 235 ± 53 |
| 47 | 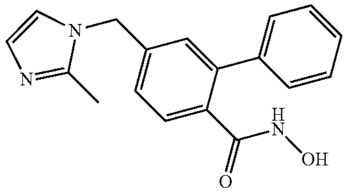 [SMILES: Cc1nccn1Cc1ccc(C(=O)NO)c(-c2ccccc2)c1] | | 140 ± 50 |
| 48 | 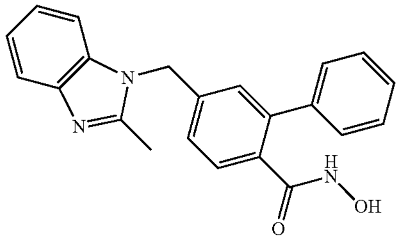 [SMILES: Cc1nc2ccccc2n1Cc1ccc(C(=O)NO)c(-c2ccccc2)c1] | | 58 ± 14 |
| 49 | 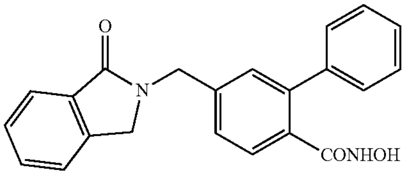 | 33,000 | 31 ± 5 |
| 50 | 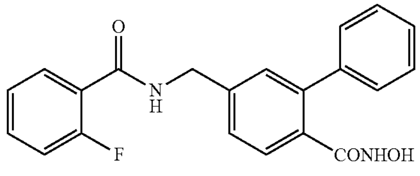 | 16,000 | 130 ± 22 |

TABLE 8-continued
Inhibitor potency of some representative compounds ($IC_{50}$, nM) against HDAC1 versus HDAC7
| | Structure | $IC_{50}$ (nM) (HDAC1) | $IC_{50}$ (nM) (HDAC7) |
|---|---|---|---|
| 51 | 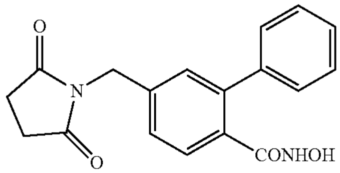 | >20,000 | 76 ± 20 |
| 52 | 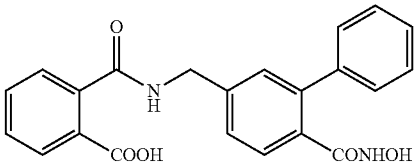 | 20,000 | 1,100 ± 200 |
| 53 | 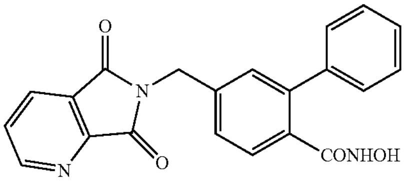 | 28,000 | 250 ± 86 |
| 54 | 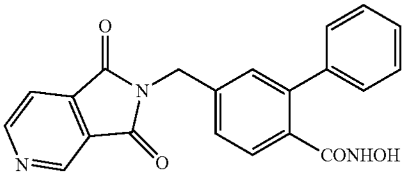 | >20,000 | 650 ± 260 |
| 55 | 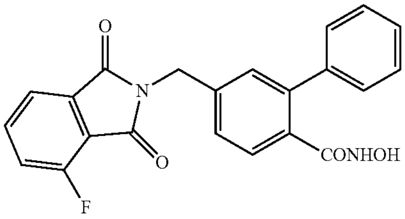 | 27,000 ± 13,000 | 214 ± 34 |
| 56 | 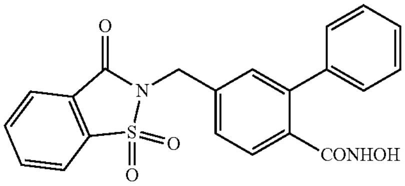 | 4,900 ± 3,400 | 10 ± 2 |
| 57 | 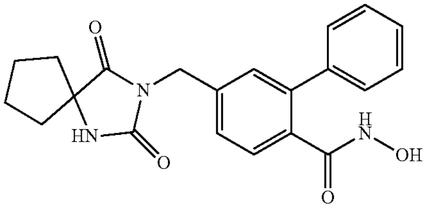 [SMILES: O=C(NO)c1ccc(CN2C(=O)NC3(CCCC3)C2=O)cc1-c1ccccc1] | | 95 ± 18 |

TABLE 8-continued
Inhibitor potency of some representative compounds ($IC_{50}$, nM) against HDAC1 versus HDAC7
| | Structure | $IC_{50}$ (nM) (HDAC1) | $IC_{50}$ (nM) (HDAC7) |
|---|---|---|---|
| 57b | 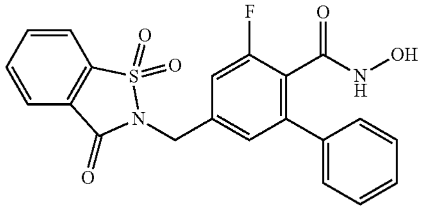 [SMILES: O=C(NO)c1c(F)cc(CN2C(=O)c3ccccc3S2(=O)=O)cc1-c1ccccc1] | | 582 ± 104 |
| 58 | 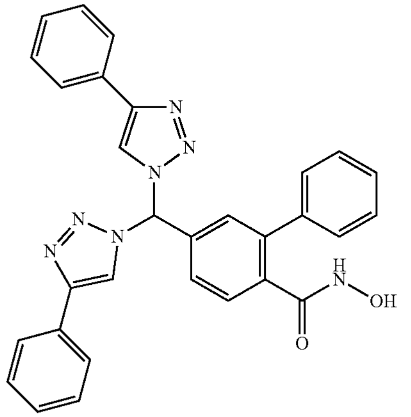 [SMILES: O=C(NO)c1ccc(C(n2cc(-c3ccccc3)nn2)n2cc(-c3ccccc3)nn2)cc1-c1ccccc1] | | 5 ± 1 |
| 59 | 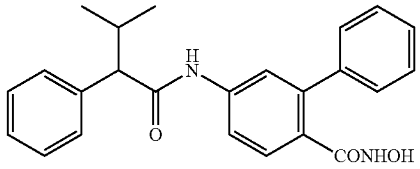 | >10,000 | 555 ± 334 |
| 60 | 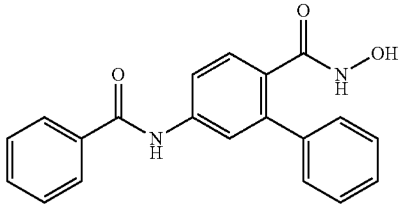 [SMILES: O=C(Nc1ccc(C(=O)NO)c(-c2ccccc2)c1)c1ccccc1] | | 325 |
| 61 | 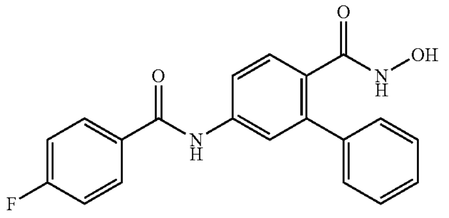 [SMILES: O=C(Nc1ccc(C(=O)NO)c(-c2ccccc2)c1)c1ccc(F)cc1] | | 645 |
| 62 | 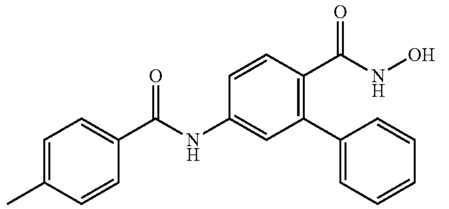 [SMILES: Cc1ccc(C(=O)Nc2ccc(C(=O)NO)c(-c3ccccc3)c2)cc1] | | 431 |

TABLE 8-continued
| Inhibitor potency of some representative compounds ($IC_{50}$, nM) against HDAC1 versus HDAC7 | | | |
|---|---|---|---|
| | Structure | $IC_{50}$ (nM) (HDAC1) | $IC_{50}$ (nM) (HDAC7) |
| 63 | 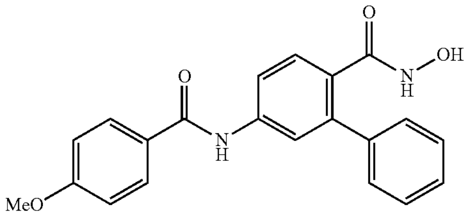 [SMILES: COc1ccc(C(=O)Nc2ccc(C(=O)NO)c(-c3ccccc3)c2)cc1] | | 323 |
| 64 | 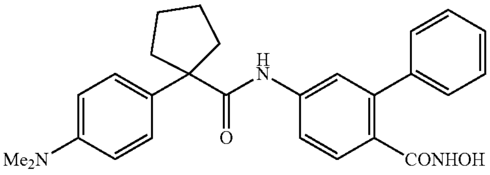 | >10,000 | 556 ± 317 |
| 65 | 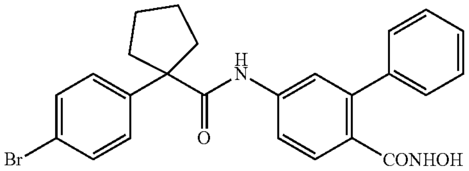 | 4900 ± 1710 | 1210 ± 700 |
| 66 | 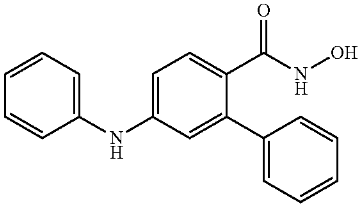 [SMILES: O=C(NO)c1ccc(Nc2ccccc2)cc1-c1ccccc1] | | 94 |
| 67 | 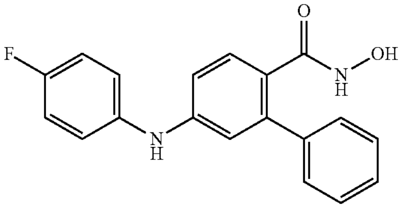 [SMILES: O=C(NO)c1ccc(Nc2ccc(F)cc2)cc1-c1ccccc1] | | 88 |
| 68 | 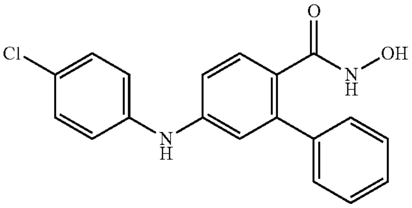 [SMILES: O=C(NO)c1ccc(Nc2ccc(Cl)cc2)cc1-c1ccccc1] | | 178 |
| 69 | 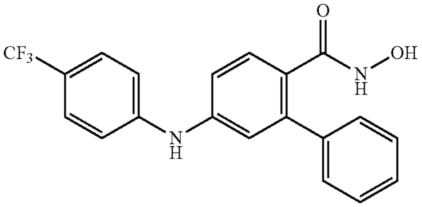 [SMILES: O=C(NO)c1ccc(Nc2ccc(C(F)(F)F)cc2)cc1-c1ccccc1] | | 578 |

TABLE 8-continued
Inhibitor potency of some representative compounds ($IC_{50}$, nM) against HDAC1 versus HDAC7
| | Structure | $IC_{50}$ (nM) (HDAC1) | $IC_{50}$ (nM) (HDAC7) |
|---|---|---|---|
| 70 | 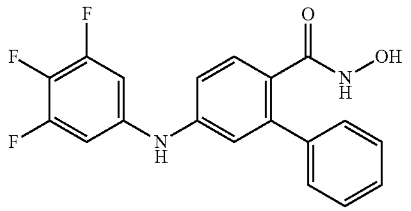 [SMILES: O=C(NO)c1ccc(Nc2cc(F)c(F)c(F)c2)cc1-c1ccccc1] | | 649 |
| 71 | 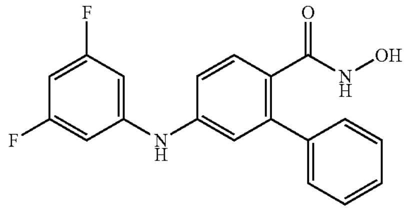 [SMILES: O=C(NO)c1ccc(Nc2cc(F)cc(F)c2)cc1-c1ccccc1] | | 206 |
| 72 | 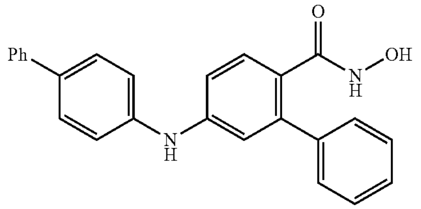 | | >10,000 |
| 73 | 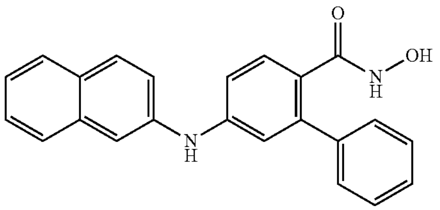 [SMILES: O=C(NO)c1ccc(Nc2ccc3ccccc3c2)cc1-c1ccccc1] | | 321 |
| 74 | 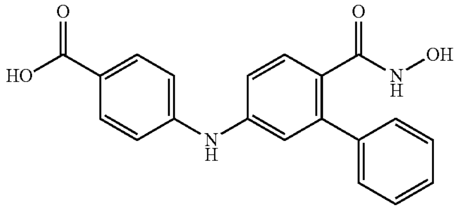 [SMILES: O=C(O)c1ccc(Nc2ccc(C(=O)NO)c(-c3ccccc3)c2)cc1] | | 68 ± 15 |
| 75 | 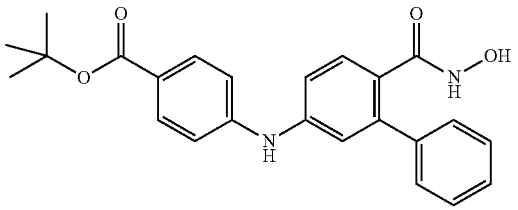 [SMILES: CC(C)(C)OC(=O)c1ccc(Nc2ccc(C(=O)NO)c(-c3ccccc3)c2)cc1] | | 54 ± 7 |
| 76 | 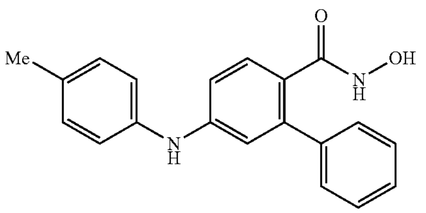 [SMILES: Cc1ccc(Nc2ccc(C(=O)NO)c(-c3ccccc3)c2)cc1] | | 81 ± 19 |

TABLE 8-continued
Inhibitor potency of some representative compounds ($IC_{50}$, nM) against HDAC1 versus HDAC7
| | Structure | $IC_{50}$ (nM) (HDAC1) | $IC_{50}$ (nM) (HDAC7) |
|---|---|---|---|
| 77 | 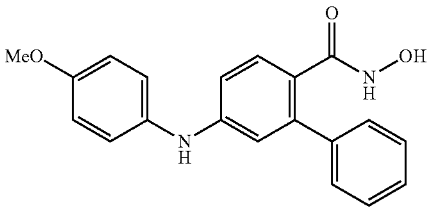 [SMILES: COc1ccc(Nc2ccc(C(=O)NO)c(-c3ccccc3)c2)cc1] | | 61 ± 9 |
| 79 | 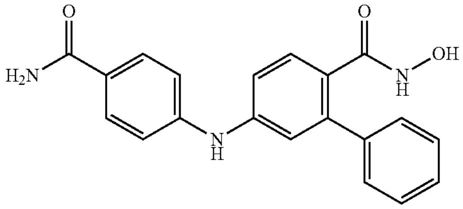 [SMILES: NC(=O)c1ccc(Nc2ccc(C(=O)NO)c(-c3ccccc3)c2)cc1] | >10,000 | 43 ± 9 |
| 80 | 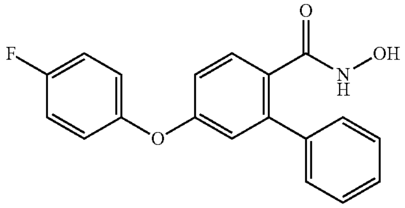 [SMILES: O=C(NO)c1ccc(Oc2ccc(F)cc2)cc1-c1ccccc1] | | 175 ± 26 |
| 81 | 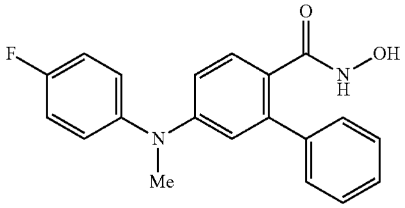 [SMILES: CN(c1ccc(F)cc1)c1ccc(C(=O)NO)c(-c2ccccc2)c1] | | 64 ± 10 |
| 82 | 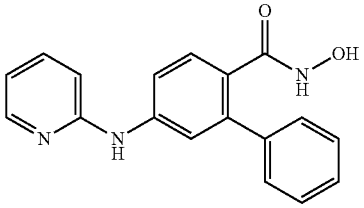 [SMILES: O=C(NO)c1ccc(Nc2ccccn2)cc1-c1ccccc1] | | 249 |
| 83 | 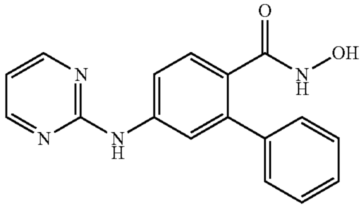 [SMILES: O=C(NO)c1ccc(Nc2ncccn2)cc1-c1ccccc1] | | 447 ± 177 |
| 84 | 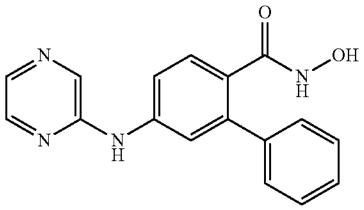 [SMILES: O=C(NO)c1ccc(Nc2cnccn2)cc1-c1ccccc1] | | 233 ± 95 |

TABLE 8-continued
Inhibitor potency of some representative compounds ($IC_{50}$, nM) against HDAC1 versus HDAC7
| | Structure | $IC_{50}$ (nM) (HDAC1) | $IC_{50}$ (nM) (HDAC7) |
|---|---|---|---|
| 85 | 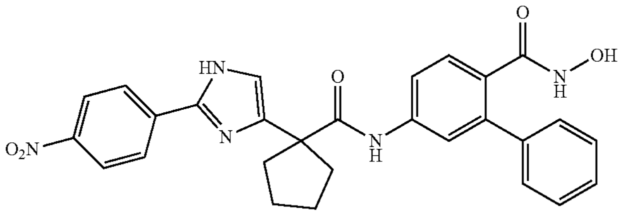 [SMILES: O=C(NO)c1ccc(NC(=O)C2(c3c[nH]c(-c4ccc([N+](=O)[O-])cc4)n3)CCCC2)cc1-c1ccccc1] | | 625 ± 318 |
| 86 | 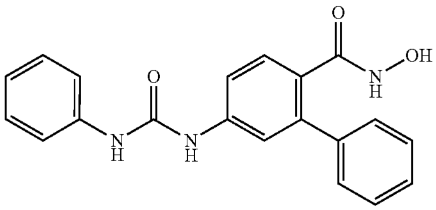 [SMILES: O=C(Nc1ccccc1)Nc1ccc(C(=O)NO)c(-c2ccccc2)c1] | | 248 |
| 87 | 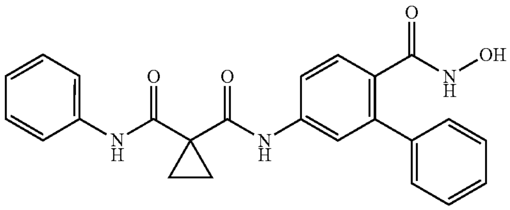 [SMILES: O=C(NO)c1ccc(NC(=O)C2(C(=O)Nc3ccccc3)CC2)cc1-c1ccccc1] | | 241 |
| 88 | 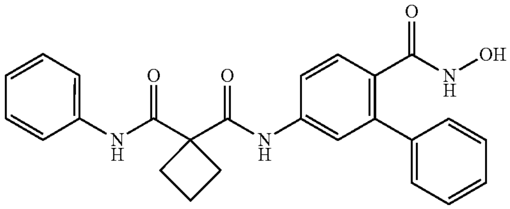 [SMILES: O=C(NO)c1ccc(NC(=O)C2(C(=O)Nc3ccccc3)CCC2)cc1-c1ccccc1] | | 75 ± 23 |
| 89 | 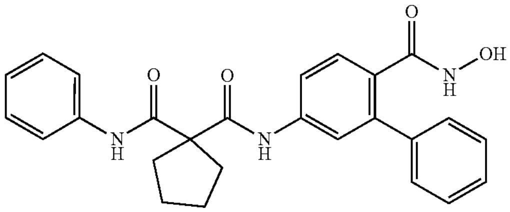 [SMILES: O=C(NO)c1ccc(NC(=O)C2(C(=O)Nc3ccccc3)CCCC2)cc1-c1ccccc1] | | 243 |
| 90 | 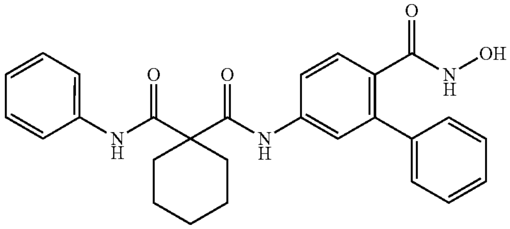 [SMILES: O=C(NO)c1ccc(NC(=O)C2(C(=O)Nc3ccccc3)CCCCC2)cc1-c1ccccc1] | | 168 |
| 92 | 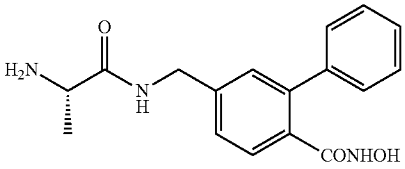 | | 3130 ± 1730 |

TABLE 8-continued
Inhibitor potency of some representative compounds ($IC_{50}$, nM) against HDAC1 versus HDAC7
| | Structure | $IC_{50}$ (nM) (HDAC1) | $IC_{50}$ (nM) (HDAC7) |
|---|---|---|---|
| 93 | 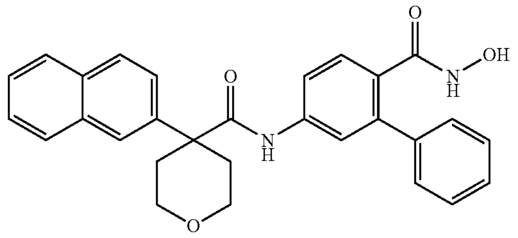 [SMILES: O=C(NO)c1ccc(NC(=O)C2(c3ccc4ccccc4c3)CCOCC2)cc1-c1ccccc1] | | 1594 |
| 94 | 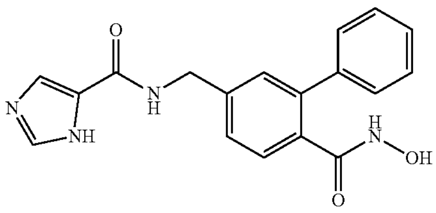 [SMILES: O=C(NCc1ccc(C(=O)NO)c(-c2ccccc2)c1)c1cnc[nH]1] | | 165 ± 45 |
| 95 | 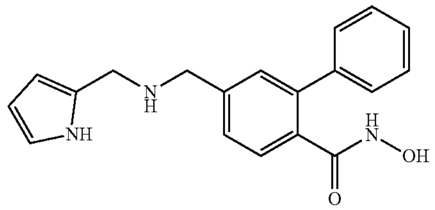 [SMILES: O=C(NO)c1ccc(CNCc2ccc[nH]2)cc1-c1ccccc1] | | 914 ± 204 |
| 96 | 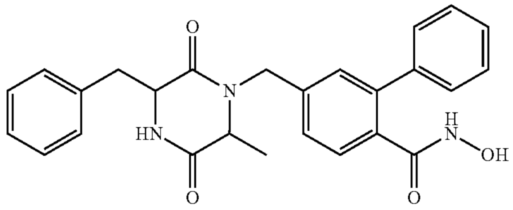 [SMILES: CC1C(=O)NC(Cc2ccccc2)C(=O)N1Cc1ccc(C(=O)NO)c(-c2ccccc2)c1] | | 322 ± 109 |
| 97 | 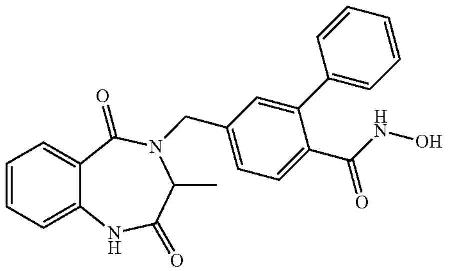 [SMILES: CC1C(=O)Nc2ccccc2C(=O)N1Cc1ccc(C(=O)NO)c(-c2ccccc2)c1] | | 74 ± 13 |
| 98 | 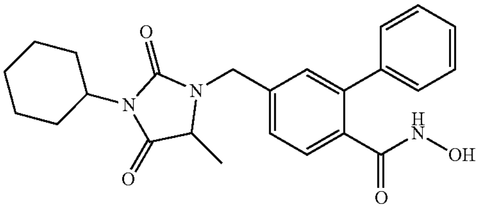 [SMILES: CC1C(=O)N(C2CCCCC2)C(=O)N1Cc1ccc(C(=O)NO)c(-c2ccccc2)c1] | | 100 ± 18 |

TABLE 8-continued
| Inhibitor potency of some representative compounds ($IC_{50}$, nM) against HDAC1 versus HDAC7 | | | |
|---|---|---|---|
| | Structure | $IC_{50}$ (nM) (HDAC1) | $IC_{50}$ (nM) (HDAC7) |
| 99 | 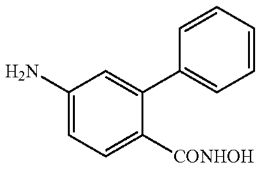 | | 945 |
| Comparative Examples | | | |
| 1 | 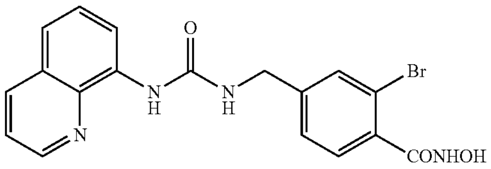 | 3839 ± 1629 | >10,000 |
| 3 | 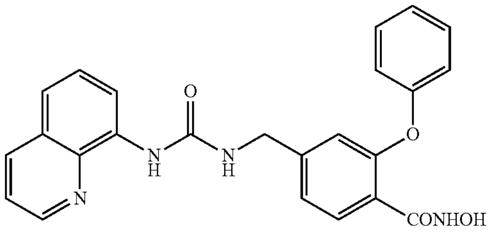 | 2520 ± 1341 | >10,000 |
| 100 | 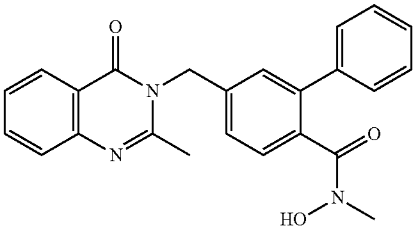 [SMILES: Cc1nc2ccccc2c(=O)n1Cc1ccc(C(=O)N(C)O)c(-c2ccccc2)c1] | | 10,000 |
| 101 | 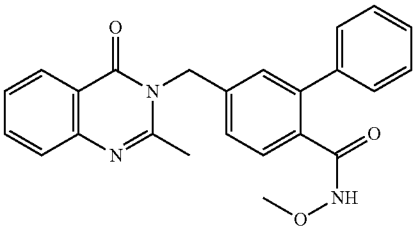 [SMILES: CONC(=O)c1ccc(Cn2c(C)nc3ccccc3c2=O)cc1-c1ccccc1] | | 10,000 |
| 102 | 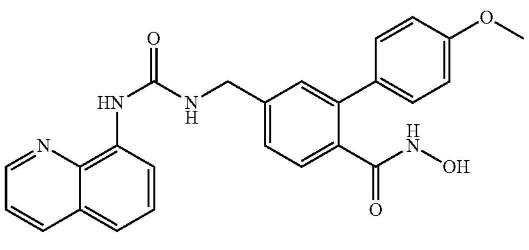 [SMILES: COc1ccc(-c2cc(CNC(=O)Nc3cccc4cccnc34)ccc2C(=O)NO)cc1] | | >10,000 |

TABLE 8-continued

Inhibitor potency of some representative compounds ($IC_{50}$, nM) against HDAC1 versus HDAC7

| | Structure | $IC_{50}$ (nM) (HDAC1) | $IC_{50}$ (nM) (HDAC7) |
|---|---|---|---|
| 103 | 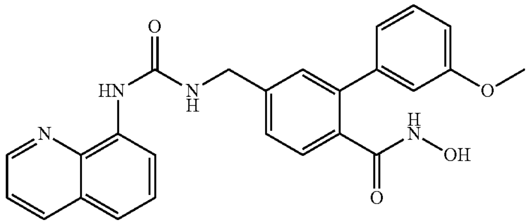 [SMILES: COc1cccc(-c2cc(CNC(=O)Nc3cccc4cccnc34)ccc2C(=O)NO)c1] | | >10,000 |
| 104 | 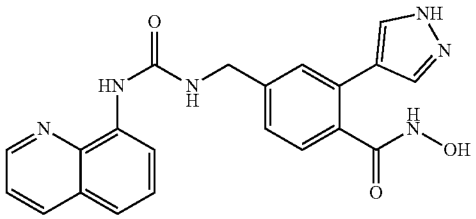 [SMILES: O=C(NCc1ccc(C(=O)NO)c(-c2cn[nH]c2)c1)Nc1cccc2cccnc12] | | >10,000 |
| 105 | 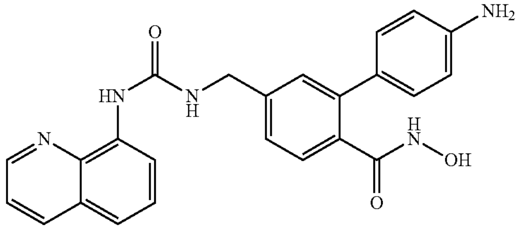 [SMILES: Nc1ccc(-c2cc(CNC(=O)Nc3cccc4cccnc34)ccc2C(=O)NO)cc1] | | >10,000 |
| 106 | 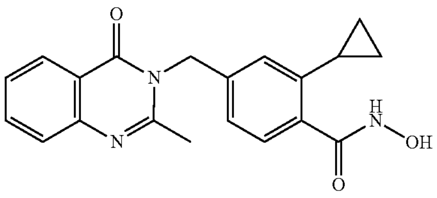 [SMILES: Cc1nc2ccccc2c(=O)n1Cc1ccc(C(=O)NO)c(C2CC2)c1] | | 8,664 ± 2,502 |

TABLE 9

Isoform selectivity of selected compounds ($IC_{50}$, nM) that bind to and inhibit representative class I, class IIa and class IIb HDACs

| Cmpd | Class I | Class IIa | | | | Class IIb |
|---|---|---|---|---|---|---|
| No. | HDAC1 | HDAC4 | HDAC5 | HDAC7 | HDAC9 | HDAC6 |
| 12 | 2,200 ± 1,200 | 42 ± 7 | 9 ± 2 | 7.3 ± 1.2 | 17 ± 3 | 1,100 ± 540 |
| 14 | 3,200 ± 800 | 22 ± 3 | 8 ± 1 | 6.4 ± 0.8 | 15 ± 3 | 1300 ± 480 |
| 36 | 32,000 ± 18,000 | 28 ± 4 | 12 ± 2 | 11 ± 2 | 133 ± 52 | 5,700 ± 1,900 |
| 55 | 27,000 ± 13,000 | 13 ± 3 | 16 ± 2 | 21 ± 3 | 183 ± 102 | 4,400 ± 1,800 |
| 56 | 4,900 ± 3,400 | 48 ± 6 | 8 ± 1 | 10 ± 2 | 93 ± 44 | 5,500 ± 3,100 |

Assay Example 4

Tissue Distribution in Rat (Compound 12)

Compound 12 (10 mg/kg, s.c.) dissolved in 50% propylene glycol/50% saline was administered to female Dark Agouti rats, 8-10 weeks old, 3x per time point. Fresh brain was homogenized in water (1 mL/g). Tissue sample was extracted with MeCN (1:3, v/v). UPLC-MS (Shimazu Nano LC system with a Phenomenex Jupiter C18 5 m, 150×2.00 mm column) was used to assess concentration of compound. Standard elution conditions: 0 to 99% B linear gradient over 11 min, then 99% B for 3 min. Solvent A: $H_2O$+0.1% formic acid. Solvent B:90% MeCN, 10% $H_2O$+0.1% formic acid. Flow rate: 0.25 mL/min. Injection volume: 10 μL. Mass spectroscopy: Applied Biosystems Sciex QSTAR Elite®. Quantification methods: both standard curve and internal standards (caffeine) gave same results. The results are provided in FIG. 1.

Anti-Inflammatory Activity in Collagen-Induced Rat Arthritis (Compound 12)

Effects of compound 12 (LL87) on progression of collagen-induced arthritis (CIA) in 8-12 week old female Dark Agouti rats. Arthritis was induced by inoculating the rats intradermally at the tail base with bovine nasal collagen type II under isoflurane anaesthetic on days 0 and 7. Collagen (200 μg per rat, group 2 and 3) was dissolved in 50 mM acetic acid (100 μL) emulsified with an equal volume of Incomplete Freund's Adjuvant (IFA) using an electric hand-held homogeniser (i.e. 200 μL per rat). Sham rats (group 1) received sterile saline (200 μL) only. The compound 12 (LL87A)-treated group (group 3) was given the compound at 10 mg/kg in 50% propylene glycol/50% saline (1 μL/g) s.c. once daily from day 7-19. Sham (group 1) and CIA control (group 2) rats were given the vehicle only s.c. There three randomly assigned groups were: Sham (6 rats, saline tail base injection, vehicle s.c. treatment from day 7); CIA (8 rats, bovine collagen type II tail base injection, vehicle s.c. treatment from day 7); CIA and compound 12 (LL87A) (9 rats, bovine collagen type II tail base injection, compound 12 (LL87A) 10 mg/kg/day s.c. treatment from day 7).

Rats were weighed every day from day 7 onwards, and weight change was calculated as percentage change from baseline. Disease Activity Index (DAI) was assessed daily from day 7 according to the following: weight loss, sickness behaviour, mobility, paw inflammation, pain/discomfort and aberrant behaviour. Each criterion was scored from 0 to 3, with 0 being normal and 3 being severely affected. Hind paws were measured daily with a digital caliper from day 15. Both width and thickness were measured, and an area was calculated and expressed as percentage change from baseline. All rats were terminated by $CO_2$ inhalation on day 20.

Figure 2:
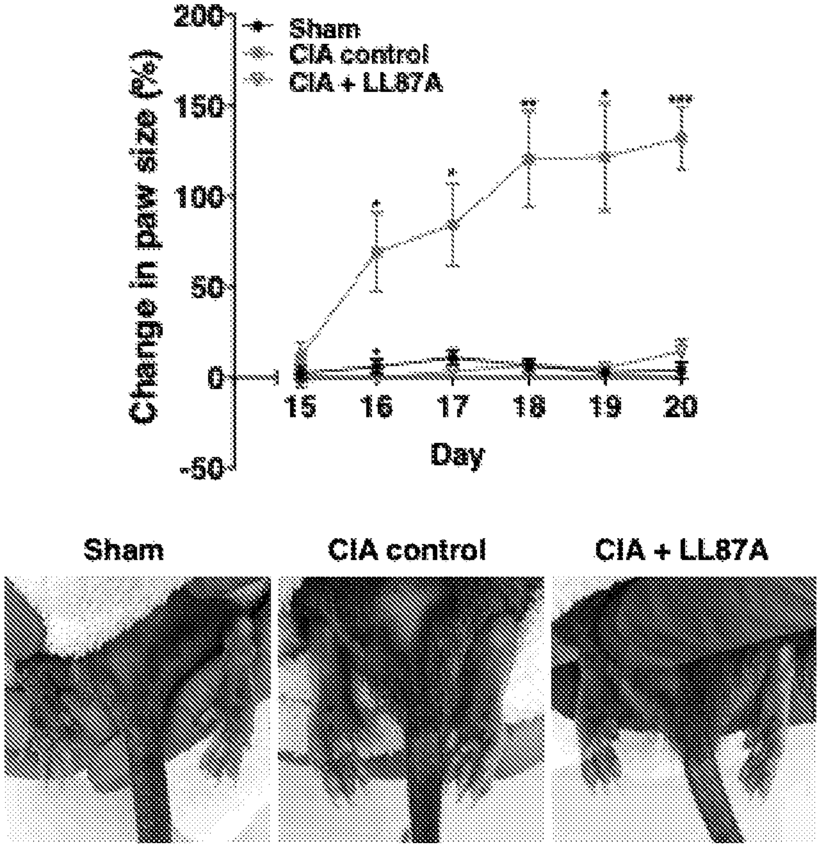
FIG. 2 is a graph and photographs showing the effect of compound 12 (LL87A) on rat hind paw swelling in a model of collagen-induced arthritis (CIA)
Figure 3:
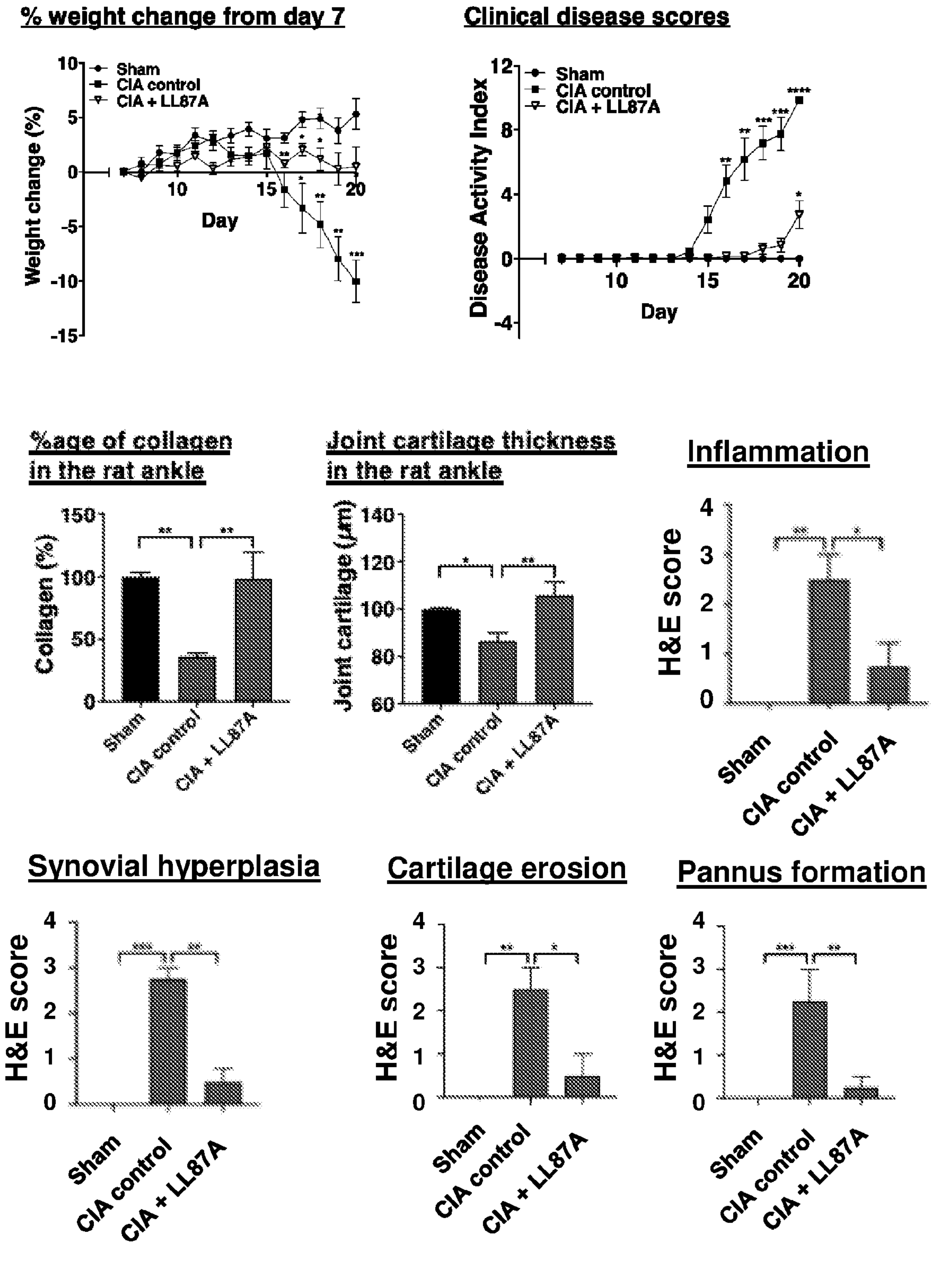
FIG. 3 provides graphs showing the effect of compound 12 (LL87A) on weight change, and clinical disease in collagen-induced arthritis (CIA) rats, and the effect of compound 12 on collagen loss and structural damage on CIA rat ankle joint cartilage.
Figure 4:
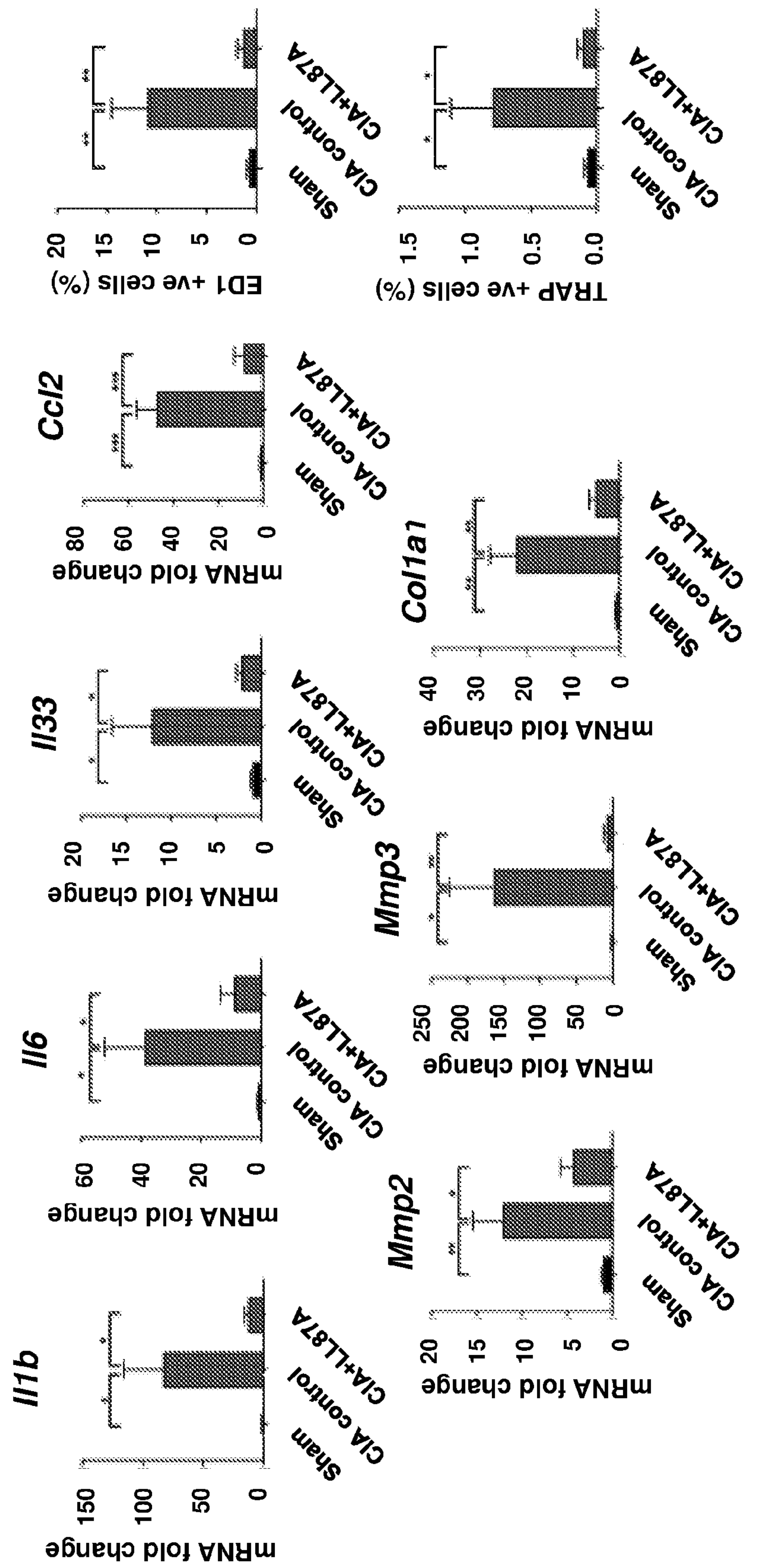
FIG. 4 provides graphs showing the effect of compound 12 on macrophages and osteoclasts in CIA rats, and also the effect of compound 12 on expression of inflammatory genes and arthritic markers in CIA rats.

Female DA rats (8-12 weeks old) were given compound 12 (LL87A) at 10 mg/kg/day s.c. from day 7 onwards in the CIA model. This illustrated significant reductions in hind paw swelling, body weight loss, clinical disease scores, knee and ankle joint damage, collagen loss and cartilage thinning, numbers of macrophages and osteoclasts, and inflammatory gene expression in the compound-treated rats compared to disease controls. Hind paw swelling from day 15-20 was significantly reduced in HDAC inhibitor-treated rats compared to CIA controls. Representative photographs of rat hind paws from each of sham, CIA control, and inhibitor-treated groups are shown in FIG. 2. See also FIGS. 3 and 4. Data are presented as mean±SEM, n=6-10. Analysis by two-way ANOVA; $^*p<0.05$, $^{}p<0.01$, $^{*}p<0.001$, $^{****}p<0.0001$ compared to sham.

Micro-computed tomography (microCT). Following euthanasia of the rats, their left hind limbs were skinned and disarticulated at the hip joint. The limbs were fixed in 10% neutral buffered formalin (NBF, Sigma-Aldrich, USA) for 48 h at 4° C., then transferred to 70% ethanol until scanning. One limb from each of sham, CIA control and LL87A-treated group was scanned using an Inveon preclinical microCT scanner (Siemens, Germany). The CT images were acquired through an X-ray source with the voltage set to 80 kV and the current set to 250 μA. The scans were performed using 360° rotation with 360 rotation steps with a medium-high magnification and a binning factor of two. The exposure time was 2000 ms with an effective isotropic pixel size of 27 μm. The total CT scanning process took approximately 90 minutes. The CT images were reconstructed by an Inveon Acquisition Workstation software (IAW version 2.4, Siemens, Germany) using a Feldkamp reconstruction software (Siemens, Germany). The CT images were visualised and analysed using Inveon Research Workstation software (IRW version 4.3, Siemens, Germany).

Histopathology and joint assessment. Following microCT scanning, the left ankle and knee were decalcified in Osteosoft® (Merck Millipore, USA) for 21 days. Decalcification was considered complete when the bony portions were penetrable by an 18 G needle. Paws were then embedded in paraffin wax and cut at 8 μm sagitally using a microtome (Leica Biosystems, Germany).

After dewaxing in xylene and rehydration in serial dilutions of alcohol, paw tissue sections were stained. They were then dehydrated through 70% alcohol and two changes of absolute alcohol, cleared in xylene, and mounted in dibutylphthalate polystyrene xylene (DPX) mountant (Sigma-Aldrich, USA). Finally, tissue sections were viewed under an Olympus BX-51 upright microscope. Images were captured using an Olympus DP-71 12 Mp colour camera and DP Capture/DP Manager software packages (Olympus, Japan).

Masson's trichrome (MTC) staining was performed using a standard protocol. MTC-stained sections were assessed for articular collagen loss. Brightfield photomicrographs (20× lens) were taken of each articular surface of each joint, with six images for each animal. FIJI/ImageJ 1.42q software (USA) was used to quantitate collagen loss, measured by loss of blue collagen-like staining by aniline blue, using an automated script created by Dr. Rink-Jan Lohman and Dr. Nick Hamilton, both from IMB, UQ. Briefly, articular cartilage was digitally traced from articular surface to subchondral bone border on MTC images, then automatically colour-deconvoluted into red and blue channels and analysed for pixel staining density per unit area, expressed as a ratio of blue to red. Lower ratios suggest reduced blue collagen-like staining of the articular cartilage, representing arthritic collagen loss. Final results were presented as percentage collagen loss from sham.

Articular cartilage thickness was also measured from the same MTC-stained sections. Three regions of three joint surfaces of each paw were measured digitally using FIJI/ImageJ 1.42q software (USA) from the chondral/bone junction to the articular surface. These thickness values were then averaged within animals and expressed in μm.

Haematoxylin and eosin (H&E) staining was performed using a standard protocol. H&E-stained sections were used to evaluate tissue health, in particular the tibio-talo-calcaneal joint. At least six 20× sections were evaluated and scored (0-3) for inflammation, synovial hyperplasia, pannus formation and bone/cartilage erosion. A total score of 12 was possible according to this scheme.

Toluidine blue staining for mast cells was performed by staining paw tissue sections with 0.1% toluidine blue (Sigma-Aldrich, USA) in 1% sodium chloride (pH 2.5) for 3 min. Active mast cells were expressed as a percentage of all toluidine blue-positive cells.

Immunohistochemistry (IHC) for ED1 and ED2 macrophages After dewaxing in xylene and rehydration in serial dilutions of alcohol, paw tissue sections were incubated in citrate buffer (0.01 M, pH 6) at 95° C. for 20 min for antigen retrieval. They were then cooled down briefly and incubated with blocking medium (PBS, 0.1% triton X-100, 10% horse serum) for 1 h at room temperature in a humidity chamber. Samples were incubated with the primary antibody overnight at 4° C.: either ED1 (ab31630, mouse monoclonal antibody to CD68, Abcam, Australia) or ED2 (mouse monoclonal antibody to CD163, Abcam, Australia) at 1:100 dilution in diluent (PBS, 0.1% triton X-100, 4% horse serum). The next day, samples were washed with PBS and incubated with the secondary antibody (donkey anti-mouse conjugated with HRP, Abcam, Australia) at 1:400 dilution in the same diluent for 2 h at room temperature. Slides were then incubated with DAB (3,3'diaminobenzidine, ab64238, Abcam, Australia) for 5 min at room temperature before counterstaining with haematoxylin. Finally, slides were dehydrated and mounted with DPX mountant (Sigma-Aldrich, USA). Slides stained with ED1 antibody were scanned by an Aperio XT Brightfield Slide Scanner (Leica Biosystems, Germany), and those stained with ED2 antibody were scanned by a Axio Scan.Z1 Scanner (Zeiss, Germany). Slides were viewed using either Aperio ImageScope slide viewing software (Leica Biosystems, Germany) for the former, or ZEN 3.1 (blue edition, Zeiss, Germany) for the latter. Tissue sections were colour deconvoluted using the IHC Image Analysis Toolbox (H-DAB) in FIJI/ImageJ 1.42q software (USA). Brown DAB staining was then quantified (percentage of area occupied by positive staining) and averaged per section.

Tartrate-resistant acid phosphatase (TRAP) staining for osteoclasts. Osteoclasts were stained with tartrate-resistant acid phosphate (TRAP) staining solution and counterstained with Fast Green according to standard protocol (University of Rochester Medical Center). Entire slides were scanned by an Axio Scan.Z1 Scanner (Zeiss, Germany) as above. Slides were viewed using ZEN 3.1 (blue edition) slide viewing software (Zeiss, Germany). Tissue sections were colour deconvoluted using the IHC Image Analysis Toolbox (Feulgen Light Green) in FIJI/ImageJ 1.42q software. Purple staining by TRAP solution per section was then quantified and averaged.

RNA isolation and gene analysis. Plantar soft tissues from the right hind rat paw were stored at −80° C. in a freezer until RNA extraction was performed. Tissues (~120 mg) were cut into small pieces with a scalpel blade and mixed with 1 mL of TRIsure™ (Bioline, Australia) and 0.5 mm zirconium oxide beads (Next Advance, USA). They were then macerated and homogenised at 4° C. using a Bullet Blender® tissue homogeniser (Next Advance, USA). Afterwards, 200 μL of chloroform (Sigma-Aldrich, USA) was added and the mixture was shaken vigorously. Samples were incubated at room temperature for 5 min before centrifugation (12,000 rpm, 15 min, 4° C.). The clear supernatant from each sample was collected for RNA isolation using ISOLATE II RNA Mini Kit (Bioline, Australia) according to manufacturer's instructions. RNA was converted to complementary DNA (cDNA) using SuperScript® III Reverse Transcriptase (Invitrogen, Australia) and Oligo(dT) 12-18 primer (Invitrogen, Australia) in a Veriti™ 96-well thermal cycler (Applied Biosystems, USA). Real-time PCR was conducted using SYBR® Green (Life Technologies, Australia) in a ViiA™ 7 Real-Time PCR System (Applied Biosystems, USA). All samples were duplicates, and target genes were normalised to housekeeping gene Hprt. Fold change was calculated relative to sham.

Rat TNF protein level in rat paw tissues. Protein extraction was performed by homogenising frozen rat paw tissues with cell lysis buffer (Abcam, Australia, 120 mg of tissues in 400 μL) and zirconium oxide beads (1 mm and 2 mm, Next Advance, USA) using a Bullet Blender® tissue homogeniser (Next Advance, USA) at 4° C. Samples were then centrifuged at 12,000 rpm for 15 min at 4° C. and their supernatants collected. rTNF was quantified by a sandwich ELISA assay (BD OptEIA™, BD Biosciences, CA, USA) according to manufacturer's instructions. The final rTNF concentrations were normalised to mg of rat paw tissues.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims appropriately interpreted by those skilled in the art.

The invention claimed is:

1. A compound or a pharmaceutically acceptable salt thereof, wherein the compound is selected from the group consisting of:

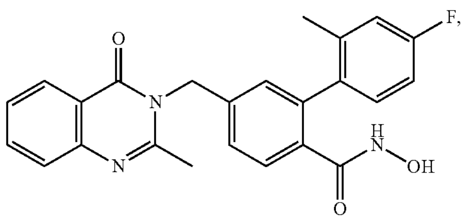

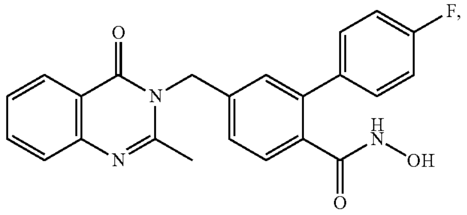

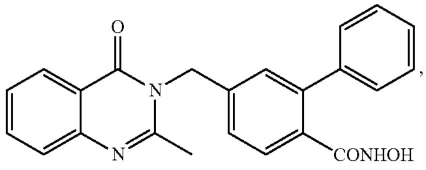

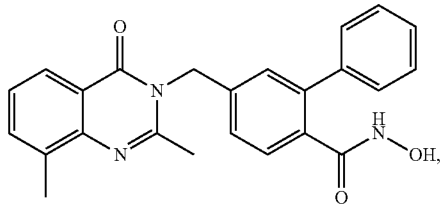

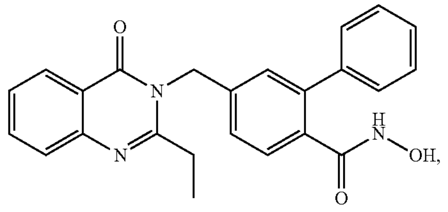

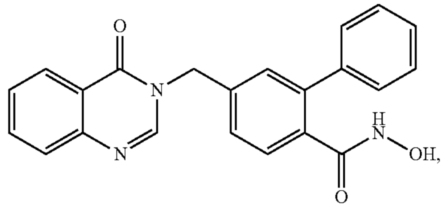

-continued

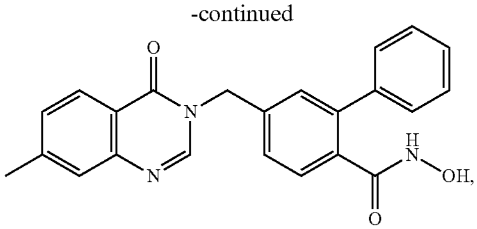

,

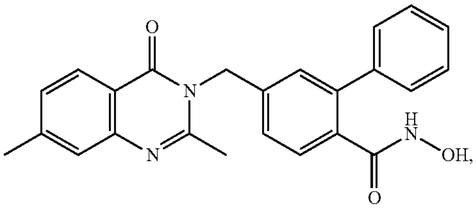

, and

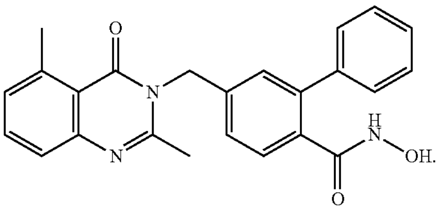

.

2. The compound or the pharmaceutically acceptable salt thereof of claim 1, wherein the compound is selected from the group consisting of:

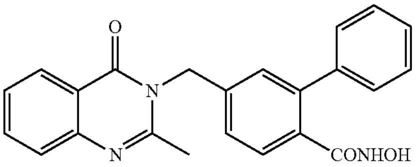

and

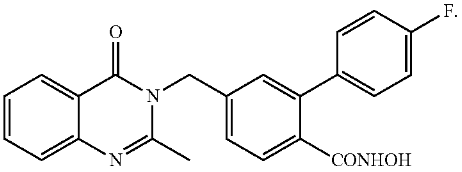

.

3. A pharmaceutical composition comprising an effective amount of the compound or pharmaceutically acceptable salt thereof of claim 1.

4. A method of treating a disease associated with Class IIa histone deacetylase activity in a subject, the method comprising administering to the subject an effective amount of the compound of claim 1 or the pharmaceutically acceptable salt thereof; wherein the disease associated with Class IIa histone deacetylase activity is an inflammatory disease.

5. A method of treating a disease associated with Class IIa histone deacetylase activity in a subject, the method comprising administering to the subject an effective amount of the compound of claim 2 or the pharmaceutically acceptable salt thereof; wherein the disease associated with Class IIa histone deacetylase activity is an inflammatory disease.

* * * * *